(12) United States Patent
Blazeck et al.

(10) Patent No.: US 9,896,691 B2
(45) Date of Patent: Feb. 20, 2018

(54) COMPOSITIONS AND METHODS FOR LIPID PRODUCTION

(71) Applicant: Board of Regents, The University of Texas System, Austin, TX (US)

(72) Inventors: John Blazeck, Austin, TX (US); Andrew Hill, Austin, TX (US); Leqian Liu, Austin, TX (US); Hal Alper, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 241 days.

(21) Appl. No.: 14/268,796

(22) Filed: May 2, 2014

(65) Prior Publication Data
US 2014/0329287 A1    Nov. 6, 2014

Related U.S. Application Data

(60) Provisional application No. 61/819,476, filed on May 3, 2013.

(51) Int. Cl.
| | |
|---|---|
| *C12P 7/64* | (2006.01) |
| *C12N 15/81* | (2006.01) |
| *C07K 14/39* | (2006.01) |
| *C12N 1/16* | (2006.01) |
| *C12N 9/04* | (2006.01) |
| *C12N 9/02* | (2006.01) |

(Continued)

(52) U.S. Cl.
CPC ............ *C12N 15/815* (2013.01); *C07K 14/39* (2013.01); *C12N 1/16* (2013.01); *C12N 9/0006* (2013.01); *C12N 9/0008* (2013.01); *C12N 9/0042* (2013.01); *C12N 9/0077* (2013.01); *C12N 9/1007* (2013.01); *C12N 9/78* (2013.01); *C12N 9/88* (2013.01); *C12N 9/93* (2013.01); *C12N 15/01* (2013.01); *C12N 15/52* (2013.01); *C12P 7/64* (2013.01); *C12P 7/6409* (2013.01); *C12P 7/6463* (2013.01); *C12R 1/645* (2013.01)

(58) Field of Classification Search
None
See application file for complete search history.

(56) References Cited

U.S. PATENT DOCUMENTS

| | | | |
|---|---|---|---|
| 8,367,395 B2 * | 2/2013 | Bailey | C11B 1/10 435/183 |
| 2009/0117253 A1 | 5/2009 | Hong et al. | |

(Continued)

FOREIGN PATENT DOCUMENTS

| | | |
|---|---|---|
| EP | 0005277 A2 | 11/1979 |
| WO | WO 2011/109548 A2 | 9/2011 |
| WO | WO 2013/059649 A1 | 4/2013 |

OTHER PUBLICATIONS

Kamisaka et al. "DGA1 (diacylglycerol acyltransferase gene) overexpression and leucine biosynthesis significantly increase lipid accumulation in the delta-snf2 disruptant of *Saccharomyces cerevisiae*", Biochemical Journal, vol. 408, pp. 61-68, 2007.*

(Continued)

*Primary Examiner* — Richard Ekstrom
(74) *Attorney, Agent, or Firm* — Meunier Carlin & Curfman LLC

(57) ABSTRACT

Described herein, inter alia, are compositions, oleagnious organisms, and methods useful for producing lipids, lipid precursors, and/or oleochemicals.

10 Claims, 23 Drawing Sheets

(51) Int. Cl.
| | |
|---|---|
| C12N 9/10 | (2006.01) |
| C12N 9/78 | (2006.01) |
| C12N 9/88 | (2006.01) |
| C12N 9/00 | (2006.01) |
| C12N 15/52 | (2006.01) |
| C12N 15/01 | (2006.01) |
| C12R 1/645 | (2006.01) |

(56) References Cited

U.S. PATENT DOCUMENTS

| | | | | |
|---|---|---|---|---|
| 2011/0300595 | A1* | 12/2011 | Lang | C12N 9/0006 435/145 |
| 2013/0143282 | A1* | 6/2013 | Stephanopoulos | C12N 15/815 435/134 |
| 2013/0149754 | A1* | 6/2013 | Dulermo | C12P 7/6409 435/134 |
| 2013/0230891 | A1* | 9/2013 | Hong | C12N 9/0083 435/134 |
| 2013/0280793 | A1* | 10/2013 | Brown | C12Y 102/01 435/257.2 |

OTHER PUBLICATIONS

Andre et al., "Biotechnological conversions of bio-diesel-derived crude glycerol by *Yarrowia lipolytica* strains", *Engineering in Life Sciences* 2009, 9(6):468-478.

Beopoulos et al., "Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts", *Applied Microbiology and Biotechnology* 2012, 93(4):1523-1537.

Beopoulos et al., "Control of Lipid Accumulation in the Yeast *Yarrowia lipolytica*", *Applied and Environmental Microbiology* 2008, 74(24):7779-7789.

Blazeck et al., "Heterologous production of pentane in the oleaginous yeast *Yarrowia lipolytica*.", *Journal of Biotechnology* 2013, 165:184-194.

Blazeck et al., "Harnessing *Yarrowia lipolytica* lipogenesis to create a platform for lipid and biofuel production", *Nature Communications*, Jan. 2014, 5 Article 3131, 10 pages.

Chuang et al., "Co-expression of heterologous desaturase genes in *Yarrowia lipolytica*.", *New Biotechnology* 2010, 27(4):277-282.

Dulermo et al., "Involvement of the G3P shuttle and beta-oxidation pathway in the control of TAG synthesis and lipid accumulation in *Yarrowia lipolytica*", *Metabolic Engineering* 2011, 13(5):482-491.

Gebre et al., "Osh6 overexpression extends the lifespan of yeast by increasing vacuole fusion", *Cell Cycle* 2012, 11(11): 2176-2188.

Han et al., "Leucyl-tRNA Synthetase is an Intracellular Leucine Sensor for the mTORC1-Signaling Pathway", *Cell* 2012, 149(2):410-424.

Kamei et al., "GABA metabolism pathway genes, UGA1 and GAD1, regulate replicative lifespan in *Saccharomyces cerevisiae*", *Biochemical and Biophysical Research Communications* 2011, 407(1):185-190.

Kamisaka et al., "DGA1 (diacylglycerol acyltransferase gene) overexpression and leucine biosynthesis significantly increase lipid accumulation in the delta snf2 disruptant of *Saccharomyces cerevisiae*", *Biochemical Journal* 2007, 408:61-68.

Morin et al., "Transcriptomic Analyses during the Transition from Biomass Production to Lipid Accumulation in the Oleaginous Yeast *Yarrowia lipolytica*", *Plos One* 2011, 6(11):e27966, 13 pages.

Staschke et al., "Integration of General Amino Acid Control and Target of Rapamycin (TOR) Regulatory Pathways in Nitrogen Assimilation in Yeast", *Journal of Biological Chemistry* 2010, 285(22):16893-16911.

Tai et al, "Engineering the push and pull of lipid biosynthesis in oleaginous yeast *Yarrowia lipolytica* for biofuel production", *Metabolic Engineering* 2013, 15:1-9.

Xue et al., "Production of omega-3 eicosapentaenoic acid by metabolic engineering of *Yarrowia lipolytica*", *Nature Biotechnology* 2013, 31(8): 734-740.

Ageitos et al., "Oily yeasts as oleaginous cell factories", *Applied Microbiology and Biotechnology*, 2011, 90(4): 1219-1227.

Ratledge, C., "Regulation of lipid accumulation in oleaginous micro-organisms", *Biochemical Society Transactions*, 2002, 30(6):1047-1050.

Sitepu et al., "An improved high-throughput Nile red fluorescence assay for estimating intracellular lipids in a variety of yeast species", *Journal of Microbiological Methods*, 2012, 91(2):321-328.

Titorenko et al., "Four Distinct Secretory Pathways Serve Protein Secretion, Cell Surface Growth, and Peroxisome Biogenesis in the Yeast *Yarrowia lipolytica*", *Molecular and Cellular Biology*, 1997, 17(9):5210-5226.

Invitation to Pay Additional Fees and Partial International Search Report dated Oct. 13, 2014 for International Application No. PCT/US2014/036663, 18 pages.

International Search Report and Written Opinion dated Dec. 15, 2014 for International Application No. PCT/US2014/036663, 38 pages.

* cited by examiner

| | | | | |
|---|---|---|---|---|
| Yali0A | 297474 | G | A | YALI0A02354g similar to S. cerevisiae OSH6, member of an oxysterol-binding protein family |
| Yali0A | 316425 | CGGA | C | YALI0A02497g no similarity |
| Yali0C | 138994 | T | C | YALI0C01001g no similarity |
| Yali0C | 139014 | A | G | YALI0C01001g no similarity |
| Yali0C | 953493 | G | A | YALI0C07150g similar to S. cerevisiae IRC20; E3 ubiquitin ligase and putative helicase |
| Yali0C | 2966661 | C | T | YALI0C22231g weakly similar to Schizosaccharomyces pombe RNA polymerase III Transcription factor (TFIIIC subunit) |
| Yali0C | 3047264 | G | A | YALI0C22726g no similarity |
| Yali0D | 1576990 | G | A | YALI0D12628g similar to Fusarium solani cutinase transcription factor 1 alpha |
| Yali0E | 2038953 | G | A | YALI0E17215g some similarity to S. cerevisiae RME1 |
| Yali0E | 2038954 | G | A | YALI0E17215g some similarity to S. cerevisiae RME1 |
| Yali0E | 2424790 | T | G | YALI0E20449g weakly similar to S. cerevisiae YOX1 |
| Yali0F | 3369592 | C | T | YALI0F26191g similar to S. cerevisiae UGA3 |

FIG. 21

                        SEQUENCE LISTING

<160> NUMBER OF SEQ ID NOS: 81

<210> SEQ ID NO 1
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 1
ttggcgcgcc atgccgcagc aagcaatgg                                    29

<210> SEQ ID NO 2
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 2
ccttaattaa ttaaccatgc agccgctcaa ac                                32

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 3
ttggcgcgcc atgtctgcca acgagaacat                                   30

<210> SEQ ID NO 4
<211> LENGTH: 30
<212> TYPE: DNA
<213> ORGANISM: Artificial Sequence
<220> FEATURE:
```

<223> OTHER INFORMATION: Synthetic polynucleotide

<400> SEQUENCE: 4
ttggcgcgcc tctgccaacg agaacatctc                                        30

<210> SEQ ID NO 5
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 5
ccttaattaa ctatgatcga gtcttggcct tg                                     32

<210> SEQ ID NO 6
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 6
ttggcgcgcc atgtcagcga aatccattca cg                                     32

<210> SEQ ID NO 7
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 7
ttggcgcgcc tcagcgaaat ccattcacga g                                      31

<210> SEQ ID NO 8
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 8
ccttaattaa ttaaactccg agaggagtgg aa                                     32

<210> SEQ ID NO 9
<211> LENGTH: 67
<212> TYPE: DNA
<213> ORGANISM: Artificial Sequence
<220> FEATURE:
<223> OTHER INFORMATION: Synthetic polynucleotide

<400> SEQUENCE: 9
ccaccgcgga taacttcgta taatgtatgc tatacgaagt tatgagtctt tattggtgat       60
gggaaga                                                                 67

<210> SEQ ID NO 10
<211> LENGTH: 67
<212> TYPE: DNA
<213> ORGANISM: Artificial Sequence
<220> FEATURE:
<223> OTHER INFORMATION: Synthetic polynucleotide

<400> SEQUENCE: 10
cggttcgaaa taacttcgta tagcatacat tatacgaagt tatcagtcgc cagcttaaag       60

-continued atatcta 67

```
<210> SEQ ID NO 11
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 11
```
ggaacggtag atctcgagcg tcccaaaacc ttctc 35

```
<210> SEQ ID NO 12
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 12
```
gtggacgggc cggcgtttgg cgcccgtttt ttcg 34

```
<210> SEQ ID NO 13
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 13
```
cattcaaagg cgcgccatga ctatcgactc acaatactac a 41

```
<210> SEQ ID NO 14
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 14
```
gcggatcctt aattaattac tcaatcattc ggaactctgg 40

```
<210> SEQ ID NO 15
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 15
```
cattcaaagg cgcgccatgg aagtccgacg acgaaa 36

```
<210> SEQ ID NO 16
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 16
```
gcggatcctt aattaactac tggttctgct tgtagttgt 39

```
<210> SEQ ID NO 17
<211> LENGTH: 32
<212> TYPE: DNA
```

```
<213> ORGANISM: Artificial Sequence
<220> FEATURE:
<223> OTHER INFORMATION: Synthetic polynucleotide

<400> SEQUENCE: 17
gactggcgcg catgagcttc ccccaacaag ta                              32

<210> SEQ ID NO 18
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 18
gtccttaatt aattatctgt tgacaggaaa gtatcgc                         37

<210> SEQ ID NO 19
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 19
gactggcgcg catgtctatc aagcgagaag agt                             33

<210> SEQ ID NO 20
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 20
gtccttaatt aactagatca gcaataaagt cgtgct                          36

<210> SEQ ID NO 21
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 21
gactggcgcg ccatgttacg actacgaacc atgc                            34

<210> SEQ ID NO 22
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 22
gtccttaatt aactagtcgt aatcccgcac atg                             33

<210> SEQ ID NO 23
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 23
actgggcgcg ccatggctaa agacaaggaa atcgactttg ac                   42
```

<210> SEQ ID NO 24
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 24
actgttaatt aatcagtaaa tgtaagccag aacatcgt                              38

<210> SEQ ID NO 25
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 25
actgttaatt aatcatgcag cctgggcctg g                                     31

<210> SEQ ID NO 26
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 26
actgggcgcg ccatgtttta caccaagccc gacccg                                36

<210> SEQ ID NO 27
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 27
actgttaatt aattagagag tcccccacat gtcaccc                               37

<210> SEQ ID NO 28
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 28
actgggcgcg ccatgcgcca aaagctgccg ttcaac                                36

<210> SEQ ID NO 29
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 29
actgttaatt aattatggct tcccttctgc cacatc                                36

<210> SEQ ID NO 30
<211> LENGTH: 36
<212> TYPE: DNA
<213> ORGANISM: Artificial Sequence
<220> FEATURE:

<223> OTHER INFORMATION: Synthetic polynucleotide

<400> SEQUENCE: 30
actgggcgcg ccatgactat cgactcacaa tactac                                    36

<210> SEQ ID NO 31
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 31
actgttaatt aattactcaa tcattcggaa ctctgg                                    36

<210> SEQ ID NO 32
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 32
agagggctag agagagggag aa                                                   22

<210> SEQ ID NO 33
<211> LENGTH: 2609
<212> TYPE: DNA
<213> ORGANISM: Yarrowia lipolytica

<400> SEQUENCE: 33
atgccgcagc aagcaatgga tatcaagggc aaggccaagt ctgtgcccat gcccgaagaa          60
gacgacctgg actcgcattt tgtgggtccc atctctcccc gacctcacgg agcagacgag         120
attgctggct acgtgggctg cgaagacgac gaagacgagc ttgaagaact gggaatgctg         180
ggccgatctg cgtccaccca cttctcttac gcggaagaac gccacctcat cgaggttgat         240
gccaagtaca gagctcttca tggccatctg cctcatcagc actctcagag tccgtgtcc          300
agatcttcgt catttgtgcg ggccgaaatg aaccacccc ctcccccacc ctccagccac          360
acccaccaac agccagagga cgatgacgca tcttccactc gatctcgatc gtcgtctcga         420
gcttctggac gcaagttcaa cagaaacaga accaagtctg gatcttcgct gagcaagggt         480
ctccagcagc tcaacatgac cggatcgctc gaagaagagc cctacgagag cgatgacgat         540
gcccgactat ctgcggaaga cgacattgtc tatgatgcta cccagaaaga cacctgcaag         600
cccatatctc ctactctcaa acgcacccgc accaaggacg acatgaagaa catgtccatc         660
aacgacgtca aaatcaccac caccacagaa gatcctcttg tggcccagga gctgtccatg         720
atgttcgaaa aggtgcagta ctgccgagac ctccgagaca agtaccaaac cgtgtcgcta         780
cagaaggacg gagacaaccc caaggatgac aagacacact ggaaaattta ccccgagcct         840
ccaccaccct cctggcacga gaccgaaaag cgattccgag gctcgtccaa aaaggagcac         900
caaaagaaag acccgacaat ggatgaattc aaattcgagg actgcgaaat ccccggaccc         960
aacgacatgg tcttcaagcg agatcctacc tgtgtctatc aggtctatga ggatgaaagc        1020
tctctcaacg aaaataagcc gtttgttgcc atcccctcaa tccgagatta ctacatggat        1080
ctggaggatc tcattgtggc ttcgtctgac ggacctgcca agtcttttgc tttccgacga        1140
ctgcaatata tagaagccaa gtggaacctc tactacctgc tcaacgagta cacgagagca        1200
accgagtcca agaccaaccc ccatcgagac ttttacaacg tacgaaaggt cgacacccac        1260

```
gttcaccact ctgcctgcat gaaccagaag catctgctgc gattcatcaa atacaagatg   1320
aagaactgcc ctgatgaagt tgtcatccac cgagacggtc gggagctgac actctcccag   1380
gtgtttgagt cacttaactt gactgcctac gacctgtcta tcgataccct tgatatgcat   1440
gctcacaagg actcgttcca tcgatttgac aagttcaacc tcaagtacaa ccctgtcggt   1500
gagtctcgac tgcgagaaat cttcctaaag accgacaact acatccaggg tcgataccta   1560
gctgagatca caaggaggt gttccaggat ctcgagaact cgaagtacca gatggcggag   1620
taccgtattt ccatctacgg tcggtccaag gacgagtggg acaagctggc tgcctgggtg   1680
ctggacaaca aactgttttc gcccaatgtt cggtggttga tccaggtgcc tcgactgtac   1740
gacatttaca agaaggctgg tctggttaac acctttgccg acattgtgca gaacgtcttt   1800
gagcctcttt tcgaggtcac caaggatccc agtacccatc ccaagctgca cgtgttcctg   1860
cagcgagttg tgggctttga ctctgtcgat gacgagtcga agctggaccg acgtttccac   1920
cgaaagttcc caactgcagc atactgggac agcgcacaga ccctcccta ctcgtactgg   1980
cagtactatc tatacgccaa catggcctcc atcaacacct ggagacagcg tttgggctat   2040
aatacttttg agttgcgacc ccatgctgga gaggctggtg acccagagca tcttctgtgc   2100
acttatctgg ttgctcaggg tatcaaccac ggtattctgt tgcgaaaggt gcccttcatt   2160
cagtaccttt actacctgga ccagatcccc attgccatgt ctcctgtgtc aacaatgcg   2220
ctgttcctca cgttcgacaa gaaccccttc tactcatact tcaagcgggg tctcaacgtg   2280
tccttgtcat cggatgatcc tctgcagttt gcttacacta aggaggctct gattgaggag   2340
tactctgtgg ctgcgctcat ttacaagctt tccaacgtgg atatgtgtga gcttgctcga   2400
aactcggtac tgcaatctgg ctttgagcga atcatcaagg agcattggat cggcgaaaac   2460
tacgagatcc atggccccga gggcaacacc atccagaaga caaacgtgcc caatgtgcgt   2520
ctggccttcc gagacgagac tttgacccac gagcttgctc tggtggacaa gtacaccaat   2580
cttgaggagt ttgagcggct gcatggtta                                    2609
```

<210> SEQ ID NO 34
<211> LENGTH: 869
<212> TYPE: PRT
<213> ORGANISM: Yarrowia lipolytica

<400> SEQUENCE: 34

```
Met Pro Gln Gln Ala Met Asp Ile Lys Gly Lys Ala Lys Ser Val Pro
1               5                   10                  15

Met Pro Glu Glu Asp Asp Leu Asp Ser His Phe Val Gly Pro Ile Ser
            20                  25                  30

Pro Arg Pro His Gly Ala Asp Glu Ile Ala Gly Tyr Val Gly Cys Glu
        35                  40                  45

Asp Asp Glu Asp Glu Leu Glu Glu Leu Gly Met Leu Gly Arg Ser Ala
    50                  55                  60

Ser Thr His Phe Ser Tyr Ala Glu Glu Arg His Leu Ile Glu Val Asp
65                  70                  75                  80

Ala Lys Tyr Arg Ala Leu His Gly His Leu Pro His Gln His Ser Gln
                85                  90                  95

Ser Pro Val Ser Arg Ser Ser Phe Val Arg Ala Glu Met Asn His
            100                 105                 110

Pro Pro Pro Pro Ser Ser His Thr His Gln Gln Pro Glu Asp Asp
        115                 120                 125
```

```
Asp Ala Ser Ser Thr Arg Ser Arg Ser Ser Arg Ala Ser Gly Arg
    130                 135                 140

Lys Phe Asn Arg Asn Arg Thr Lys Ser Gly Ser Ser Leu Ser Lys Gly
145                 150                 155                 160

Leu Gln Gln Leu Asn Met Thr Gly Ser Leu Glu Glu Glu Pro Tyr Glu
                165                 170                 175

Ser Asp Asp Asp Ala Arg Leu Ser Ala Glu Asp Asp Ile Val Tyr Asp
                180                 185                 190

Ala Thr Gln Lys Asp Thr Cys Lys Pro Ile Ser Pro Thr Leu Lys Arg
            195                 200                 205

Thr Arg Thr Lys Asp Asp Met Lys Asn Met Ser Ile Asn Asp Val Lys
    210                 215                 220

Ile Thr Thr Thr Thr Glu Asp Pro Leu Val Ala Gln Glu Leu Ser Met
225                 230                 235                 240

Met Phe Glu Lys Val Gln Tyr Cys Arg Asp Leu Arg Asp Lys Tyr Gln
                245                 250                 255

Thr Val Ser Leu Gln Lys Asp Gly Asp Asn Pro Lys Asp Asp Lys Thr
                260                 265                 270

His Trp Lys Ile Tyr Pro Glu Pro Pro Pro Ser Trp His Glu Thr
            275                 280                 285

Glu Lys Arg Phe Arg Gly Ser Ser Lys Lys Glu His Gln Lys Lys Asp
    290                 295                 300

Pro Thr Met Asp Glu Phe Lys Phe Glu Asp Cys Glu Ile Pro Gly Pro
305                 310                 315                 320

Asn Asp Met Val Phe Lys Arg Asp Pro Thr Cys Val Tyr Gln Val Tyr
                325                 330                 335

Glu Asp Glu Ser Ser Leu Asn Glu Asn Lys Pro Phe Val Ala Ile Pro
                340                 345                 350

Ser Ile Arg Asp Tyr Tyr Met Asp Leu Glu Asp Leu Ile Val Ala Ser
            355                 360                 365

Ser Asp Gly Pro Ala Lys Ser Phe Ala Phe Arg Arg Leu Gln Tyr Leu
    370                 375                 380

Glu Ala Lys Trp Asn Leu Tyr Tyr Leu Leu Asn Glu Tyr Thr Glu Thr
385                 390                 395                 400

Thr Glu Ser Lys Thr Asn Pro His Arg Asp Phe Tyr Asn Val Arg Lys
                405                 410                 415

Val Asp Thr His Val His His Ser Ala Cys Met Asn Gln Lys His Leu
                420                 425                 430

Leu Arg Phe Ile Lys Tyr Lys Met Lys Asn Cys Pro Asp Glu Val Val
    435                 440                 445

Ile His Arg Asp Gly Arg Glu Leu Thr Leu Ser Gln Val Phe Glu Ser
450                 455                 460

Leu Asn Leu Thr Ala Tyr Asp Leu Ser Ile Asp Thr Leu Asp Met His
465                 470                 475                 480

Ala His Lys Asp Ser Phe His Arg Phe Asp Lys Phe Asn Leu Lys Tyr
                485                 490                 495

Asn Pro Val Gly Glu Ser Arg Leu Arg Glu Ile Phe Leu Lys Thr Asp
                500                 505                 510

Asn Tyr Ile Gln Gly Arg Tyr Leu Ala Glu Ile Thr Lys Glu Val Phe
            515                 520                 525

Gln Asp Leu Glu Asn Ser Lys Tyr Gln Met Ala Glu Tyr Arg Ile Ser
    530                 535                 540

Ile Tyr Gly Arg Ser Lys Asp Glu Trp Asp Lys Leu Ala Ala Trp Val
```

Leu Asp Asn Lys Leu Phe Ser Pro Asn Val Arg Trp Leu Ile Gln Val
545                 550                 555                 560

Pro Arg Leu Tyr Asp Ile Tyr Lys Lys Ala Gly Leu Val Asn Thr Phe
            565                 570                 575

Ala Asp Ile Val Gln Asn Val Phe Glu Pro Leu Phe Glu Val Thr Lys
        580                 585                 590

Asp Pro Ser Thr His Pro Lys Leu His Val Phe Leu Gln Arg Val Val
    595                 600                 605

Gly Phe Asp Ser Val Asp Asp Glu Ser Lys Leu Asp Arg Arg Phe His
610                 615                 620

Arg Lys Phe Pro Thr Ala Ala Tyr Trp Asp Ser Ala Gln Asn Pro Pro
625                 630                 635                 640

Tyr Ser Tyr Trp Gln Tyr Tyr Leu Tyr Ala Asn Met Ala Ser Ile Asn
            645                 650                 655

Thr Trp Arg Gln Arg Leu Gly Tyr Asn Thr Phe Glu Leu Arg Pro His
        660                 665                 670

Ala Gly Glu Ala Gly Asp Pro Glu His Leu Leu Cys Thr Tyr Leu Val
    675                 680                 685

Ala Gln Gly Ile Asn His Gly Ile Leu Leu Arg Lys Val Pro Phe Ile
690                 695                 700

705                 710                 715                 720

Gln Tyr Leu Tyr Tyr Leu Asp Gln Ile Pro Ile Ala Met Ser Pro Val
            725                 730                 735

Ser Asn Asn Ala Leu Phe Leu Thr Phe Asp Lys Asn Pro Phe Tyr Ser
        740                 745                 750

Tyr Phe Lys Arg Gly Leu Asn Val Ser Leu Ser Ser Asp Asp Pro Leu
    755                 760                 765

Gln Phe Ala Tyr Thr Lys Glu Ala Leu Ile Glu Glu Tyr Ser Val Ala
770                 775                 780

Ala Leu Ile Tyr Lys Leu Ser Asn Val Asp Met Cys Glu Leu Ala Arg
785                 790                 795                 800

Asn Ser Val Leu Gln Ser Gly Phe Glu Arg Ile Ile Lys Glu His Trp
            805                 810                 815

Ile Gly Glu Asn Tyr Glu Ile His Gly Pro Glu Gly Asn Thr Ile Gln
        820                 825                 830

Lys Thr Asn Val Pro Asn Val Arg Leu Ala Phe Arg Asp Glu Thr Leu
    835                 840                 845

Thr His Glu Leu Ala Leu Val Asp Lys Tyr Thr Asn Leu Glu Glu Phe
850                 855                 860

Glu Arg Leu His Gly
865

<210> SEQ ID NO 35
<211> LENGTH: 1218
<212> TYPE: DNA
<213> ORGANISM: Yarrowia lipolytica

<400> SEQUENCE: 35
atggaacccg aaactaagaa gaccaagact gactccaaga agattgttct tctcggcggc     60
gacttctgtg cccccgaggt gattgccgag gccgtcaagg tgctcaagtc tgttgctgag    120
gcctccggca ccgagtttgt gtttgaggac cgactcattg gaggagctgc cattgagaag    180
gagggcgagc ccatcaccga cgctactctc gacatctgcc gaaaggctga ctctattatg    240
ctcggtgctg tcggaggcgc tgccaacacc gtatggacca ctcccgacgg acgaaccgac    300

-continued

```
gtgcgacccg agcagggtct cctcaagctg cgaaaggacc tgaacctgta cgccaacctg    360
cgaccctgcc agctgctgtc gcccaagctc gccgatctct cccccatccg aaacgttgag    420
ggcaccgact tcatcattgt ccgagagctc gtcggaggta tctactttgg agagcgaaag    480
gaggatgacg atctggcgt cgcttccgac accgagacct actccgttcc tgaggttgag    540
cgaattgccc gaatggccgc cttcctggcc cttcagcaca ccccctct tcccgtgtgg      600
tctcttgaca aggccaacgt gctggcctcc tctcgacttt ggcgaaagac tgtcactcga    660
gtcctcaagg acgaattccc ccagctcgag ctcaaccacc agctgatcga ctcggccgcc    720
atgatcctca tcaagcagcc ctccaagatg aatggtatca tcatcaccac caacatgttt    780
ggcgatatca tctccgacga ggcctccgtc atccccggtt ctctgggtct gctgccctcc    840
gcctctctgg cttctctgcc cgacaccaac gaggcgttcg gtctgtacga gccctgtcac    900
ggatctgccc ccgatctcgg caagcagaag gtcaacccca ttgccaccat tctgtctgcc    960
gccatgatgc tcaagttctc tcttaacatg aagcccgccg tgacgctgt tgaggctgcc   1020
gtcaaggagt ccgtcgaggc tggtatcact accgccgata tcggaggctc ttcctccacc   1080
tccgaggtcg gagacttgtt gccaacaagg tcaaggagct gctcaagaag gagtaagtcg   1140
tttctacgac gcattgatgg aaggagcaaa ctgacgcgcc tgcgggttgg tctaccggca   1200
gggtccgcta gtgtataa                                                  1218
```

<210> SEQ ID NO 36
<211> LENGTH: 400
<212> TYPE: PRT
<213> ORGANISM: Yarrowia lipolytica

<400> SEQUENCE: 36

```
Met Glu Pro Glu Thr Lys Lys Thr Lys Thr Asp Ser Lys Lys Ile Val
 1               5                  10                  15

Leu Leu Gly Gly Asp Phe Cys Gly Pro Glu Val Ile Ala Glu Ala Val
                20                  25                  30

Lys Val Leu Lys Ser Val Ala Glu Ala Ser Gly Thr Glu Phe Val Phe
            35                  40                  45

Glu Asp Arg Leu Ile Gly Gly Ala Ala Ile Glu Lys Glu Gly Glu Pro
        50                  55                  60

Ile Thr Asp Ala Thr Leu Asp Ile Cys Arg Lys Ala Asp Ser Ile Met
65                  70                  75                  80

Leu Gly Ala Val Gly Gly Ala Ala Asn Thr Val Trp Thr Thr Pro Asp
                85                  90                  95

Gly Arg Thr Asp Val Arg Pro Glu Gln Gly Leu Leu Lys Leu Arg Lys
            100                 105                 110

Asp Leu Asn Leu Tyr Ala Asn Leu Arg Pro Cys Gln Leu Leu Ser Pro
        115                 120                 125

Lys Leu Ala Asp Leu Ser Pro Ile Arg Asn Val Glu Gly Thr Asp Phe
    130                 135                 140

Ile Ile Val Arg Glu Leu Val Gly Gly Ile Tyr Phe Gly Glu Arg Lys
145                 150                 155                 160

Glu Asp Asp Gly Ser Gly Val Ala Ser Asp Thr Glu Thr Tyr Ser Val
                165                 170                 175

Pro Glu Val Glu Arg Ile Ala Arg Met Ala Ala Phe Leu Ala Leu Gln
            180                 185                 190

His Asn Pro Pro Leu Pro Val Trp Ser Leu Asp Lys Ala Asn Val Leu
        195                 200                 205
```

Ala Ser Ser Arg Leu Trp Arg Lys Thr Val Thr Arg Val Leu Lys Asp
        210                 215                 220

Glu Phe Pro Gln Leu Glu Leu Asn His Gln Leu Ile Asp Ser Ala Ala
225                 230                 235                 240

Met Ile Leu Ile Lys Gln Pro Ser Lys Met Asn Gly Ile Ile Ile Thr
            245                 250                 255

Thr Asn Met Phe Gly Asp Ile Ile Ser Asp Glu Ala Ser Val Ile Pro
            260                 265                 270

Gly Ser Leu Gly Leu Leu Pro Ser Ala Ser Leu Ala Ser Leu Pro Asp
        275                 280                 285

Thr Asn Glu Ala Phe Gly Leu Tyr Glu Pro Cys His Gly Ser Ala Pro
        290                 295                 300

Asp Leu Gly Lys Gln Lys Val Asn Pro Ile Ala Thr Ile Leu Ser Ala
305                 310                 315                 320

Ala Met Met Leu Lys Phe Ser Leu Asn Met Lys Pro Ala Gly Asp Ala
            325                 330                 335

Val Glu Ala Ala Val Lys Glu Ser Val Glu Ala Gly Ile Thr Thr Ala
            340                 345                 350

Asp Ile Gly Gly Ser Ser Thr Ser Glu Val Gly Asp Leu Leu Pro
        355                 360                 365

Thr Arg Ser Arg Ser Cys Ser Arg Arg Ser Lys Ser Phe Leu Arg Arg
        370                 375                 380

Ile Asp Gly Arg Ser Lys Leu Thr Arg Leu Arg Val Gly Leu Pro Ala
385                 390                 395                 400

<210> SEQ ID NO 37
<211> LENGTH: 861
<212> TYPE: DNA
<213> ORGANISM: Yarrowia lipolytica

<400> SEQUENCE: 37
atgccctcct acgaagctcg agctaacgtc cacaagtccg cctttgccgc tcgagtgctc      60
aagctcgtgg cagccaagaa aaccaacctg tgtgcttctc tggatgttac caccaccaag    120
gagctcattg agcttgccga taaggtcgga ccttatgtgt gcatgatcaa gacccatatc    180
gacatcattg acgacttcac ctacgccggc actgtgctcc ccctcaagga acttgctctt    240
aagcacggtt tcttcctgtt cgaggacaga agttcgcag atattggcaa cactgtcaag    300
caccagtaca gaacggtgt ctaccgaatc gccgagtggt ccgatatcac caacgcccac    360
ggtgtacccg gaaccggaat cattgctggc ctgcgagctg gtgccgagga aactgtctct    420
gaacagaaga aggaggacgt ctctgactac gagaactccc agtacaagga gttcctggtc    480
ccctctccca cgagaagct ggccagaggt ctgctcatgc tggccgagct gtcttgcaag    540
ggctctctgg ccactggcga gtactccaag cagaccattg agcttgcccg atccgacccc    600
gagtttgtgg ttggcttcat tgcccagaac cgacctaagg cgactctga ggactggctt    660 attctgaccc ccgggtggg tcttgacgac aagggagacg ctctcggaca gcagtaccga    720
actgttgagg atgtcatgtc taccggaacg gatatcataa ttgtcggccg aggtctgtac    780
ggccagaacc gagatcctat tgaggaggcc aagcgatacc agaaggctgg ctgggaggct    840
taccagaaga ttaactgtta g                                                861

<210> SEQ ID NO 38
<211> LENGTH: 286
<212> TYPE: PRT

<213> ORGANISM: Yarrowia lipolytica

<400> SEQUENCE: 38

```
Met Pro Ser Tyr Glu Ala Arg Ala Asn Val His Lys Ser Ala Phe Ala
1               5                   10                  15

Ala Arg Val Leu Lys Leu Val Ala Ala Lys Thr Asn Leu Cys Ala
            20                  25                  30

Ser Leu Asp Val Thr Thr Thr Lys Glu Leu Ile Glu Leu Ala Asp Lys
            35                  40                  45

Val Gly Pro Tyr Val Cys Met Ile Lys Thr His Ile Asp Ile Ile Asp
        50                  55                  60

Asp Phe Thr Tyr Ala Gly Thr Val Leu Pro Lys Glu Leu Ala Leu
65                  70                  75                  80

Lys His Gly Phe Phe Leu Phe Glu Asp Arg Lys Phe Ala Asp Ile Gly
                    85                  90                  95

Asn Thr Val Lys His Gln Tyr Lys Asn Gly Val Tyr Arg Ile Ala Glu
                100                 105                 110

Trp Ser Asp Ile Thr Asn Ala His Gly Val Pro Gly Thr Gly Ile Ile
            115                 120                 125

Ala Gly Leu Arg Ala Gly Ala Glu Glu Thr Val Ser Glu Gln Lys Lys
        130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Val Gly Phe Ile Ala
        195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
                245                 250                 255

Arg Gly Leu Tyr Gly Gln Asn Arg Asp Pro Ile Glu Glu Ala Lys Arg
            260                 265                 270

Tyr Gln Lys Ala Gly Trp Glu Ala Tyr Gln Lys Ile Asn Cys
        275                 280                 285
```

<210> SEQ ID NO 39
<211> LENGTH: 1953
<212> TYPE: DNA
<213> ORGANISM: Yarrowia lipolytica

<400> SEQUENCE: 39

```
atgtctgcca acgagaacat ctcccgattc gacgccctg tgggcaagga gcaccccgcc      60
tacgagctct ccataacca cacacgatct ttcgtctatg gtctccagcc tcgagcctgc     120
cagggtatgc tggacttcga cttcatctgt aagcgagaga acccctccgt ggccggtgtc     180
atctatccct tcggcggcca gttcgtcacc aagatgtact ggggcaccaa ggagactctt     240
ctccctgtct accagcaggt cgagaaggcc gctgccaagc accccgaggt cgatgtcgtg     300
gtcaactttg cctcctctcg atccgtctac tcctctacca tggagctgct cgagtacccc     360
cagttccgaa ccatcgccat tattgccgag ggtgtccccg agcgacgagc ccgagagatc     420
```

```
ctccacaagg cccagaagaa gggtgtgacc atcattggtc ccgctaccgt cggaggtatc    480
aagcccggtt gcttcaaggt tggaaacacc ggaggtatga tggacaacat tgtcgcctcc    540
aagctctacc gacccggctc cgttgcctac gtctccaagt ccggaggaat gtccaacgag    600
ctgaacaaca ttatctctca caccaccgac ggtgtctacg agggtattgc tattggtggt    660
gaccgatacc ctggtactac cttcattgac catatcctgc gatacgaggc cgaccccaag    720
tgtaagatca tcgtcctcct tggtgaggtt ggtggtgttg aggagtaccg agtcatcgag    780
gctgttaaga acggccagat caagaagccc atcgtcgctt gggccattgg tacttgtgcc    840
tccatgttca agactgaggt tcagttcggc cacgccggct ccatggccaa ctccgacctg    900
gagactgcca aggctaagaa cgccgccatg aagtctgctg gcttctacgt ccccgatacc    960
ttcgaggaca tgcccgaggt ccttgccgag ctctacgaga gatggtcgc caagggcgag   1020 ctgtctcgaa tctctgagcc tgaggtcccc aagatcccca ttgactactc ttgggcccag   1080
gagcttggtc ttatccgaaa gcccgctgct ttcatctcca ctatttccga tgaccgaggc   1140
caggagcttc tgtacgctgg catgcccatt tccgaggttt caaggagga cattggtatc   1200 ggcggtgtca tgtctctgct gtggttccga cgacgactcc ccgactacgc ctccaagttt   1260
cttgagatgg ttctcatgct tactgctgac cacggtcccg ccgtatccgg tgccatgaac   1320
accattatca ccacccgagc tggtaaggat ctcatttctt ccctggttgc tggtctcctg   1380
accattggta cccgattcgg aggtgctctt gacggtgctg ccaccgagtt caccactgcc   1440
tacgacaagg gtctgtcccc ccgacagttc gttgatacca tgcgaaagca gaacaagctg   1500
attcctggta ttggccatcg agtcaagtct cgaaacaacc ccgatttccg agtcgagctt   1560
gtcaaggact ttgttaagaa gaacttcccc tccacccagc tgctcgacta cgccttgct   1620 gtcgaggagg tcaccacctc caagaaggac aacctgattc tgaacgttga cggtgctatt   1680
gctgttcctt ttgtcgatct catgcgatct tgcggtgcct ttactgtgga ggagactgag   1740
gactacctca gaacggtgt tctcaacggt ctgttcgttc cggtcgatc cattggtctc   1800 attgcccacc atctcgatca gaagcgactc aagaccggtc tgtaccgaca tccttgggac   1860
gatatcacct acctggttgg ccaggaggct atccagaaga gcgagtcga gatcagcgcc   1920 ggcgacgttt ccaaggccaa gactcgatca tag                                1953
```

<210> SEQ ID NO 40
<211> LENGTH: 650
<212> TYPE: PRT
<213> ORGANISM: Yarrowia lipolytica

<400> SEQUENCE: 40

```
Met Ser Ala Asn Glu Asn Ile Ser Arg Phe Asp Ala Pro Val Gly Lys
1               5                   10                  15

Glu His Pro Ala Tyr Glu Leu Phe His Asn His Thr Arg Ser Phe Val
            20                  25                  30

Tyr Gly Leu Gln Pro Arg Ala Cys Gln Gly Met Leu Asp Phe Asp Phe
        35                  40                  45

Ile Cys Lys Arg Glu Asn Pro Ser Val Ala Gly Val Ile Tyr Pro Phe
    50                  55                  60

Gly Gly Gln Phe Val Thr Lys Met Tyr Trp Gly Thr Lys Glu Thr Leu
65                  70                  75                  80

Leu Pro Val Tyr Gln Gln Val Glu Lys Ala Ala Lys His Pro Glu
                85                  90                  95
```

```
Val Asp Val Val Val Asn Phe Ala Ser Ser Arg Ser Val Tyr Ser Ser
            100                 105                 110

Thr Met Glu Leu Leu Glu Tyr Pro Gln Phe Arg Thr Ile Ala Ile Ile
            115                 120                 125

Ala Glu Gly Val Pro Glu Arg Arg Ala Arg Glu Ile Leu His Lys Ala
        130                 135                 140

Gln Lys Lys Gly Val Thr Ile Ile Gly Pro Ala Thr Val Gly Gly Ile
145                 150                 155                 160

Lys Pro Gly Cys Phe Lys Val Gly Asn Thr Gly Gly Met Met Asp Asn
                165                 170                 175

Ile Val Ala Ser Lys Leu Tyr Arg Pro Gly Ser Val Ala Tyr Val Ser
            180                 185                 190

Lys Ser Gly Gly Met Ser Asn Glu Leu Asn Asn Ile Ile Ser His Thr
        195                 200                 205

Thr Asp Gly Val Tyr Glu Gly Ile Ala Ile Gly Gly Asp Arg Tyr Pro
    210                 215                 220

Gly Thr Thr Phe Ile Asp His Ile Leu Arg Tyr Glu Ala Asp Pro Lys
225                 230                 235                 240

Cys Lys Ile Ile Val Leu Leu Gly Glu Val Gly Gly Val Glu Glu Tyr
                245                 250                 255

Arg Val Ile Glu Ala Val Lys Asn Gly Gln Ile Lys Lys Pro Ile Val
            260                 265                 270

Ala Trp Ala Ile Gly Thr Cys Ala Ser Met Phe Lys Thr Glu Val Gln
        275                 280                 285

Phe Gly His Ala Gly Ser Met Ala Asn Ser Asp Leu Glu Thr Ala Lys
    290                 295                 300

Ala Lys Asn Ala Ala Met Lys Ser Ala Gly Phe Tyr Val Pro Asp Thr
305                 310                 315                 320

Phe Glu Asp Met Pro Glu Val Leu Ala Glu Leu Tyr Glu Lys Met Val
                325                 330                 335

Ala Lys Gly Glu Leu Ser Arg Ile Ser Glu Pro Glu Val Pro Lys Ile
            340                 345                 350

Pro Ile Asp Tyr Ser Trp Ala Gln Glu Leu Gly Leu Ile Arg Lys Pro
        355                 360                 365

Ala Ala Phe Ile Ser Thr Ile Ser Asp Asp Arg Gly Gln Glu Leu Leu
    370                 375                 380

Tyr Ala Gly Met Pro Ile Ser Glu Val Phe Lys Glu Asp Ile Gly Ile
385                 390                 395                 400

Gly Gly Val Met Ser Leu Leu Trp Phe Arg Arg Arg Leu Pro Asp Tyr
                405                 410                 415

Ala Ser Lys Phe Leu Glu Met Val Leu Met Leu Thr Ala Asp His Gly
            420                 425                 430

Pro Ala Val Ser Gly Ala Met Asn Thr Ile Ile Thr Thr Arg Ala Gly
        435                 440                 445

Lys Asp Leu Ile Ser Ser Leu Val Ala Gly Leu Leu Thr Ile Gly Thr
450                 455                 460

Arg Phe Gly Gly Ala Leu Asp Gly Ala Ala Thr Glu Phe Thr Thr Ala
465                 470                 475                 480

Tyr Asp Lys Gly Leu Ser Pro Arg Gln Phe Val Asp Thr Met Arg Lys
                485                 490                 495

Gln Asn Lys Leu Ile Pro Gly Ile Gly His Arg Val Lys Ser Arg Asn
            500                 505                 510

Asn Pro Asp Phe Arg Val Glu Leu Val Lys Asp Phe Val Lys Lys Asn
```

```
            515                 520                 525
Phe Pro Ser Thr Gln Leu Leu Asp Tyr Ala Leu Ala Val Glu Glu Val
    530                 535                 540
Thr Thr Ser Lys Lys Asp Asn Leu Ile Leu Asn Val Asp Gly Ala Ile
545                 550                 555                 560
Ala Val Ser Phe Val Asp Leu Met Arg Ser Cys Gly Ala Phe Thr Val
            565                 570                 575
Glu Glu Thr Glu Asp Tyr Leu Lys Asn Gly Val Leu Asn Gly Leu Phe
            580                 585                 590
Val Leu Gly Arg Ser Ile Gly Leu Ile Ala His His Leu Asp Gln Lys
            595                 600                 605
Arg Leu Lys Thr Gly Leu Tyr Arg His Pro Trp Asp Asp Ile Thr Tyr
    610                 615                 620
Leu Val Gly Gln Glu Ala Ile Gln Lys Lys Arg Val Glu Ile Ser Ala
625                 630                 635                 640
Gly Asp Val Ser Lys Ala Lys Thr Arg Ser
            645                 650
```

<210> SEQ ID NO 41
<211> LENGTH: 1494
<212> TYPE: DNA
<213> ORGANISM: Yarrowia lipolytica

<400> SEQUENCE: 41

```
atgtcagcga aatccattca cgaggccgac ggcaaggccc tgctcgcaca ctttctgtcc      60
aaggcgcccg tgtgggccga gcagcagccc atcaacacgt tgaaatggg cacacccaag     120
ctggcgtctc tgacgttcga ggacggcgtg gccccgagc agatcttcgc cgccgctgaa     180
aagacctacc cctggctgct ggagtccggc gccaagtttg tggccaagcc cgaccagctc    240
atcaagcgac gaggcaaggc cggcctgctg gtactcaaca agtcgtggga ggagtgcaag    300
ccctggatcg ccgagcgggc cgccaagccc atcaacgtgg agggcattga cggagtgctg    360
cgaacgttcc tggtcgagcc ctttgtgccc cacgaccaga agcacgagta ctacatcaac    420
atccactccg tgcgagaggg cgactggatc ctcttctacc acgagggagg agtcgacgtc    480
ggcgacgtgg acgccaaggc cgccaagatc ctcatccccg ttgacattga gaacgagtac    540
ccctccaacg ccacgctcac caaggagctg ctggcacacg tgccgaggga ccagcaccag    600
accctgctcg acttcatcaa ccggctctac gccgtctacg tcgatctgca gtttacgtat    660
ctggagatca cccccctggt cgtgatcccc accgccaggg cgtcgaggt ccactacctg    720
gatcttgccg gcaagctcga ccagaccgca gagtttgagt gcggccccaa gtgggctgct    780
gcgcggtccc ccgccgctct gggccaggtc gtcaccattg acgccggctc caccaaggtg    840
tccatcgacg ccggccccgc catggtcttc cccgctcctt tcggtcgaga gctgtccaag    900
gaggaggcgt acattgcgga gctcgattcc aagaccggag cttctctgaa gctgactgtt    960
ctcaatgcca agggccgaat ctggacccct gtggctggtg gaggagcctc cgtcgtctac   1020
gccgacgcca ttgcgtctgc cggctttgct gacgagctcg ccaactacgg cgagtactct   1080
ggcgctccca cgagaccca gacctacgag tacgccaaaa ccgtactgga tctcatgacc   1140
cggggcgacg ctcaccccga gggcaaggta ctgttcattg gcggaggaat cgccaacttc   1200
acccaggttg gatccacctt caagggcatc atcgggcct ccgggactac cagtcttct   1260
ctgcacaacc acaaggtgaa gatttacgtg cgacgaggcg gtcccaactg gcaggagggt   1320
ctgcggttga tcaagtcggc tggcgacgag ctgaatctgc ccatggagat ttacggcccc   1380
```

```
gacatgcacg tgtcgggtat tgttcctttg gctctgcttg gaaagcggcc caagaatgtc    1440 aagcctttg gcaccggacc ttctactgag gcttccactc ctctcggagt ttaa           1494
```

<210> SEQ ID NO 42
<211> LENGTH: 497
<212> TYPE: PRT
<213> ORGANISM: Yarrowia lipolytica

<400> SEQUENCE: 42

```
Met Ser Ala Lys Ser Ile His Glu Ala Asp Gly Lys Ala Leu Leu Ala
1               5                   10                  15

His Phe Leu Ser Lys Ala Pro Val Trp Ala Glu Gln Gln Pro Ile Asn
            20                  25                  30

Thr Phe Glu Met Gly Thr Pro Lys Leu Ala Ser Leu Thr Phe Glu Asp
        35                  40                  45

Gly Val Ala Pro Glu Gln Ile Phe Ala Ala Glu Lys Thr Tyr Pro
    50                  55                  60

Trp Leu Leu Glu Ser Gly Ala Lys Phe Val Ala Lys Pro Asp Gln Leu
65                  70                  75                  80

Ile Lys Arg Arg Gly Lys Ala Gly Leu Leu Val Leu Asn Lys Ser Trp
                85                  90                  95

Glu Glu Cys Lys Pro Trp Ile Ala Glu Arg Ala Ala Lys Pro Ile Asn
            100                 105                 110

Val Glu Gly Ile Asp Gly Val Leu Arg Thr Phe Leu Val Glu Pro Phe
        115                 120                 125

Val Pro His Asp Gln Lys His Glu Tyr Tyr Ile Asn Ile His Ser Val
    130                 135                 140

Arg Glu Gly Asp Trp Ile Leu Phe Tyr His Glu Gly Gly Val Asp Val
145                 150                 155                 160

Gly Asp Val Asp Ala Lys Ala Ala Lys Ile Leu Ile Pro Val Asp Ile
                165                 170                 175

Glu Asn Glu Tyr Pro Ser Asn Ala Thr Leu Thr Lys Glu Leu Leu Ala
            180                 185                 190

His Val Pro Glu Asp Gln His Gln Thr Leu Leu Asp Phe Ile Asn Arg
        195                 200                 205

Leu Tyr Ala Val Tyr Val Asp Leu Gln Phe Thr Tyr Leu Glu Ile Asn
    210                 215                 220

Pro Leu Val Val Ile Pro Thr Ala Gln Gly Val Glu Val His Tyr Leu
225                 230                 235                 240

Asp Leu Ala Gly Lys Leu Asp Gln Thr Ala Glu Phe Glu Cys Gly Pro
                245                 250                 255

Lys Trp Ala Ala Ala Arg Ser Pro Ala Ala Leu Gly Gln Val Val Thr
            260                 265                 270

Ile Asp Ala Gly Ser Thr Lys Val Ser Ile Asp Ala Gly Pro Ala Met
        275                 280                 285

Val Phe Pro Ala Pro Phe Gly Arg Glu Leu Ser Lys Glu Glu Ala Tyr
    290                 295                 300

Ile Ala Glu Leu Asp Ser Lys Thr Gly Ala Ser Leu Lys Leu Thr Val
305                 310                 315                 320

Leu Asn Ala Lys Gly Arg Ile Trp Thr Leu Val Ala Gly Gly Gly Ala
                325                 330                 335

Ser Val Val Tyr Ala Asp Ala Ile Ala Ser Ala Gly Phe Ala Asp Glu
            340                 345                 350
```

```
Leu Ala Asn Tyr Gly Glu Tyr Ser Gly Ala Pro Asn Glu Thr Gln Thr
            355                 360                 365

Tyr Glu Tyr Ala Lys Thr Val Leu Asp Leu Met Thr Arg Gly Asp Ala
    370                 375                 380

His Pro Glu Gly Lys Val Leu Phe Ile Gly Gly Ile Ala Asn Phe
385                 390                 395                 400

Thr Gln Val Gly Ser Thr Phe Lys Gly Ile Ile Arg Ala Phe Arg Asp
                405                 410                 415

Tyr Gln Ser Ser Leu His Asn His Lys Val Lys Ile Tyr Val Arg Arg
                420                 425                 430

Gly Gly Pro Asn Trp Gln Glu Gly Leu Arg Leu Ile Lys Ser Ala Gly
            435                 440                 445

Asp Glu Leu Asn Leu Pro Met Glu Ile Tyr Gly Pro Asp Met His Val
        450                 455                 460

Ser Gly Ile Val Pro Leu Ala Leu Leu Gly Lys Arg Pro Lys Asn Val
465                 470                 475                 480

Lys Pro Phe Gly Thr Gly Pro Ser Thr Glu Ala Ser Thr Pro Leu Gly
                485                 490                 495

Val
```

<210> SEQ ID NO 43
<211> LENGTH: 1890
<212> TYPE: DNA
<213> ORGANISM: Artificial Sequence
<220> FEATURE:
<223> OTHER INFORMATION: Synthetic polynucleotide

<400> SEQUENCE: 43

```
atgttacgac tacgaaccat gcgacccaca cagaccagcg tcagggcggc gcttgggccc      60
accgctgcgg cccgaaacat gtcctcctcc agcccctcca gcttcgaata ctcgtcctac     120
gtcaagggca cgcgggaaat cggccaccga aaggcgccca caacccgtct gtcggttgag     180
ggccccatct acgtgggctt cgacggcatt cgtcttctca acctgccgca tctcaacaag     240
ggctcgggat tcccctcaa cgagcgacgg gaattcggac tcagtggtct tctgccctct     300
gccgaagcca ccctggagga acaggtcgac cgagcatacc aacaattcaa aaagtgtggc     360
actcccttag ccaaaaacgg gttctgcacc tcgctcaagt ccaaaacga ggtgctctac     420
tacgccctgc tgctcaagca cgttaaggag gtcttcccca tcatctatac accgactcag     480
ggagaagcca ttgaacagta ctcgcggctg ttccggcggc ccgaaggctg cttcctcgac     540
atcaccagtc cctacgacgt ggaggagcgt ctgggagcgc ttggagacca tgacgacatt     600
gactacattg tcgtgactga ctccgagggt attctcggaa ttggagacca aggagtgggc     660
ggtattggta tttccatcgc caagctggct ctcatgactc tatgtgctgg agtcaaccc      720
tcacgagtca ttcctgtggt tctggatacg ggaaccaaca accaggagct gctgcacgac     780
cccctgtatc tcggccgacg aatgccccga gtgcgaggaa agcagtacga cgacttcatc     840
gacaactttg tgcagtctgc ccgaaggctg tatcccaagg cggtgatcca tttcgaggac     900
tttgggctcg ctaacgcaca caagatcctc gacaagtatc gaccggagat cccctgcttc     960
aacgacgaca tccagggcac tggagccgtc actctggcct ccatcacggc cgctctcaag    1020
gtgctgggca aaaatatcac agatactcga attctcgtgt acggagctgg ttcggccggc    1080
atgggtattg ctgaacaggt ctatgataac ctggttgccc agggtctcga cgacaagact    1140
gcgcgacaaa acatctttct catggaccga ccgggtctac tgaccaccgc acttaccgac    1200
```

-continued

```
gagcagatga gcgacgtgca gaagccgttt gccaaggaca aggccaatta cgagggagtg    1260
gacaccaaga ctctggagca cgtggttgct gccgtcaagc cccatattct cattggatgt    1320
tccactcagc ccggcgcctt taacgagaag gttgtcaagg agatgcttaa acacacccct    1380
cgacccatca ttctccctct ttccaacccc acacgtcttc atgaggctgt ccctgcagat    1440
ctgtacaagt ggaccgacgg caaggctctg gttgccaccg gctcgccctt tgacccagtc    1500
aacggcaagg agacgtctga gaacaataac tgctttgttt tccccggaat cgggctggga    1560
gccattctgt ctcgatcaaa gctcatcacc aacaccatga ttgctgctgc catcgagtgc    1620
ctcgccgaac aggcccccat tctcaagaac cacgacgagg gagtacttcc cgacgtagct    1680
ctcatccaga tcatttcggc ccgggtggcc actgccgtgg ttcttcaggc caaggctgag    1740
ggcctagcca ctgtcgagga agagctcaag cccggcacca aggaacatgt gcagattccc    1800
gacaactttg acgagtgtct cgcctgggtc gagactcaga tgtggcggcc cgtctaccgg    1860
cctctcatcc atgtgcggga ttacgactag                                     1890
```

<210> SEQ ID NO 44
<211> LENGTH: 629
<212> TYPE: PRT
<213> ORGANISM: Artificial Sequence
<220> FEATURE:
<223> OTHER INFORMATION: Synthetic polypeptide

<400> SEQUENCE: 44

```
Met Leu Arg Leu Arg Thr Met Arg Pro Thr Gln Thr Ser Val Arg Ala
1               5                   10                  15

Ala Leu Gly Pro Thr Ala Ala Arg Asn Met Ser Ser Ser Ser Pro
            20                  25                  30

Ser Ser Phe Glu Tyr Ser Ser Tyr Val Lys Gly Thr Arg Glu Ile Gly
        35                  40                  45

His Arg Lys Ala Pro Thr Thr Arg Leu Ser Val Glu Gly Pro Ile Tyr
    50                  55                  60

Val Gly Phe Asp Gly Ile Arg Leu Leu Asn Leu Pro His Leu Asn Lys
65                  70                  75                  80

Gly Ser Gly Phe Pro Leu Asn Glu Arg Arg Glu Phe Gly Leu Ser Gly
                85                  90                  95

Leu Leu Pro Ser Ala Glu Ala Thr Leu Glu Glu Gln Val Asp Arg Ala
            100                 105                 110

Tyr Gln Gln Phe Lys Lys Cys Gly Thr Pro Leu Ala Lys Asn Gly Phe
        115                 120                 125

Cys Thr Ser Leu Lys Phe Gln Asn Glu Val Leu Tyr Tyr Ala Leu Leu
    130                 135                 140

Leu Lys His Val Lys Glu Val Phe Pro Ile Ile Tyr Thr Pro Thr Gln
145                 150                 155                 160

Gly Glu Ala Ile Glu Gln Tyr Ser Arg Leu Phe Arg Arg Pro Glu Gly
                165                 170                 175

Cys Phe Leu Asp Ile Thr Ser Pro Tyr Asp Val Glu Glu Arg Leu Gly
            180                 185                 190

Ala Phe Gly Asp His Asp Asp Ile Asp Tyr Ile Val Val Thr Asp Ser
        195                 200                 205

Glu Gly Ile Leu Gly Ile Gly Asp Gln Gly Val Gly Gly Ile Gly Ile
    210                 215                 220

Ser Ile Ala Lys Leu Ala Leu Met Thr Leu Cys Ala Gly Val Asn Pro
225                 230                 235                 240
```

Ser Arg Val Ile Pro Val Val Leu Asp Thr Gly Thr Asn Asn Gln Glu
            245                 250                 255

Leu Leu His Asp Pro Leu Tyr Leu Gly Arg Arg Met Pro Arg Val Arg
        260                 265                 270

Gly Lys Gln Tyr Asp Asp Phe Ile Asp Asn Phe Val Gln Ser Ala Arg
    275                 280                 285

Arg Leu Tyr Pro Lys Ala Val Ile His Phe Glu Asp Phe Gly Leu Ala
290                 295                 300

Asn Ala His Lys Ile Leu Asp Lys Tyr Arg Pro Glu Ile Pro Cys Phe
305                 310                 315                 320

Asn Asp Asp Ile Gln Gly Thr Gly Ala Val Thr Leu Ala Ser Ile Thr
                325                 330                 335

Ala Ala Leu Lys Val Leu Gly Lys Asn Ile Thr Asp Thr Arg Ile Leu
            340                 345                 350

Val Tyr Gly Ala Gly Ser Ala Gly Met Gly Ile Ala Glu Gln Val Tyr
        355                 360                 365

Asp Asn Leu Val Ala Gln Gly Leu Asp Asp Lys Thr Ala Arg Gln Asn
    370                 375                 380

Ile Phe Leu Met Asp Arg Pro Gly Leu Leu Thr Thr Ala Leu Thr Asp
385                 390                 395                 400

Glu Gln Met Ser Asp Val Gln Lys Pro Phe Ala Lys Asp Lys Ala Asn
                405                 410                 415

Tyr Glu Gly Val Asp Thr Lys Thr Leu Glu His Val Val Ala Ala Val
            420                 425                 430

Lys Pro His Ile Leu Ile Gly Cys Ser Thr Gln Pro Gly Ala Phe Asn
        435                 440                 445

Glu Lys Val Val Lys Glu Met Leu Lys His Thr Pro Arg Pro Ile Ile
    450                 455                 460

Leu Pro Leu Ser Asn Pro Thr Arg Leu His Glu Ala Val Pro Ala Asp
465                 470                 475                 480

Leu Tyr Lys Trp Thr Asp Gly Lys Ala Leu Val Ala Thr Gly Ser Pro
                485                 490                 495

Phe Asp Pro Val Asn Gly Lys Glu Thr Ser Glu Asn Asn Asn Cys Phe
            500                 505                 510

Val Phe Pro Gly Ile Gly Leu Gly Ala Ile Leu Ser Arg Ser Lys Leu
        515                 520                 525

Ile Thr Asn Thr Met Ile Ala Ala Ala Ile Glu Cys Leu Ala Glu Gln
    530                 535                 540

Ala Pro Ile Leu Lys Asn His Asp Glu Gly Val Leu Pro Asp Val Ala
545                 550                 555                 560

Leu Ile Gln Ile Ile Ser Ala Arg Val Ala Thr Ala Val Val Leu Gln
                565                 570                 575

Ala Lys Ala Glu Gly Leu Ala Thr Val Glu Glu Leu Lys Pro Gly
            580                 585                 590

Thr Lys Glu His Val Gln Ile Pro Asp Asn Phe Asp Glu Cys Leu Ala
        595                 600                 605

Trp Val Glu Thr Gln Met Trp Arg Pro Val Tyr Arg Pro Leu Ile His
    610                 615                 620

Val Arg Asp Tyr Asp
625

<210> SEQ ID NO 45
<211> LENGTH: 1545
<212> TYPE: DNA

<213> ORGANISM: Yarrowia lipolytica

<400> SEQUENCE: 45

```
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa ttttcatgct atgctgcgca     180
attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg gccgctactt ccccataact ctgcacaaga cggtggatct ggagcccacg     360
cacacatact accctctgga cgtccaggag tatcacctga ttgctgagag atactggccg     420
cagaacaagt acctccgagc aatcatctcc accatcgagt actttctgcc cgccttcatg     480
aaacggtctc tttctatcaa cgagcaggag cagcctgccg agcgagatcc tctcctgtct     540
cccgtttctc ccagctctcc gggttctcaa cctgacaagt ggattaacca cgacagcaga     600
tatagccgtg gagaatcatc tggctccaac ggccacgcct cgggctccga acttaacggc     660
aacggcaaca atggcaccac taaccgacga cctttgtcgt ccgcctctgc tggctccact     720
gcatctgatt ccacgcttct taacgggtcc ctcaactcct cgccaaccaa gatcattggc     780
gaaaacgacc cacagctgtc gcccacaaaa ctcaagccca ctggcagaaa atacatcttc     840
ggctaccacc cccacggcat tatcggcatg ggagcctttg gtggaattgc caccgaggga     900
gctggatggt ccaagctctt tccgggcatc cctgtttctc ttatgactct caccaacaac     960
ttccgagtgc ctctctacag agagtaccct atgagtctgg gagtcgcttc tgtctccaag    1020
aagtcctgca aggccctcct caagcgaaac cagtctatct gcattgtcgt tggtggagca    1080
caggaaagtc ttctggccag acccggtgtc atggacctgg tgctactcaa gcgaaagggt    1140
tttgttcgac ttggtatgga ggtcggaaat gtcgcccttg ttcccatcat ggcctttggt    1200
gagaacgacc tctatgacca ggttagcaac gacaagtcgt ccaagctgta ccgattccag    1260
cagtttgtca gaacttcct ggattcacc cttcctttga tgcatgcccg aggcgtcttc    1320
aactacgatg tcggtcttgt cccctacagg cgacccgtca acattgtggt tggttccccc    1380
attgacttgc cttatctccc acaccccacc gacgaagaag tgtccgaata ccacgaccga    1440
tacatcgccg agctgcagcg aatctacaac gagcacaagg atgaatattt catcgattgg    1500
accgaggagg gcaaaggagc cccagagttc cgaatgattg agtaa               1545
```

<210> SEQ ID NO 46
<211> LENGTH: 514
<212> TYPE: PRT
<213> ORGANISM: Yarrowia lipolytica

<400> SEQUENCE: 46

```
Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80
```

-continued

```
Pro Ser Asn Gly Gly Val Val Lys Arg Tyr Ser Pro Ile Ser Arg Asn
                85                  90                  95
Phe Phe Ile Trp Lys Leu Phe Gly Arg Tyr Phe Pro Ile Thr Leu His
            100                 105                 110
Lys Thr Val Asp Leu Glu Pro Thr His Thr Tyr Tyr Pro Leu Asp Val
        115                 120                 125
Gln Glu Tyr His Leu Ile Ala Glu Arg Tyr Trp Pro Gln Asn Lys Tyr
    130                 135                 140
Leu Arg Ala Ile Ile Ser Thr Ile Glu Tyr Phe Leu Pro Ala Phe Met
145                 150                 155                 160
Lys Arg Ser Leu Ser Ile Asn Glu Gln Glu Gln Pro Ala Glu Arg Asp
                165                 170                 175
Pro Leu Leu Ser Pro Val Ser Pro Ser Ser Pro Gly Ser Gln Pro Asp
            180                 185                 190
Lys Trp Ile Asn His Asp Ser Arg Tyr Ser Arg Gly Glu Ser Ser Gly
        195                 200                 205
Ser Asn Gly His Ala Ser Gly Ser Glu Leu Asn Gly Asn Gly Asn Asn
    210                 215                 220
Gly Thr Thr Asn Arg Arg Pro Leu Ser Ser Ala Ser Ala Gly Ser Thr
225                 230                 235                 240
Ala Ser Asp Ser Thr Leu Leu Asn Gly Ser Leu Asn Ser Tyr Ala Asn
                245                 250                 255
Gln Ile Ile Gly Glu Asn Asp Pro Gln Leu Ser Pro Thr Lys Leu Lys
            260                 265                 270
Pro Thr Gly Arg Lys Tyr Ile Phe Gly Tyr His Pro His Gly Ile Ile
        275                 280                 285
Gly Met Gly Ala Phe Gly Gly Ile Ala Thr Glu Gly Ala Gly Trp Ser
    290                 295                 300
Lys Leu Phe Pro Gly Ile Pro Val Ser Leu Met Thr Leu Thr Asn Asn
305                 310                 315                 320
Phe Arg Val Pro Leu Tyr Arg Glu Tyr Leu Met Ser Leu Gly Val Ala
                325                 330                 335
Ser Val Ser Lys Lys Ser Cys Lys Ala Leu Leu Lys Arg Asn Gln Ser
            340                 345                 350
Ile Cys Ile Val Val Gly Gly Ala Gln Glu Ser Leu Leu Ala Arg Pro
        355                 360                 365
Gly Val Met Asp Leu Val Leu Leu Lys Arg Lys Gly Phe Val Arg Leu
    370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Ser Lys Leu
                405                 410                 415
Tyr Arg Phe Gln Gln Phe Val Lys Asn Phe Leu Gly Phe Thr Leu Pro
            420                 425                 430
Leu Met His Ala Arg Gly Val Phe Asn Tyr Asp Val Gly Leu Val Pro
        435                 440                 445
Tyr Arg Arg Pro Val Asn Ile Val Val Gly Ser Pro Ile Asp Leu Pro
    450                 455                 460
Tyr Leu Pro His Pro Thr Asp Glu Glu Val Ser Glu Tyr His Asp Arg
465                 470                 475                 480
Tyr Ile Ala Glu Leu Gln Arg Ile Tyr Asn Glu His Lys Asp Glu Tyr
                485                 490                 495
Phe Ile Asp Trp Thr Glu Glu Gly Lys Gly Ala Pro Glu Phe Arg Met
```

Ile Glu

<210> SEQ ID NO 47
<211> LENGTH: 1581
<212> TYPE: DNA
<213> ORGANISM: Yarrowia lipolytica

<400> SEQUENCE: 47

```
atggaagtcc gacgacgaaa atcgacgtg ctcaaggccc agaaaaacgg ctacgaatcg      60
ggcccaccat ctcgacaatc gtcgcagccc tcctcaagag catcgtccag aacccgcaac    120
aaacactcct cgtccaccct gtcgctcagc ggactgacca tgaaagtcca gaagaaacct    180
gcgggacccc cggcgaactc caaaacgcca ttcctacaca tcaagcccgt gcacacgtgc    240
tgctccacat caatgctttc gcgcgattat gacggctcca accccagctt caagggcttc    300
aaaaacatcg gcatgatcat tctcattgtg gaaatctac ggctcgcatt cgaaaactac     360
ctcaaatacg gcatttccaa cccgttcttc gaccccaaaa ttactccttc cgagtggcag    420
ctctcaggct tgctcatagt cgtggcctac gcacatatcc tcatggccta cgctattgag    480
agcgctgcca agctgctgtt cctctctagc aaacaccact acatggccgt ggggcttctg    540
cataccatga acactttgtc gtccatctcg ttgctgtcct acgtcgtcta ctactacctg    600
cccaaccccg tggcaggcac aatagtcgag tttgtggccg ttattctgtc tctcaaactc    660
gcctcatacg ccctcactaa ctcggatctc cgaaaagccg caattcatgc cagaagctc     720
gacaagacgc aagacgataa cgaaaaggaa tccacctcgt cttcctcttc ttcagatgac    780
gcagagactt tggcagacat tgacgtcatt cctgcatact acgcacagct gccctacccc    840
cagaatgtga cgctgtcgaa cctgctgtac ttctggtttg ctcccacact ggtctaccag    900
cccgtgtacc ccaagacgga gcgtattcga cccaagcacg tgatccgaaa cctgtttgag    960
ctcgtctctc tgtgcatgct tattcagttt ctcatcttcc agtacgccta ccccatcatg   1020
cagtcgtgtc tggctctgtt cttccagccc aagctcgatt atgccaacat ctccgagcgc   1080
ctcatgaagt tggcctccgt gtctatgatg gtctggctca ttggattcta cgcttttcttc  1140
cagaacggtc tcaatcttat tgccgagctc acctgttttg aaacagaac cttctaccag    1200
cagtggtgga attcccgctc cattggccag tactggactc tatggaacaa gccagtcaac   1260
cagtacttta gacaccacgt ctacgtgcct cttctcgctc ggggcatgtc gcggttcaat   1320
gcgtcggtgg tggttttctt tttctccgcc gtcatccatg aactgcttgt cggcatcccc   1380
actcacaaca tcatcggagc cgccttcttc ggcatgatgt cgcaggtgcc tctgatcatg   1440
gctactgaga accttcagca tattaactcc tctctgggcc ccttccttgg caactgtgca   1500
ttctggttca ccttttttcct gggacaaccc acttgtgcat tcctttatta tctggcttac   1560
aactacaagc agaaccagta g                                              1581
```

<210> SEQ ID NO 48
<211> LENGTH: 526
<212> TYPE: PRT
<213> ORGANISM: Yarrowia lipolytica

<400> SEQUENCE: 48

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30
```

```
Arg Ala Ser Ser Arg Thr Arg Asn Lys His Ser Ser Thr Leu Ser
     35                  40                  45

Leu Ser Gly Leu Thr Met Lys Val Gln Lys Pro Ala Gly Pro Pro
 50                  55                  60

Ala Asn Ser Lys Thr Pro Phe Leu His Ile Lys Pro Val His Thr Cys
 65                  70                  75                  80

Cys Ser Thr Ser Met Leu Ser Arg Asp Tyr Asp Gly Ser Asn Pro Ser
                 85                  90                  95

Phe Lys Gly Phe Lys Asn Ile Gly Met Ile Ile Leu Ile Val Gly Asn
                100                 105                 110

Leu Arg Leu Ala Phe Glu Asn Tyr Leu Lys Tyr Gly Ile Ser Asn Pro
            115                 120                 125

Phe Phe Asp Pro Lys Ile Thr Pro Ser Glu Trp Gln Leu Ser Gly Leu
            130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
    195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
            245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
    275                 280                 285

Leu Tyr Phe Trp Phe Ala Pro Thr Leu Val Tyr Gln Pro Val Tyr Pro
    290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Gln Pro Lys Leu
            340                 345                 350

Asp Tyr Ala Asn Ile Ser Glu Arg Leu Met Lys Leu Ala Ser Val Ser
            355                 360                 365

Met Met Val Trp Leu Ile Gly Phe Tyr Ala Phe Phe Gln Asn Gly Leu
370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
            405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Phe Phe
            435                 440                 445
```

```
Ser Ala Val Ile His Glu Leu Leu Val Gly Ile Pro Thr His Asn Ile
450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
            485                 490                 495

Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
            515                 520                 525

<210> SEQ ID NO 49
<211> LENGTH: 3810
<212> TYPE: DNA
<213> ORGANISM: Yarrowia lipolytica

<400> SEQUENCE: 49
atggctaaag acaaggaaat cgactttgac tacacgggag aactggtgat ggacgatttc      60
gagttcccca tcgacgacat gctccacaac gacggagatg actttgtcaa gaaggaaacg     120
tgggacgagg gttttggttt cggaacaaat ggcgccgtgg gtgcgcagat ggacgtccag     180
accagcccat ttagcgaccc tgttttggc ggcgtgggag caggccctga catgatgggt      240
ctcatggata caaacatgaa ccacatcaac ggtagtcaca acatgaacag cgtcgtcaag     300
caggaggact actacacacc gtccatgggc actccatga ccccaacaa gcaacagtcc      360 atgacccctc aacagcagca tcacatgaac acaaccagc cctctcagct ccaatctttg      420
catcaacagt cccagaaggc tcaaccacag cagcaacaac aacagccaca tcagtcgaca     480
ggagtcgata gcataatcac aaaggcatac accagggcag caggagacct accgtacgga     540
cgaaagtact cacgacaact caacaagtac cccgaggacg tggagtattc atctttcgac     600
ccatcgctat ggagcaattt gctgaccaac tcggaaactc cgtaccaata ccagatacat     660
gtccattcca tgcccggaaa atcacgtgtg agacccaaa tcaaatgtgc attatcaatc     720
taccctccgc ctccacagca gtccgttcga cttccgacag acaccatttc gcgtcccaag    780
ttccagctca agcagggcca cattccagac tcgtgtctct ccttggaagt atacattgtg    840
ggcgagcaga cccccagcaa gcccgtcaat ttgtgttcta gatgcatcaa acgagaacag    900
aagcgagcct gtcgaaagaa actctttgac gagtcggagg agctgtcgtg gtcgagact     960 cgtcaacgac gtctggctgt cttcaactgc tccgaggtgc ttgagttcaa ggatgtggaa    1020
cggcgagtat acatccccga gtccggcact acagttaccg ccaagcagct ggttctgccc    1080
ctgcgtctgg cttgctactg tagacaccac ggggagaaaa agggatttcg aatcctcttt    1140
tgtcttagag acgagggagg ccagattgtg gtgtgggcc agagtggaac gaccgtcatg    1200
atcactgacg accacaaggt tgtgggagac gcggttgcca tgccgactac agccactgct    1260
cctgccaccg ctggctcttc acaaccccc acccaggttc ctaccccgc tgcatcttcg     1320 tcgacgagct atcgtcctcg aaactcgctt cctctatcgc ctacttccat ggaagactct    1380
tcgtcggagt tcacctcgga ccattctcat tactccaact atggttctaa acgacgacga    1440
gacggctctt ccatcagcga ttggagcggc atgatgaacg tgcgaggcat ggatagacag    1500
gcttccatta ccagcattcc cgaaatggtt ggtggcatgt cgaacatgac tgtggccagt    1560
gcttcgggta cgccactaa tctgctgct cacaacatga acaaccccgc agacgaaaac    1620
ctgcccgtca tcaagcgaat catcccctcg cagggttcca ttcgaggcgg cattgaagta    1680
```

```
accctgcttg gatctggctt caagtccaat ctggtggctg ttttcggtga caacaaggcc    1740
gtgggcaccc actgctggtc tgattcgacc atcgtgaccc atctgccgcc ttcgaccatc    1800
gtgggtcccg ttgtggtgtc tttcgaaggt tttgtgctcg acaagcctca gattttacc     1860
tattttgacg acacagacgg ccagttgatt gagttggcgc tccaggttgt gggtctcaag    1920
atgaacggac ggctggaaga cgcccgaaac attgccatgc gaatcgtggg caacaatgga    1980
ggcgttgcgg gcgcacaagg cgccatggca ggcgggaaca tgtctaacgg agacgttgga    2040
atggaaagtg ctgctgcaga cagttcggtt caacccgtat cgcctcccac agaccacgaa    2100
gatgtggttc tgcgatgtct ggctctcaca gacattcctg gaggccgaat tgccaactgg    2160
caactcacca acgccgaggg acagaccatg gttcatctgg ccagtattct gggttactcg    2220
cgtgttctgg tggctcttgt ggctcgagga gctcgtgtgg atgtttccga caatggtgga    2280
ttcactcctc ttcatttcgc tgctctcttt ggccgtcgaa agattgccaa gaaactactt    2340
cggtgcaacg ctgaccccta caacgtaacg cgaattggcg aaaccgtgtt tgatgttgct    2400
tgtcctcaca ttctcgatct tctggtcggt cctcagggca tgcctatggc cgttcagacg    2460
tcgtatactc ccgattacca tcgtcagcgt cgatcttcat cttcttccac tctggcttcc    2520
attgcatcca tccaggattc gcgtgagtac ggtttctatg accatggaat gatttccaac    2580
ctgtcgcata ttccgtccac gtgctccatt cgatcatcga cttctcagtt tgacgctgaa    2640
gacgagtggg acgagcgaga tgaggaggat ggagactttg acgacgattc agatgaggac    2700
tcagacgatg actcagacgc gctcttcatg tctgttagaa agcacgccaa ggccaagtct    2760
gtggaatctc ctctctctga ggaggaagag cgacttgtgc gacacattga ggccgaagac    2820
caggctgtgg aggcccgtgt ggctgccgga atcgtcagta gcaatgtacc cgacgtggtg    2880
tcttccaatg actcggatca cgtgagatct gacacttcca ctgagaacaa gtccttttca    2940
cggtactttg accgtactct cagcatggca tcttgggacg atgttctggc ttacatttac    3000
agacccaagc gagctactgt gcccaacaag cggtcttctg gagctcctcc ttcagtcaga    3060
tccacaagat cgcctctttc ggaccatccc atcacgtctt cgggagacga gtccgaccga    3120
accatttctg cacatgcccc ttccggcggt gccggtcgag gccggtctca ttcgtccatc    3180
tcgcgaatgt ggcgatacct gaagaactcg tctgccgatg aggccacccg gtctcgatct    3240
cgagatgcaa acggagccgg tgctcccccct gcctacgaag aaatcttccc tggccatggg    3300
gttgtccacg acaagaaggt tgtgcagatg gccgctgctt ctgctgccga gaactcgtct    3360
gggcctgttg gagcctcatc ttcagcagtt gcgtccactt ctgcggctgc cgctgtggtg    3420
ccctccccac tagcccccat tgtggaggac gaggagcagc tggtagaggc ctggagacga    3480
cagcgacgat ccatggctaa cgatcgcatg ttatttgcct tctggctgcc tgtgctgctc    3540
atggctattg gttatatggt catcaaggcg tttggtctgt tccccgacca ggtctctgcc    3600
gttgagtctg tggctgagac tgtgggtgtc cactgccgtg gagcagttgc caagctatgg    3660
ttcaagcagt accctgttca ccgaggccag ccactcaagg acacctgttc atttgagccc    3720
aacagtctgg tagagtcagc tcttcgtcag atgaatgggt ggtccgaccg ggaggttccc    3780
attcatcaag cccaggccca ggctgcatga                                      3810
```

<210> SEQ ID NO 50
<211> LENGTH: 1269
<212> TYPE: PRT
<213> ORGANISM: Yarrowia lipolytica
<400> SEQUENCE: 50

-continued

```
Met Ala Lys Asp Lys Glu Ile Asp Phe Asp Tyr Thr Gly Glu Leu Val
1               5                   10                  15

Met Asp Asp Phe Glu Phe Pro Ile Asp Asp Met Leu His Asn Asp Gly
                20                  25                  30

Asp Asp Phe Val Lys Lys Glu Thr Trp Asp Gly Phe Gly Phe Gly
            35                  40                  45

Thr Asn Gly Ala Val Gly Ala Gln Met Asp Val Gln Thr Ser Pro Phe
        50                  55                  60

Ser Asp Pro Val Phe Gly Gly Val Gly Ala Gly Pro Asp Met Met Gly
65                  70                  75                  80

Leu Met Asp Thr Asn Met Asn His Ile Asn Gly Ser His Asn Met Asn
                85                  90                  95

Ser Val Val Lys Gln Glu Asp Tyr Tyr Thr Pro Ser Met Gly Thr Pro
                100                 105                 110

Met Asn Pro Gln Gln Gln Gln Ser Met Thr Pro Gln Gln Gln His His
            115                 120                 125

Met Asn His Asn Gln Pro Ser Gln Leu Gln Ser Leu His Gln Gln Ser
        130                 135                 140

Gln Lys Ala Gln Pro Gln Gln Gln Gln Gln Pro His Gln Ser Thr
145                 150                 155                 160

Gly Val Asp Ser Ile Ile Thr Lys Ala Tyr Thr Arg Ala Ala Gly Asp
                165                 170                 175

Leu Pro Tyr Gly Arg Lys Tyr Ser Arg Gln Leu Asn Lys Tyr Pro Glu
                180                 185                 190

Asp Val Glu Tyr Ser Ser Phe Asp Pro Ser Leu Trp Ser Asn Leu Leu
            195                 200                 205

Thr Asn Ser Glu Thr Pro Tyr Gln Tyr Gln Ile His Val His Ser Met
        210                 215                 220

Pro Gly Lys Ser Arg Val Glu Thr Gln Ile Lys Cys Ala Leu Ser Ile
225                 230                 235                 240

Tyr Pro Pro Pro Gln Gln Ser Val Arg Leu Pro Thr Asp Thr Ile
                245                 250                 255

Ser Arg Pro Lys Phe Gln Leu Lys Gln Gly His Ile Pro Asp Ser Cys
            260                 265                 270

Leu Ser Leu Glu Val Tyr Ile Val Gly Glu Gln Asn Pro Ser Lys Pro
        275                 280                 285

Val Asn Leu Cys Ser Arg Cys Ile Lys Arg Glu Gln Lys Arg Ala Cys
        290                 295                 300

Arg Lys Lys Leu Phe Asp Glu Ser Glu Glu Leu Ser Trp Val Glu Thr
305                 310                 315                 320

Arg Gln Arg Arg Leu Ala Val Phe Asn Cys Ser Glu Val Leu Glu Phe
            325                 330                 335

Lys Asp Val Glu Arg Arg Val Tyr Ile Pro Glu Ser Gly Thr Thr Val
            340                 345                 350

Thr Ala Lys Gln Leu Val Leu Pro Leu Arg Leu Ala Cys Tyr Cys Arg
        355                 360                 365

His His Gly Glu Lys Lys Gly Phe Arg Ile Leu Phe Cys Leu Arg Asp
        370                 375                 380

Glu Gly Gly Gln Ile Val Gly Val Gly Gln Ser Gly Thr Thr Val Met
385                 390                 395                 400

Ile Thr Asp Asp His Lys Val Val Gly Asp Ala Val Ala Met Pro Thr
                405                 410                 415
```

-continued

```
Thr Ala Thr Ala Pro Ala Thr Ala Gly Ser Ser Gln Pro Pro Thr Gln
                420                 425                 430

Val Pro Thr Pro Ala Ala Ser Ser Ser Thr Ser Tyr Arg Pro Arg Asn
                435                 440                 445

Ser Leu Pro Leu Ser Pro Thr Ser Met Glu Asp Ser Ser Ser Glu Phe
            450                 455                 460

Thr Ser Asp His Ser His Tyr Ser Asn Tyr Gly Ser Lys Arg Arg Arg
465                 470                 475                 480

Asp Gly Ser Ser Ile Ser Asp Trp Ser Gly Met Met Asn Val Arg Gly
                485                 490                 495

Met Asp Arg Gln Ala Ser Ile Thr Ser Ile Pro Glu Met Val Gly Gly
                500                 505                 510

Met Ser Asn Met Thr Val Ala Ser Ala Ser Gly Ser Ala Thr Asn Leu
            515                 520                 525

Ala Ala His Asn Met Asn Asn Pro Ala Asp Glu Asn Leu Pro Val Ile
            530                 535                 540

Lys Arg Ile Ile Pro Ser Gln Gly Ser Ile Arg Gly Gly Ile Glu Val
545                 550                 555                 560

Thr Leu Leu Gly Ser Gly Phe Lys Ser Asn Leu Val Ala Val Phe Gly
                565                 570                 575

Asp Asn Lys Ala Val Gly Thr His Cys Trp Ser Asp Ser Thr Ile Val
            580                 585                 590

Thr His Leu Pro Pro Ser Thr Ile Val Gly Pro Val Val Ser Phe
            595                 600                 605

Glu Gly Phe Val Leu Asp Lys Pro Gln Ile Phe Thr Tyr Phe Asp Asp
610                 615                 620

Thr Asp Gly Gln Leu Ile Glu Leu Ala Leu Gln Val Val Gly Leu Lys
625                 630                 635                 640

Met Asn Gly Arg Leu Glu Asp Ala Arg Asn Ile Ala Met Arg Ile Val
                645                 650                 655

Gly Asn Asn Gly Gly Val Ala Gly Ala Gln Gly Ala Met Ala Gly Gly
                660                 665                 670

Asn Met Ser Asn Gly Asp Val Gly Met Glu Ser Ala Ala Ala Asp Ser
            675                 680                 685

Ser Val Gln Pro Val Ser Pro Pro Thr Asp His Glu Asp Val Val Leu
            690                 695                 700

Arg Cys Leu Ala Leu Thr Asp Ile Pro Gly Gly Arg Ile Ala Asn Trp
705                 710                 715                 720

Gln Leu Thr Asn Ala Glu Gly Gln Thr Met Val His Leu Ala Ser Ile
                725                 730                 735

Leu Gly Tyr Ser Arg Val Leu Val Ala Leu Val Ala Arg Gly Ala Arg
            740                 745                 750

Val Asp Val Ser Asp Asn Gly Gly Phe Thr Pro Leu His Phe Ala Ala
            755                 760                 765

Leu Phe Gly Arg Arg Lys Ile Ala Lys Lys Leu Leu Arg Cys Asn Ala
            770                 775                 780

Asp Pro Tyr Lys Arg Asn Arg Ile Gly Glu Thr Val Phe Asp Val Ala
785                 790                 795                 800

Cys Pro His Ile Leu Asp Leu Leu Val Gly Pro Gln Gly Met Pro Met
                805                 810                 815

Ala Val Gln Thr Ser Tyr Thr Pro Asp Tyr His Arg Gln Arg Arg Ser
            820                 825                 830

Ser Ser Ser Ser Thr Leu Ala Ser Ile Ala Ser Ile Gln Asp Ser Arg
```

-continued

```
            835                 840                 845
Glu Tyr Gly Phe Tyr Asp His Gly Met Ile Ser Asn Leu Ser His Ile
            850                 855                 860
Pro Ser Thr Cys Ser Ile Arg Ser Ser Thr Ser Gln Phe Asp Ala Glu
865                 870                 875                 880
Asp Glu Trp Asp Glu Arg Asp Glu Glu Asp Gly Asp Phe Asp Asp
                    885                 890                 895
Ser Asp Glu Asp Ser Asp Asp Ser Asp Ala Leu Phe Met Ser Val
            900                 905                 910
Arg Lys His Ala Lys Ala Lys Ser Val Glu Ser Pro Leu Ser Glu Glu
            915                 920                 925
Glu Glu Arg Leu Val Arg His Ile Glu Ala Glu Asp Gln Ala Val Glu
            930                 935                 940
Ala Arg Val Ala Ala Gly Ile Val Ser Ser Asn Val Pro Asp Val Val
945                 950                 955                 960
Ser Ser Asn Asp Ser Asp His Val Arg Ser Asp Thr Ser Thr Glu Asn
                    965                 970                 975
Lys Ser Phe Ser Arg Tyr Phe Asp Arg Thr Leu Ser Met Ala Ser Trp
                    980                 985                 990
Asp Asp Val Leu Ala Tyr Ile Tyr Arg Pro Lys Arg Ala Thr Val Pro
                    995                1000                1005
Asn Lys Arg Ser Ser Gly Ala Pro Pro Ser Val Arg Ser Thr Arg
            1010                1015                1020
Ser Pro Leu Ser Asp His Pro Ile Thr Ser Ser Gly Asp Glu Ser
            1025                1030                1035
Asp Arg Thr Ile Ser Ala His Ala Pro Ser Gly Gly Ala Gly Arg
            1040                1045                1050
Gly Arg Ser His Ser Ser Ile Ser Arg Met Trp Arg Tyr Leu Lys
            1055                1060                1065
Asn Ser Ser Ala Asp Glu Ala Thr Arg Ser Arg Ser Arg Asp Ala
            1070                1075                1080
Asn Gly Ala Gly Ala Pro Pro Ala Tyr Glu Glu Ile Phe Pro Gly
            1085                1090                1095
His Gly Val Val His Asp Lys Lys Val Val Gln Met Ala Ala Ala
            1100                1105                1110
Ser Ala Ala Glu Asn Ser Ser Gly Pro Val Gly Ala Ser Ser Ser
            1115                1120                1125
Ala Val Ala Ser Thr Ser Ala Ala Ala Val Val Pro Ser Pro
            1130                1135                1140
Leu Ala Pro Ile Val Glu Asp Glu Glu Gln Leu Val Glu Ala Trp
            1145                1150                1155
Arg Arg Gln Arg Arg Ser Met Ala Asn Asp Arg Met Leu Phe Ala
            1160                1165                1170
Phe Trp Leu Pro Val Leu Leu Met Ala Ile Gly Tyr Met Val Ile
            1175                1180                1185
Lys Ala Phe Gly Leu Phe Pro Asp Gln Val Ser Ala Val Glu Ser
            1190                1195                1200
Val Ala Glu Thr Val Gly Val His Cys Arg Gly Ala Val Ala Lys
            1205                1210                1215
Leu Trp Phe Lys Gln Tyr Pro Val His Arg Gly Gln Pro Leu Lys
            1220                1225                1230
Asp Thr Cys Ser Phe Glu Pro Asn Ser Leu Val Glu Ser Ala Leu
            1235                1240                1245
```

Arg Gln Met Asn Gly Trp Ser Asp Arg Glu Val Pro Ile His Gln
    1250                1255                1260

Ala Gln Ala Gln Ala Ala
    1265

<210> SEQ ID NO 51
<211> LENGTH: 3810
<212> TYPE: DNA
<213> ORGANISM: Artificial Sequence
<220> FEATURE:
<223> OTHER INFORMATION: Synthetic polynucleotide

<400> SEQUENCE: 51

| | | | | | |
|---|---|---|---|---|---|
| atggctaaag | acaaggaaat | cgactttgac | tacacgggag | aactggtgat | ggacgatttc | 60 |
| gagttcccca | tcgacgacat | gctccacaac | gacggagatg | actttgtcaa | gaaggaaacg | 120 |
| tgggacgagg | gttttggttt | cggaacaaat | ggcgccgtgg | gtgcgcagat | ggacgtccag | 180 |
| accagcccat | ttagcgaccc | tgttttggc | ggcgtgggag | caggccctga | catgatgggt | 240 |
| ctcatggata | caaacatgaa | ccacatcaac | ggtagtcaca | catgaacag | cgtcgtcaag | 300 |
| caggaggact | actacacacc | gtccatgggc | actcccatga | ccccaaca | gcaacagtcc | 360 |
| atgacccctc | aacagcagca | tcacatgaac | cacaaccagc | cctctcagct | ccaatctttg | 420 |
| catcaacagt | cccagaaggc | tcaaccacag | cagcaacaac | aacagccaca | tcagtcgaca | 480 |
| ggagtcgata | gcataatcac | aaaggcatac | accagggcag | caggagaccct | accgtacgga | 540 |
| cgaaagtact | cacgcaaact | caacaagtac | cccgaggacg | tggagtattc | atctttcgac | 600 |
| ccatcgctat | ggagcaattt | gctgaccaac | tcggaaactc | cgtaccaata | ccagatacat | 660 |
| gtccattcca | tgcccggaaa | atcacgtgtg | gagacccaaa | tcaaatgtgc | attatcaatc | 720 |
| taccctccgc | ctccacagca | gtccgttcga | cttccgacag | acaccatttc | gcgtcccaag | 780 |
| ttccagctca | gcagggcca | cattccgac | tcgtgtctct | ccttggaagt | atacattgtg | 840 |
| ggcgagcaga | accccagcaa | gcccgtcaat | ttgtgttcta | gatgcatcaa | acgagaacag | 900 |
| aagcgagcct | gtcgaaagaa | actctttgac | gagtcggagg | agctgtcgtg | ggtcagagact | 960 |
| cgtcaacgac | gtctggctgt | cttcaactgc | tccgaggtgc | ttgagttcaa | ggatgtggaa | 1020 |
| cggcgagtat | acatccccga | gtccggcact | acagttaccg | ccaagcagct | ggttctgccc | 1080 |
| ctgcgtctgg | cttgctactg | tagacaccac | ggggagaaaa | agggattcg | aatcctcttt | 1140 |
| tgtcttagag | acgagggagg | ccagattgtg | ggtgtgggcc | agagtggaac | gaccgtcatg | 1200 |
| atcactgacg | accacaaggt | tgtgggagac | gcggttgcca | tgccgactac | agccactgct | 1260 |
| cctgccaccg | ctggctcttc | acaacccccc | acccaggttc | ctaccccgc | tgcatcttcg | 1320 |
| tcgacgagct | atcgtcctcg | aaactcgctt | cctctatcgc | ctacttccat | ggaagactct | 1380 |
| tcgtcggagt | tcacctcgga | ccattctcat | tactccaact | atggttctaa | acgacgacga | 1440 |
| gacggctctt | ccatcagcga | ttggagcggc | atgatgaacg | tgcgaggcat | ggatagacag | 1500 |
| gcttccatta | ccagcattcc | cgaaatggtt | ggtggcatgt | cgaacatgac | tgtggccagt | 1560 |
| gcttcgggta | cgccactaa | tctggctgct | cacaacatga | caacccccgc | agacgaaaac | 1620 |
| ctgcccgtca | tcaagcgaat | catccccctcg | cagggttcca | ttcgaggcgg | cattgaagta | 1680 |
| accctgcttg | gatctggctt | caagtccaat | ctggtggctg | ttttcggtga | caacaaggcc | 1740 |
| gtgggcaccc | actgctggtc | tgattcgacc | atcgtgaccc | atctgccgcc | ttcgaccatc | 1800 |
| gtgggtcccg | ttgtggtgtc | tttcgaaggt | tttgtgctcg | acaagcctca | gattttacc | 1860 |

-continued

```
tattttgacg acacagacgg ccagttgatt gagttggcgc tccaggttgt gggtctcaag    1920
atgaacagac ggctggaaga cgcccgaaac attgccatgc gaatcgtggg caacaatgga    1980
ggcgttgcgg gcgcacaagg cgccatggca ggcgggaaca tgtctaacgg agacgttgga    2040
atggaaagtg ctgctgcaga cagttcggtt caacccgtat cgcctccac agaccacgaa     2100
gatgtggttc tgcgatgtct ggctctcaca gacattcctg gaggccgaat tgccaactgg    2160
caactcacca cgccgaggg acagaccatg gttcatctgg ccagtattct gggttactcg     2220
cgtgttctgg tggctcttgt ggctcgagga gctcgtgtgg atgtttccga caatggtgga    2280
ttcactcctc ttcatttcgc tgctctcttt ggccgtcgaa agattgccaa gaaactactt    2340
cggtgcaacg ctgaccccta caaacgtaac cgaattggcg aaaccgtgtt tgatgttgct    2400
tgtcctcaca ttctcgatct ctggtcggt cctcagggca tgcctatggc cgttcagacg     2460
tcgtatactc ccgattacca tcgtcagcgt cgatcttcat cttcttccac tctggcttcc    2520
attgcatcca tccaggattc gcgtgagtac ggtttctatg accatggaat gatttccaac    2580
ctgtcgcata ttccgtccac gtgctccatt cgatcatcga cttctcagtt tgacgctgaa    2640
gacgagtggg acgagcgaga tgaggaggat ggagactttg acgacgattc agatgaggac    2700
tcagacgatg actcagacgc gctcttcatg tctgttagaa agcacgccaa ggccaagtct    2760
gtggaatctc ctctctctga ggaggaagag cgacttgtgc gacacattga ggccgaagac    2820
caggctgtgg aggcccgtgt ggctgccgga atcgtcagta gcaatgtacc cgacgtggtg    2880
tcttccaatg actcggatca cgtgagatct gacacttcca ctgagaacaa gtccttttca    2940
cggtactttg accgtactct cagcatggca tcttgggacg atgttctggc ttacatttac    3000
agacccaagc gagctactgt gcccaacaag cggtcttctg gagctcctcc ttcagtcaga    3060
tccacaagat cgcctctttc ggaccatccc atcacgtctt cgggagacga gtccgaccga    3120
accatttctg cacatgcccc ttccggcggt gccggtcgag gccggtctca ttcgtccatc    3180
tcgcgaatgt ggcgatacct gaagaactcg tctgccgatg aggccacccg gtctcgatct    3240
cgagatgcaa acggagccgg tgctccccct gcctacgaag aaatcttccc tggccatggg    3300
gttgtccacg acaagaaggt tgtgcagatg ccgctgctt ctgctgccga gaactcgtct     3360
gggcctgttg gagcctcatc ttcagcagtt gcgtccactt ctgcggctgc cgctgtggtg    3420
ccctccccac tagcccccat tgtggaggac gaggagcagc tggtagaggc ctggagacga    3480
cagcgacgat ccatggctaa cgatcgcatg ttatttgcct tctggctgcc tgtgctgctc    3540
atggctattg ttatatggt catcaaggcg tttggtctgt tccccgacca ggtctctgcc    3600
gttgagtctg tggctgagac tgtgggtgtc cactgccgtg gagcagttgc caagctatgg    3660
ttcaagcagt accctgttca ccgaggccag ccactcaagg acacctgttc atttgagccc    3720
aacagtctgg tagagtcagc tcttcgtcag atgaatgggt ggtccgaccg ggaggttccc    3780
attcatcaag cccaggccca ggctgcatga                                      3810
```

<210> SEQ ID NO 52
<211> LENGTH: 1269
<212> TYPE: PRT
<213> ORGANISM: Artificial Sequence
<220> FEATURE:
<223> OTHER INFORMATION: Synthetic polypeptide
<400> SEQUENCE: 52

```
Met Ala Lys Asp Lys Glu Ile Asp Phe Asp Tyr Thr Gly Glu Leu Val
1               5                   10                  15
```

Met Asp Asp Phe Glu Phe Pro Ile Asp Asp Met Leu His Asn Asp Gly
                20                  25                  30

Asp Asp Phe Val Lys Lys Glu Thr Trp Asp Glu Gly Phe Gly Phe Gly
            35                  40                  45

Thr Asn Gly Ala Val Gly Ala Gln Met Asp Val Gln Thr Ser Pro Phe
        50                  55                  60

Ser Asp Pro Val Phe Gly Gly Val Gly Ala Gly Pro Asp Met Met Gly
65                  70                  75                  80

Leu Met Asp Thr Asn Met Asn His Ile Asn Gly Ser His Asn Met Asn
                85                  90                  95

Ser Val Val Lys Gln Glu Asp Tyr Tyr Thr Pro Ser Met Gly Thr Pro
            100                 105                 110

Met Asn Pro Gln Gln Gln Ser Met Thr Pro Gln Gln His His
            115                 120                 125

Met Asn His Asn Gln Pro Ser Gln Leu Gln Ser Leu His Gln Gln Ser
            130                 135                 140

Gln Lys Ala Gln Pro Gln Gln Gln Gln Pro His Gln Ser Thr
145                 150                 155                 160

Gly Val Asp Ser Ile Ile Thr Lys Ala Tyr Thr Arg Ala Ala Gly Asp
                165                 170                 175

Leu Pro Tyr Gly Arg Lys Tyr Ser Arg Gln Leu Asn Lys Tyr Pro Glu
            180                 185                 190

Asp Val Glu Tyr Ser Ser Phe Asp Pro Ser Leu Trp Ser Asn Leu Leu
            195                 200                 205

Thr Asn Ser Glu Thr Pro Tyr Gln Tyr Gln Ile His Val His Ser Met
210                 215                 220

Pro Gly Lys Ser Arg Val Glu Thr Gln Ile Lys Cys Ala Leu Ser Ile
225                 230                 235                 240

Tyr Pro Pro Pro Gln Ser Val Arg Leu Pro Thr Asp Thr Ile
            245                 250                 255

Ser Arg Pro Lys Phe Gln Leu Lys Gln Gly His Ile Pro Asp Ser Cys
            260                 265                 270

Leu Ser Leu Glu Val Tyr Ile Val Gly Glu Gln Asn Pro Ser Lys Pro
            275                 280                 285

Val Asn Leu Cys Ser Arg Cys Ile Lys Arg Glu Gln Lys Arg Ala Cys
            290                 295                 300

Arg Lys Lys Leu Phe Asp Glu Ser Glu Glu Leu Ser Trp Val Glu Thr
305                 310                 315                 320

Arg Gln Arg Arg Leu Ala Val Phe Asn Cys Ser Glu Val Leu Glu Phe
                325                 330                 335

Lys Asp Val Glu Arg Arg Val Tyr Ile Pro Glu Ser Gly Thr Thr Val
            340                 345                 350

Thr Ala Lys Gln Leu Val Leu Pro Leu Arg Leu Ala Cys Tyr Cys Arg
        355                 360                 365

His His Gly Glu Lys Lys Gly Phe Arg Ile Leu Phe Cys Leu Arg Asp
            370                 375                 380

Glu Gly Gly Gln Ile Val Gly Val Gly Gln Ser Gly Thr Thr Val Met
385                 390                 395                 400

Ile Thr Asp Asp His Lys Val Val Gly Asp Ala Val Ala Met Pro Thr
                405                 410                 415

Thr Ala Thr Ala Pro Ala Thr Ala Gly Ser Ser Gln Pro Pro Thr Gln
            420                 425                 430

Val Pro Thr Pro Ala Ala Ser Ser Ser Thr Ser Tyr Arg Pro Arg Asn

-continued

```
                435                 440                 445
Ser Leu Pro Leu Ser Pro Thr Ser Met Glu Asp Ser Ser Glu Phe
450                 455                 460

Thr Ser Asp His Ser His Tyr Ser Asn Tyr Gly Ser Lys Arg Arg
465                 470                 475                 480

Asp Gly Ser Ser Ile Ser Asp Trp Ser Gly Met Met Asn Val Arg Gly
                485                 490                 495

Met Asp Arg Gln Ala Ser Ile Thr Ser Ile Pro Glu Met Val Gly Gly
                500                 505                 510

Met Ser Asn Met Thr Val Ala Ser Ala Ser Gly Ser Ala Thr Asn Leu
                515                 520                 525

Ala Ala His Asn Met Asn Asn Pro Ala Asp Glu Asn Leu Pro Val Ile
                530                 535                 540

Lys Arg Ile Ile Pro Ser Gln Gly Ser Ile Arg Gly Gly Ile Glu Val
545                 550                 555                 560

Thr Leu Leu Gly Ser Gly Phe Lys Ser Asn Leu Val Ala Val Phe Gly
                565                 570                 575

Asp Asn Lys Ala Val Gly Thr His Cys Trp Ser Asp Ser Thr Ile Val
                580                 585                 590

Thr His Leu Pro Pro Ser Thr Ile Val Gly Pro Val Val Ser Phe
                595                 600                 605

Glu Gly Phe Val Leu Asp Lys Pro Gln Ile Phe Thr Tyr Phe Asp Asp
                610                 615                 620

Thr Asp Gly Gln Leu Ile Glu Leu Ala Leu Gln Val Val Gly Leu Lys
625                 630                 635                 640

Met Asn Arg Arg Leu Glu Asp Ala Arg Asn Ile Ala Met Arg Ile Val
                645                 650                 655

Gly Asn Asn Gly Gly Val Ala Gly Ala Gln Gly Ala Met Ala Gly Gly
                660                 665                 670

Asn Met Ser Asn Gly Asp Val Gly Met Glu Ser Ala Ala Ala Asp Ser
                675                 680                 685

Ser Val Gln Pro Val Ser Pro Pro Thr Asp His Glu Asp Val Val Leu
                690                 695                 700

Arg Cys Leu Ala Leu Thr Asp Ile Pro Gly Gly Arg Ile Ala Asn Trp
705                 710                 715                 720

Gln Leu Thr Asn Ala Glu Gly Gln Thr Met Val His Leu Ala Ser Ile
                725                 730                 735

Leu Gly Tyr Ser Arg Val Leu Val Ala Leu Val Ala Arg Gly Ala Arg
                740                 745                 750

Val Asp Val Ser Asp Asn Gly Gly Phe Thr Pro Leu His Phe Ala Ala
                755                 760                 765

Leu Phe Gly Arg Arg Lys Ile Ala Lys Lys Leu Leu Arg Cys Asn Ala
                770                 775                 780

Asp Pro Tyr Lys Arg Asn Arg Ile Gly Glu Thr Val Phe Asp Val Ala
785                 790                 795                 800

Cys Pro His Ile Leu Asp Leu Leu Val Gly Pro Gln Gly Met Pro Met
                805                 810                 815

Ala Val Gln Thr Ser Tyr Thr Pro Asp Tyr His Arg Gly Arg Arg Ser
                820                 825                 830

Ser Ser Ser Ser Thr Leu Ala Ser Ile Ala Ser Ile Gln Asp Ser Arg
                835                 840                 845

Glu Tyr Gly Phe Tyr Asp His Gly Met Ile Ser Asn Leu Ser His Ile
                850                 855                 860
```

```
Pro Ser Thr Cys Ser Ile Arg Ser Thr Ser Gln Phe Asp Ala Glu
865                 870                 875                 880

Asp Glu Trp Asp Glu Arg Asp Glu Glu Asp Gly Asp Phe Asp Asp
                885                 890                 895

Ser Asp Glu Asp Ser Asp Asp Ser Asp Ala Leu Phe Met Ser Val
            900                 905                 910

Arg Lys His Ala Lys Ala Lys Ser Val Glu Ser Pro Leu Ser Glu Glu
            915                 920                 925

Glu Glu Arg Leu Val Arg His Ile Glu Ala Glu Asp Gln Ala Val Glu
930                 935                 940

Ala Arg Val Ala Ala Gly Ile Val Ser Ser Asn Val Pro Asp Val Val
945                 950                 955                 960

Ser Ser Asn Asp Ser Asp His Val Arg Ser Asp Thr Ser Thr Glu Asn
            965                 970                 975

Lys Ser Phe Ser Arg Tyr Phe Asp Arg Thr Leu Ser Met Ala Ser Trp
            980                 985                 990

Asp Asp Val Leu Ala Tyr Ile Tyr Arg Pro Lys Arg Ala Thr Val Pro
            995                 1000                1005

Asn Lys Arg Ser Ser Gly Ala Pro Pro Ser Val Arg Ser Thr Arg
    1010                1015                1020

Ser Pro Leu Ser Asp His Pro Ile Thr Ser Ser Gly Asp Glu Ser
    1025                1030                1035

Asp Arg Thr Ile Ser Ala His Ala Pro Ser Gly Gly Ala Gly Arg
    1040                1045                1050

Gly Arg Ser His Ser Ser Ile Ser Arg Met Trp Arg Tyr Leu Lys
    1055                1060                1065

Asn Ser Ser Ala Asp Glu Ala Thr Arg Ser Arg Ser Arg Asp Ala
    1070                1075                1080

Asn Gly Ala Gly Ala Pro Pro Ala Tyr Glu Glu Ile Phe Pro Gly
    1085                1090                1095

His Gly Val Val His Asp Lys Lys Val Val Gln Met Ala Ala Ala
    1100                1105                1110

Ser Ala Ala Glu Asn Ser Ser Gly Pro Val Gly Ala Ser Ser Ser
    1115                1120                1125

Ala Val Ala Ser Thr Ser Ala Ala Ala Val Val Pro Ser Pro
    1130                1135                1140

Leu Ala Pro Ile Val Glu Asp Glu Glu Gln Leu Val Glu Ala Trp
    1145                1150                1155

Arg Arg Gln Arg Arg Ser Met Ala Asn Asp Arg Met Leu Phe Ala
    1160                1165                1170

Phe Trp Leu Pro Val Leu Leu Met Ala Ile Gly Tyr Met Val Ile
    1175                1180                1185

Lys Ala Phe Gly Leu Phe Pro Asp Gln Val Ser Ala Val Glu Ser
    1190                1195                1200

Val Ala Glu Thr Val Gly Val His Cys Arg Gly Ala Val Ala Lys
    1205                1210                1215

Leu Trp Phe Lys Gln Tyr Pro Val His Arg Gly Gln Pro Leu Lys
    1220                1225                1230

Asp Thr Cys Ser Phe Glu Pro Asn Ser Leu Val Glu Ser Ala Leu
    1235                1240                1245

Arg Gln Met Asn Gly Trp Ser Asp Arg Glu Val Pro Ile His Gln
    1250                1255                1260
```

Ala Gln Ala Gln Ala Ala
    1265

<210> SEQ ID NO 53
<211> LENGTH: 3003
<212> TYPE: DNA
<213> ORGANISM: Artificial Sequence
<220> FEATURE:
<223> OTHER INFORMATION: Synthetic polynucleotide

<400> SEQUENCE: 53

```
atggctaaag acaaggaaat cgactttgac tacacgggag aactggtgat ggacgatttc      60
gagttcccca tcgacgacat gctccacaac gacggagatg actttgtcaa gaaggaaacg     120
tgggacgagg gttttggttt cggaacaaat ggcgccgtgg gtgcgcagat ggacgtccag     180
accagcccat ttagcgaccc tgttttggc ggcgtgggag caggccctga catgatgggt      240
ctcatggata caaacatgaa ccacatcaac ggtagtcaca catgaacag cgtcgtcaag      300
caggaggact actacacacc gtccatgggc actcccatga accccaaca gcaacagtcc      360
atgacccctc aacagcagca tcacatgaac cacaaccagc cctctcagct ccaatctttg      420
catcaacagt cccagaaggc tcaaccacag cagcaacaac aacagccaca tcagtcgaca      480
ggagtcgata gcataatcac aaaggcatac accagggcag caggagacct accgtacgga      540
cgaaagtact cacgcaaact caacaagtac cccgaggacg tggagtattc atctttcgac      600
ccatcgctat ggagcaattt gctgaccaac tcggaaactc cgtaccaata ccagatacat      660
gtccattcca tgcccggaaa atcacgtgtg gagacccaaa tcaaatgtgc attatcaatc      720
taccctccgc ctccacagca gtccgttcga cttccgacag acaccatttc gcgtcccaag      780
ttccagctca gcagggcca cattccagac tcgtgtctct ccttggaagt atacattgtg      840
ggcgagcaga accccagcaa gcccgtcaat ttgtgttcta gatgcatcaa acgagaacag      900
aagcgagcct gtcgaaagaa actctttgac gagtcggagg agctgtcgtg ggtcgagact      960
cgtcaacgac gtctggctgt cttcaactgc tccgaggtgc ttgagttcaa ggatgtggaa     1020
cggcgagtat acatccccga gtccggcact acagttaccg ccaagcagct ggttctgccc     1080
ctgcgtctgg cttgctactg tagacaccac ggggagaaaa agggatttcg aatcctcttt     1140
tgtcttagag acgagggagg ccagattgtg ggtgtgggcc agagtggaac gaccgtcatg     1200
atcactgacg accacaaggt tgtgggagac gcggttgcca tgccgactac agccactgct     1260
cctgccaccg ctggctcttc acaaccccc acccaggttc ctaccccgc tgcatcttcg      1320
tcgacgagct atcgtcctcg aaactcgctt cctctatcgc ctacttccat ggaagactct     1380
tcgtcggagt tcacctcgga ccattctcat tactccaact atggttctaa acgacgacga     1440
gacggctctt ccatcagcga ttggagcggc atgatgaacg tgcgaggcat ggatagacag     1500
gcttccatta ccagcattcc cgaaatggtt ggtggcatgt cgaacatgac tgtggccagt     1560
gcttcgggta cgccactaa tctgctgct cacaacatga caaccccgc agacgaaaac      1620
ctgcccgtca tcaagcgaat catcccctcg cagggttcca ttcgaggcgg cattgaagta     1680
accctgcttg gatctggctt caagtccaat ctggtggctg ttttcggtga caacaaggcc     1740
gtgggcaccc actgctggtc tgattcgacc atcgtgaccc atctgccgcc ttcgaccatc     1800
gtgggtcccg ttgtggtgtc tttcgaaggt tttgtgctcg acaagcctca gatttttacc     1860
tattttgacg acacagacgg ccagttgatt gagttggcgc tccaggttgt gggtctcaag     1920
atgaacggac ggctggaaga cgcccgaaac attgccatgc gaatcgtggg caacaatgga     1980
```

-continued

```
ggcgttgcgg gcgcacaagg cgccatggca ggcgggaaca tgtctaacgg agacgttgga    2040
atggaaagtg ctgctgcaga cagttcggtt caacccgtat cgcctcccac agaccacgaa    2100
gatgtggttc tgcgatgtct ggctctcaca gacattcctg gaggccgaat tgccaactgg    2160
caactcacca cgccgaggg acagaccatg gttcatctgg ccagtattct gggttactcg    2220
cgtgttctgg tggctcttgt ggctcgagga gctcgtgtgg atgtttccga caatggtgga    2280
ttcactcctc ttcatttcgc tgctctcttt ggccgtcgaa agattgccaa gaaactactt    2340
cggtgcaacg ctgacccta caaacgtaac cgaattggcg aaaccgtgtt tgatgttgct    2400
tgtcctcaca ttctcgatct tctggtcggt cctcagggca tgcctatggc cgttcagacg    2460
tcgtatactc ccgattacca tcgtcagcgt cgatcttcat cttcttccac tctggcttcc    2520
attgcatcca tccaggattc gcgtgagtac ggtttctatg accatggaat gatttccaac    2580
ctgtcgcata ttccgtccac gtgctccatt cgatcatcga cttctcagtt tgacgctgaa    2640
gacgagtggg acgagcgaga tgaggaggat ggagactttg acgacgattc agatgaggac    2700
tcagacgatg actcagacgc gctcttcatg tctgttagaa agcacgccaa ggccaagtct    2760
gtggaatctc ctctctctga ggaggaagag cgacttgtgc gacacattga ggccgaagac    2820
caggctgtgg aggcccgtgt ggctgccgga atcgtcagta gcaatgtacc cgacgtggtg    2880
tcttccaatg actcggatca cgtgagatct gacacttcca ctgagaacaa gtccttttca    2940
cggtactttg accgtactct cagcatggca tcttgggacg atgttctggc ttacatttac    3000
tga                                                                  3003
```

<210> SEQ ID NO 54
<211> LENGTH: 1000
<212> TYPE: PRT
<213> ORGANISM: Artificial Sequence
<220> FEATURE:
<223> OTHER INFORMATION: Synthetic polypeptide

<400> SEQUENCE: 54

```
Met Ala Lys Asp Lys Glu Ile Asp Phe Asp Tyr Thr Gly Glu Leu Val
1               5                  10                  15

Met Asp Asp Phe Glu Phe Pro Ile Asp Asp Met Leu His Asn Asp Gly
            20                  25                  30

Asp Asp Phe Val Lys Lys Glu Thr Trp Asp Glu Gly Phe Gly Phe Gly
        35                  40                  45

Thr Asn Gly Ala Val Gly Ala Gln Met Asp Val Gln Thr Ser Pro Phe
    50                  55                  60

Ser Asp Pro Val Phe Gly Val Gly Ala Gly Pro Asp Met Met Gly
65                  70                  75                  80

Leu Met Asp Thr Asn Met Asn His Ile Asn Gly Ser His Asn Met Asn
                85                  90                  95

Ser Val Val Lys Gln Glu Asp Tyr Tyr Thr Pro Ser Met Gly Thr Pro
            100                 105                 110

Met Asn Pro Gln Gln Gln Gln Ser Met Thr Pro Gln Gln Gln His His
        115                 120                 125

Met Asn His Asn Gln Pro Ser Gln Leu Gln Ser Leu His Gln Gln Ser
    130                 135                 140

Gln Lys Ala Gln Pro Gln Gln Gln Gln Gln Pro His Gln Ser Thr
145                 150                 155                 160

Gly Val Asp Ser Ile Ile Thr Lys Ala Tyr Thr Arg Ala Ala Gly Asp
                165                 170                 175
```

-continued

Leu Pro Tyr Gly Arg Lys Tyr Ser Arg Gln Leu Asn Lys Tyr Pro Glu
            180                 185                 190

Asp Val Glu Tyr Ser Ser Phe Asp Pro Ser Leu Trp Ser Asn Leu Leu
        195                 200                 205

Thr Asn Ser Glu Thr Pro Tyr Gln Tyr Gln Ile His Val His Ser Met
    210                 215                 220

Pro Gly Lys Ser Arg Val Glu Thr Gln Ile Lys Cys Ala Leu Ser Ile
225                 230                 235                 240

Tyr Pro Pro Pro Gln Gln Ser Val Arg Leu Pro Thr Asp Thr Ile
            245                 250                 255

Ser Arg Pro Lys Phe Gln Leu Lys Gln Gly His Ile Pro Asp Ser Cys
        260                 265                 270

Leu Ser Leu Glu Val Tyr Ile Val Gly Glu Gln Asn Pro Ser Lys Pro
    275                 280                 285

Val Asn Leu Cys Ser Arg Cys Ile Lys Arg Glu Gln Lys Arg Ala Cys
        290                 295                 300

Arg Lys Lys Leu Phe Asp Glu Ser Glu Leu Ser Trp Val Glu Thr
305                 310                 315                 320

Arg Gln Arg Arg Leu Ala Val Phe Asn Cys Ser Glu Val Leu Glu Phe
            325                 330                 335

Lys Asp Val Glu Arg Val Tyr Ile Pro Glu Ser Gly Thr Thr Val
        340                 345                 350

Thr Ala Lys Gln Leu Val Leu Pro Leu Arg Leu Ala Cys Tyr Cys Arg
            355                 360                 365

His His Gly Glu Lys Lys Gly Phe Arg Ile Leu Phe Cys Leu Arg Asp
    370                 375                 380

Glu Gly Gly Gln Ile Val Gly Val Gly Gln Ser Gly Thr Thr Val Met
385                 390                 395                 400

Ile Thr Asp Asp His Lys Val Val Gly Asp Ala Val Ala Met Pro Thr
            405                 410                 415

Thr Ala Thr Ala Pro Ala Thr Ala Gly Ser Ser Gln Pro Pro Thr Gln
        420                 425                 430

Val Pro Thr Pro Ala Ala Ser Ser Thr Ser Tyr Arg Pro Arg Asn
        435                 440                 445

Ser Leu Pro Leu Ser Pro Thr Ser Met Glu Asp Ser Ser Glu Phe
    450                 455                 460

Thr Ser Asp His Ser His Tyr Ser Asn Tyr Gly Ser Lys Arg Arg Arg
465                 470                 475                 480

Asp Gly Ser Ser Ile Ser Asp Trp Ser Gly Met Met Asn Val Arg Gly
            485                 490                 495

Met Asp Arg Gln Ala Ser Ile Thr Ser Ile Pro Glu Met Val Gly Gly
        500                 505                 510

Met Ser Asn Met Thr Val Ala Ser Ala Ser Gly Ser Ala Thr Asn Leu
    515                 520                 525

Ala Ala His Asn Met Asn Asn Pro Ala Asp Glu Asn Leu Pro Val Ile
        530                 535                 540

Lys Arg Ile Ile Pro Ser Gln Gly Ser Ile Arg Gly Ile Glu Val
545                 550                 555                 560

Thr Leu Leu Gly Ser Gly Phe Lys Ser Asn Leu Val Ala Val Phe Gly
            565                 570                 575

Asp Asn Lys Ala Val Gly Thr His Cys Trp Ser Asp Ser Thr Ile Val
        580                 585                 590

Thr His Leu Pro Pro Ser Thr Ile Val Gly Pro Val Val Val Ser Phe

```
                    595                 600                 605
Glu Gly Phe Val Leu Asp Lys Pro Gln Ile Phe Thr Tyr Phe Asp Asp
    610                 615                 620

Thr Asp Gly Gln Leu Ile Glu Leu Ala Leu Gln Val Val Gly Leu Lys
625                 630                 635                 640

Met Asn Gly Arg Leu Glu Asp Ala Arg Asn Ile Ala Met Arg Ile Val
                645                 650                 655

Gly Asn Asn Gly Gly Val Ala Gly Ala Gln Gly Ala Met Ala Gly Gly
                660                 665                 670

Asn Met Ser Asn Gly Asp Val Gly Met Glu Ser Ala Ala Ala Asp Ser
            675                 680                 685

Ser Val Gln Pro Val Ser Pro Pro Thr Asp His Glu Asp Val Val Leu
690                 695                 700

Arg Cys Leu Ala Leu Thr Asp Ile Pro Gly Gly Arg Ile Ala Asn Trp
705                 710                 715                 720

Gln Leu Thr Asn Ala Glu Gly Gln Thr Met Val His Leu Ala Ser Ile
                725                 730                 735

Leu Gly Tyr Ser Arg Val Leu Val Ala Leu Val Ala Arg Gly Ala Arg
            740                 745                 750

Val Asp Val Ser Asp Asn Gly Gly Phe Thr Pro Leu His Phe Ala Ala
        755                 760                 765

Leu Phe Gly Arg Arg Lys Ile Ala Lys Lys Leu Leu Arg Cys Asn Ala
770                 775                 780

Asp Pro Tyr Lys Arg Asn Arg Ile Gly Glu Thr Val Phe Asp Val Ala
785                 790                 795                 800

Cys Pro His Ile Leu Asp Leu Leu Val Gly Pro Gln Gly Met Pro Met
                805                 810                 815

Ala Val Gln Thr Ser Tyr Thr Pro Asp Tyr His Arg Gln Arg Arg Ser
            820                 825                 830

Ser Ser Ser Ser Thr Leu Ala Ser Ile Ala Ser Ile Gln Asp Ser Arg
        835                 840                 845

Glu Tyr Gly Phe Tyr Asp His Gly Met Ile Ser Asn Leu Ser His Ile
    850                 855                 860

Pro Ser Thr Cys Ser Ile Arg Ser Ser Thr Ser Gln Phe Asp Ala Glu
865                 870                 875                 880

Asp Glu Trp Asp Glu Arg Asp Glu Glu Asp Gly Asp Phe Asp Asp Asp
                885                 890                 895

Ser Asp Glu Asp Ser Asp Asp Ser Asp Ala Leu Phe Met Ser Val
            900                 905                 910

Arg Lys His Ala Lys Ala Lys Ser Val Glu Ser Pro Leu Ser Glu Glu
        915                 920                 925

Glu Glu Arg Leu Val Arg His Ile Glu Ala Glu Asp Gln Ala Val Glu
    930                 935                 940

Ala Arg Val Ala Ala Gly Ile Val Ser Ser Asn Val Pro Asp Val Val
945                 950                 955                 960

Ser Ser Asn Asp Ser Asp His Val Arg Ser Asp Thr Ser Thr Glu Asn
                965                 970                 975

Lys Ser Phe Ser Arg Tyr Phe Arg Thr Leu Ser Met Ala Ser Trp
            980                 985                 990

Asp Asp Val Leu Ala Tyr Ile Tyr
        995                 1000

<210> SEQ ID NO 55
```

```
<211> LENGTH: 772
<212> TYPE: DNA
<213> ORGANISM: Artificial Sequence
<220> FEATURE:
<223> OTHER INFORMATION: Synthetic polynucleotide

<400> SEQUENCE: 55
atgtctggac cttccaccct cgccacggga ctgcaccctc tccccacaga gaccccaaag      60
ttccccacca acatcatgga ccgattctcc ctcaagggta aggttgcctc cgtcaccggc     120
tcctcgtcag gtatcggcta ctgcgtggcc gaggcctacg cccaggccgg tgccgacgtg     180
gccatctggt acaactccca ccccgccgac gcaaaggctg agcacctcgc taagacctac     240
ggcgtcaagg ccaaggccta caagtgccct gtcaccgacg ccgccgccgt ggagtccacc     300
atccagcaga tcgagaagga ctttggcacc attgacatct cgtcgccaa cgctggtgtc      360
ccctggaccg ccggccccat gatcgacgtg cccgacaaca aggagtggga caaggtcatc     420
aacctggatc tcaacggtgc ctactactgc gccaagtacg ccggccagat cttcaagaag     480
aagggcaagg atccttcat cttcaccgcc tccatgtccg gccacattgt caacatcccc      540
cagatgcagg cctgctacaa cgccgccaag gccgctctgc tgcacctgtc tcgatcgctg     600
gccgtcgagt gggccggctt tgcccgatgc aacacagtct cccctggcta catggccacc     660
gagatctccg actttgtccc caaggagacc aaggagaagt ggtggcagct cattcccatg     720
ggccgagagg gagacccctc cgagctctag cctacctcta ccttgcctct ga             772

<210> SEQ ID NO 56
<211> LENGTH: 200
<212> TYPE: DNA
<213> ORGANISM: Artificial Sequence
<220> FEATURE:
<223> OTHER INFORMATION: Synthetic polynucleotide

<400> SEQUENCE: 56
cacaaatatt cttgatttac tttggttttg ccctattcgg aaattttatt gatatctaat      60
agaagtatta agtaaaaat gtactaatac ttaattgtaa tgtcatcaga ataacattt       120
gaggaaaata tttcaaacct aattgatata tatattagag atgtcccgct tctctgtcat     180
taatatattc aagcaatcga                                                 200

<210> SEQ ID NO 57
<211> LENGTH: 840
<212> TYPE: DNA
<213> ORGANISM: Artificial Sequence
<220> FEATURE:
<223> OTHER INFORMATION: Synthetic polynucleotide

<400> SEQUENCE: 57
atgaagttca cctccgctac tctcctcgcc cttgccgccc ttgtcgttgc cgacaacgcc      60
gttgtctctc agatcaacga tggccagatc caggctcctc ccgctggtgg tgagggtgcc     120
aagcccgccc ctgctccttc tggagctgcc cccggtgccc ccggtgctgg tgctcccggc     180
gctggtgctc ccggcgctgg tgccctggc gctggcgagg gtgctaagcc ctctggagct      240
gcccccggtg ccccggcgc tggtgctccc ggtgctggtg agggtgctaa gccttctggc      300
ggtgccccg tgctggcgc tcctggtgct ggcgagggtg ctaagccctc tggtggtgcc       360
cctggtgccc ccggcgctgg tgctcccggt gctggtgagg gtgctaagcc ctctggtggt     420
gccccggtg ccccggcgc tggtgagggt gccaagccct ccggctctgc tcccggtgct       480
cctggcgctg gtgagggtgc caagccctcc ggctctgctc ccggtgctcc tggcgctggt     540
```

-continued

```
gagggtgcca agccctctgg ctctgctccc ggtgctcctg gtgctggtga gggtgccaag      600
ccctctggct ctgctcccgg tgctcctgga gctggtgcag gtgctaagcc ctccgctgga      660
ggtgagcacc ccgctgctga ggccactggt gtcgtcactc agatccacga cggccagatc      720
caggctcccg agcagaccca gcccccgct gccggccctg cccaggctaa cggtgctgcc       780
accctcggtg cccagatcgt tgccggtgtt gtcgccgctg ccggtgtcgc tctcttctaa      840
```

<210> SEQ ID NO 58
<211> LENGTH: 1542
<212> TYPE: DNA
<213> ORGANISM: Artificial Sequence
<220> FEATURE:
<223> OTHER INFORMATION: Synthetic polynucleotide

<400> SEQUENCE: 58

```
atggccgaca caagcctct gtgcacgatt accacgcccg aaccgtcacc caagcgtcga       60
aagatctctg ccgaggagaa agaaaagatg cgacttgaaa aggaacagat caagaagcag      120
aaagaggaag agcgagagca gcttcgaaga cagaaggaag aagagaaaga gctactgaga      180
aagcagaaag aggaggagaa ggaacaactg aggaaacaga aggaggagga aagagggct      240 aaagaggagg agagagggct agagagaggg agaaaacgac gacgagaaga ggaacgaaag      300
aaggctgccg aagagaagga gcttgagcga gccaagattg cagaggagaa ggctaagttg      360
gctgaagaga aggaggccaa gagacttgaa aaagaagctg aactcaagaa gaaggagcaa      420
gaacagactc gaatcatgtc tttctttaac aagaagacca aaaagaagac caagaaggaa      480
gctgttaaca gtgacaagtg tttggacttt gataaagact tcctacccott ccacatcaaa      540 gataccgtgt gtatggcaga caagacggag tgtgaagtga tggatcagga tcctgttgac      600
tggctcaaca gtctcaacct ttctgatgac agcaacaccg ccgaagcaga agaaccacct      660
gttcccgtca aaaccatcat tactcacatc cagaccgctg ccactctggg tctcaatcct      720
gataattaca cggtactcc tttagacacg ctggtcaatg ctcttcctag acgatacttg      780
cagttctatg gtgacgagcg acccgcatac ctgggcacgt actccaagag ctgctcgcgt      840
gatctgttgc agaaccctct cttccaggtg cctggttttgg actacgagta cgacagtgag      900
gcagactggg aagatgaagg agaagatatt gaagatgatg aaattagtgg agacgaggag      960
atggaggacg acgaaatggc cgactttgtg tgttctgatg atgccaagag tcccagcacc     1020
atgacttcaa aggtcacgac agcccaggaa cctgttgttg tctggggctg ctcagatatg     1080
gttggtatga ctttttggagg actgattgtc caggggggcaa ttgacccatt caagactat     1140 tggactgttg caaaagttga gcagaagacc gatactaaga gtgacgtgac aatgactagt     1200
gcgacatcag cttctggtac agctattaaa tctactacaa ccaaaaccga actcagcccg     1260
tttgaagtcc tctccaaaac tctgtcacct tccccagcgg ttgcttcagc cacgaaacag     1320
tttctggctg ctgccaagcc tcagaagctc attgctggag cgacctgac tgctcttttg      1380 aagcgagtag atggatccga cgataacaag acgctgttga ccgagctgct tgtaagcag      1440 tatcccagt acacacgcaa gatggtcacg gccaccattc agcactatgc tgagcgacag      1500
ggtcctaaga gcgacaagcg gtgggttctg aaggatatct ag                         1542
```

<210> SEQ ID NO 59
<211> LENGTH: 1944
<212> TYPE: DNA
<213> ORGANISM: Yarrowia lipolytica

<400> SEQUENCE: 59

```
atgagcttcc cccaacaagt aatagcgccg ggccaacggc tcaacgagct tctggaggcc      60
atcaaacagg agttcgactc cgtgaccaac gaggcgtccg tctaccggct gcacaaggac     120
gagtttgacg tcaaggtgaa ccagcagacg tcagatctgg ccagattcg acagtcggtc     180
tacgagctag aaatggcgca ccgaaagatg aaggagcgct acgaggagga aatcatgcgg     240
ctcaagagcg agctggaggc cgaggtggac cccgctgcga accccgcaca ctcccagcag     300
cagcaacagc agcaacagca acagcagcaa cagcagcagc agaaccagca ggcacaggac     360
caacaagcac gggccgcgca caacaggca gcccagcagc aggccctcgc ccagcagcag     420
ccgcccagc agcaggctct ggcccaacag caggcccagg ctcaacagca ggcccaggcc      480
caggcccacc acatgggtgg tgtgccccct cgcaaggac agccccgtc gctgctgcgt      540
ccatcatcca acgtgttcag cggcatcatg tccggtcagc ccggcacctc ttctctggct     600
cccccgcagg acagcccggt tcagcccag cctggtcagc ccaacctgg tcaaccccag     660
ccctactccg gctacgtggg tgctaacggc tacacgtctt cgccacataa cggaccccc     720
gtcatcagcg caatggcctc gcccaacagc aagaagcgac aggtgtcgac ccccgttccc     780
ggcaaggcgt ctccccaggt ggcccccaa gagatgcaac agcagcagca acagcagggc     840
cctccacagc agcagcaacc tccccagcag cagcaacaga ccccgaaga gatgggcaac     900
tacctgggcg acatggacat tgagcgggta cctccggagc tcaaaaaca aaaggccgac     960
tggtttgtcg tttacaacca gcgagcacca cggctgctgg acgtggatat tgtgcagtcg    1020
ctggaccaca actctgtagt gtgctgtgtg cggttctccg ctgacggcaa gtacattgcc    1080
actggctgta accgatctgc ccagattttc gacgtgcaga ctggccagct catctgccgg    1140
ctgcaggacc actcggtcga ccgagaaggc gacctgtaca tccggtccgt gtgtttctcg    1200
ccggacggta agtacctggc caccggcgcc gaggacaagc agatccgagt gtgggacatt    1260
aaatctcaga gcatacggca cgtgttcact ggccacgagc aggacattta tcgctggac    1320
ttttcgcgaa acggccgaca cattgcctct ggctctggcg accgcacagt ccgaatgtgg    1380
gatattgaga gcggccagtg tactctaacc ctgtcgatcg aggacggcgt caccacggtg    1440
gccatctcgc ccgacggcaa gtttgtggct gcaggcagct tggacaagtc tgtgcgaatc    1500
tgggacacct ctaccggttt cctggttgag cgtctggagg ccctgatgg acacaaggac    1560
tccgtctata gtgtagcttt cacccccaac ggtatggatc ttgtttccgg ctcgctggac    1620
aagacgatca agctgtggga gctgcaggct cctcgaggca ttcaggccaa ccagcgagga    1680
ggcgtctgcg tcaagacgct gtgtggacac aaggactttg ttctgagtgt ggccagcacg    1740
ctggatgggc agtggattct ttccggctcc aaggaccggg gtgtgcaatt ctgggacct    1800
cgaacgggcc aggtgcaact catgctgcag ggtcatcgaa attcggtcat cagtgtggct    1860
cctagtccca tgggcgggtt gtttgctact ggaagtggag attgcaaggc tcgaatctgg    1920
cgatactttc ctgtcaacag ataa                                            1944
```

<210> SEQ ID NO 60
<211> LENGTH: 647
<212> TYPE: PRT
<213> ORGANISM: Yarrowia lipolytica

<400> SEQUENCE: 60

```
Met Ser Phe Pro Gln Gln Val Ile Ala Pro Gly Gln Arg Leu Asn Glu
 1               5                  10                  15
```

-continued

```
Leu Leu Glu Ala Ile Lys Gln Glu Phe Asp Ser Val Thr Asn Glu Ala
            20                  25                  30

Ser Val Tyr Arg Leu His Lys Asp Glu Phe Asp Val Lys Val Asn Gln
        35                  40                  45

Gln Thr Ser Asp Leu Gly Gln Ile Arg Gln Ser Val Tyr Glu Leu Glu
    50                  55                  60

Met Ala His Arg Lys Met Lys Glu Arg Tyr Glu Glu Ile Met Arg
65                  70                  75                  80

Leu Lys Ser Glu Leu Glu Ala Arg Gly Gly Pro Ala Ala Asn Pro Ala
                85                  90                  95

His Ser Gln Gln Gln Gln Gln Gln Gln Gln Gln Gln Gln Gln Gln Gln
            100                 105                 110

Gln Gln Asn Gln Gln Ala Gln Asp Gln Gln Ala Arg Ala Ala Gln Gln
        115                 120                 125

Gln Ala Gln Gln Gln Ala Leu Ala Gln Gln Gln Ala Ala Gln Gln
    130                 135                 140

Gln Ala Leu Ala Gln Gln Ala Gln Ala Gln Gln Ala Gln Ala
145                 150                 155                 160

Gln Ala His His Met Gly Gly Val Pro Pro Ser Gln Gly Gln Pro Pro
                165                 170                 175

Ser Leu Leu Arg Pro Ser Ser Asn Val Phe Ser Gly Ile Met Ser Gly
            180                 185                 190

Gln Pro Gly Thr Ser Ser Leu Ala Pro Pro Gln Gly Gln Pro Gly Gln
        195                 200                 205

Pro Gln Pro Gly Gln Pro Gln Pro Gly Gln Pro Gln Pro Tyr Ser Gly
    210                 215                 220

Tyr Val Gly Ala Asn Gly Tyr Thr Ser Ser Pro His Asn Gly Pro Pro
225                 230                 235                 240

Val Ile Ser Ala Met Ala Ser Pro Asn Ser Lys Lys Arg Gln Val Ser
                245                 250                 255

Thr Pro Val Pro Gly Lys Ala Ser Pro Gln Val Ala Pro Gln Glu Met
            260                 265                 270

Gln Gln Gln Gln Gln Gln Gln Gly Pro Pro Gln Gln Gln Gln Pro Pro
        275                 280                 285

Gln Gln Gln Gln Gln Ser Pro Glu Glu Met Gly Asn Tyr Leu Gly Asp
    290                 295                 300

Met Asp Ile Glu Arg Val Pro Pro Glu Leu Lys Lys Gln Lys Ala Asp
305                 310                 315                 320

Trp Phe Val Val Tyr Asn Gln Arg Ala Pro Arg Leu Leu Asp Val Asp
                325                 330                 335

Ile Val Gln Ser Leu Asp His Asn Ser Val Val Cys Cys Val Arg Phe
            340                 345                 350

Ser Ala Asp Gly Lys Tyr Ile Ala Thr Gly Cys Asn Arg Ser Ala Gln
        355                 360                 365

Ile Phe Asp Val Gln Thr Gly Gln Leu Ile Cys Arg Leu Gln Asp Asp
    370                 375                 380

Ser Val Asp Arg Glu Gly Asp Leu Tyr Ile Arg Ser Val Cys Phe Ser
385                 390                 395                 400

Pro Asp Gly Lys Tyr Leu Ala Thr Gly Ala Glu Asp Lys Gln Ile Arg
                405                 410                 415

Val Trp Asp Ile Lys Ser Gln Ser Ile Arg His Val Phe Thr Gly His
            420                 425                 430

Glu Gln Asp Ile Tyr Ser Leu Asp Phe Ser Arg Asn Gly Arg His Ile
```

```
          435                 440                 445
Ala Ser Gly Ser Gly Asp Arg Thr Val Arg Met Trp Asp Ile Glu Ser
    450                 455                 460

Gly Gln Cys Thr Leu Thr Leu Ser Ile Glu Asp Gly Val Thr Thr Val
465                 470                 475                 480

Ala Ile Ser Pro Asp Gly Lys Phe Val Ala Gly Ser Leu Asp Lys
                485                 490                 495

Ser Val Arg Ile Trp Asp Thr Ser Thr Gly Phe Leu Val Glu Arg Leu
            500                 505                 510

Glu Ala Pro Asp Gly His Lys Asp Ser Val Tyr Ser Val Ala Phe Thr
        515                 520                 525

Pro Asn Gly Met Asp Leu Val Ser Gly Ser Leu Asp Lys Thr Ile Lys
    530                 535                 540

Leu Trp Glu Leu Gln Ala Pro Arg Gly Ile Gln Ala Asn Gln Arg Gly
545                 550                 555                 560

Gly Val Cys Val Lys Thr Leu Cys Gly His Lys Asp Phe Val Leu Ser
                565                 570                 575

Val Ala Ser Thr Leu Asp Gly Gln Trp Ile Leu Ser Gly Ser Lys Asp
            580                 585                 590

Arg Gly Val Gln Phe Trp Asp Pro Arg Thr Gly Gln Val Gln Leu Met
        595                 600                 605

Leu Gln Gly His Arg Asn Ser Val Ile Ser Val Ala Pro Ser Pro Met
    610                 615                 620

Gly Gly Leu Phe Ala Thr Gly Ser Gly Asp Cys Lys Ala Arg Ile Trp
625                 630                 635                 640

Arg Tyr Phe Pro Val Asn Arg
                645

<210> SEQ ID NO 61
<211> LENGTH: 900
<212> TYPE: DNA
<213> ORGANISM: Yarrowia lipolytica

<400> SEQUENCE: 61
atgtctatca agcgagaaga gtcctttact cccaccccg aggacctggg atctcccctg     60
acagctgatt ctcctggctc tcccgagtct ggagacaagc gaaagaagga tctcactctg    120 cccttcctg ctggtgctct tccccctcga aagagagcta agacagagaa cgaaaaggag    180
cagagacgca tcgagcggat catgcgaaac cggcaggcgg cacatgcgtc tcgagagaag    240
aagcgacgac atttggagga cctggagaag aagtgctcgg agttgtcgtc cgaaaacaac    300
gatctacacc accaggtgac tgagtccaag aagaccaaca tgcacctcat ggaacaacac    360
tactcgctgg tggccaagct gcagcagctc tcgtcgctcg tcaacatggc caagtcttcc    420
ggagctttgg ccggcgttga tgtccccgac atgagcgatg tgtctatggc ccccaagttg    480
gagatgccca ccgcggctcc ttcccagccc atgggtctcg ccagcgcgcc caccctcttc    540
aaccacgata atgagaccgt cgtccccgac tctcctattg tgaagaccga ggaagtcgac    600
tctacaaact ttctcctcca cacggagtcc tcctcccccc ccgaactagc tgagagcact    660
ggctcaggct cgccatcgtc gactctgtcc tgcgacgaaa ctgattatct tgtggaccgg    720
gcgcgtcatc cagcagtgat gactgtcgca actactgacc agcagcgtcg gcacaagatt    780
tcattttcat caaggacgag cccgttgacg acgagcttgg actgcatgga ctgtcggatg    840
acttcaccct gtttgaagac aacaagcagc ctgcccagca cgactttatt gctgatctag    900
```

<210> SEQ ID NO 62
<211> LENGTH: 299
<212> TYPE: PRT
<213> ORGANISM: Yarrowia lipolytica

<400> SEQUENCE: 62

Met Ser Ile Lys Arg Glu Glu Ser Phe Thr Pro Thr Pro Glu Asp Leu
1               5                   10                  15

Gly Ser Pro Leu Thr Ala Asp Ser Pro Gly Ser Pro Glu Ser Gly Asp
            20                  25                  30

Lys Arg Lys Lys Asp Leu Thr Leu Pro Leu Pro Ala Gly Ala Leu Pro
        35                  40                  45

Pro Arg Lys Arg Ala Lys Thr Glu Asn Glu Lys Glu Gln Arg Arg Ile
50                  55                  60

Glu Arg Ile Met Arg Asn Arg Gln Ala Ala His Ala Ser Arg Glu Lys
65                  70                  75                  80

Lys Arg Arg His Leu Glu Asp Leu Glu Lys Lys Cys Ser Glu Leu Ser
                85                  90                  95

Ser Glu Asn Asn Asp Leu His His Gln Val Thr Glu Ser Lys Lys Thr
            100                 105                 110

Asn Met His Leu Met Glu Gln His Tyr Ser Leu Val Ala Lys Leu Gln
        115                 120                 125

Gln Leu Ser Ser Leu Val Asn Met Ala Lys Ser Ser Gly Ala Leu Ala
130                 135                 140

Gly Val Asp Val Pro Asp Met Ser Asp Val Ser Met Ala Pro Lys Leu
145                 150                 155                 160

Glu Met Pro Thr Ala Ala Pro Ser Gln Pro Met Gly Leu Ala Ser Ala
                165                 170                 175

Pro Thr Leu Phe Asn His Asp Asn Glu Thr Val Val Pro Asp Ser Pro
            180                 185                 190

Ile Val Lys Thr Glu Glu Val Asp Ser Thr Asn Phe Leu Leu His Thr
        195                 200                 205

Glu Ser Ser Ser Pro Pro Glu Leu Ala Glu Ser Thr Gly Ser Gly Ser
210                 215                 220

Pro Ser Ser Thr Leu Ser Cys Asp Glu Thr Asp Tyr Leu Val Asp Arg
225                 230                 235                 240

Ala Arg His Pro Ala Val Met Thr Val Ala Thr Thr Asp Gln Gln Arg
                245                 250                 255

Arg His Lys Ile Ser Phe Ser Ser Arg Thr Ser Pro Leu Thr Thr Ser
            260                 265                 270

Leu Asp Cys Met Asp Cys Arg Met Thr Ser Pro Cys Leu Lys Thr Thr
        275                 280                 285

Ser Ser Leu Pro Ser Thr Thr Leu Leu Leu Ile
290                 295

<210> SEQ ID NO 63
<211> LENGTH: 738
<212> TYPE: DNA
<213> ORGANISM: Yarrowia lipolytica

<400> SEQUENCE: 63
atgcgccaaa agctgccgtt caacccgctc cagtcgcttc tcccgcgaat ctttgtgcgg    60
ggcaaaaaac acgatgcgcg cagccgctgg gaaatgcgcc agatgaaaga caagcatgtg   120
gccatggcca aggctgacgg attccggtct cgagccgcgt acaagctaca ggaactcgac   180

-continued

```
tccatgttcc ggctgttcaa gcccggcatg acggtggtgg atttgggctt tgcgcccggc    240
gcatggagtc aagtggctgc tcagcgagtg cggcctggag gcagagttat tggagtggat    300
atccttcctt gcattcctcc tccaggagtg tccagcatcc agggaaattt cctgtccaaa    360
gaaacacaaa acgagctcaa acgtgtgctg gccgtctcgg cgatgggagt tcccaaggac    420
aaggactctg gtggcgccat aggcactgct cctccgtctt atctggacac tgaacgcgag    480
cttggcagta ttaacagcaa cagcaacgaa ccccaatttg gcgacgacta cccggtagat    540
atagtgctta gtgacatgtg cgaaacgtta ccccaggaac acggattttt tcaaagaact    600
attaatgacc catactatag gatggccaat gtttccggca tagctgtgag ggaccatgct    660
gccagtattg tgagtgaagg aaggaagcgc attgggtgtg tgcagccag cttcgatgtg    720 gcagaaggga agccataa                                                 738
```

<210> SEQ ID NO 64
<211> LENGTH: 245
<212> TYPE: PRT
<213> ORGANISM: Yarrowia lipolytica

<400> SEQUENCE: 64

```
Met Arg Gln Lys Leu Pro Phe Asn Pro Leu Gln Ser Leu Leu Pro Arg
 1               5                  10                  15

Ile Phe Val Arg Gly Lys Lys His Asp Ala Arg Ser Arg Trp Glu Met
                20                  25                  30

Arg Gln Met Lys Asp Lys His Val Ala Met Ala Lys Ala Asp Gly Phe
            35                  40                  45

Arg Ser Arg Ala Ala Tyr Lys Leu Gln Glu Leu Asp Ser Met Phe Arg
        50                  55                  60

Leu Phe Lys Pro Gly Met Thr Val Val Asp Leu Gly Phe Ala Pro Gly
 65                  70                  75                  80

Ala Trp Ser Gln Val Ala Ala Gln Arg Val Arg Pro Gly Arg Val
                85                  90                  95

Ile Gly Val Asp Ile Leu Pro Cys Ile Pro Pro Gly Val Ser Ser
            100                 105                 110

Ile Gln Gly Asn Phe Leu Ser Lys Glu Thr Gln Asn Glu Leu Lys Arg
        115                 120                 125

Val Leu Ala Val Ser Ala Met Gly Val Pro Lys Asp Lys Asp Ser Gly
    130                 135                 140

Gly Ala Ile Gly Thr Ala Pro Pro Ser Tyr Leu Asp Thr Glu Arg Glu
145                 150                 155                 160

Leu Gly Ser Ile Asn Ser Asn Ser Asn Glu Pro Gln Phe Gly Asp Asp
                165                 170                 175

Tyr Pro Val Asp Ile Val Leu Ser Asp Met Cys Glu Thr Leu Pro Gln
            180                 185                 190

Glu His Gly Phe Phe Gln Arg Thr Ile Asn Asp Pro Tyr Tyr Arg Met
        195                 200                 205

Ala Asn Val Ser Gly Ile Ala Val Arg Asp His Ala Ala Ser Ile Val
    210                 215                 220

Ser Glu Gly Arg Lys Arg Ile Gly Cys Gly Ala Ala Ser Phe Asp Val
225                 230                 235                 240

Ala Glu Gly Lys Pro
                245
```

<210> SEQ ID NO 65
<211> LENGTH: 1590

<212> TYPE: DNA
<213> ORGANISM: Yarrowia lipolytica

<400> SEQUENCE: 65

```
atgttttaca ccaagcccga cccggtggtt gattattccc gcctcaagga catggacatg      60
tatcctgagt acgacaatgg ccagaacatg ggcttttcca acatgaacat gaccgatctt     120
tacgacggcg gtcttaacat gtcgtcgatg gcgcaacccg tggcgttgaa ccagatgggc     180
agcatgggcc ccatgggctc tttaagtaac atgcccatgg gttttgtgtc ccagaaccag     240
cctcaaactc aggctcaggc ccaggcccag agccagaacc agaatcagaa ccagaaccag     300
aaccagaacc agcctcagaa tcacaacacc catgttatga gcgataacca caaccatacc     360
cacaccaaca atactcacaa caccaacgtc acccacaaca ccccctccat gggtggtcac     420
acaacctctg tcgggggcca cgacaccaat gactcggccc atgttggggg tcacgccagc     480
aatgtcacat ccccgacccc ggcaaccccct gcctccacat cttccgtacc cgcaacctcg     540
cctcagattc ccttcaccgt cgcgccaccc gcaccgtcag gcaaatatgt gaccgatgac     600
gagcgatggc aggcactggt cgaccgagac cccgaggctg acggcgcctt catctactgc     660
gtcaccagca ccaaggtgta ctgccggccc acgtgctcgg cccggctcgc gctgcggtcc     720
aacattgtgt atttttgacac catgaaggag gctgtggccg ccggctaccg ccctgccga      780
cggtgcaacc ccgacgtgag cgagatgaac tcgcagcgac gcgccgtggg ctccgtgtgt     840
aacctcatcc actcgctgga gcccgacaag gtgccacgtg tcaagaagct agccgagtcc     900
gtcggcctca cgctctggca cttttcaccgt ctcttcaagc ggtacacggg cctcacgcct     960
cgacagtaca tcactgagtt ccacaagcga aagcgccttg ggctgccgca gttgcaagtc    1020
agcaaggtgg taaccaagaa gagctatgag cgacagcagc gtcgccaggg cagcaacggt    1080
tccacgcccc agcagtctcc ccaagtcggc gcctcttcgc cagccggcga ggtggaggcc    1140
atcaagctcg agaccccgt cgaaaccgtc cagccgctat actacgacag caacggcgtg    1200
actcacaacg ctgccaacgt cggggctcac agctccaatg tcactcacaa cactagccat    1260
gtcggaagca acgcaacctc cgccacgagc tccattgcca ctcctctttc caacacaacg    1320
tcacccgaca cctcgacgcc ggcccaggac tcggcataca tcattgccca cggttccaac    1380
gccagcaacg ccgctcctgt ggttgctccg gggcctgcca ccggctctgg cgacaactgg    1440
atcaagacgg agccctcgat ggattttatg cctcggtacg agccgcggta cgaccagtct    1500
atctccattg acgcccccat gtttattcct gatggtaacg agtatcatca aacgggggag    1560
atgttgggtg acatgtgggg gactctctaa                                      1590
```

<210> SEQ ID NO 66
<211> LENGTH: 529
<212> TYPE: PRT
<213> ORGANISM: Yarrowia lipolytica

<400> SEQUENCE: 66

```
Met Phe Tyr Thr Lys Pro Asp Pro Val Val Asp Tyr Ser Arg Leu Lys
  1               5                  10                  15

Asp Met Asp Met Tyr Pro Glu Tyr Asp Asn Gly Gln Asn Met Gly Phe
             20                  25                  30

Ser Asn Met Asn Met Thr Asp Leu Tyr Asp Gly Gly Leu Asn Met Ser
         35                  40                  45

Ser Met Ala Gln Pro Val Ala Leu Asn Gln Met Gly Ser Met Gly Pro
     50                  55                  60
```

```
Met Gly Ser Leu Ser Asn Met Pro Met Gly Phe Val Ser Gln Asn Gln
 65                  70                  75                  80

Pro Gln Thr Gln Ala Gln Ala Gln Ser Gln Asn Gln Asn Gln
                 85                  90                  95

Asn Gln Asn Gln Asn Gln Asn Gln Pro Gln Asn His Asn Thr His Val
                100                 105                 110

Met Ser Asp Asn His Asn His Thr His Thr Asn Asn Thr His Asn Thr
            115                 120                 125

Asn Val Thr His Asn Thr Pro Ser Met Gly Gly His Thr Thr Ser Val
        130                 135                 140

Gly Gly His Asp Thr Asn Asp Ser Ala His Val Gly Gly His Ala Ser
145                 150                 155                 160

Asn Val Thr Ser Pro Thr Pro Ala Thr Pro Ala Ser Thr Ser Ser Val
                165                 170                 175

Pro Ala Thr Ser Pro Gln Ile Pro Phe Thr Val Ala Pro Pro Ala Pro
                180                 185                 190

Ser Gly Lys Tyr Val Thr Asp Asp Glu Arg Trp Gln Ala Leu Val Asp
            195                 200                 205

Arg Asp Pro Glu Ala Asp Gly Ala Phe Ile Tyr Cys Val Thr Ser Thr
210                 215                 220

Lys Val Tyr Cys Arg Pro Thr Cys Ser Ala Arg Leu Ala Leu Arg Ser
225                 230                 235                 240

Asn Ile Val Tyr Phe Asp Thr Met Lys Glu Ala Val Ala Ala Gly Tyr
                245                 250                 255

Arg Pro Cys Arg Arg Cys Asn Pro Asp Val Ser Glu Met Asn Ser Gln
            260                 265                 270

Arg Arg Ala Val Gly Ser Val Cys Asn Leu Ile His Ser Leu Glu Pro
        275                 280                 285

Asp Lys Val Pro Arg Val Lys Lys Leu Ala Glu Ser Val Gly Leu Thr
        290                 295                 300

Leu Trp His Phe His Arg Leu Phe Lys Arg Tyr Thr Gly Leu Thr Pro
305                 310                 315                 320

Arg Gln Tyr Ile Thr Glu Phe His Lys Arg Lys Arg Leu Gly Leu Pro
                325                 330                 335

Gln Leu Gln Val Ser Lys Val Val Thr Lys Lys Ser Tyr Glu Arg Gln
            340                 345                 350

Gln Arg Arg Gln Gly Ser Asn Gly Ser Thr Pro Gln Gln Ser Pro Gln
        355                 360                 365

Val Gly Ala Ser Ser Pro Ala Gly Glu Val Glu Ala Ile Lys Leu Glu
        370                 375                 380

Thr Pro Val Glu Thr Val Gln Pro Leu Tyr Tyr Asp Ser Asn Gly Val
385                 390                 395                 400

Thr His Asn Ala Ala Asn Val Gly Ala His Ser Ser Asn Val Thr His
                405                 410                 415

Asn Thr Ser His Val Gly Ser Asn Ala Thr Ser Ala Thr Ser Ser Ile
                420                 425                 430

Ala Thr Pro Leu Ser Asn Thr Thr Ser Pro Asp Thr Ser Thr Pro Ala
            435                 440                 445

Gln Asp Ser Ala Tyr Ile Ile Ala His Gly Ser Asn Ala Ser Asn Ala
        450                 455                 460

Ala Pro Val Val Ala Pro Gly Pro Ala Thr Gly Ser Gly Asp Asn Trp
465                 470                 475                 480

Ile Lys Thr Glu Pro Ser Met Asp Phe Met Pro Arg Tyr Glu Pro Arg
```

```
                485                 490                 495
Tyr Asp Gln Ser Ile Ser Ile Asp Ala Pro Met Phe Ile Pro Asp Gly
            500                 505                 510
Asn Glu Tyr His His Asn Gly Glu Met Leu Gly Asp Met Trp Gly Thr
            515                 520                 525
Leu

<210> SEQ ID NO 67
<211> LENGTH: 1709
<212> TYPE: DNA
<213> ORGANISM: Yarrowia lipolytica

<400> SEQUENCE: 67
atgatttctg ctattcgtcc cgccgttcga tcttccgttc gtgttgcccc tatggccaac    60
accgccttcc gggcctactc tacccaggat gtgagtattt cttttctttc atcaattggt   120
tgctgtgcga cggatttcgt tgcgtcagcc tgattgcaac agccttaggc cccattttcg   180
acctgttctt gcctcggcaa aagttttttcc gaatgcatgt gacacgtcga atgtggtgct   240
ttcaagcagc agcagcagca taaaatatgg aatgtgttgt gtgcagaagt cgacattaca   300
taaccccgcg gcaaccatac gagatggcag tcataacaat tgcaattgag caatacaaac   360
cacactgcaa cccactaaaa agaaacacga ctaacaaata gggtcttaag gagcgattcg   420
ccgagctcat ccccgagaac gtcgagaaga tcaagaagct ccgaaggag aagggtaaca   480 ccgtcatcgg cgaggtcatc ctcgaccagg cttacggtgg tatgcgaggt attaagggtc   540
tcgtctggga gggatccgtc ctcgaccccg aggagggtat ccgattccga ggtctgacta   600
tccccgacct ccagaagcag ctcccccacg ccctggcgg aaaggagcct ctccccgagg   660
gtcttttctg gctcctgctc accggcgaga tccccactga tgctcaggtc aagggtctgt   720
ccgctgactg ggcctctcga gccgagatcc ccaagcatgt tgaggagctc atcgaccgat   780 gccccccac cctccacccc atggctcagc tcggtattgc cgtcaacgct ctggagtccg   840
agtctcagtt caccaaggct tacgagaagg gtgttaacaa gaaggagtac tggcagtaca   900
cctacgagga ttcatgaac ctcattgcca agctccccgt cattgcttct cgaatctacc   960 gaaaccttt caaggacgga aagattgttg ctccattga caactctctt gactactctg  1020
ctaacttcgc ctctctgctc ggctttggcg acaacaagga gttcattgag cttctgcgac  1080
tctacctcac catccacgct gaccacgagg gaggtaacgt ctctgcccac accaccaagc  1140
ttgttggttc tgctctctcc tctcccttcc tctctctgtc cgctggtctc aacggtcttg  1200
ccggtcctct ccacggccga gctaaccagg aggtccttga gtggattctc gagatgaagt  1260
ccaagattgg ctctgatgtc accaaggagg acattgagaa gtacctctgg gatacccta  1320 aggccggtcg agtcgtcccc ggttacggac acgccgttct ccgaaagacc gatcctcgat  1380
acaccgccca gcgagagttc gccctcgagc acatgcccga ctacgacctc ttccacctcg  1440
tttccaccat ctacgaggtt gccccaagg ttctcaccga gcacggcaag accaagaacc  1500
cctggcccaa tgtggactcc cactccggtg tcctcctcca gtactacggt ctcactgagc  1560
agtcttacta cactgttctc ttcggtgttt cccgagctat cggtgtcctg ccccagctca  1620
tcatggaccg agcttacggt gctcccatcg agcgacccaa gtccttctct accgagaagt  1680
acgctgagct cgttggcctc aagctctaa                                   1709

<210> SEQ ID NO 68
<211> LENGTH: 465
```

<212> TYPE: PRT
<213> ORGANISM: Yarrowia lipolytica

<400> SEQUENCE: 68

```
Met Ile Ser Ala Ile Arg Pro Ala Val Arg Ser Ser Val Arg Val Ala
1               5                   10                  15

Pro Met Ala Asn Thr Ala Phe Arg Ala Tyr Ser Thr Gln Asp Gly Leu
            20                  25                  30

Lys Glu Arg Phe Ala Glu Leu Ile Pro Glu Asn Val Glu Lys Ile Lys
        35                  40                  45

Lys Leu Arg Lys Glu Lys Gly Asn Thr Val Ile Gly Glu Val Ile Leu
    50                  55                  60

Asp Gln Ala Tyr Gly Gly Met Arg Gly Ile Lys Gly Leu Val Trp Glu
65                  70                  75                  80

Gly Ser Val Leu Asp Pro Glu Glu Gly Ile Arg Phe Arg Gly Leu Thr
                85                  90                  95

Ile Pro Asp Leu Gln Lys Gln Leu Pro His Ala Pro Gly Gly Lys Glu
            100                 105                 110

Pro Leu Pro Glu Gly Leu Phe Trp Leu Leu Leu Thr Gly Glu Ile Pro
        115                 120                 125

Thr Asp Ala Gln Val Lys Gly Leu Ser Ala Asp Trp Ala Ser Arg Ala
130                 135                 140

Glu Ile Pro Lys His Val Glu Glu Leu Ile Asp Arg Cys Pro Pro Thr
145                 150                 155                 160

Leu His Pro Met Ala Gln Leu Gly Ile Ala Val Asn Ala Leu Glu Ser
                165                 170                 175

Glu Ser Gln Phe Thr Lys Ala Tyr Glu Lys Gly Val Asn Lys Lys Glu
            180                 185                 190

Tyr Trp Gln Tyr Thr Tyr Glu Asp Ser Met Asn Leu Ile Ala Lys Leu
        195                 200                 205

Pro Val Ile Ala Ser Arg Ile Tyr Arg Asn Leu Phe Lys Asp Gly Lys
    210                 215                 220

Ile Val Gly Ser Ile Asp Asn Ser Leu Asp Tyr Ser Ala Asn Phe Ala
225                 230                 235                 240

Ser Leu Leu Gly Phe Gly Asp Asn Lys Glu Phe Ile Glu Leu Leu Arg
                245                 250                 255

Leu Tyr Leu Thr Ile His Ala Asp His Glu Gly Gly Asn Val Ser Ala
            260                 265                 270

His Thr Thr Lys Leu Val Gly Ser Ala Leu Ser Ser Pro Phe Leu Ser
        275                 280                 285

Leu Ser Ala Gly Leu Asn Gly Leu Ala Gly Pro Leu His Gly Arg Ala
    290                 295                 300

Asn Gln Glu Val Leu Glu Trp Ile Leu Glu Met Lys Ser Lys Ile Gly
305                 310                 315                 320

Ser Asp Val Thr Lys Glu Asp Ile Glu Lys Tyr Leu Trp Asp Thr Leu
                325                 330                 335

Lys Ala Gly Arg Val Val Pro Gly Tyr Gly His Ala Val Leu Arg Lys
            340                 345                 350

Thr Asp Pro Arg Tyr Thr Ala Gln Arg Glu Phe Ala Leu Glu His Met
        355                 360                 365

Pro Asp Tyr Asp Leu Phe His Leu Val Ser Thr Ile Tyr Glu Val Ala
    370                 375                 380

Pro Lys Val Leu Thr Glu His Gly Lys Thr Lys Asn Pro Trp Pro Asn
385                 390                 395                 400
```

Val Asp Ser His Ser Gly Val Leu Leu Gln Tyr Tyr Gly Leu Thr Glu
            405                 410                 415

Gln Ser Tyr Tyr Thr Val Leu Phe Gly Val Ser Arg Ala Ile Gly Val
        420                 425                 430

Leu Pro Gln Leu Ile Met Asp Arg Ala Tyr Gly Ala Pro Ile Glu Arg
    435                 440                 445

Pro Lys Ser Phe Ser Thr Glu Lys Tyr Ala Glu Leu Val Gly Leu Lys
450                 455                 460

Leu
465

<210> SEQ ID NO 69
<211> LENGTH: 7270
<212> TYPE: DNA
<213> ORGANISM: Yarrowia lipolytica

<400> SEQUENCE: 69

| | | | | | |
|---|---|---|---|---|---|
| atgcgactgc | aattgaggac | actaacacgt | cggttttttca | ggtgagtaaa | cgacggtggc | 60 |
| cgtggccacg | acagccgagg | cgtcacgatg | ggccagacga | gcacattctc | gccgccacaa | 120 |
| cctcgccagc | acaagaaact | aacccagtat | ggcttcagga | tcttcaacgc | agatgtggc | 180 |
| tcccttggtg | accccaaca | ttcacaaagg | tctcgcctct | catttctttg | gactcaattc | 240 |
| tgtccacaca | gccaagccct | caaaagtcaa | ggagtttgtg | gcttctcacg | gaggtcatac | 300 |
| agttatcaac | aaggtgagta | tttgacgttt | agactgtata | acaggcggcc | gcagtgcaac | 360 |
| aacgaccaaa | aagggtcgaa | aaagggtcga | aacggacac | aaaagctgga | aacaagagt | 420 |
| gtaatacatt | cttacacgtc | caattgttag | acaaacacgg | ctgttcggtc | ccaaaaccac | 480 |
| cagtatcacc | tattttccac | ttgtgtctcg | gatctgatca | taatctgatc | tcaagatgaa | 540 |
| atttacgcca | ccgacatgat | attgtgattt | tcggattctc | cagaccgagc | agattccagc | 600 |
| aataccacca | cttgcccacc | ttcagcggcc | tctcggcgcg | attcgccact | ttccccaacg | 660 |
| agtgttacta | acccaggtcc | tcatcgctaa | caacggtatt | gccgcagtaa | aggagatccg | 720 |
| ttcagtacga | aaatgggcct | acgagacctt | ggcgacgag | cgagcaatct | cgttcaccgt | 780 |
| catggccacc | cccgaagatc | tcgctgccaa | cgccgactac | attagaatgg | ccgatcagta | 840 |
| cgtcgaggtg | cccggaggaa | ccaacaacaa | caactacgcc | aacgtcgagc | tgattgtcga | 900 |
| cgtggctgag | cgattcggcg | tcgatgccgt | gtgggccgga | tggggccatg | ccagtgaaaa | 960 |
| tccccctgctc | cccgagtcgc | tagcggcctc | tccccgcaag | attgtcttca | tcggccctcc | 1020 |
| cggagctgcc | atgagatctc | tgggagacaa | aatttcttct | accattgtgg | cccagcacgc | 1080 |
| aaaggtcccg | tgtatcccgt | ggtctggaac | cggagtggac | gaggttgtgg | ttgacaagag | 1140 |
| caccaacctc | gtgtccgtgt | ccgaggaggt | gtacaccaag | ggctgcacca | ccggtcccaa | 1200 |
| gcagggtctg | gagaaggcta | agcagattgg | attccccgtg | atgatcaagg | cttccgaggg | 1260 |
| aggaggagga | aagggtattc | gaaaggttga | gcgagaggag | gacttcgagg | ctgcttacca | 1320 |
| ccaggtcgag | ggagagatcc | ccggctcgcc | catcttcatt | atgcagcttg | caggcaatgc | 1380 |
| ccggcatttg | gaggtgcagc | ttctggctga | tcagtacggc | aacaatattt | cactgtttgg | 1440 |
| tcgagattgt | tcggttcagc | gacggcatca | aaagattatt | gaggaggctc | ctgtgactgt | 1500 |
| ggctggccag | cagaccttca | ctgccatgga | gaaggctgcc | gtgcgactcg | gtaagcttgt | 1560 |
| cggatatgtc | tctgcaggta | ccgttgaata | tctgtattcc | catgaggacg | acaagttcta | 1620 |
| cttcttggag | ctgaatcctc | gtcttcaggt | cgaacatcct | accaccgaga | tggtcaccgg | 1680 |

```
tgtcaacctg cccgctgccc agcttcagat cgccatgggt atcccsctcg atcgaatcaa    1740
ggacattcgt ctcttttacg gtgttaaccc tcacaccacc actccaattg atttcgactt    1800
ctcgggcgag gatgctgata agacacagcg acgtcccgtc ccccgaggtc acaccactgc    1860
ttgccgaatc acatccgagg accctggaga gggtttcaag ccctccggag gtactatgca    1920
cgagctcaac ttccgatcct cgtccaacgt gtggggttac ttctccgttg gtaaccaggg    1980
aggtatccat tcgttctcgg attcgcagtt tggtcacatc ttcgccttcg gtgagaaccg    2040
aagtgcgtct cgaaagcaca tggttgttgc tttgaaggaa ctatctattc gaggtgactt    2100
ccgaaccacc gtcgagtacc tcatcaagct gctggagaca ccggacttcg aggacaacac    2160
catcaccacc ggctggctgg atgagcttat ctccaacaag ctgactgccg agcgacccga    2220
ctcgttcctc gctgttgttt gtggtgctgc taccaaggcc catcgagctt ccgaggactc    2280
tattgccacc tacatggctt cgctagagaa gggccaggtc cctgctcgag acattctcaa    2340
gacccttttc cccgttgact tcatctacga gggccagcgg tacaagttca ccgccacccg    2400
gtcgtctgag gactcttaca cgctgttcat caacggttct cgatgcgaca ttggagttag    2460
acctcttttct gacggtggta ttctgtgtct tgtaggtggg agatcccaca atgtctactg    2520
gaaggaggag gttggagcca cgcgactgtc tgttgactcc aagacctgcc ttctcgaggt    2580
ggagaacgac cccactcagc ttcgatctcc ctctcccgt aagctggtta agttcctggt    2640
cgagaacggc gaccacgtgc gagccaacca gccctatgcc gagattgagg tcatgaagat    2700
gtacatgact ctcactgctc aggaggacgg tattgtccag ctgatgaagc agcccggttc    2760
caccatcgag gctggcgaca tcctcggtat cttggcccctt gatgatcctt ccaaggtcaa    2820
gcatgccaag ccctttgagg ccagcttcc cgagcttgga cccccactc tcagcggtaa    2880
caagcctcat cagcgatacg agcactgcca gaacgtgctc cataacattc tgcttggttt    2940
cgataaccag gtggtgatga agtccactct tcaggagatg gttggtctgc tccgaaaccc    3000
tgagcttcct tatctccagt gggctcatca ggtgtcttct ctgcacaccc gaatgagcgc    3060
caagctggat gctactcttg ctggtctcat tgacaaggcc aagcagcgag gtggcgagtt    3120
tcctgccaag cagcttctgc gagcccttga aaggaggcg agctctggcg aggtcgatgc    3180
gctcttccag caaactcttg ctcctctgtt tgaccttgct cgagagtacc aggacggtct    3240
tgctatccac gagcttcagg ttgctgcagg ccttctgcag gcctactacg actctgaggc    3300
ccggttctgc ggacccaacg tacgtgacga ggatgtcatt ctcaagcttc gagaggagaa    3360
ccgagattct cttcgaaagg ttgtgatggc ccagctgtct cattctcgag tcggagccaa    3420
gaacaacctt gtgctggccc ttctcgatga atacaaggtg gccgaccagg ctggcaccga    3480
ctctcctgcc tccaacgtgc acgttgcaaa gtacttgcga cctgtgctgc gaaagattgt    3540
ggagctggaa tctcgagctt ctgccaaggt atctctgaaa gcccgagaga ttctcatcca    3600
gtgcgctctg ccctctctaa aggagcgaac tgaccagctt gagcacattc tgcgatcttc    3660
tgtcgtcgag tctcgatacg gagaggttgg tctggagcac cgaactcccc gagccgatat    3720
tctcaaggag gttgtcgact ccaagtacat tgtctttgat gtgcttgccc agttcttttgc    3780
ccacgatgat ccctggatcg tccttgctgc cctggagctg tacatccgac gagcttgcaa    3840
ggcctactcc atcctggaca tcaactacca ccaggactcg gacctgcctc ccgtcatctc    3900
gtggcgattt agactgccta ccatgtcgtc tgctttgtac aactcagtag tgtcttctgg    3960
ctccaaaacc cccacttccc cctcggtgtc tcgagctgat tccgtctccg acttttcgta    4020
```

-continued

```
caccgttgag cgagactctg ctcccgctcg aaccggagcg attgttgccg tgcctcatct    4080
ggatgatctg gaggatgctc tgactcgtgt tctggagaac ctgcccaaac ggggcgctgg    4140
tcttgccatc tctgttggtg ctagcaacaa gagtgccgct gcttctgctc gtgacgctgc    4200
tgctgctgcc gcttcatccg ttgacactgg cctgtccaac atttgcaacg ttatgattgg    4260
tcgggttgat gagtctgatg acgacgacac tctgattgcc cgaatctccc aggtcattga    4320
ggactttaag gaggactttg aggcctgttc tctgcgacga atcaccttct ccttcggcaa    4380
ctcccgaggt acttatccca agtatttcac gttccgaggc cccgcatacg aggaggaccc    4440
cactatccga cacattgagc ctgctctggc cttccagctg gagctcgccc gtctgtccaa    4500
cttcgacatc aagcctgtcc acaccgacaa ccgaaacatc cacgtgtacg aggctactgg    4560
caagaacgct gcttccgaca gcggttctt cacccgaggt atcgtacgac ctggtcgtct    4620
tcgagagaac atccccacct cggagtatct catttccgag gctgaccggc tcatgagcga    4680
tattttggac gctctagagg tgattggaac caccaactcg gatctcaacc acattttcat    4740
caacttctca gccgtctttg ctctgaagcc cgaggaggtt gaagctgcct ttggcggttt    4800
cctggagcga tttggccgac gtctgtggcg acttcgagtc accggtgccg agatccgaat    4860
gatggtatcc gaccccgaaa ctggctctgc tttccctctg cgagcaatga tcaacaacgt    4920
ctctggttac gttgtgcagt ctgagctgta cgctgaggcc aagaacgaca agggccagtg    4980
gattttcaag tctctgggca agcccggctc catgcacatg cggtctatca acactcccta    5040
ccccaccaag gagtggctgc agcccaagcg gtacaaggcc catctgatgg gtaccaccta    5100
ctgctatgac ttccccgagc tgttccgaca gtccattgag tcggactgga agaagtatga    5160
cggcaaggct cccgacgatc tcatgacttg caacgagctg attctcgatg aggactctgg    5220
cgagctgcag gaggtgaacc gagagcccgg cgccaacaac gtcggtatgg ttgcgtggaa    5280
gtttgaggcc aagaccccg agtaccctcg aggccgatct ttcatcgtgg tggccaacga    5340
tatcaccttc cagattggtt cgtttggccc tgctgaggac cagttcttct tcaaggtgac    5400
ggagctggct cgaaagctcg gtattcctcg aatctatctg tctgccaact ctggtgctcg    5460
aatcggcatt gctgacgagc tcgttggcaa gtacaaggtt gcgtggaacg acagactgaa    5520
cccctccaag ggcttcaagt acctttactt caccccctgag tctcttgcca ccctcaagcc    5580
cgacactgtt gtcaccactg agattgagga ggagggtccc aacggcgtgg agaagcgtca    5640
tgtgatcgac tacattgtcg gagagaagga cggtctcgga gtcgagtgtc tgcggggctc    5700
tggtctcatt gcaggcgcca cttctcgagc ctacaaggat atcttcactc tcactcttgt    5760
cacctgtcga tccgttggta tcggtgctta ccttgttcgt cttggtcaac gagccatcca    5820
gattgagggc cagcccatca ttctcactgg tgcccccgcc atcaacaagc tgcttggtcg    5880
agaggtctac tcttccaact tgcagcttgg tggtactcag atcatgtaca acaacggtgt    5940
gtctcatctg actgcccgag atgatctcaa cggtgtccac aagatcatgc agtggctgtc    6000
atacatccct gcttctcgag gtcttccagt gcctgttctc cctcacaaga ccgatgtgtg    6060
ggatcgagac gtgacgttcc agcctgtccg aggcgagcag tacgatgtta gatggcttat    6120
ttctggccga actctcgagg atggtgcttt cgagtctggt ctctttgaca aggactcttt    6180
ccaggagact ctgtctggct gggccaaggg tgttgttgtt ggtcgagctc gtcttggcgg    6240
cattcccttc ggtgtcattg gtgtcgagac tgcgaccgtc gacaatacta ccctgccgaa    6300
tcccgccaac ccggactcta ttgagatgag cacctctgaa gccggccagg tttggtaccc    6360
caactcggcc ttcaagacct ctcaggccat caacgacttc aaccatggtg aggcgcttcc    6420
```

-continued

```
tctcatgatt cttgctaact ggcgaggctt ttctggtggt cagcgagaca tgtacaatga   6480
ggttctcaag tacggatctt tcattgttga tgctctggtt gactacaagc agcccatcat   6540
ggtgtacatc cctcccaccg gtgagctgcg aggtggttct tgggttgtgg ttgaccccac   6600
catcaactcg gacatgatgg agatgtacgc tgacgtcgag tctcgaggtg gtgtgctgga   6660
gcccgaggga atggtcggta tcaagtaccg acgagacaag ctactggaca ccatggctcg   6720
tctggatccc gagtactcct ctctcaagaa gcagcttgag gagtctcccg attctgagga   6780
gctcaaggtc aagctcagcg tgcgagagaa gtctctcatg cccatctacc agcagatctc   6840
cgtgcagttt gccgacttgc atgaccgagc tggccgaatg gaggccaagg gtgtcattcg   6900
tgaggctctt gtgtggaagg atgctcgtcg attcttcttc tggcgaatcc gacgacgatt   6960
agtcgaggag tacctcatta ccaagatcaa tagcattctg ccctcttgca ctcggcttga   7020
gtgtctggct cgaatcaagt cgtggaagcc tgccactctt gatcagggct ctgaccgggg   7080
tgttgccgag tggtttgacg agaactctga tgccgtctct gctcgactca gcgagctcaa   7140
gaaggacgct tctgcccagt cgtttgcttc tcaactgaga aaggaccgac agggtactct   7200
ccagggcatg aagcaggctc tcgcttctct ttctgaggct gagcgggctg agctgctcaa   7260
ggggttgtga                                                          7270
```

<210> SEQ ID NO 70
<211> LENGTH: 2266
<212> TYPE: PRT
<213> ORGANISM: Yarrowia lipolytica

<400> SEQUENCE: 70

```
Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
                20                  25                  30

His Lys Gly Leu Ala Ser His Phe Phe Gly Leu Asn Ser Val His Thr
            35                  40                  45

Ala Lys Pro Ser Lys Val Lys Glu Phe Val Ala Ser His Gly Gly His
        50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Asn Tyr Ala Asn Val Glu Leu Ile Val Asp
    130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175

Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Val Asp Lys Ser
```

```
            210                 215                 220
Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Lys Gly Ile Arg Lys
            260                 265                 270

Val Glu Arg Glu Glu Asp Phe Glu Ala Ala Tyr His Gln Val Glu Gly
                275                 280                 285

Glu Ile Pro Gly Ser Pro Ile Phe Ile Met Gln Leu Ala Gly Asn Ala
            290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg Arg His Gln Lys Ile
                325                 330                 335

Ile Glu Glu Ala Pro Val Thr Val Ala Gly Gln Gln Thr Phe Thr Ala
                340                 345                 350

Met Glu Lys Ala Ala Val Arg Leu Gly Lys Leu Val Gly Tyr Val Ser
            355                 360                 365

Ala Gly Thr Val Glu Tyr Leu Tyr Ser His Glu Asp Asp Lys Phe Tyr
            370                 375                 380

Phe Leu Glu Leu Asn Pro Arg Leu Gln Val Glu His Pro Thr Thr Glu
385                 390                 395                 400

Met Val Thr Gly Val Asn Leu Pro Ala Ala Gln Leu Gln Ile Ala Met
                405                 410                 415

Gly Ile Pro Leu Asp Arg Ile Lys Asp Ile Arg Leu Phe Tyr Gly Val
                420                 425                 430

Asn Pro His Thr Thr Pro Ile Asp Phe Asp Phe Ser Gly Glu Asp
            435                 440                 445

Ala Asp Lys Thr Gln Arg Arg Pro Val Pro Arg Gly His Thr Thr Ala
            450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Asn Val Trp Gly
                485                 490                 495

Tyr Phe Ser Val Gly Asn Gln Gly Gly Ile His Ser Phe Ser Asp Ser
                500                 505                 510

Gln Phe Gly His Ile Phe Ala Phe Gly Glu Asn Arg Ser Ala Ser Arg
            515                 520                 525

Lys His Met Val Val Ala Leu Lys Glu Leu Ser Ile Arg Gly Asp Phe
            530                 535                 540

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
            580                 585                 590

Ala Ala Thr Lys Ala His Arg Ala Ser Glu Asp Ser Ile Ala Thr Tyr
            595                 600                 605

Met Ala Ser Leu Glu Lys Gly Gln Val Pro Ala Arg Asp Ile Leu Lys
            610                 615                 620

Thr Leu Phe Pro Val Asp Phe Ile Tyr Glu Gly Gln Arg Tyr Lys Phe
625                 630                 635                 640
```

```
Thr Ala Thr Arg Ser Ser Glu Asp Ser Tyr Thr Leu Phe Ile Asn Gly
            645                 650                 655

Ser Arg Cys Asp Ile Gly Val Arg Pro Leu Ser Asp Gly Gly Ile Leu
        660                 665                 670

Cys Leu Val Gly Gly Arg Ser His Asn Val Tyr Trp Lys Glu Glu Val
        675                 680                 685

Gly Ala Thr Arg Leu Ser Val Asp Ser Lys Thr Cys Leu Leu Glu Val
        690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                725                 730                 735

Ala Glu Ile Glu Val Met Lys Met Tyr Met Thr Leu Thr Ala Gln Glu
                740                 745                 750

Asp Gly Ile Val Gln Leu Met Lys Gln Pro Gly Ser Thr Ile Glu Ala
            755                 760                 765

Gly Asp Ile Leu Gly Ile Leu Ala Leu Asp Asp Pro Ser Lys Val Lys
770                 775                 780

His Ala Lys Pro Phe Glu Gly Gln Leu Pro Leu Gly Pro Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
                820                 825                 830

Thr Leu Gln Glu Met Val Gly Leu Leu Arg Asn Pro Glu Leu Pro Tyr
            835                 840                 845

Leu Gln Trp Ala His Gln Val Ser Ser Leu His Thr Arg Met Ser Ala
            850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Thr Leu Ala Pro
                900                 905                 910

Leu Phe Asp Leu Ala Arg Glu Tyr Gln Asp Gly Leu Ala Ile His Glu
                915                 920                 925

Leu Gln Val Ala Ala Gly Leu Leu Gln Ala Tyr Tyr Asp Ser Glu Ala
            930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
            980                 985                 990

Asp Glu Tyr Lys Val Ala Asp Gln Ala Gly Thr Asp Ser Pro Ala Ser
                995                1000                1005

Asn Val His Val Ala Lys Tyr Leu Arg Pro Val Leu Arg Lys Ile
    1010                1015                1020

Val Glu Leu Glu Ser Arg Ala Ser Ala Lys Val Ser Leu Lys Ala
    1025                1030                1035

Arg Glu Ile Leu Ile Gln Cys Ala Leu Pro Ser Leu Lys Glu Arg
    1040                1045                1050
```

```
Thr Asp Gln Leu Glu His Ile Leu Arg Ser Ser Val Val Glu Ser
1055                1060                1065

Arg Tyr Gly Glu Val Gly Leu Glu His Arg Thr Pro Arg Ala Asp
1070                1075                1080

Ile Leu Lys Glu Val Val Asp Ser Lys Tyr Ile Val Phe Asp Val
1085                1090                1095

Leu Ala Gln Phe Phe Ala His Asp Asp Pro Trp Ile Val Leu Ala
1100                1105                1110

Ala Leu Glu Leu Tyr Ile Arg Arg Ala Cys Lys Ala Tyr Ser Ile
1115                1120                1125

Leu Asp Ile Asn Tyr His Gln Asp Ser Asp Leu Pro Pro Val Ile
1130                1135                1140

Ser Trp Arg Phe Arg Leu Pro Thr Met Ser Ser Ala Leu Tyr Asn
1145                1150                1155

Ser Val Val Ser Ser Gly Ser Lys Thr Pro Thr Ser Pro Ser Val
1160                1165                1170

Ser Arg Ala Asp Ser Val Ser Asp Phe Ser Tyr Thr Val Glu Arg
1175                1180                1185

Asp Ser Ala Pro Ala Arg Thr Gly Ala Ile Val Ala Val Pro His
1190                1195                1200

Leu Asp Asp Leu Glu Asp Ala Leu Thr Arg Val Leu Glu Asn Leu
1205                1210                1215

Pro Lys Arg Gly Ala Gly Leu Ala Ile Ser Val Gly Ala Ser Asn
1220                1225                1230

Lys Ser Ala Ala Ala Ser Ala Arg Asp Ala Ala Ala Ala Ala Ala
1235                1240                1245

Ser Ser Val Asp Thr Gly Leu Ser Asn Ile Cys Asn Val Met Ile
1250                1255                1260

Gly Arg Val Asp Glu Ser Asp Asp Asp Thr Leu Ile Ala Arg
1265                1270                1275

Ile Ser Gln Val Ile Glu Asp Phe Lys Glu Asp Phe Glu Ala Cys
1280                1285                1290

Ser Leu Arg Arg Ile Thr Phe Ser Phe Gly Asn Ser Arg Gly Thr
1295                1300                1305

Tyr Pro Lys Tyr Phe Thr Phe Arg Gly Pro Ala Tyr Glu Glu Asp
1310                1315                1320

Pro Thr Ile Arg His Ile Glu Pro Ala Leu Ala Phe Gln Leu Glu
1325                1330                1335

Leu Ala Arg Leu Ser Asn Phe Asp Ile Lys Pro Val His Thr Asp
1340                1345                1350

Asn Arg Asn Ile His Val Tyr Glu Ala Thr Gly Lys Asn Ala Ala
1355                1360                1365

Ser Asp Lys Arg Phe Phe Thr Arg Gly Ile Val Arg Pro Gly Arg
1370                1375                1380

Leu Arg Glu Asn Ile Pro Thr Ser Glu Tyr Leu Ile Ser Glu Ala
1385                1390                1395

Asp Arg Leu Met Ser Asp Ile Leu Asp Ala Leu Glu Val Ile Gly
1400                1405                1410

Thr Thr Asn Ser Asp Leu Asn His Ile Phe Ile Asn Phe Ser Ala
1415                1420                1425

Val Phe Ala Leu Lys Pro Glu Glu Val Glu Ala Ala Phe Gly Gly
1430                1435                1440

Phe Leu Glu Arg Phe Gly Arg Arg Leu Trp Arg Leu Arg Val Thr
```

```
            1445                1450                1455

Gly Ala Glu Ile Arg Met Met Val Ser Asp Pro Glu Thr Gly Ser
        1460                1465                1470

Ala Phe Pro Leu Arg Ala Met Ile Asn Asn Val Ser Gly Tyr Val
        1475                1480                1485

Val Gln Ser Glu Leu Tyr Ala Glu Ala Lys Asn Asp Lys Gly Gln
        1490                1495                1500

Trp Ile Phe Lys Ser Leu Gly Lys Pro Gly Ser Met His Met Arg
        1505                1510                1515

Ser Ile Asn Thr Pro Tyr Pro Thr Lys Glu Trp Leu Gln Pro Lys
        1520                1525                1530

Arg Tyr Lys Ala His Leu Met Gly Thr Thr Tyr Cys Tyr Asp Phe
        1535                1540                1545

Pro Glu Leu Phe Arg Gln Ser Ile Glu Ser Asp Trp Lys Lys Tyr
        1550                1555                1560

Asp Gly Lys Ala Pro Asp Asp Leu Met Thr Cys Asn Glu Leu Ile
        1565                1570                1575

Leu Asp Glu Asp Ser Gly Glu Leu Gln Glu Val Asn Arg Glu Pro
        1580                1585                1590

Gly Ala Asn Asn Val Gly Met Val Ala Trp Lys Phe Glu Ala Lys
        1595                1600                1605

Thr Pro Glu Tyr Pro Arg Gly Arg Ser Phe Ile Val Val Ala Asn
        1610                1615                1620

Asp Ile Thr Phe Gln Ile Gly Ser Phe Gly Pro Ala Glu Asp Gln
        1625                1630                1635

Phe Phe Phe Lys Val Thr Glu Leu Ala Arg Lys Leu Gly Ile Pro
        1640                1645                1650

Arg Ile Tyr Leu Ser Ala Asn Ser Gly Ala Arg Ile Gly Ile Ala
        1655                1660                1665

Asp Glu Leu Val Gly Lys Tyr Lys Val Ala Trp Asn Asp Glu Thr
        1670                1675                1680

Asp Pro Ser Lys Gly Phe Lys Tyr Leu Tyr Phe Thr Pro Glu Ser
        1685                1690                1695

Leu Ala Thr Leu Lys Pro Asp Thr Val Val Thr Thr Glu Ile Glu
        1700                1705                1710

Glu Glu Gly Pro Asn Gly Val Glu Lys Arg His Val Ile Asp Tyr
        1715                1720                1725

Ile Val Gly Glu Lys Asp Gly Leu Gly Val Glu Cys Leu Arg Gly
        1730                1735                1740

Ser Gly Leu Ile Ala Gly Ala Thr Ser Arg Ala Tyr Lys Asp Ile
        1745                1750                1755

Phe Thr Leu Thr Leu Val Thr Cys Arg Ser Val Gly Ile Gly Ala
        1760                1765                1770

Tyr Leu Val Arg Leu Gly Gln Arg Ala Ile Gln Ile Glu Gly Gln
        1775                1780                1785

Pro Ile Ile Leu Thr Gly Ala Pro Ala Ile Asn Lys Leu Leu Gly
        1790                1795                1800

Arg Glu Val Tyr Ser Ser Asn Leu Gln Leu Gly Gly Thr Gln Ile
        1805                1810                1815

Met Tyr Asn Asn Gly Val Ser His Leu Thr Ala Arg Asp Asp Leu
        1820                1825                1830

Asn Gly Val His Lys Ile Met Gln Trp Leu Ser Tyr Ile Pro Ala
        1835                1840                1845
```

Ser Arg Gly Leu Pro Val Pro Val Leu Pro His Lys Thr Asp Val
1850                1855                1860

Trp Asp Arg Asp Val Thr Phe Gln Pro Val Arg Gly Glu Gln Tyr
1865                1870                1875

Asp Val Arg Trp Leu Ile Ser Gly Arg Thr Leu Glu Asp Gly Ala
1880                1885                1890

Phe Glu Ser Gly Leu Phe Asp Lys Asp Ser Phe Gln Glu Thr Leu
1895                1900                1905

Ser Gly Trp Ala Lys Gly Val Val Gly Arg Ala Arg Leu Gly
1910                1915                1920

Gly Ile Pro Phe Gly Val Ile Gly Val Glu Thr Ala Thr Val Asp
1925                1930                1935

Asn Thr Thr Pro Ala Asp Pro Ala Asn Pro Asp Ser Ile Glu Met
1940                1945                1950

Ser Thr Ser Glu Ala Gly Gln Val Trp Tyr Pro Asn Ser Ala Phe
1955                1960                1965

Lys Thr Ser Gln Ala Ile Asn Asp Phe Asn His Gly Glu Ala Leu
1970                1975                1980

Pro Leu Met Ile Leu Ala Asn Trp Arg Gly Phe Ser Gly Gly Gln
1985                1990                1995

Arg Asp Met Tyr Asn Glu Val Leu Lys Tyr Gly Ser Phe Ile Val
2000                2005                2010

Asp Ala Leu Val Asp Tyr Lys Gln Pro Ile Met Val Tyr Ile Pro
2015                2020                2025

Pro Thr Gly Glu Leu Arg Gly Gly Ser Trp Val Val Val Asp Pro
2030                2035                2040

Thr Ile Asn Ser Asp Met Met Glu Met Tyr Ala Asp Val Glu Ser
2045                2050                2055

Arg Gly Gly Val Leu Glu Pro Glu Gly Met Val Gly Ile Lys Tyr
2060                2065                2070

Arg Arg Asp Lys Leu Leu Asp Thr Met Ala Arg Leu Asp Pro Glu
2075                2080                2085

Tyr Ser Ser Leu Lys Lys Gln Leu Glu Glu Ser Pro Asp Ser Glu
2090                2095                2100

Glu Leu Lys Val Lys Leu Ser Val Arg Glu Lys Ser Leu Met Pro
2105                2110                2115

Ile Tyr Gln Gln Ile Ser Val Gln Phe Ala Asp Leu His Asp Arg
2120                2125                2130

Ala Gly Arg Met Glu Ala Lys Gly Val Ile Arg Glu Ala Leu Val
2135                2140                2145

Trp Lys Asp Ala Arg Arg Phe Phe Phe Trp Arg Ile Arg Arg Arg
2150                2155                2160

Leu Val Glu Glu Tyr Leu Ile Thr Lys Ile Asn Ser Ile Leu Pro
2165                2170                2175

Ser Cys Thr Arg Leu Glu Cys Leu Ala Arg Ile Lys Ser Trp Lys
2180                2185                2190

Pro Ala Thr Leu Asp Gln Gly Ser Asp Arg Gly Val Ala Glu Trp
2195                2200                2205

Phe Asp Glu Asn Ser Asp Ala Val Ser Ala Arg Leu Ser Glu Leu
2210                2215                2220

Lys Lys Asp Ala Ser Ala Gln Ser Phe Ala Ser Gln Leu Arg Lys
2225                2230                2235

```
Asp Arg Gln Gly Thr Leu Gln Gly Met Lys Gln Ala Leu Ala Ser
    2240                2245                2250
Leu Ser Glu Ala Glu Arg Ala Glu Leu Leu Lys Gly Leu
    2255                2260                2265
```

<210> SEQ ID NO 71
<211> LENGTH: 1134
<212> TYPE: DNA
<213> ORGANISM: Yarrowia lipolytica

<400> SEQUENCE: 71

```
atgtggggaa gttcacatgc attcgctggt gaatctgatc tgacactaca actacacacc     60
aggtccaaca tgagcgacaa tacgacaatc aaaaagccga tccgacccaa accgatccgg    120
acggaacgcc tgccttacgc tggggccgca gaaatcatcc gagccaacca gaaagaccac    180
tactttgagt ccgtgcttga acagcatctc gtcacgtttc tgcagaaatg aagggagta    240
cgatttatcc accagtacaa ggaggagctg gagacggcgt ccaagtttgc atatctcggt    300
ttgtgtacgc ttgtgggctc caagactctc ggagaagagt acaccaatct catgtacact    360
atcagagacc gaacagctct accggggtg gtgagacggt tggctacgt gctttccaac     420
actctgtttc cataccgtt tgtgcgctac atgggcaagt gcgcgccaa actgatgcgc     480
gagtatcccc atctggtgga gtacgacgaa gatgagcctg tgcccagccc ggaaacatgg    540
aaggagcggg tcatcaagac gtttgtgaac aagtttgaca agttcacggc gctggagggg    600
tttaccgcga tccacttggc gattttctac gtctacggct cgtactacca gctcagtaag    660
cggatctggg gcatgcgtta tgtatttgga caccgactgg acaagaatga gcctcgaatc    720
ggttacgaga tgctcggtct gctgattttc gcccggtttg ccacgtcatt tgtgcagacg    780
ggaagagagt acctcggagc gctgctggaa agagcgtgg agaaagaggc aggggagaag    840
gaagatgaaa aggaagcggt tgtgccgaaa aagaagtcgt caattccgtt cattgaggat    900
acagaagggg agacggaaga caagatcgat ctggaggacc ctcgacagct caagttcatt    960
cctgaggcgt ccagagcgtg cactctgtgt ctgtcataca ttagtgcgcc ggcatgtacg   1020
ccatgtggac actttttctg ttgggactgt atttccgaat gggtgagaga gaagcccgag   1080
tgtcccttgt gtcggcaggg tgtgagagag cagaacttgt tgcctatcag ataa         1134
```

<210> SEQ ID NO 72
<211> LENGTH: 377
<212> TYPE: PRT
<213> ORGANISM: Yarrowia lipolytica

<400> SEQUENCE: 72

```
Met Trp Gly Ser Ser His Ala Phe Ala Gly Glu Ser Asp Leu Thr Leu
  1               5                  10                  15
Gln Leu His Thr Arg Ser Asn Met Ser Asp Asn Thr Thr Ile Lys Lys
             20                  25                  30
Pro Ile Arg Pro Lys Pro Ile Arg Thr Glu Arg Leu Pro Tyr Ala Gly
         35                  40                  45
Ala Ala Glu Ile Ile Arg Ala Asn Gln Lys Asp His Tyr Phe Glu Ser
     50                  55                  60
Val Leu Glu Gln His Leu Val Thr Phe Leu Gln Lys Trp Lys Gly Val
 65                  70                  75                  80
Arg Phe Ile His Gln Tyr Lys Glu Glu Leu Glu Thr Ala Ser Lys Phe
                 85                  90                  95
Ala Tyr Leu Gly Leu Cys Thr Leu Val Gly Ser Lys Thr Leu Gly Glu
```

```
                    100                 105                 110
Glu Tyr Thr Asn Leu Met Tyr Thr Ile Arg Asp Arg Thr Ala Leu Pro
            115                 120                 125
Gly Val Val Arg Arg Phe Gly Tyr Val Leu Ser Asn Thr Leu Phe Pro
        130                 135                 140
Tyr Leu Phe Val Arg Tyr Met Gly Lys Leu Arg Ala Lys Leu Met Arg
145                 150                 155                 160
Glu Tyr Pro His Leu Val Glu Tyr Asp Glu Asp Glu Pro Val Pro Ser
                165                 170                 175
Pro Glu Thr Trp Lys Glu Arg Val Ile Lys Thr Phe Val Asn Lys Phe
            180                 185                 190
Asp Lys Phe Thr Ala Leu Glu Gly Phe Thr Ala Ile His Leu Ala Ile
        195                 200                 205
Phe Tyr Val Tyr Gly Ser Tyr Tyr Gln Leu Ser Lys Arg Ile Trp Gly
    210                 215                 220
Met Arg Tyr Val Phe Gly His Arg Leu Asp Lys Asn Glu Pro Arg Ile
225                 230                 235                 240
Gly Tyr Glu Met Leu Gly Leu Leu Ile Phe Ala Arg Phe Ala Thr Ser
                245                 250                 255
Phe Val Gln Thr Gly Arg Glu Tyr Leu Gly Ala Leu Leu Glu Lys Ser
            260                 265                 270
Val Glu Lys Glu Ala Gly Glu Lys Glu Asp Lys Glu Ala Val Val
        275                 280                 285
Pro Lys Lys Lys Ser Ser Ile Pro Phe Ile Glu Asp Thr Glu Gly Glu
    290                 295                 300
Thr Glu Asp Lys Ile Asp Leu Glu Asp Pro Arg Gln Leu Lys Phe Ile
305                 310                 315                 320
Pro Glu Ala Ser Arg Ala Cys Thr Leu Cys Leu Ser Tyr Ile Ser Ala
                325                 330                 335
Pro Ala Cys Thr Pro Cys Gly His Phe Phe Cys Trp Asp Cys Ile Ser
            340                 345                 350
Glu Trp Val Arg Glu Lys Pro Glu Cys Pro Leu Cys Arg Gln Gly Val
        355                 360                 365
Arg Glu Gln Asn Leu Leu Pro Ile Arg
    370                 375

<210> SEQ ID NO 73
<211> LENGTH: 2364
<212> TYPE: DNA
<213> ORGANISM: Yarrowia lipolytica

<400> SEQUENCE: 73
atgaccgaca aggactggga tcttgtctac aaggtccacg ttttcggtgc ctacaaggtt      60
acccgagctg cctggcctta cttccgaaag cagaagtacg gtcgagttat ctctacctct     120
tccgctgctg gtctttacgg aaacttcggc cagaccaact actccgctgc caagctcgcc     180
ctggttggtt tcggtgagac tctcgccaag gagggtgcca agtacaacat tacttccaac     240
gtcatcgctc ctcttgctgc ttcccgaatg accgagacag tcatgcccga ggatatcctc     300
aagctcctca gcctgagta cgttgttcct ctggtcggct acctcaccca cgactctgtc     360
accgagtctt atggtattta cgaggtcggt gctggttaca tggctaaaat ccgatgggag     420
cgaggcaacg tgctgttttt caagggcgac gacactttca cccgtctgc tattctgaag     480 cgatgggatg aggtcaccct cttttgagagc cccacctacc ctaacggccc tgctgacttc     540
```

```
ttcaaatacg ctgaggagtc tgttaagcga cccgagaacc cccagggacc caccgtctcc    600
ttcaaggacc aggttgtcat tgtcactgga gccggtgctg gcattggccg agcttactct    660
cacctccttg ctaagcttgg tgccaaggtc gttgttaacg atttcggtaa ccctcagaag    720
gttgtcgatg aaattaaggc cctcggtggt atcgccgtcg ctgacaagaa caacgtcatc    780
cacggtgaga aggttgttca gaccgctatc gacgccttcg gtgctgtcca cgccgttgtc    840
aacaacgctg gtattctccg agacaagtct ttcgccaaca tggatgatga gatgtggcag    900
ctgatctttg atgtccacct caacggtact tactccgtta ccaaggccgc gtggccccac    960
ttccttaagc agaagtacgg ccgtgtcatc aacaccacct caacttctgg tatctacggt   1020
aacttcggcc aggccaacta ctctgccgcc aaggctggta tcctcggttt ctcccgagct   1080
cttgctcgag agggtgagaa gtacaacatt cttgtcaaca ccattgcccc taacgctggt   1140
actgccatga ctgcttctgt cttcactgag gagatgctcg agctcttcaa gcccgatttc   1200
atcgcaccca tcaccgtcct gcttgcttcc gatcaggctc ccgtcaccgg tgatctgttt   1260
gagactggtt ctgcttggat cggacagact cgatggcagc gagctggtgg taaggccttc   1320
aacaccaaga agggtgtcac ccccgaaatg gttcgagaca gctgggctaa gatcgtcgac   1380
ttcgatgatg gtaactccac ccatcccacc actccctccg agtctactac tcagattctt   1440
gagaacatct tcaacgtgcc tgatgaggag gttgaggaga ctgctctcgt tgctggtccc   1500
ggtggtcccg gtatcctcaa caaggagggc gaacctttcg actacactta cacttaccga   1560
gacctcattc tttacaacct tggtctcggt gccaaggcta atgagctcaa gtatgtcttc   1620
gagggtgatg atgacttcca gaccgtgccc actttcggtg ttatcccctta catgggtggc   1680
ctcatcacta ccaactatgg cgacttcgtt cctaacttca accctatgat gcttctccac   1740
ggtgagcagt accttgaaat ccgacagtgg cctattccta ccaatgctac attggagaac   1800
aaggctaagg tcatcgatgt cgttgacaag ggcaaggctg ccctccttgt cactgctacc   1860
accaccacga caaggagac tggtgaggag gtttttctaca acgagtcttc tctcttcatc   1920
cgaggctctg gtggtttcgg tggtaagtct accggtactg accgtggcgc tgccactgct   1980
gccaacaagc cccctgctcg agctcctgac ttcgttaagg agatcaagat ccaggaggac   2040
caggctgcca tttaccgact ttctggtgat acaacccctc ttcacatcga ccctgctttt   2100
gctgctgttg gtaactttga ccgaccatt ctccacggtc tctgctcttt tggtgtctcc   2160
ggtaaggctc tttacgatca gtttggtcct ttcaagaacg ctaaggtccg atttgctggt   2220
cacgtcttcc ctggtgagac cctgaaggtt gagggctgga aggagggcaa caaggtcatt   2280
ttccagacca aggttgttga gcgaggtact accgccatca gcaatgccgc cattgagctc   2340
ttccccaagg atgctaagct ctaa                                          2364
```

<210> SEQ ID NO 74
<211> LENGTH: 787
<212> TYPE: PRT
<213> ORGANISM: Yarrowia lipolytica

<400> SEQUENCE: 74

Met Thr Asp Lys Asp Trp Asp Leu Val Tyr Lys Val His Val Phe Gly
1               5                   10                  15

Ala Tyr Lys Val Thr Arg Ala Ala Trp Pro Tyr Phe Arg Lys Gln Lys
            20                  25                  30

Tyr Gly Arg Val Ile Ser Thr Ser Ser Ala Ala Gly Leu Tyr Gly Asn
        35                  40                  45

```
Phe Gly Gln Thr Asn Tyr Ser Ala Ala Lys Leu Ala Leu Val Gly Phe
    50                  55                  60

Gly Glu Thr Leu Ala Lys Glu Gly Ala Lys Tyr Asn Ile Thr Ser Asn
65                  70                  75                  80

Val Ile Ala Pro Leu Ala Ala Ser Arg Met Thr Glu Thr Val Met Pro
                85                  90                  95

Glu Asp Ile Leu Lys Leu Leu Lys Pro Glu Tyr Val Pro Leu Val
            100                 105                 110

Gly Tyr Leu Thr His Asp Ser Val Thr Glu Ser Tyr Gly Ile Tyr Glu
            115                 120                 125

Val Gly Ala Gly Tyr Met Ala Lys Ile Arg Trp Glu Arg Gly Asn Gly
    130                 135                 140

Ala Val Phe Lys Gly Asp Asp Thr Phe Thr Pro Ser Ala Ile Leu Lys
145                 150                 155                 160

Arg Trp Asp Glu Val Thr Ser Phe Glu Ser Pro Thr Tyr Pro Asn Gly
                165                 170                 175

Pro Ala Asp Phe Phe Lys Tyr Ala Glu Glu Ser Val Lys Arg Pro Glu
            180                 185                 190

Asn Pro Gln Gly Pro Thr Val Ser Phe Lys Asp Gln Val Val Ile Val
        195                 200                 205

Thr Gly Ala Gly Ala Gly Ile Gly Arg Ala Tyr Ser His Leu Leu Ala
    210                 215                 220

Lys Leu Gly Ala Lys Val Val Asn Asp Phe Gly Asn Pro Gln Lys
225                 230                 235                 240

Val Val Asp Glu Ile Lys Ala Leu Gly Gly Ile Ala Val Ala Asp Lys
                245                 250                 255

Asn Asn Val Ile His Gly Glu Lys Val Val Gln Thr Ala Ile Asp Ala
            260                 265                 270

Phe Gly Ala Val His Ala Val Asn Asn Ala Gly Ile Leu Arg Asp
    275                 280                 285

Lys Ser Phe Ala Asn Met Asp Asp Glu Met Trp Gln Leu Ile Phe Asp
290                 295                 300

Val His Leu Asn Gly Thr Tyr Ser Val Thr Lys Ala Ala Trp Pro His
305                 310                 315                 320

Phe Leu Lys Gln Lys Tyr Gly Arg Val Ile Asn Thr Thr Ser Thr Ser
                325                 330                 335

Gly Ile Tyr Gly Asn Phe Gly Gln Ala Asn Tyr Ser Ala Ala Lys Ala
            340                 345                 350

Gly Ile Leu Gly Phe Ser Arg Ala Leu Ala Arg Glu Gly Glu Lys Tyr
        355                 360                 365

Asn Ile Leu Val Asn Thr Ile Ala Pro Asn Ala Gly Thr Ala Met Thr
    370                 375                 380

Ala Ser Val Phe Thr Glu Glu Met Leu Glu Leu Phe Lys Pro Asp Phe
385                 390                 395                 400

Ile Ala Pro Ile Thr Val Leu Leu Ala Ser Asp Gln Ala Pro Val Thr
                405                 410                 415

Gly Asp Leu Phe Glu Thr Gly Ser Ala Trp Ile Gly Gln Thr Arg Trp
            420                 425                 430

Gln Arg Ala Gly Gly Lys Ala Phe Asn Thr Lys Lys Gly Val Thr Pro
        435                 440                 445

Glu Met Val Arg Asp Ser Trp Ala Lys Ile Val Asp Phe Asp Asp Gly
    450                 455                 460

Asn Ser Thr His Pro Thr Thr Pro Ser Glu Ser Thr Thr Gln Ile Leu
```

Glu Asn Ile Phe Asn Val Pro Asp Glu Val Glu Thr Ala Leu
465                 470                 475                 480

Val Ala Gly Pro Gly Pro Gly Ile Leu Asn Lys Glu Gly Pro
            485                 490                 495

Phe Asp Tyr Thr Tyr Thr Tyr Arg Asp Leu Ile Leu Tyr Asn Leu Gly
                515                 520                 525

Leu Gly Ala Lys Ala Asn Glu Leu Lys Tyr Val Phe Glu Gly Asp Asp
        530                 535                 540

Asp Phe Gln Thr Val Pro Thr Phe Gly Val Ile Pro Tyr Met Gly Gly
545                 550                 555                 560

Leu Ile Thr Thr Asn Tyr Gly Asp Phe Val Pro Asn Phe Asn Pro Met
                565                 570                 575

Met Leu Leu His Gly Glu Gln Tyr Leu Glu Ile Arg Gln Trp Pro Ile
            580                 585                 590

Pro Thr Asn Ala Thr Leu Glu Asn Lys Ala Lys Val Ile Asp Val Val
            595                 600                 605

Asp Lys Gly Lys Ala Ala Leu Leu Val Thr Ala Thr Thr Thr Asn
610                 615                 620

Lys Glu Thr Gly Glu Glu Val Phe Tyr Asn Glu Ser Ser Leu Phe Ile
625                 630                 635                 640

Arg Gly Ser Gly Gly Phe Gly Gly Lys Ser Thr Gly Thr Asp Arg Gly
                645                 650                 655

Ala Ala Thr Ala Ala Asn Lys Pro Pro Ala Arg Ala Pro Asp Phe Val
        660                 665                 670

Lys Glu Ile Lys Ile Gln Glu Asp Gln Ala Ala Ile Tyr Arg Leu Ser
            675                 680                 685

Gly Asp Tyr Asn Pro Leu His Ile Asp Pro Ala Phe Ala Ala Val Gly
            690                 695                 700

Asn Phe Asp Arg Pro Ile Leu His Gly Leu Cys Ser Phe Gly Val Ser
705                 710                 715                 720

Gly Lys Ala Leu Tyr Asp Gln Phe Gly Pro Phe Lys Asn Ala Lys Val
                725                 730                 735

Arg Phe Ala Gly His Val Phe Pro Gly Glu Thr Leu Lys Val Glu Gly
            740                 745                 750

Trp Lys Glu Gly Asn Lys Val Ile Phe Gln Thr Lys Val Val Glu Arg
        755                 760                 765

Gly Thr Thr Ala Ile Ser Asn Ala Ala Ile Glu Leu Phe Pro Lys Asp
    770                 775                 780

Ala Lys Leu
785

<210> SEQ ID NO 75
<211> LENGTH: 2694
<212> TYPE: DNA
<213> ORGANISM: Yarrowia lipolytica

<400> SEQUENCE: 75
atgctggctt ctcgagtttc catcaaggct gtgagtatcg atggtgaaga agacaccga      60 caatcgccac gttgtgccac agacacagac gcgttctac acacacacac acaagagtcg    120
acgtgtggtt tagccgaggt atttcgacag ggaggaaaaa cgacaacgaa aggaccgaca    180
gataccaaag caacccaatc accacctcaa tcaatgatcc ccgcccgcgg gaatgcggaa    240
aaggcttctg cgacattaca acaaagccaa ctctgttgat tgttgtttg cgacattggc     300

| | |
|---|---|
| tttgtgccgg tcccaaaatt acctcgacca accacacggc ggcaattgaa gacaatgcaa | 360 |
| attaaatagc acatactaac ccagccccgc cttgcacgat ctctcgcgac taccactaat | 420 |
| gcctccctca acttggactc caaggtccga atgaacaact gggaggccaa caacttcctc | 480 |
| aacttcaaga agcacaccga gaacgtccag attgtcaagg agcgactcaa ccgacccctg | 540 |
| acctacgctg agaagattct ctacggccat ctcgacaagc ccatgagca ggagattgtc | 600 |
| cgaggtcagt cctacctcaa gctgcgaccc gatcgagccg cctgccagga tgccaccgcc | 660 |
| cagatggcca ttctgcagtt catgtctgcc ggtatcccca ccgtccagac ccccaccacc | 720 |
| gtccactgtg accatcttat ccaggcccag gttggtggtg agcaggatct tgctcgagcc | 780 |
| atcgacatca acaaggaggt ctacaacttc cttggcaccg cctccgccaa gtacgacatt | 840 |
| ggtttctgga aggccggatc cggtattatc accagatca ttctcgagaa ctacgccttc | 900 |
| cccggtgccc ttctcattgg ttccgactct cataccccca acgccggtgg tctcggtatg | 960 |
| ctcgccatcg gtgtcggtgg tgccgatgtc gtcgacgtca tggccggtct cccctgggag | 1020 |
| cttaaggccc ccaagattat cggtgtcaag ctgaccggta agctctctgg ctggacctcc | 1080 |
| cccaaggata ttatcctgaa ggtcgctggt atcctcaccg tcaagggtgg aaccggtgct | 1140 |
| atcgtcgagt acttcggtga tggtgtcgat aacctgtcct gcactggtat gggaaccatc | 1200 |
| tgtaacatgg gtgccgagat tggtgctacc acctccacct tccccttcaa cgagcgaatg | 1260 |
| gccgactacc ttaacgccac tggccgaaag gagattgccg actttgctcg actttacaac | 1320 |
| cacttcctct ctgccgatga gggttgtgag tacgatcagc tcatcgagat tgacctgaac | 1380 |
| acccttgagc cttacgtcaa cggtcccttc actcccgatc ttgccacccc catctccaag | 1440 |
| ctcaaggatg tcgccgtcga gaacggatgg cccccttgagg tcaaggtcgg tcttatcggc | 1500 |
| tcttgcacca actcctctta cgaggatatg gagcgatccg cctccattgc caaggacgcc | 1560 |
| atggcccacg gtcttaagtc caagtccatc tacaccgtca cccccggttc cgagcagatc | 1620 |
| cgagccacca ttgagcgaga tggtcagctc cagaccttcc tcgacttcgg tggtatcgtc | 1680 |
| cttgctaacg cttgtggccc ctgcattggt cagtgggacc gacgagacat caagaagggt | 1740 |
| gagaagaaca ccattgtctc ttcttacaac cgaaacttca ctggccgaaa cgattctaac | 1800 |
| cctgccaccc acgctttcgt cacctctccc gatctcgtca ccgctttcgc cattgctggt | 1860 |
| gacctccgat tcaaccctct cactgactcc ctgaaggatt ctgagggtaa ggagttcaag | 1920 |
| ctcaaggagc ccactggaaa gggtctgccc gaccgaggtt acgacccgg catggacacc | 1980 |
| taccaggctc ccccgccga ccgatctgcc gtcgaggttg atgtttcccc cacttccgac | 2040 |
| cgactccaga tcctcaagcc cttcaagcct tgggacggca aggacggtat tgacatgccc | 2100 |
| atcctcatca agtctcttgg taagaccacc actgaccata tctctcaggc cggtccctgg | 2160 |
| cttaagtacc gaggccatct ccagaacatc tccaacaact acatgattgg agccatcaac | 2220 |
| gctgagaacg aggaggccaa caacgtccga aaccagatca ctggcgagtg ggaggagtt | 2280 |
| cccgagactg ccattgctta ccgagacaac ggtatccgat gggttgttgt cggaggtgat | 2340 |
| aacttcggtg agggttcttc tcgagagcac gctgctcttg agccccgatt cctcggtggt | 2400 |
| ttcgccatca tcaccaagtc ttttgcccga attcacgaga ctaacctgaa gaagcagggt | 2460 |
| ctcctgcccc ttaacttcgt caacggtgct gactacgaca agatccagcc ctccgataag | 2520 |
| atctccattc ttggtcttaa ggaccttgcc ccggcaagaa acgtcaccat tgaggttacc | 2580 |
| cccaaggacg gtgccaagtg gaccaccgag gtttctcaca cctacaactc tgagcagctc | 2640 | gagtggttca agtacggctc tgccctcaac aagatggctg cctccaagaa ataa    2694

<210> SEQ ID NO 76
<211> LENGTH: 779
<212> TYPE: PRT
<213> ORGANISM: Yarrowia lipolytica

<400> SEQUENCE: 76

```
Met Leu Ala Ser Arg Val Ser Ile Lys Ala Pro Arg Leu Ala Arg Ser
1               5                   10                  15

Leu Ala Thr Thr Thr Asn Ala Ser Leu Asn Leu Asp Ser Lys Val Arg
            20                  25                  30

Met Asn Asn Trp Glu Ala Asn Asn Phe Leu Asn Phe Lys Lys His Thr
        35                  40                  45

Glu Asn Val Gln Ile Val Lys Glu Arg Leu Asn Arg Pro Leu Thr Tyr
    50                  55                  60

Ala Glu Lys Ile Leu Tyr Gly His Leu Asp Lys Pro His Glu Gln Glu
65                  70                  75                  80

Ile Val Arg Gly Gln Ser Tyr Leu Lys Leu Arg Pro Asp Arg Ala Ala
                85                  90                  95

Cys Gln Asp Ala Thr Ala Gln Met Ala Ile Leu Gln Phe Met Ser Ala
            100                 105                 110

Gly Ile Pro Thr Val Gln Thr Pro Thr Thr Val His Cys Asp His Leu
        115                 120                 125

Ile Gln Ala Gln Val Gly Gly Glu Gln Asp Leu Ala Arg Ala Ile Asp
    130                 135                 140

Ile Asn Lys Glu Val Tyr Asn Phe Leu Gly Thr Ala Ser Ala Lys Tyr
145                 150                 155                 160

Asp Ile Gly Phe Trp Lys Ala Gly Ser Gly Ile Ile His Gln Ile Ile
                165                 170                 175

Leu Glu Asn Tyr Ala Phe Pro Gly Ala Leu Leu Ile Gly Ser Asp Ser
            180                 185                 190

His Thr Pro Asn Ala Gly Gly Leu Gly Met Leu Ala Ile Gly Val Gly
        195                 200                 205

Gly Ala Asp Val Val Asp Val Met Ala Gly Leu Pro Trp Glu Leu Lys
    210                 215                 220

Ala Pro Lys Ile Ile Gly Val Lys Leu Thr Gly Lys Leu Ser Gly Trp
225                 230                 235                 240

Thr Ser Pro Lys Asp Ile Ile Leu Lys Val Ala Gly Ile Leu Thr Val
                245                 250                 255

Lys Gly Gly Thr Gly Ala Ile Val Glu Tyr Phe Gly Asp Gly Val Asp
            260                 265                 270

Asn Leu Ser Cys Thr Gly Met Gly Thr Ile Cys Asn Met Gly Ala Glu
        275                 280                 285

Ile Gly Ala Thr Thr Ser Thr Phe Pro Phe Asn Glu Arg Met Ala Asp
    290                 295                 300

Tyr Leu Asn Ala Thr Gly Arg Lys Glu Ile Ala Asp Phe Ala Arg Leu
305                 310                 315                 320

Tyr Asn His Phe Leu Ser Ala Asp Glu Gly Cys Glu Tyr Asp Gln Leu
                325                 330                 335

Ile Glu Ile Asp Leu Asn Thr Leu Glu Pro Tyr Val Asn Gly Pro Phe
            340                 345                 350

Thr Pro Asp Leu Ala Thr Pro Ile Ser Lys Leu Lys Asp Val Ala Val
        355                 360                 365
```

```
Glu Asn Gly Trp Pro Leu Glu Val Lys Val Gly Leu Ile Gly Ser Cys
    370                 375                 380

Thr Asn Ser Ser Tyr Glu Asp Met Glu Arg Ser Ala Ser Ile Ala Lys
385                 390                 395                 400

Asp Ala Met Ala His Gly Leu Lys Ser Lys Ser Ile Tyr Thr Val Thr
                405                 410                 415

Pro Gly Ser Glu Gln Ile Arg Ala Thr Ile Glu Arg Asp Gly Gln Leu
            420                 425                 430

Gln Thr Phe Leu Asp Phe Gly Ile Val Leu Ala Asn Ala Cys Gly
            435                 440                 445

Pro Cys Ile Gly Gln Trp Asp Arg Arg Asp Ile Lys Lys Gly Glu Lys
    450                 455                 460

Asn Thr Ile Val Ser Ser Tyr Asn Arg Asn Phe Thr Gly Arg Asn Asp
465                 470                 475                 480

Ser Asn Pro Ala Thr His Ala Phe Val Thr Ser Pro Asp Leu Val Thr
                485                 490                 495

Ala Phe Ala Ile Ala Gly Asp Leu Arg Phe Asn Pro Leu Thr Asp Ser
            500                 505                 510

Leu Lys Asp Ser Glu Gly Lys Glu Phe Lys Leu Lys Glu Pro Thr Gly
    515                 520                 525

Lys Gly Leu Pro Asp Arg Gly Tyr Asp Pro Gly Met Asp Thr Tyr Gln
530                 535                 540

Ala Pro Pro Ala Asp Arg Ser Ala Val Glu Val Asp Val Ser Pro Thr
545                 550                 555                 560

Ser Asp Arg Leu Gln Ile Leu Lys Pro Phe Lys Pro Trp Asp Gly Lys
                565                 570                 575

Asp Gly Ile Asp Met Pro Ile Leu Ile Lys Ser Leu Gly Lys Thr Thr
            580                 585                 590

Thr Asp His Ile Ser Gln Ala Gly Pro Trp Leu Lys Tyr Arg Gly His
    595                 600                 605

Leu Gln Asn Ile Ser Asn Asn Tyr Met Ile Gly Ala Ile Asn Ala Glu
    610                 615                 620

Asn Glu Glu Ala Asn Asn Val Arg Asn Gln Ile Thr Gly Glu Trp Gly
625                 630                 635                 640

Gly Val Pro Glu Thr Ala Ile Ala Tyr Arg Asp Asn Gly Ile Arg Trp
                645                 650                 655

Val Val Val Gly Gly Asp Asn Phe Gly Gly Ser Ser Arg Glu His
            660                 665                 670

Ala Ala Leu Glu Pro Arg Phe Leu Gly Gly Phe Ala Ile Ile Thr Lys
    675                 680                 685

Ser Phe Ala Arg Ile His Glu Thr Asn Leu Lys Lys Gln Gly Leu Leu
    690                 695                 700

Pro Leu Asn Phe Val Asn Gly Ala Asp Tyr Asp Lys Ile Gln Pro Ser
705                 710                 715                 720

Asp Lys Ile Ser Ile Leu Gly Leu Lys Asp Leu Ala Pro Gly Lys Asn
                725                 730                 735

Val Thr Ile Glu Val Thr Pro Lys Asp Gly Ala Lys Trp Thr Thr Glu
            740                 745                 750

Val Ser His Thr Tyr Asn Ser Glu Gln Leu Glu Trp Phe Lys Tyr Gly
    755                 760                 765

Ser Ala Leu Asn Lys Met Ala Ala Ser Lys Lys
    770                 775
```

<210> SEQ ID NO 77
<211> LENGTH: 1464
<212> TYPE: DNA
<213> ORGANISM: Artificial Sequence
<220> FEATURE:
<223> OTHER INFORMATION: Synthetic polynucleotide

<400> SEQUENCE: 77

| | |
|---|---|
| atggatctgg cgaaaatcac cgacggcttc gtcaagcacg agacctcgtc gtcgtcctct | 60 |
| tcttgctcca ccaccaacac agggcccacc ccagacttgt ctccagtgac gccctccaag | 120 |
| gaatgtgaga agcggccacg agaggacgac cctgaagagt cgcacgacac gagcgccggc | 180 |
| gccaacagca acaacaacgc tagcgtgtct ctcatgtcca ccccagagcc caagtcgtcg | 240 |
| tctcccccg gactgtcgca tttcgcacac ctgatgcaaa agtcggacac catgtaccga | 300 |
| cagaacctca actcggacca gtacatctac tcggacgagg agaaggagaa ccacaagact | 360 |
| tcgggcaagc cccacacccc ccaggtgcct catacgccct ccagtgtgcc gacacaacaa | 420 |
| ccccaatatg catttatttc acattccatc acctcgtacc cgtcgaacga gcctcagatt | 480 |
| gacaacgcac ggctggcgcg ccgaaaacga cgccgaacgt ctcccacgga actcgcgctg | 540 |
| ctggagcagg agtttgcccg caaccagaag cctcccaagc acattcgcgt cgacattgcc | 600 |
| cgccgagtcg acatgactga aaaggctgtg caggtgtggt tccagaacaa gcggcagagc | 660 |
| gtgcgaaaga gcatgaacaa gagcatgacc gatgacacct cttttcgccga ctcttcgttc | 720 |
| gctgaaacta cctttgacga gacagacggt aactccacat tcctgtccaa ttccaacgtc | 780 |
| agcaccagcg taagcaacaa gtcaatcact tcttccatca cagacaacaa gtcgccctg | 840 |
| gcacagtcaa ccaccgccga ctctggtgcc aacgccaacg ccaacgccaa cgccaacgcc | 900 |
| aacaacaaca ccgcatccac ttcctccaca aacgactccg aaattgcatc cgtcgccccc | 960 |
| aaaacaaacg gcagctcatt ctctgttttc gaagataccc ccgagactcc cgcgaaaaag | 1020 |
| aaacccagtg ctccgcgact gtccatgcgt ggtgggaagg ctactgttat ctacgccggc | 1080 |
| aagcccaagg gtgtcacgct gtcctcggga agacgtcttg gggtccctgc cacaccctcc | 1140 |
| tctcccgcca acaacaatct tggcctggga ggctcgcctc tggccacatc gtctcctatg | 1200 |
| acccagcgga ccgcgtcgca actgaaccag gcatctgcat cttctcccct atcggctgtt | 1260 |
| aagtccaagt cttttggaac tgccgaggaa agcctggctg cgacgctcaa gaagcggctt | 1320 |
| ccgtccatgc actacgacct gcccgtgacc aacaagacgt cgtctgtgcg ccatggcgtg | 1380 |
| agctctcccg tggtcgacgc cggcagccgt gaggccgagt gtatttccaa tctcctctct | 1440 |
| cttcgaaacg gaggacgatg gtaa | 1464 |

<210> SEQ ID NO 78
<211> LENGTH: 1548
<212> TYPE: DNA
<213> ORGANISM: Artificial Sequence
<220> FEATURE:
<223> OTHER INFORMATION: Synthetic polynucleotide

<400> SEQUENCE: 78

| | |
|---|---|
| atgttgcgag ccctgaatac cgtccagcga cttccagca cccgagccat gtccacctct | 60 |
| tccatttcgt ctctgcttaa gaaccccaat cttctgcgaa accagggcta tgtcaatggt | 120 |
| cagtgggtct cctccaagac cggagacact ttcagcgttg agaacccagc cactggcgag | 180 |
| actctgggcc aggtgcccga gttctctgtc gccgaggccg atgaggctgt ccagcacgca | 240 |
| cagactgcct tcaagacctt caaacatacc actggacgag agcgatccaa gatgctgcga | 300 |

```
aagtggtacg atctgatgca ggagaatgct ggtgatctgg ccaccctggt gactctggag    360
aacggtaagt ccctcgctga cgccaagggc gagattggct acggagcatc tttcttcgag    420
tggttctccg aggaagctcc tcgaatctac ggagacatca ttccatccgc caaccccgcc    480
aaccgaatct acacaatcaa gcagcccatc ggagtctgcg aatcatcac ccctggaac     540 ttcccctcgg ccatgatcac ccgaaaggct gctgctgctg ttgctgctgg ctgtaccatg    600
gtgatcaagc tggttccga aacctcctac tctgcccttg ctctggctta cctggctgaa     660
caggccggca tccctaaggg tgttgtcaac gtggtcacta ctaagaagaa cactcgagct    720
tttggtaacg ccctgtgcga gaaccccacc gtcaaaaagg tttctttcac gggctccact    780
ggtgtcggaa agacccttat gggcgcatcg gcctccactc ttaagaagct gtcctttgag    840
ctcggtggca acgctccctt cattgtgttt gaggacgccg atattgaccg ggctgtcgac    900
ggagctattg cgtccaagtt ccgaggcact ggccagacct gtgtctgtgc aaaccgaatt    960
tatgtgcacg agagcatcgc cgagaagttt gctgagcgaa tggcagccgt ggtcaaggac   1020
ttcaaggttg gaaacggtct cgaccctaac accacccatg ccctcttat ccacgaggga   1080 gccaagggca agatccagga gcaggttgac gatgctgtca agaagggagg aaaggtactc   1140
attggaggct ccgacgcccc tgagatcgga aaggcctttt tccagcctac cgtcatttcc   1200
ggggccaagt ctgatatgct gattgcctcc gaggagacgt ttggtcccat tgctgccatc   1260
ttccccttta gaccgacgc tgaggtcatt gagcttgcca acaaggcaga ggtcggtctg    1320
gccggctact tctactccaa ggacgtgtac cgaatccaac aggttgccga ggctctcgag   1380
gtcggaatgg tcggtgttaa caccggtctg atgacggagt gtgctctgcc ctttggcggt   1440
atcaaggagt ctggctttgg ccgagagggc tccaagtacg gcctggatga ctacatggtg   1500
ctcaagacta ttgttgtgtc tggcgtcgag ccccacattc agccttaa               1548
```

<210> SEQ ID NO 79
<211> LENGTH: 627
<212> TYPE: DNA
<213> ORGANISM: Artificial Sequence
<220> FEATURE:
<223> OTHER INFORMATION: Synthetic polynucleotide

<400> SEQUENCE: 79

```
atgtattcat tcgacttcaa ctttgacacg gcatatccgc cacagactga atattccaaa     60
caagacgact gtctgggata catgcccatc acgcctcctt acctggactg gagctcgctg    120
acattcccgc cggttgaata cgcacccatc gtcgataacg tgctcccgga agaaccctcg    180
gagccctcgg acgtgtcttc ttcttccgga gaagaaagcc cctactttt cgacgaatac    240 tgcaccattc cctctctggt cgaccagctc aagaaaaacc caacatttg gccatggca     300 aacaccgtca agaaaggagc ctacgtgtgt agccactgca ctaagcaggg caccccgtc    360 aagttcaaaa ccatggtcga ctttgccacc cacctcgact cgcattctca tgaccgaagc    420
tgcaaatgcg ccgacacaaa atgtccctgg tccattgtgg gcttctctac tcgatcggaa    480
atgcgaagac acacaaactc ggtccatcga caaacaccct tcacatgcaa aatctgtgac    540
cgcgggtttg tacgagaaga ctctctcaaa cggcatgtca aactactcca catttctccc    600
ctcaaaacca gacgaaagag tacctga                                        627
```

<210> SEQ ID NO 80
<211> LENGTH: 1683
<212> TYPE: DNA
<213> ORGANISM: Artificial Sequence

```
<220> FEATURE:
<223> OTHER INFORMATION: Synthetic polynucleotide

<400> SEQUENCE: 80
atgcaccacc acctcaaccc caaggcgctc ttttctggtg agtatggcgg acagaaatgg      60
acggaggaac gtggcagagc cgattgacca gccacgcagg ccgaccaagc cccattgagt     120
gagccattgg acgtccttgg cccgaataga cgctctctcc caggtttgcc ggaaaaacga     180
gctgttatat ccgaacgagc tgtttgtgcc caaaaaagcc cctactaacc cccaggccga     240
aaggagagca cctctcccca gacacaagcc gcgtccggct ccggagccgt gtctccaggc     300
cgacctctgg attcgtccac caacgtcgaa gatgtggatg agcttgacgg agacggccag     360
aacatcatca tgggaattat cgcgcagctg cgacccggcg ctgatctgtc tcgaatcaca     420
cttcccacct tcattctcga gcgaaagtcc atgctcgagc gaatcacaaa ctccctgcag     480
caccccacat atgtcattga ggccacgcc accaaggacc ccatgcagcg gttcatccaa      540
gtggtaaagt ggtaccactc cggctggcac atcacccca aggccgtcaa aaagcccctg      600
aaccccattc tcggcgagtt cttcacatgc tactgggact cgacgacgg ttcccacgga      660
tactacatct ccgagcagac ctcccaccac cctcccaagt catcctactt ttacatgatc     720
cctgagcaca acatccgagt cgacggtaca ctggctccca gtcccgtttt cctgggtaac     780
tcagctgctt ctctcatgga gggcgccacc attctcaagt tcctggacat tgtagatgcc     840
aagggcgctc ccgaggagta cgaaatcact tcgcccaatg cctacgcccg aggtattctc     900
tttgaacggc tcaagtacga gtactgcgac cactcgatca tcaagtgtcc cgctctggac     960
ctgactctgg acctggactt caaggccaag ggcttcattt ccggtacata caatgccttc    1020
gagggccaga tcaagaagat ctccaccggc gaggccttt acgatgttta tggaaagtgg     1080
gatgaaatca tcgagctcaa gaacctcaag accggcgaga agtcggtgct gtttgacgtg    1140
actaaggccg ccctgcaccc tcccaaggtg cgacccatcg ctgagcaggc cgccaccgag    1200
tcccgacgac tgtgggagcc cgtcaccgac gctcttgcta agcgagacca caccgttgct    1260
accgacgaaa agttcaagat tgaggacaaa cagcgaacgc tggccaagga gcgagaagag    1320
cacggcgtca agttcctgcc caaactgttc aagcccgccc ccgctcccct ggacttcatt    1380
ctgtataagg atctgcacgg cactcccgaa gagatcacca aggagattct cagcatagtc    1440
cccattctgc ccggccaaca gttcaccaag gactttgaaa tgtccggcga agaaatac      1500
aagctggaga gagcggcca ggccagcagc gagactcagc ccaccgccac gaccactgcg     1560
gctgccccc aagcaggcgc tgtccccaca accctgcta acggcagac tccctggcc        1620
aagacttctg atcttcagga ggctcttccc accgaagagg acgagttcca cgacgcccag    1680
tag                                                                  1683

<210> SEQ ID NO 81
<211> LENGTH: 5510
<212> TYPE: DNA
<213> ORGANISM: Artificial Sequence
<220> FEATURE:
<223> OTHER INFORMATION: Synthetic polynucleotide

<400> SEQUENCE: 81
atgacaagtg atgcgataaa cgccatggaa aacgacagta cgacggtggt agaggtggaa      60
acgacatttg tgaacgataa cgtggtccgt ggcttcctcg atgttgcacg tgatacgctg     120
ccagacgtcc aaggactcct tccactggtc caagtgcagc tggtggcgga tatctcaaga     180
```

```
gagatgctgg agggcgaaga agtgctggaa atcaccgatc cagagtcaca tggcgtcaaa      240
aataccgaag caggtgacga aacgaactca cgtgacccca tcgtcgcttc tgcgcctgct      300
accctggttc ctaacgagag cacattagag attcatgtca cgcccaagta caccaccaag      360
gacaagaaac gaggccgcaa aaagaccaag aaggacgaag attggttggt aacatgcttg      420
ggtgttgttc aactaggaaa cgtggaaacc agtgaccacg tgcttaccgc tttgaaacag      480
gctctttcgg tagccaaatt taacccgcga atcgagtca gtgtcttttc agtgaatcct       540
cacgtcactg ttaccaaaaa caatggtgtt tacagcattt ccatcacttt tggagtcttt      600
gcgaagcctt ttgatggcca cgtcaaccct gagatccata tggcaggtca cctcaacatt      660
gtgaatgtca tccgacagtt cctgggcgta actaagataa acagctaca taagaacgac       720 tatgtgactc ctgaatactt ctacgagtgc ctggaactca aggatgatac cgaggttgag      780
atcaacagag atcttcagcc ggaagggatg agatcaaaac ttttggatta ccagcttgaa      840
actgtggggt gggttctgga tagagaaaag ggagaatcgc gtgagaagac gatagaggga      900
attccttcac catggaaacg gttcagggct catggtatca actggttggt tgattttgtg      960
ggtctcaaca ttggtcctga aaggaggtg atggagattt tgacacgaga tacgaaacca      1020
acaactgagg accccgagat tcaagcagta tcacgtgacg cagatttaa ggctggatat      1080 ggacttattg ctgatgaaat gggtcttgga aagacagttg agctactagc tgtagtcctg      1140
aataacccca gacctgaatt tccaccgcaa acacactacg atctgtactc tgacagagac      1200
gtgttaccta ccaagacgac tctcatttta tgtcctgcca gtatcagtca acagtggatt      1260
gctgaggtta ctaaacatgc tcccagtctc tctgtctttc tgtacactgg tcgagcagct      1320
ttggatgctc aaagagagaa ggaaggtact cccgataccg atattgaggt tggaattgac      1380
tcagatactg attcagaagg ccctcttgtt tcaaaacatg cacaatttct ctctcagttc      1440
gacattgtag tcacatccta tgaagttgca tctcgcgagg ttgccaacgc tctttacaac      1500
cctctgagag tcgtgtaac tcgcaccaag acgaagctaa agtcgaaaga tacccgagat      1560
gtcgatctcg tgcaagaccg gctttccctc caatctccac tgagtcagct tcagttctgg      1620
cgtgtgattc tggacgaggt tcagatggtg ggaaacacgg tctccaacgc agctgttgta      1680
gctcgtatta ttccccgagt gcatgcatgg ggagtcagtg gtactcctat aaagaagggc      1740
atgcctgact tacttggcat gtgtgtgttt ttgagatgtg aacccggcga gttttatgga      1800
agaagtgatt gtgagtatac taaaggaaca gtcagagtgg catgtgacaa aaaaacaaaa      1860
aaccatatgg ctcaatgaag ggctacgact aacacagatg cgtataacta ctcttggcaa      1920
aacggatacc tcagcacaac tatgacagca tctggagtaa gtcatcaaaa acactgggag      1980
atgctcatgc ttgacaagcc tcggtttcga gacgttattc gtcaaatgtc tattcgacat      2040
actaagcgac aggtcagaga tcaactagta ttgcctcctc aggaaagaca ccatgtgaga      2100
ctcagattca atctagtcga ggaagaaaac taccgacacc tgcgtgaagg tgttgagagt      2160
gccgtcagtg aggcagtggc tagttctctc atgagagaag agagggaagc tacacgtgag      2220
gcagctgtgg tggataggta tggcgttctg ccttcaagtg tcactccccc tgtgagcaac      2280
agacctagag gcactttcaa catcggaggc tctaatccct atgctagtat catggcgaat      2340
atcaacaaca cagtcattga acctgaaatt gagattgatc ccagtatcac ttctagtgga      2400
gagggtgacg ccaacatgt ctacactacc tggtcgggtg ctgtagacac gtatggtggt       2460
gagtctagcg gtacagctgc tagtagcacc gatgctgacg gcgatgataa cgctcaatct      2520
cccacatctg atacagctag caacactgac atcaatgtta gtgctattcc cgatatagag      2580
```

```
gtatcccga ctgccacccc tacagcctcc accagatccc aaaatggaac ttctgctcct    2640
ccagcatctt ccgctcctgc ggatttaaca acagcaaccc tctcttcctg gctgttacgg    2700
ttacgacaaa cctgctgcca tcctcgagtc ggttctggta acaagaaggc tctcggaaac    2760
ggtattcttc aaactgtcag tcacgtgctg acgccatgt gcgaccaggc gctcacccag    2820
ctgctgaacg acgagcgaag tctgtttgtc gaagagctgg agaaggcacg agttcacgag    2880
ttcaacaaac aaccagacat tggactcaca gtgcttcagt cacgtgtttc tgaagtcgag    2940
gttcgaactg gtgagatccg agatatggct gttgctgcgg ctacgcggta tgctatgaag    3000
aagaaggagg taatttccga gtggaagcgt attggtgagg ttgataacaa gcgcaagttg    3060
gaggagagtg atgacggtgc tgctaatgtt aagaaagtca aggtcgaaaa agaggagaag    3120
gaggaagaag tggcaaagga ggaggtttcc gaagatttta aaatggaggg aactgagaac    3180
aactccattt ttggagctcc aactgctttt ctgggctctg attcggagtc tgagagcact    3240
ggtaagatgt ccaaaccatt acaaaagtac ctgaacaact ccgaggaact tcagacggag    3300
aaggagcgaa acaggctttt tctgcaccgg tacaggagct ggatggatct tatgcatcgg    3360 tactatttt tcattgctac ttttcatttc caagttggag aagcgtgagt atgacaaaga    3420
tttgtaatga cgtggtggtt ctactggggt catgagaggt catgagacat actaacacag    3480
taaaaaagtg gctgaggaga agaaagaaaa gaggatggg aaggacgatg aagaagga    3540 agatgaagag aaggaagaga ttgaggtcaa gaaagaggag gatgaaggga ccaagagtga    3600
cgagtgagta tagagatatc atgagtggca gaataacttg tgccattcgc tcctcttatg    3660
tatatgtgta ctaacacagt ctggaaacgc actattacac gctggcagaa caaatccgaa    3720
cccagctact tcaacgccct attgagagag tagaccaaga cgtgggtcga cttgaacggg    3780
ccaaggagct ggagatggtt cagatccctg ttgataccttt gactcgagat ctagtacagg    3840 cttctcctttt ccttgaggca cgtgtttcgg gtctactcga gatcatcaac caacagtccg    3900
aatatcttga agaatggatg accagagttc gagagctgtt ggttgcacgt gacgagaagg    3960
acgtgaaaga aacagataag aagaagaata aggagatgt cgagaaagtt gaaggcgaaa    4020
acactgatcc ttatgcttct ggattagaca accaacaata tgcgtcggac taccttgatg    4080
ctatatcgta cctgctgcaa ctcagagatg aagctctcaa tgccaagact acggcctcag    4140
cagccgacaa gatccaagtt aacttgtggt accacaatga ctacgaagaa gagcttaccg    4200
atcttcaggt ggccctcaag gaagctctgg acgcttgtca tgtgagtccc actcttggtg    4260
ccctcaaacc tatcgttgct gctctgaaga cggactctgg agctgtttca ttgtcaattt    4320
acaacccgaa atggcctccc aagttgctgt ccaagctcaa tccgatcgtt aagacagtta    4380
cctcgacaac caaggcttgc agagacctgt tgtcagtcgt tagaagctgt ttcaactcga    4440
aggttgtcta ttacaagcag ctgcagcaac tgtctgacaa tgtgagcagt ctggaggaac    4500
tcatcgagcc tggttatgtc acactggaac gcctgaacgc caaaataaac catctcgtac    4560
ctttaatcaa gcgtacaaag ggccgaatca catacttaca gagtctcaaa ggtgatgatg    4620
acacaactgg agtttccaac atgactggaa ttcataaaat gtgtgtcatc tgtcaggatg    4680
attatattat cgtgggatcc atcactgtct gtggccatta cttttgcaga aactgcctgg    4740
aagagtggtg gcagacacat aatacgtgtc caatgtgcaa gactgtattg tcccgcgacg    4800
atgtgttctc tttcacccaa caggacaagg aagacaagtc acgtgcaggt tctttcgctg    4860
ctcggatcaa tcaagatgac gccattggag caatgtatgc gccagtgtcg gaggacactc    4920
```

```
aacagttgat gagcaaacag agcatcaaga gtgcgtatgg cacaaagatt gaccacgtta    4980
tcaagtatat caagatgctc actcatcggg ctcctggcac tcagattgtc atcttttctc    5040
agtgggcaga gattctcaca ttgttagctt cagccctcac tgagaacaag attgcatacg    5100
cggagccgaa aacactgatg tctttcttgc aatcggaaga agtcacgtgt ttcctcttga    5160
acgcaaagtt ccagtccact ggcctgactc ttgtaaatgc cactcacgtc attctatgcg    5220
agcccattct caacgctgct cttgaggctc aggccatcag tcgaatccac cgaatgggcc    5280
agactcagac tacccacgtg actatcttca ctatggccga tactgttgaa gaagaggttc    5340
tgcgtcttgc tattaacaag cggttgaaaa gtatggacgg tgatgagacg tttgaggaga    5400
atgaatctcg acatgtgaca tcaggagtgg gtgcgctcgc caccgataaa tccggagagg    5460
tggtcaaccg tcaggatatg tgggacgctt tgtttcccag tgacgggtaa                5510
```

COMPOSITIONS AND METHODS FOR LIPID PRODUCTION

CROSS-REFERENCES TO RELATED APPLICATIONS

This application claims the benefit of U.S. Provisional Patent Application No. 61/819,476, filed May 3, 2013, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under N000141110669 awarded by Office of Naval Research. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 93331-003510US-907029_ST25.TXT, created on Apr. 29, 2014, 210,560 bytes, machine format IBM-PC, MS-Windows operating system, is hereby incorporated herein by reference in its entirety and for all purposes.

BACKGROUND

Increasing oil consumption makes continued dependence on petroleum reserves untenable. Microbial production of renewable alternatives can reduce petroleum footprints through the in vivo synthesis of ethanol, biodiesel, and industrial precursors (Curran et al. 2013; Elshahed 2010; Li et al. 2008; Xu et al. 2013; Yim et al. 2011). Economic viability is highly dependent upon microbial choice, and an ideal host efficiently generates high titers independent of fermentation condition, through native or imported biosynthetic metabolism (Alper and Stephanopoulos 2009). In this regard, Yarrowia lipolytica's genetic tractability, efficient utilization of many energy sources, and native capacity to accumulate lipids make it an ideal platform for oleo-chemical synthesis (Barth and Gaillardin 1996; Beopoulos et al. 2009a; Papanikolaou and Aggelis 2002).

Here we have employed a large-scale combinatorial approach to maximize lipid production in Y. lipolytica through both genomic engineering and combinatorial and inverse metabolic engineering multiplexed with phenotypic induction.

Y. lipolytica has a fully defined metabolic engineering toolbox that enables intracellular flux control through genomic manipulation (Blazeck et al. 2013b; Dujon et al. 2004; Fickers et al. 2003; Juretzek et al. 2001; Matsuoka et al. 1993). Y. lipolytica is commonly utilized for heterologous protein excretion and to examine and manipulate lipid and fatty acid metabolism (Beopoulos et al. 2009b; Beopoulos et al. 2008; Dulermo and Nicaud 2011; Madzak et al. 2004; Thevenieau et al. 2009), and has proven amenable to downstream manipulation of its fatty acid content to alter desaturation levels (Chuang et al. 2010) or to synthesize novel oleo-chemicals (Blazeck et al. 2013a). Thus, Y. lipolytica lipid reserves are ideal for in vivo catalysis to alkanes (Schirmer et al. 2010), fatty acid esters (Shi et al. 2012) or for standard transesterification-based conversion and use as biodiesel. In particular, biodiesel production grants a high net energy gain compared to other alternative fuels with minimal environmental impact, and harvesting lipid reserves from a microbial source such as Y. lipolytica enables easily scaled-up production without compromising food supply (Christophe et al. 2012; Hill et al. 2006; Kirstine and Galbally 2012; Subramaniam et al. 2010). Y. lipolytica's natural lipid content consists of predominantly C16:0, C16:1, C18:0, C18:1, and C18:2 fatty acids (Beopoulos et al. 2008; Blazeck et al. 2013a; Tai and Stephanopoulos 2013), very similar to the fatty acid content of biodiesel derived from soybeans and rapeseed (Gruzdiene and Anelauskaite 2011; Hammond et al. 2005). Economic viability can be greatly improved by fully utilizing all sugars from lignocellulosic biomass or by using carbon from industrial waste streams. In this regard, Y. lipolytica can efficient utilize hydrophobic and waste carbon sources, such as crude glycerol (Andre et al. 2009; Fickers et al. 2005; Makri et al. 2010; Rywinska et al. 2013), and has shown excellent heterologous gene expression when utilizing glucose, sucrose, glycerol, or oleic acid as a carbon source (Blazeck et al. 2013b). Finally, Y. lipolytica is regarded as a "safe-to-use" organism (Groenewald et al. 2013).

Lipid accumulation in Y. lipolytica can be induced by nitrogen starvation and has been associated with the activity of four enzymes: AMP Deaminase (AMPDp), ATP-Citrate Lyase (ACLp), Malic Enzyme (MAEp) and Acetyl-CoA Carboxylase (ACCp) (Beopoulos et al. 2009a; Dulermo and Nicaud 2011). AMPDp cleaves AMP into $NH_4^+$ and inosine 5'-monophosphate to replenish intracellular nitrogen levels; AMP deficiency inhibits the citric acid cycle resulting in citric acid accumulation. ACLp cleaves citric acid into oxaloacetate and acetyl-CoA, and ACCp carboxylates acetyl-CoA into malonyl-CoA fatty acid building blocks. Fatty acid synthesis is further encouraged by a MEAp-mediated increase in NADPH levels (Beopoulos et al. 2009a). Fatty acids can be directly stored in intracellular lipid bodies or further incorporated in triacylglycerides before storage (Beopoulos et al. 2008). Triacylglyceride synthesis follows the Kennedy Pathway to fuse three fatty acids to a glycerol-3-phosphate (G3P) backbone (Kennedy 1961). The ultimate step is catalyzed by the DGA1 or DGA2 acyl-CoA:diacylglycerol acyltransferases (Beopoulos et al. 2009a; Beopoulos et al. 2012). G3P backbone is synthesized from dihydroxyacetone phosphate (DHAP) by the cytosolic, $NAD^+$-dependent glycerol-3-phosphate dehydrogenase (GPD1) and recycled into glycolysis by the mitochondrial, $FAD^+$-dependent glycerol-3-phosphate dehydrogenase isoform (GUT2) (Dulermo and Nicaud 2011). TAG hydrolysis mobilizes free fatty acids for peroxisomal degradation through the four step β-oxidation cycle (Beopoulos et al. 2011)—oxidation by one of six acyl-CoA oxidases (POX1-6), hydration and dehydrogenation by the multifunctional enzyme (MFE1), and thiolysis by a 3-ketoacyl-CoA-thiolase (POT1 or PAT1) (Beopoulos et al. 2009a). The PEX10p transcription factor has been implicated in peroxisomal biogenesis and Δpex10 mutants display increased triacylglyceride content (Blazeck et al. 2013a; Hong et al. 2012; Zhu et al. 2012).

Genomic modifications to Y. lipolytica's fatty acid, lipid, and central carbon metabolism have shown promise towards increasing lipid accumulation capacity. Deletion of the six POX genes increased ex novo incorporation of oleic acid in Y. lipolytica, while deletion of the single MFE1 gene had a similar effect (Beopoulos et al. 2008; Dulermo and Nicaud 2011). Increasing G3P backbone levels by combining GUT2p deletion and GPD1p overexpression in these β-oxidation deficient backgrounds further increased ex novo lipid accumulation to 65-75% triacylglyceride content (Dulermo and Nicaud 2011). Overexpression of DGA1p increased de novo triacylglyceride accumulation fourfold over control levels to 33.8% triacylglyceride content, and co-overexpression of ACC1p further increased triacylglyceride accumulation to a final yield of 41% triacylglyceride content (Tai and Stephanopoulos 2013). To date, no study has attempted to combine the beneficial effects of engineering *Y. lipolytica*'s fatty acid, lipid and central metabolism in a single strain. Additionally, *Y. lipolytica*'s dependence on media formulation for lipid accumulation has not been adequately explored, nor has its ability to randomly accumulate mutations that enhance lipid accumulation. Furthermore, no attempt has been made to utilize mutation-based evolutionary selection to identify novel lipogenic genotypes. Thus, the ultimate capacity of *Y. lipolytica* to accumulate lipids and other oleochemicals has not been unlocked. To this end, we have employed a large scale combinatorial approach to maximize lipid production while accounting for unexpected interactions between genotype and environmentally-induced phenotype. The present invention provides solutions to these and other problems in the art.

BRIEF SUMMARY

In a first aspect is provided a genetically modified oleaginous organism (e.g. yeast cell, oleaginous yeast cell, *Yarrowia lipolytica*, algae, or plant cell) wherein the dry weight of said yeast cell includes greater than 60% wt/wt lipids, lipid precursors, and/or oleochemicals.

In a second aspect is provided a method of producing a lipid, lipid precursor, or oleochemical (e.g., lipid, lipid precursor, oleochemical) including: 1) culturing a yeast cell as described herein (including embodiments or as described in the examples, tables, figures, and/or claims) in a growth medium; and 2) isolating the lipid, lipid precursor, or oleochemical (e.g., lipid, lipid precursor, oleochemical) (e.g. from the medium or yeast cell).

In a third aspect is provided a method of isolating a genetically modified yeast cell from a plurality of yeast cells, including greater than 60% wt/wt lipids, lipid precursors, and/or oleochemicals in dry weight, including allowing a genetically modified yeast cell to separate from a population of yeast cells within the plurality of yeast cells by floating above the population of yeast cells within an aqueous medium thereby isolating the genetically modified yeast cell, wherein the population of yeast cells includes a lower percentage wt/wt of lipids, lipid precursors, and/or oleochemicals than said genetically modified yeast cell.

BRIEF DESCRIPTION OF THE DRAWINGS

FIG. 21. List of consensus mutations in strain E26 and E13 identified in open reading frame through next generation sequencing analysis. Among them, YLOSH6; YLIRC20; YLRME1; YLYOX1; YLUGA2 contains missense mutations in annotated protein.

DETAILED DESCRIPTION

Figure 1:
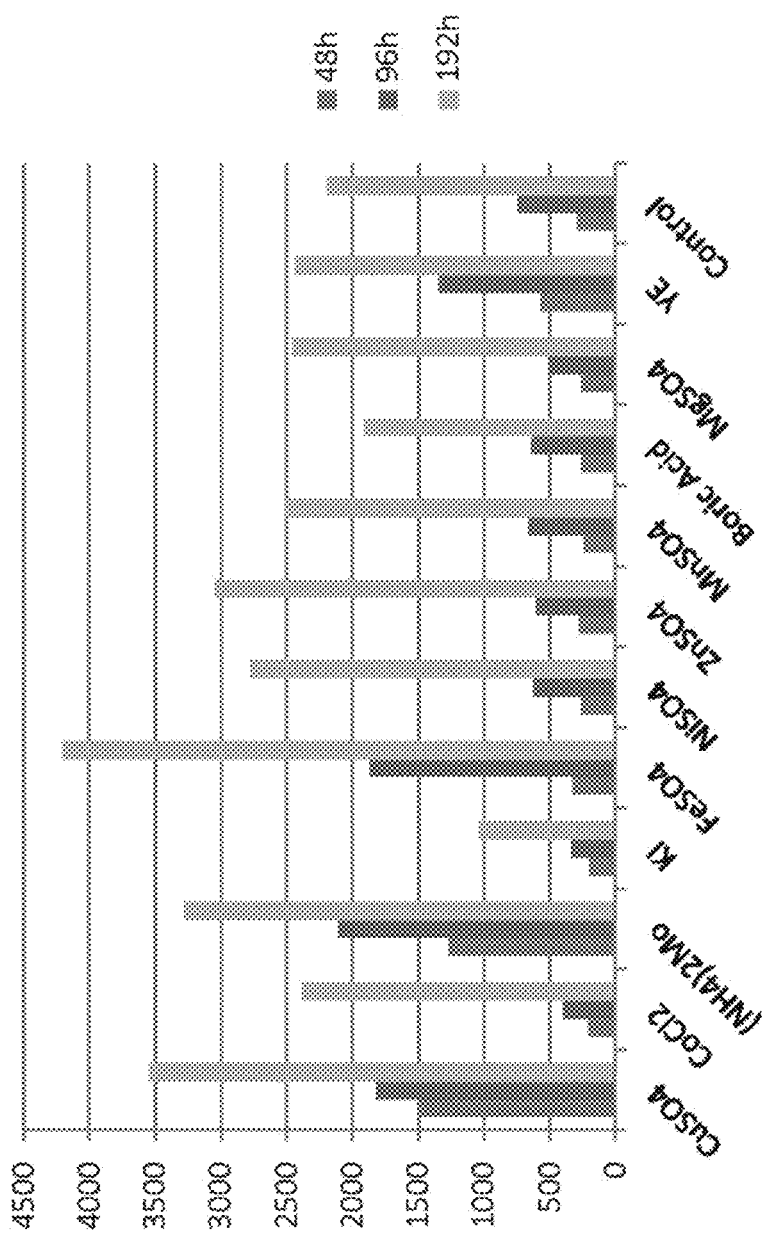
FIG. 1. Nile Red assay quantifying lipid content of PO1f WT strain in C160N0.2 media supplemented with individual micronutrients after 2, 4, and 8 days of cultivation.

Our work described herein represents the largest scale engineering effort in an oleaginous organism to date. We analyzed the effect of nitrogen starvation and carbon level on a wildtype *Y. lipolytica* strain and a strain with two genomic modifications to increase lipid (e.g. triacylglyceride) accumulation. By testing twenty media formulations containing between 10 g/L and 320 g/L glucose and 0.04 g/L and 10 g/L ammonium sulfate, we demonstrated that increasing carbon to nitrogen ratio (C:N ratio) generally induces lipid (e.g. triacylglyceride) accumulation, that carbon level is more important than nitrogen level towards this induction, and that this optimum carbon level is dependent upon genomic background. We further determined that lipid (e.g. triacylglyceride) accumulation could be increased through the addition of certain metallic cofactors in the wildtype background as well as for some *Y. lipolytica* strains already engineered for increased lipid (e.g. triacylglyceride) content. In an effort to rationally engineer *Y. lipolytica* for increased lipid (e.g. triacylglyceride) accumulation while accounting for unpredictable cumulative effects arising from simultaneously altering fatty acid, lipid, and central carbon metabolism, we overexpressed multiple (e.g. five) enzymes implicated in lipid (e.g. triacylglyceride) accumulation in multiple (e.g. four) background strains differentially deficient in fatty acid degradation. These native enzymatic overexpressions were driven by high-strength constitutive promoters, occurred singly or in tandem with a second enzyme overexpression, and alleviated one of two auxotrophies (leucine and uracil). This combinatorial approach generated over 50 distinct genotypes that produced a large range in lipid (e.g. triacylglyceride) accumulation ability, culminating in upwards of 40-fold above control when using Nile-red based fluorescence and nearly 5-fold when using concentration (g/L) or percent lipid by cell mass (% dcw). In the process, we discovered a correlation between the auxotrophic marker used to select for protein overexpression and a strain's capacity to accumulate oleo-content. Specifically, the ability to endogenously produce the amino acid leucine, conferred by a selectable leucine auxotrophic marker, is beneficial (e.g. essential) to enable high lipid titer. We further examined a few (e.g. thirteen) of these strains to determine how C:N ratio and genotype interacted towards producing lipid (e.g. triacylglyceride) content on a larger scale. We observed a strong tendency towards high lipid (e.g. triacylglyceride) levels in most high producers at a single media formulation—cultivated in 80 g/L glucose and 5 g/L ammonium sulfate. We selected a MFE1, PEX10 double knockout strain with no auxotrophies overexpressing the DGA1p lipid synthesis as our final rationally engineered strain, and demonstrated its triacylglyceride accumulation ability on a variety of carbon sources, demonstrating its robust capacity to accumulate triacylglycerides regardless of media composition.

Through our time working with *Y. lipolytica*, we became aware of its surprising capacity to randomly (or forcibly through the use of an exogenous mutagen such as EMS) generate isolatable sub-strains that reproducibly displayed higher than wildtype triacylglyceride levels. In fact, one such strain, dubbed L36, displayed remarkable accumulation ability. Whole-genome sequencing of this strain pinpointed a mutation in the MGA2 transcriptional regulator as the most likely genomic explanation. Complementation assays of an MGA2p truncation mutant into wildtype background reached 50% of L36 lipid levels. We sought to harness this general capacity for beneficial mutation by subjecting wildtype, L36, and two of our highest producing rationally engineered strains to ethylmethanesulfonate (EMS) mutagenesis and positive selection. By combining large-scale investigations of phenotypic induction, genomic engineering, and positive random mutations, this work establishes a framework for engineering oleaginous organisms for increased lipid production. In this regard, we have pinpointed specific media formulations, genomic modifications, and genomic mutations that positively effect lipid (e.g. triacylglyceride) biosynthesis. The resultant strains are ideal for direct biodiesel precursor synthesis, lipid synthesis, oleochemical synthesis, lipid precursor synthesis, or for in vivo catalysis of fatty acid reserves to value added chemicals. Lipid accumulation characterized with flow cytometry using cells stained with Nile Red on 192 h time point with yeast synthetic medium containing 160 g/L glucose and 0.2 g/L ammonium sulfate and 96 h time point with yeast synthetic medium containing 80 g/L glucose and 5 g/L ammonium sulfate. Introducing MGA2-36 to the engineered strain leads to elevated level of lipid accumulation, suggesting MGA2-36 can be used a lipid enhancer in the rationally engineered lipid production strain. Lipid accumulation characterized with flow cytometry using cells stained with Nile Red on 192 h time point with yeast synthetic medium containing 160 g/L glucose and 0.2 g/L ammonium sulfate. PO1fΔmga2 leu+ showed improved level of lipid accumulation comparing to PO1f leu+ indicating mga2 knockout could improve lipid accumulation. Introducing a transmembrane domain truncated MGA2-36 in PO1f could elevate the lipid level inside the cell.

I. DEFINITIONS

The term "oleaginous organism" means an organism (e.g. a cell such as a yeast cell) that is capable of producing a lipid, lipid precursor, oleochemical, or oil (or combinations thereof) at a level exceeding the amount required for normal cellular survival and propagation of the organism (e.g. cell, yeast cell), such as for example necessary for structural integrity (e.g. membrane formation and maintenance) and cellular maintenance. Examples of amounts exceeding the amount required for normal cellular survival and propagation include an amount of lipids, oils, lipid precursors, and oleochemicals greater than 20% wt/wt total dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%). In embodiments, the oleaginous organism is an oleaginous yeast. In some embodiments, the oleaginous yeast is from a genus selected from the group consisting of *Apiotrichum, Candida, Cryptococcus, Debaromyces, Endomycopsis, Geotrichum, Hyphopichia, Lipomyces, Lypomyces, Pichia, Rodosporidium, Rhodotorula, Sporobolomyces, Starmerella, Torulaspora, Trichosporon, Wickerhamomyces, Yarrowia,* and *Zygoascus.* In embodiments, the oleaginous yeast is selected from the group consisting of *Apiotrichum curvatum, Candida apicola, Candida curvata, Candida revkaufi, Candida pulcherrima, Candida tropicalis, Candida utilis, Cryptococcus curvatus, Cryptococcus terricolus, Debaromyces hansenii, Endomycopsis vernalis, Geotrichum carabidarum, Geotrichum cucujoidarum, Geotrichum histeridarum, Geotrichum silvicola, Geotrichum vulgare, Hyphopichia burtonii, Lipomyces lipoferus, Lipomyces lipofer, Lypomyces orentalis, Lipomyces starkeyi, Lipomyces tetrasporous, Pichia mexicana, Rodosporidium sphaerocarpum, Rhodosporidium toruloides, Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis, Rhodotorula minuta, Rhodotorula mucilaginosa, Rhodotorula mucilaginosa Rhodotorula mucilaginosa, Rhodotorula terpenoidalis, Rhodotorula toruloides, Sporobolomyces alborubescens, Starmerella bombicola, Torulaspora delbruekii, Torulaspora pretoriensis, Trichosporon behrend, Trichosporon brassicae, Trichosporon cutaneum, Trichosporon domesticum, Trichosporon fermentans, Trichosporon laibachii, Trichosporon loubieri, Trichosporon loubieri var. loubieri, Trichosporon montevideense, Trichosporon pullulans, Wickerhamomyces canadensis, Yarrowia lipolytica,* and *Zygoascus meyerae.*

The term "buoyancy" is used according to its plain ordinary meaning and refers to the upward force exerted by a fluid, which opposes the weight of an immersed object (e.g. oleaginous organism or oleaginous yeast cell). Pressure increases with depth, resulting in a net force tending to accelerate object upward, wherein the magnitude of the force is proportional to the difference between the top and bottom of the fluid and is equivalent to the weight of the fluid that would otherwise occupy the space occupied by the object (i.e. the displace fluid). In embodiments, an oleaginous organism or yeast cell is considered "buoyant" when it does not settle (e.g. due to gravitation force alone, due to centrifugal force, due to an applied force, or due to a combination of forces such as centrifugation) to the bottom of a vessel holding a liquid (e.g. media) in which the oleaginous organism or yeast cell resides. For example, a cell may be buoyant if it floats above the bottom of the vessel, at an intermediate position between the bottom level and top level of the liquid, or on top of the upper surface of the liquid. An example of a measurement of the buoyancy of an object (e.g. cell) is the weight of the fluid the object would displace if the object were placed in the fluid. Another example of a measurement of the buoyancy of an object (e.g. cell) is a comparison of the average density of the object and the average density of the liquid to be displaced, taking into account the depth of the liquid in a column of the liquid. The term "buoyant density" is used according to its plain ordinary meaning and refers to a measure of the tendency of a substance to float in some other substance.

The term "carbon substrate" means a carbon source that a microorganism (e.g. oleaginous organism or oleaginous yeast) will metabolize to derive energy (e.g. monosaccharides, oligosaccharides, polysaccharides, alkanes, fatty acids, esters of fatty acids, monoglycerides, carbon dioxide, methanol, formaldehyde, formate or carbon-containing amines). The term "carbon source" refers to a carbon containing composition (e.g. compound, mixture of compounds) that an organism (e.g. oleaginous organism, yeast cell) may metabolize for use by the organism or that may be used for organism viability. A "majority carbon source" refers to a carbon containing composition that accounts for greater than 50% of the available carbon sources for an organism (e.g. in a media, in a growth media, in a defined media for growing yeast cells, or in a defined media for producing lipids by yeast cells) at a specified time (e.g. media when starting a yeast culture, media in a bioreactor when growing yeast, or media when producing lipids from yeast). In embodiments, an oleaginous yeast may be cultured using a medium comprising one or more carbon sources selected from the group consisting of glucose, fructose, sucrose, lactose, galactose, xylose, mannose, rhamnose, arabinose, glycerol, acetate, depolymerized sugar beet pulp, black liquor, corn starch, depolymerized cellulosic material, corn stover, sugar beet pulp, switchgrass, milk whey, molasses, potato, rice, sorghum, sugar cane, wheat, and mixtures thereof (e.g. mixtures of glycerol and glucose, mixtures of glucose and xylose, mixtures of fructose and glucose, mixtures of sucrose and depolymerized sugar beet pulp, black liquor, corn starch, depolymerized cellulosic material, corn stover, sugar beet pulp, switchgrass, milk whey, molasses, potato, rice, sorghum, sugar cane, and/or wheat). In embodiments, an oleaginous yeast is cultured using a medium comprising one or more carbon sources selected from the group consisting of depolymerized sugar beet pulp, black liquor, corn starch, depolymerized cellulosic material, corn stover, sugar beet pulp, switchgrass, milk whey, molasses, potato, rice, sorghum, sugar cane, thick cane juice, sugar beet juice, and wheat. In embodiments, an oleaginous yeast is cultured using a medium comprising lignocellulosic biomass. In embodiments carbon sources may be monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, or barley malt). Additionally, carbon sources may include alkanes, fatty acids, esters of fatty acids, monoglycerides, diglycerides, triglycerides, phospholipids, various commercial sources of fatty acids including vegetable oils (e.g., soybean oil) or animal fats.

Nitrogen may be supplied from an inorganic (e.g., $(NH_4)_2SO_4$) or organic source (e.g., urea, glutamate). The term "nitrogen source" refers to a nitrogen containing composition (e.g. compound, mixture of compounds, salt) that an organism (e.g. oleaginous organism, yeast cell) may metabolize for use by the organism or that may be used for organism viability. A "majority nitrogen source" refers to a nitrogen containing composition that accounts for greater than 50% of the available nitrogen sources for an organism (e.g. in a media, in a growth media, in a defined media for growing yeast cells, or in a defined media for producing lipids by yeast cells) at a specified time (e.g. media when starting a yeast culture, media in a bioreactor when growing yeast, or media when producing lipids from yeast).

The term "Biomass" refers to material produced by growth and/or propagation of cells. "Lignocellulosic biomass" is used according to it plain ordinary meaning and refers to plant dry matter comprising carbohydrate (e.g. cellulose or hemicellulose) and polymer (e.g. lignin). Lignocellulosic biomass may include agricultural residues (e.g. corn stover or sugarcane bagasse), energy crops (e.g. poplar trees, willow, *Miscanthus purpureum, Pennisetum purpureum*, elephant grass, maize, Sudan grass, millet, white sweet clover, rapeseed, giant *miscanthus*, switchgrass, jatropha, *Miscanthus giganteus*, or sugarcane), wood residues (e.g. sawmill or papermill discard), or municipal paper waste.

The term "Culture", "cultivate", and "ferment" are used interchangeably and refer to the intentional growth, propagation, proliferation, and/or enablement of metabolism, catabolism, and/or anabolism of one or more cells (e.g. oleaginous organism or oleaginous yeast). The combination of both growth and propagation may be termed proliferation. Examples include production by an organism of lipids, lipid precursors, and/or oleochemicals or production of a lipid, lipid precursor, and/or oleochemical of interest. Culture does not refer to the growth or propagation of microorganisms in nature or otherwise without human intervention.

The terms "dry weight" and "dry cell weight" are used interchangeably and refer to a weight determined in the relative absence of water. In embodiments, oleaginous yeast biomass comprising a fraction or percentage of a particular component by dry weight means that the fraction or percentage is calculated based on the weight of the biomass after substantially all water has been removed.

The term "growth" means an increase in cell size, total cellular contents, and/or cell mass or weight of a cell (e.g. oleaginous organism or oleaginous yeast).

The term "lipid" refers to a class of molecules that are soluble in nonpolar solvents (e.g. ether or chloroform), are relatively or completely insoluble in water, and include one or more hydrocarbon chains which are hydrophobic. In embodiments, a lipid may be a triacylglyeride (i.e. fat), fatty acid (e.g. saturated or unsaturated); glyceride or glycerolipid (e.g. monoglyceride, diglyceride, triglyceride, neutral fat, phosphoglyceride, or glycerophospholipid); sphingolipid; sterol lipid (e.g. cholesterol or a steroid hormone); prenol lipid (e.g. terpenoid); fatty alcohol; wax; polyketide; sugar-linked lipid, glycolipid, or protein-linked lipid.

The term "oil" means a triacylglyceride (or triglyceride oil), produced by an organism (e.g. oleaginous organism, oleaginous yeast, plant, and/or animal). An oil is generally liquid at normal ambient temperatures and pressures. In embodiments, oil may be vegetable or seed oils derived from plants (e.g. soy, rapeseed, canola, palm, palm kernel, coconut, corn, olive, sunflower, cotton seed, *cuphea*, peanut, camelina sativa, mustard seed, cashew nut, oats, lupine, kenaf, *calendula*, hemp, coffee, linseed, hazelnut, *euphorbia*, pumpkin seed, coriander, camellia, sesame, safflower, rice, tung oil tree, cocoa, copra, pium poppy, castor beans, pecan, jojoba, jatropha, *macadamia*, Brazil nuts, avocado, or combinations thereof). An oil may include a plurality of different triacylglycerides. For example, a vegetable or seed oil may include more than one triacylglyceride and use of the name of that vegetable or seed oil (e.g. soy, rapeseed, canola, palm, etc.) when referring to an oil generated by an oleaginous organism will be understood to mean an oil including most (e.g. all) of the triacylglycerides normally in the vegetable or seed oil (e.g. at different ratios relative to each other or the same or similar ratios relative to each other). In other embodiments, an oil may be a plurality of triacylglyceride and other lipid molecules produced by an oleaginous organism.

The term "propagation" refers to an increase in cell number via cell division.

The terms "V/V", "vol/vol", or "v/v", referring to proportions by volume, means the ratio of the volume of one substance in a composition to the volume of the total composition including the substance.

The term "W/W", "wt/wt", or "w/w", referring to proportions by weight, means the ratio of the weight of one substance in a composition to the weight of the total composition including the substance. For example, 5% w/w substance X means that 5% of the composition's weight is composed of substance X and the remainder of the weight of the composition (i.e. 95%) is composed of other substances.

The term "promoter" or "regulatory element" refers to a region or sequence determinants located upstream or downstream from the start of transcription and which are involved in recognition and binding of RNA polymerase and other proteins to initiate transcription. Promoters need not be of yeast origin, for example, promoters derived from viruses or from other organisms can be used in the compositions or methods described herein.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). In embodiments, a recombinant nucleic acid is a nucleic acid in an oleaginous organism (e.g. oleaginous yeast) that has been manipulated by a human, for example a recombinant nucleic acid comprising a coding region for a protein that is overexpressed in an oleaginous organism relative to the absence of the recombinant nucleic acid or a recombinant nucleic acid that results in disruption of a coding region or promoter region of an oleaginous organism and reduces or eliminates expression of a protein relative the absence of the recombinant nucleic acid. One of skill will recognize that nucleic acids (e.g. polynucleotides) can be manipulated in many ways and are not limited to the examples above.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones. The term encompasses nucleic acids containing known analogues of natural nucleotides which have similar or improved binding properties, for the purposes desired, as the reference nucleic acid. A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The term "expression cassette" refers to a nucleic acid construct, which when introduced into a host cell, results in transcription and/or translation of a RNA or polypeptide, respectively.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J.*

Mol. Biol. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al. One of skill will recognize that these values can be appropriately adjusted to determine corresponding identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

The term "modulator" refers to a composition that increases or decreases the level of a target molecule or the level of activity or function of a target molecule or the physical state of the target of the molecule. In embodiments a modulator is a recombinant nucleic acid that is capable of increasing or decreasing the amount of a protein in a cell or the level of activity of a protein in a cell or transcription of a second nucleic acid in a cell. In embodiments, a modulator increases or decreases the level of activity of a protein or the amount of the protein in a cell. The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, a recombinant nucleic acid that modulates the level of activity of a protein may increase the activity or amount of the protein relative the absence of the recombinant nucleic acid. In embodiments, an increase in the activity or amount of a protein may include overexpression of the protein. "Overexpression" is used in accordance with its plain meaning and refers to an increased level of expression of a protein relative to a control (e.g. cell or expression system not including a recombinant nucleic acid that contributes to the overexpression of a protein). In embodiments, a decrease in the activity or amount of a protein may include a mutation (e.g. point mutant, loss of function mutation, missense mutation, deletion, or insertion of heterologous nucleic acid; all/any of which may be in the coding region for a protein or in an operably linked region (e.g. promoter)) of the protein. The term "increased" refers to a detectable increase compared to a control. In some embodiments, the increase is by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, 10000, 20000, 30000, 40000, 50000, 60000, 70000, 80000, 90000, 100000%, or more compared to the control. In embodiments, the increase is by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, 10000, 20000, 30000, 40000, 50000, 60000, 70000, 80000, 90000, 100000%, or more compared to the control. In embodiments, the increase is by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, 10000, 20000, 30000, 40000, 50000, 60000, 70000, 80000, 90000, 100000%, compared to the control. Similarly, the term "decreased" refers to a measurable decrease compared to a control. In some embodiments, the decrease is by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or more compared to the control. In embodiments, the decrease is by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or more compared to the control. In embodiments, the decrease is by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, compared to the control. One of ordinary skill will be able to identify a relevant control.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a host organism (e.g. oleaginous organism or oleaginous yeast). In embodiments, the nucleic acid molecule may be a plasmid that replicates autonomously or it may integrate into the genome of the host organism (e.g. oleaginous organism or oleaginous yeast). Host organisms containing the transformed nucleic acid molecule may be referred to as "transgenic" or "recombinant" or "transformed" organisms (e.g. oleaginous organism or oleaginous yeast). A "genetically modified" organism (e.g. genetically modified yeast cell) is an organism (e.g. yeast cell) that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids. Genetically modified organisms may be made by rational modification of a nucleic acid or may be made by use of a mutagen or mutagenesis protocol that results in a mutation that was not identified (e.g. intended or targeted) prior to the use of the mutagen or mutagenesis protocol (e.g. UV exposure, EMS exposure, mutagen exposure, random genomic mutagenesis, transformation of a library of different nucleic acid constructs). Genetically modified organisms that include a modification (e.g. modification, insertion, deletion, mutation) not previously known or intended prior to making of the genetically modified organism may be identified through screening a plurality of organism including one or more genetically modified organisms by using a selection criteria that identifies the genetically modified organism of interest (e.g. an increased level of lipids, lipid precursors, and/or oleochemicals; floats above an organism not including the same genetic modification). In embodiments, a genetically modified organism includes a recombinant nucleic acid.

Methods for synthesizing sequences and bringing sequences together are well established and known to those of skill in the art. For example, in vitro mutagenesis and selection, site-directed mutagenesis, error prone PCR (Melnikov et al., Nucleic Acids Research, 27(4):1056-1062 (Feb. 15, 1999)), "gene shuffling" or other means can be employed to obtain mutations of naturally occurring genes.

Mutagenesis (e.g. chemical mutagenesis or site directed mutagenesis) may be used to modulate lipid production or storage in an oleaginous organism (e.g. oleaginous yeast). For example, a mutant construct or mutagen is transformed into an oleaginous yeast cell and the ability of the resulting transformed oleaginous yeast cell to produce or store one or more lipids is assayed and compared to the control cell. In some embodiments, it may be useful to disrupt or inactivate a host organism's native gene to modulate lipid production or storage. For example, a recombinant DNA fragment (e.g. a selectable marker gene) may be inserted into the gene to be disrupted in order to interrupt its coding sequence and the resulting recombinant nucleic acid then transformed into a host cell. Another example of a method of gene disruption is the use of transposable elements or transposons, which is well known to those of skill in the art.

In general, means for the purification of lipids, may include extraction with organic solvents, sonication, supercritical fluid extraction, saponification physical means such as presses, extraction, treatment with urea, fractional crystallization, HPLC, fractional distillation, silica gel chromatography, high-speed centrifugation or distillation, or combinations of these techniques.

In embodiments, the protein AMP Deaminase (AMPD) is a protein able to be translated from the nucleic acid corresponding to YALI0E11495 of the Genolevures database (i.e. found at http://www.genolevures.org/), wherein YALI0 stands for *Yarrowia lipolytica* and A,B,C,D,E,F specifies chromosome. In embodiments, the nucleic acid or gene AMP Deaminase (AMPD) is the nucleic acid or gene corresponding to YALI0E11495 of the Genolevures database (i.e. found at http://www.genolevures.org/). In embodiments, AMP Deaminase (AMPD) is a protein or nucleic acid/gene of a yeast strain corresponding to YALI0E11495 of *Yarrowia lipolytica* as described above. In embodiments, AMP Deaminase (AMPD) is a protein or nucleic acid/gene of an oleaginous organism corresponding to YALI0E11495 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Leucine Biosynthesis Gene (LEU2), also known as 3-isopropylmalate dehydrogenase, is a protein able to be translated from the nucleic acid corresponding to GenBank AF260230 or YALI0C00407 g of the Genolevures database (i.e. found at http://www.genolevures.org/), wherein YALI0 stands for *Yarrowia lipolytica* and A,B,C,D,E,F specifies chromosome. In embodiments, the nucleic acid or gene Leucine Biosynthesis Gene (LEU2) is the nucleic acid or gene corresponding to GenBank AF260230 or YALI0C00407 g of the Genolevures database (i.e. found at http://www.genolevures.org/). In embodiments, Leucine Biosynthesis Gene (LEU2) is a protein or nucleic acid/gene of a yeast strain corresponding to AF260230 of *Yarrowia lipolytica* as described above. In embodiments, Leucine Biosynthesis Gene (LEU2) is a protein or nucleic acid/gene of an oleaginous organism corresponding to AF260230 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Uracil Biosynthesis gene (URA3), also known as Orotidine 5'-phosphate decarboxylase, is a protein able to be translated from the nucleic acid corresponding to GenBank YLU40564 or YALI0E26741 g of the Genolevures database (i.e. found at http://www.genolevures.org/), wherein YALI0 stands for *Yarrowia lipolytica* and A,B,C,D,E,F specifies chromosome. In embodiments, the nucleic acid or gene Uracil Biosynthesis gene (URA3) is the nucleic acid or gene corresponding to GenBank YLU40564 or YALI0E26741 g of the Genolevures database (i.e. found at http://www.genolevures.org/). In embodiments, Uracil Biosynthesis gene (URA3) is a protein or nucleic acid/gene of a yeast strain corresponding to YLU40564 of *Yarrowia lipolytica* as described above. In embodiments, Uracil Biosynthesis gene (URA3) is a protein or nucleic acid/gene of an oleaginous organism corresponding to YLU40564 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein ATP-Citrate Lyase (ACL) is a protein including the protein ACL1, also called ATP-Citrate Lyase 1, able to be translated from the nucleic acid corresponding to YALI0E34793 of the Genolevures database (i.e. found at http://www.genolevures.org/), wherein YALI0 stands for *Yarrowia lipolytica* and A,B,C,D,E,F specifies chromosome. In embodiments, the nucleic acid or gene ATP-Citrate Lyase (ACL) includes the nucleic acid or gene ACL1 corresponding to YALI0E34793 of the Genolevures database (i.e. found at http://www.genolevures.org/). In embodiments, the protein ATP-Citrate Lyase (ACL) is a protein including the protein ACL2, also called ATP-Citrate Lyase 2, able to be translated from the nucleic acid corresponding to YALI0D24431 of the Genolevures database (i.e. found at http://www.genolevures.org/). In embodiments, the nucleic acid or gene ATP-Citrate Lyase (ACL) includes the nucleic acid or gene ACL2 corresponding to YALI0D24431 of the Genolevures database (i.e. found at http://www.genolevures.org/). In embodiments, ATP-Citrate Lyase (ACL) includes a protein or nucleic acid/gene of a yeast strain corresponding to YALI0D24431 of *Yarrowia lipolytica* as described above. In embodiments, ATP-Citrate Lyase (ACL) includes a protein or nucleic acid/gene of an oleaginous organism corresponding to YALI0D24431 of *Yarrowia lipolytica* as described above. In embodiments, the protein ATP-Citrate Lyase (ACL) is a protein including the protein ACL1 able to be translated from the nucleic acid corresponding to YALI0E34793 of the Genolevures database and the protein ACL2 able to be translated from the nucleic acid corresponding to YALI0D24431 of the Genolevures database (i.e. found at http://www.genolevures.org/). In embodiments, the nucleic acid or gene ATP-Citrate Lyase (ACL) includes the nucleic acid or gene ACL1 corresponding to YALI0E34793 and the nucleic acid or gene ACL2 corresponding to YALI0D24431 of the Genolevures database (i.e. found at http://www.genolevures.org/). In embodiments, ATP-Citrate Lyase (ACL) includes proteins or nucleic acids/genes of a yeast strain corresponding to YALI0E34793 and YALI0D24431 of *Yarrowia lipolytica* as described above. In embodiments, ATP-Citrate Lyase (ACL) includes proteins or nucleic acids/genes of an oleaginous organism corresponding to YALI0E34793 and YALI0D24431 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Malic Enzyme (MAE, MEA, MEA1) is a protein able to be translated from the nucleic acid corresponding to YALI0E18634 of the Genolevures database (i.e. found at http://www.genolevures.org/), wherein YALI0 stands for *Yarrowia lipolytica* and A,B,C,D,E,F specifies chromosome. In embodiments, the nucleic acid or gene Malic Enzyme (MAE, MEA, MEA1) is the nucleic acid or gene corresponding to YALI0E18634 of the Genolevures database (i.e. found at http://www.genolevures.org/). In embodiments, Malic Enzyme (MAE, MEA, MEA1) is a protein or nucleic acid/gene of a yeast strain corresponding to YALI0E18634 of *Yarrowia lipolytica* as described above. In embodiments, Malic Enzyme (MAE, MEA, MEA1) is a protein or nucleic acid/gene of an oleaginous organism corresponding to YALI0E18634 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein acyl-CoA: diacylglycerol acyltransferase (DGA1), also called acyl-CoA:diacylglycerol acyltransfer 1 is a protein able to be translated from the nucleic acid corresponding to YALI0E32769 of the Genolevures database (i.e. found at http://www.genolevures.org/), wherein YALI0 stands for *Yarrowia lipolytica* and A,B,C,D,E,F specifies chromosome. In embodiments, the nucleic acid or gene acyl-CoA:diacylglycerol acyltransferase (DGA1) is the nucleic acid or gene corresponding to YALI0E32769 of the Genolevures database (i.e. found at http://www.genolevures.org/). In embodiments, acyl-CoA: diacylglycerol acyltransferase (DGA1) is a protein or nucleic acid/gene of a yeast strain corresponding to YALI0E32769 of *Yarrowia lipolytica* as described above. In embodiments, acyl-CoA:diacylglycerol acyltransferase (DGA1) is a protein or nucleic acid/gene of an oleaginous organism corresponding to YALI0E32769 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein acyl-CoA: diacylglycerol acyltransferase (DGA2), also called acyl-CoA:diacylglycerol acyltransfer 2, is a protein able to be translated from the nucleic acid corresponding to YALI0D07986 of the Genolevures database (i.e. found at http://www.genolevures.org/), wherein YALI0 stands for *Yarrowia lipolytica* and A,B,C,D,E,F specifies chromosome. In embodiments, the nucleic acid or gene acyl-CoA:diacylglycerol acyltransferases (DGA2) is the nucleic acid or gene corresponding to YALI0D07986 of the Genolevures database (i.e. found at http://www.genolevures.org/). In embodiments, acyl-CoA: diacylglycerol acyltransferases (DGA2) is a protein or nucleic acid/gene of a yeast strain corresponding to YALI0D07986 of *Yarrowia lipolytica* as described above. In embodiments, acyl-CoA:diacylglycerol acyltransferases (DGA2) is a protein or nucleic acid/gene of an oleaginous organism corresponding to YALI0D07986 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Lipid synthesis regulator (MGA2) is a protein able to be translated from the nucleic acid corresponding to YALI0B12342 of the Genolevures database (i.e. found at http://www.genolevures.org/), wherein YALI0 stands for *Yarrowia lipolytica* and A,B,C,D,E,F specifies chromosome. In embodiments, the nucleic acid or gene Lipid synthesis regulator (MGA2) is the nucleic acid or gene corresponding to YALI0B12342 of the Genolevures database (i.e. found at http://www.genolevures.org/). In embodiments, Lipid synthesis regulator (MGA2) is a protein or nucleic acid/gene of a yeast strain corresponding to YALI0B12342 of *Yarrowia lipolytica* as described above. In embodiments, Lipid synthesis regulator (MGA2) is a protein or nucleic acid/gene of an oleaginous organism corresponding to YALI0B12342 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Chromatin assembly gene (RLF2 subunit p90) is a protein able to be translated from the nucleic acid corresponding to YALI0F21637 g of the Genolevures database (i.e. found at http://www.genolevures.org/), wherein YALI0 stands for *Yarrowia lipolytica* and A,B,C,D,E,F specifies chromosome. In embodiments, the nucleic acid or gene Chromatin assembly gene (RLF2 subunit p90) is the nucleic acid or gene corresponding to YALI0F21637 g of the Genolevures database (i.e. found at http://www.genolevures.org/). In embodiments, Chromatin assembly gene (RLF2 subunit p90) is a protein or nucleic acid/gene of a yeast strain corresponding to YALI0F21637 g of *Yarrowia lipolytica* as described above. In embodiments, Chromatin assembly gene (RLF2 subunit p90) is a protein or nucleic acid/gene of an oleaginous organism corresponding to YALI0F21637 g of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Mitochondrial 2' O-ribose methyltransferase (MRM2) is a protein able to be translated from the nucleic acid corresponding to YALI0E31933 of the Genolevures database (i.e. found at http://www.genolevures.org/), wherein YALI0 stands for *Yarrowia lipolytica* and A,B,C,D,E,F specifies chromosome. In embodiments, the nucleic acid or gene Mitochondrial 2' O-ribose methyltransferase (MRM2) is the nucleic acid or gene corresponding to YALI0E31933 of the Genolevures database (i.e. found at http://www.genolevures.org/). In embodiments, Mitochondrial 2' O-ribose methyltransferase (MRM2) is a protein or nucleic acid/gene of a yeast strain corresponding to YALI0E31933 of *Yarrowia lipolytica* as described above. In embodiments, Mitochondrial 2' O-ribose methyltransferase (MRM2) is a protein or nucleic acid/gene of an oleaginous organism corresponding to YALI0E31933 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Transcription Factor (PEX10) is a protein able to be translated from the nucleic acid corresponding to YALI0C01023 g of the Genolevures database (i.e. found at http://www.genolevures.org/), wherein YALI0 stands for *Yarrowia lipolytica* and A,B,C,D,E,F specifies chromosome. In embodiments, the nucleic acid or gene Transcription Factor (PEX10) is the nucleic acid or gene corresponding to YALI0C01023 g of the Genolevures database (i.e. found at http://www.genolevures.org/). In embodiments, Transcription Factor (PEX10) is a protein or nucleic acid/gene of a yeast strain corresponding to YALI0C01023 g of *Yarrowia lipolytica* as described above. In embodiments, Transcription Factor (PEX10) is a protein or nucleic acid/gene of an oleaginous organism corresponding to YALI0C01023 g of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein multifunctional enzyme (MFE1) is a protein able to be translated from the nucleic acid corresponding to YALI0E15378 of the Genolevures database (i.e. found at http://www.genolevures.org/), wherein YALI0 stands for *Yarrowia lipolytica* and A,B,C,D,E,F specifies chromosome. In embodiments, the nucleic acid or gene multifunctional enzyme (MFE1) is the nucleic acid or gene corresponding to YALI0E15378 of the Genolevures database (i.e. found at http://www.genolevures.org/). In embodiments, multifunctional enzyme (MFE1) is a protein or nucleic acid/gene of a yeast strain corresponding to YALI0E15378 of *Yarrowia lipolytica* as described above. In embodiments, multifunctional enzyme (MFE1) is a protein or nucleic acid/gene of an oleaginous organism corresponding to YALI0E15378 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein O-6-methylguanine-DNA methyltransferase (MGMT, O6M) is a protein able to be translated from the nucleic acid corresponding to YALI0C10010p of the Genolevures database (i.e. found at http://www.genolevures.org/), wherein YALI0 stands for *Yarrowia lipolytica* and A,B,C,D,E,F specifies chromosome. In embodiments, the nucleic acid or gene O-6-methylguanine-DNA methyltransferase (MGMT, O6M) is the nucleic acid or gene corresponding to YALI0C10010p of the Genolevures database (i.e. found at http://www.genolevures.org/). In embodiments, O-6-methylguanine-DNA methyltransferase (MGMT, O6M) is a protein or nucleic acid/gene of a yeast strain corresponding to YALI0C10010p of *Yarrowia lipolytica* as described above. In embodiments, O-6-methylguanine-DNA methyltransferase (MGMT, O6M) is a protein or nucleic acid/gene of an oleaginous organism corresponding to YALI0C10010p of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Aconitase (ACO1) is a protein able to be translated from the nucleic acid corresponding to YALI0D09361 of the Genolevures database (i.e. found at http://www.genolevures.org/), wherein YALI0 stands for *Yarrowia lipolytica* and A,B,C,D,E,F specifies chromosome. In embodiments, the nucleic acid or gene Aconitase (ACO1) is the nucleic acid or gene corresponding to YALI0D09361 of the Genolevures database (i.e. found at http://www.genolevures.org/). In embodiments, Aconitase (ACO1) is a protein or nucleic acid/gene of a yeast strain corresponding to YALI0D09361 of *Yarrowia lipolytica* as described above. In embodiments, O Aconitase (ACO1) is a protein or nucleic acid/gene of an oleaginous organism corresponding to YALI0D09361 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Citrate Synthase (CIT1) is a protein able to be translated from the nucleic acid corresponding to YALI0E02684 of the Genolevures database (i.e. found at http://www.genolevures.org/), wherein YALI0 stands for *Yarrowia lipolytica* and A,B,C,D,E,F specifies chromosome. In embodiments, the nucleic acid or gene Citrate Synthase (CIT1) is the nucleic acid or gene corresponding to YALI0E02684 of the Genolevures database (i.e. found at http://www.genolevures.org/). In embodiments, Citrate Synthase (CIT1) is a protein or nucleic acid/gene of a yeast strain corresponding to YALI0E02684 of *Yarrowia lipolytica* as described above. In embodiments, Citrate Synthase (CIT1) is a protein or nucleic acid/gene of an oleaginous organism corresponding to YALI0E02684 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein Acetyl-CoA Carboxylase (ACC) is a protein able to be translated from the nucleic acid corresponding to YALI0C11407 of the Genolevures database (i.e. found at http://www.genolevures.org/), wherein YALI0 stands for *Yarrowia lipolytica* and A,B,C,D,E,F specifies chromosome. In embodiments, the nucleic acid or gene Acetyl-CoA Carboxylase (ACC) is the nucleic acid or gene corresponding to YALI0C11407 of the Genolevures database (i.e. found at http://www.genolevures.org/). In embodiments, Acetyl-CoA Carboxylase (ACC) is a protein or nucleic acid/gene of a yeast strain corresponding to YALI0C11407 of *Yarrowia lipolytica* as described above. In embodiments, Acetyl-CoA Carboxylase (ACC) is a protein or nucleic acid/gene of an oleaginous organism corresponding to YALI0C11407 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein RME1 zinc-finger transcription factor (RME1) is a protein able to be translated from the nucleic acid corresponding to YALI0E17215 of the Genolevures database (i.e. found at http://www.genolevures.org/), wherein YALI0 stands for *Yarrowia lipolytica* and A,B,C,D,E,F specifies chromosome. In embodiments, the nucleic acid or gene RME1 zinc-finger transcription factor (RME1) is the nucleic acid or gene corresponding to YALI0E17215 of the Genolevures database (i.e. found at http://www.genolevures.org/). In embodiments, RME1 zinc-finger transcription factor (RME1) is a protein or nucleic acid/gene of a yeast strain corresponding to YALI0E17215 of *Yarrowia lipolytica* as described above. In embodiments, RME1 zinc-finger transcription factor (RME1) is a protein or nucleic acid/gene of an oleaginous organism corresponding to YALI0E17215 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein YOX1 homeodomain protein (YOX1) is a protein able to be translated from the nucleic acid corresponding to YALI0E20449 of the Genolevures database (i.e. found at http://www.genolevures.org/), wherein YALI0 stands for *Yarrowia lipolytica* and A,B,C,D,E,F specifies chromosome. In embodiments, the nucleic acid or gene YOX1 homeodomain protein (YOX1) is the nucleic acid or gene corresponding to YALI0E20449 of the Genolevures database (i.e. found at http://www.genolevures.org/). In embodiments, YOX1 homeodomain protein (YOX1) is a protein or nucleic acid/gene of a yeast strain corresponding to YALI0E20449 of *Yarrowia lipolytica* as described above. In embodiments, YOX1 homeodomain protein (YOX1) is a protein or nucleic acid/gene of an oleaginous organism corresponding to YALI0E20449 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein UGA2 succinate semialdehyde dehydrogenase (UGA2) is a protein able to be translated from the nucleic acid corresponding to YALI0F26191 of the Genolevures database (i.e. found at http://www.genolevures.org/), wherein YALI0 stands for *Yarrowia lipolytica* and A,B,C,D,E,F specifies chromosome. In embodiments, the nucleic acid or gene UGA2 succinate semialdehyde dehydrogenase (UGA2) is the nucleic acid or gene corresponding to YALI0F26191 of the Genolevures database (i.e. found at http://www.genolevures.org/). In embodiments, UGA2 succinate semialdehyde dehydrogenase (UGA2) is a protein or nucleic acid/gene of a yeast strain corresponding to YALI0F26191 of *Yarrowia lipolytica* as described above. In embodiments, UGA2 succinate semialdehyde dehydrogenase (UGA2) is a protein or nucleic acid/gene of an oleaginous organism corresponding to YALI0F26191 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein OSH6 oxysterol-binding protein homolog 6 (OSH6) is a protein able to be translated from the nucleic acid corresponding to YALI0A02354 of the Genolevures database (i.e. found at http://www.genolevures.org/), wherein YALI0 stands for *Yarrowia lipolytica* and A,B,C,D,E,F specifies chromosome. In embodiments, the nucleic acid or gene OSH6 oxysterol-binding protein homolog 6 (OSH6) is the nucleic acid or gene corresponding to YALI0A02354 of the Genolevures database (i.e. found at http://www.genolevures.org/). In embodiments, OSH6 oxysterol-binding protein homolog 6 (OSH6) is a protein or nucleic acid/gene of a yeast strain corresponding to YALI0A02354 of *Yarrowia lipolytica* as described above. In embodiments, OSH6 oxysterol-binding protein homolog 6 (OSH6) is a protein or nucleic acid/gene of an oleaginous organism corresponding to YALI0A02354 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

In embodiments, the protein IRC20 E3 ubiquitin-protein ligase and helicase (IRC20) is a protein able to be translated from the nucleic acid corresponding to YALI0C07150 of the Genolevures database (i.e. found at http://www.genolevures.org/), wherein YALI0 stands for *Yarrowia lipolytica* and A,B,C,D,E,F specifies chromosome. In embodiments, the nucleic acid or gene IRC20 E3 ubiquitin-protein ligase and helicase (IRC20) is the nucleic acid or gene corresponding to YALI0C07150 of the Genolevures database (i.e. found at http://www.genolevures.org/). In embodiments, IRC20 E3 ubiquitin-protein ligase and helicase (IRC20) is a protein or nucleic acid/gene of a yeast strain corresponding to YALI0C07150 of *Yarrowia lipolytica* as described above. In embodiments, IRC20 E3 ubiquitin-protein ligase and helicase (IRC20) is a protein or nucleic acid/gene of an oleaginous organism corresponding to YALI0C07150 of *Yarrowia lipolytica* as described above. In embodiments, the protein and/or nucleic acid is a wildtype version of the protein or nucleic acid. In embodiments, the protein and/or nucleic acid is a mutant form of the protein and/or nucleic acid (e.g. point mutant, loss of function mutation, missense mutation, deletion, or insertion of heterologous nucleic acid).

As used to describe a protein or nucleic/acid of another organism in comparison to a protein or nucleic/acid of *Yarrowia lipolytica*, the term "corresponds" or "corresponding" is used according to its ordinary meaning and refers to a protein or nucleic acid/gene that includes similar or identical sequence of amino acid or nucleotides respectively and/or performs a similar or identical function and/or has a similar of identical activity as the protein or nucleic acid/gene in *Yarrowia lipolytica* as described above. In some embodiments, a protein or nucleic acid corresponding to a protein or nucleic acid from *Yarrowia lipolytica* is a homolog. In embodiments, the protein and/or nucleic acid of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20) includes an amino acid and/or nucleotide sequence included in the protein and/or nucleic acid sequence for Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20) respectively, described herein (e.g. Examples section and/or sequence listing). In embodiments, the protein and/or nucleic acid of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20) is the amino acid and/or nucleotide sequence of the protein and/or nucleic acid sequence for Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20) respectively, described herein (e.g. Examples section and/or sequence listing).

The term "wildtype" as used herein when referring to an oleaginous organism (e.g. yeast strain or *Yarrowia lipolytica* strain) means an organism that has not been genetically modified to improve production of a lipid (e.g. increase yield of a lipid, alter the structure of a lipid produced by the organism, reduce production of one lipid to improve production of a second lipid, or modulate the production of a lipid). In embodiments, a wildtype yeast strain may be auxotrophic for one or more compounds (e.g. leucine and/or uracil). In embodiments, a wildtype *Yarrowia lipolytica* strain is PO1f (ATCC #MYA-2613), a leucine and uracil auxotroph devoid of any secreted protease activity (Madzak et al., 2000).

The term "oleochemical" is used herein in accordance with its well known meaning and refers to chemicals or compounds derived from lipids or fats. In embodiments, an oleochemical is a lipid or fat derived from a different lipid or fat. In embodiments an oleochemical is a chemical or compound produced by an oleaginous organism. In embodiments, an oleochemical is a chemical or compound derived from a lipid or lipid precursor produced by an oleaginous organism (e.g., fatty acid esters such as methyl esters, ethyl esters, propyl esters, or butyl esters that are derived from a fatty acid produced by an oleaginous organism by transesterification). In embodiments, an oleochemical may include further in vivo or in vitro modification of a lipid or lipid precursor enabled by endogenous or heterologous modifying enzymes or chemical reactions.

The term "lipid precursor" is used in accordance with its well known meaning and refers to a pathway intermediate (e.g., acetyl-CoA or malonyl-CoA) in the biosynthesis of a lipid. In embodiments, a lipid precursor may be any molecule along the biosynthetic pathway making triglycerides including free citrate, acetyl-CoA, free fatty acids, pyruvate, citric acid cycle intermediates, diacylglycerides, and/or triacylglycerides.

The term "micronutrient" is used in accordance with its well known meaning and refers to nutrients used by an organism (e.g. oleaginous organisms, yeast, oleaginous yeast) for growth, proliferation, propagation, survival, one or more essential biological functions, production of a lipid, lipid precursor, or oleochemical, which are required for such functions in small quantities. Examples of micronutrients include, but are not limited to, minerals, vitamins, and elements (e.g. cobalt, iron, magnesium, potassium, zinc, nickel, molybdenum, manganese, copper, and/or boron).

II. OLEAGINOUS ORGANISMS

In a first aspect is provided a genetically modified oleaginous organism (e.g. yeast cell, oleaginous yeast cell,

*Yarrowia lipolytica*, algae, or plant cell) wherein the dry weight of the oleaginous organism includes greater than 20% wt/wt lipids, lipid precursors, and/or oleochemicals (e.g., lipid, lipids, lipid precursors, lipid precursor, oleochemicals, or oleochemical).

In embodiments, the oleaginous organism (e.g. yeast cell, oleaginous yeast cell, *Yarrowia lipolytica*, algae, or plant cell) includes greater than 30% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 40% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 50% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 60% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 70% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 80% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 90% wt/wt lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes about an average of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight. In embodiments, the oleaginous organism (e.g. yeast cell, oleaginous yeast cell, *Yarrowia lipolytica*, algae, or plant cell) includes greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight.

In embodiments, the oleaginous organism (e.g. yeast cell, oleaginous yeast cell, *Yarrowia lipolytica*, algae, or plant cell) produces about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 g/L culture (e.g. in a bioreactor) of lipids, lipid precursors, and/or oleochemicals (e.g., lipid, lipids, lipid precursors, lipid precursor, oleochemicals, or oleochemical). In embodiments, the oleaginous organism (e.g. yeast cell, oleaginous yeast cell, *Yarrowia lipolytica*, algae, or plant cell) produces at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 g/L culture (e.g. in a bioreactor) of lipids, lipid precursors, and/or oleochemicals (e.g., lipid, lipids, lipid precursors, lipid precursor, oleochemicals, or oleochemical). In embodiments, the oleaginous organism (e.g. yeast cell, oleaginous yeast cell, *Yarrowia lipolytica*, algae, or plant cell) produces 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 g/L culture (e.g. in a bioreactor) of lipids, lipid precursors, and/or oleochemicals (e.g., lipid, lipids, lipid precursors, lipid precursor, oleochemicals, or oleochemical).

In embodiments, the oleaginous organism is a yeast cell. In embodiments, the oleaginous organism is an oleaginous yeast cell. In embodiments, the yeast cell is selected from the group consisting of the genera *Yarrowia*, *Candida*, *Rhodotorula*, *Rhodosporidium*, *Cryptococcus*, *Trichosporon* and *Lipomyces*. In embodiments, the yeast cell is selected from the group consisting of *Rhodosporidium toruloides*, *Lipomyces starkeyii*, *Lipomyces lipoferus*, *Apiotrichum curvatum*, *Candida curvata*, *Cryptococcus curvatus*, *Trichosporon fermentans*, *Candida revkaufi*, *Candida pulcherrima*, *Candida tropicalis*, *Candida utilis*, *Trichosporon pullans*, *Trichosporon cutaneum*, *Rhodotorula glutinus*, *Rhodotorula graminis* and *Yarrowia lipolytica*. In embodiments, the yeast cell is selected from the group consisting of *Lipomyces starkeyii*, *Rhodosporidium toruloides*, *Apiotrichum curvatum*, *Candida curvata*, *Cryptococcus curvatus*, *Trichosporon fermentans*, *Rhodotorula glutinis*, and *Yarrowia lipolytica*. In embodiments, the yeast cell is *Yarrowia lipolytica*.

In embodiments, the oleaginous organism (e.g. yeast cell, oleaginous yeast cell, *Yarrowia lipolytica*, algae, or plant cell) is buoyant in an aqueous medium. In embodiments, the yeast cell includes a greater buoyancy (i.e. greater tendency to float, lower density) than a yeast cell that includes less than about 99% lipids, lipid precursors, and/or oleochemicals (e.g., lipid, lipids, lipid precursors, lipid precursor, oleochemicals, or oleochemical) by dry weight (e.g. less than about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight). In embodiments, the yeast cell includes a greater buoyancy (i.e. greater tendency to float, lower density) than a yeast cell that includes less than 99% lipids, lipid precursors, and/or oleochemicals (e.g., lipid, lipids, lipid precursors, lipid precursor, oleochemicals, or oleochemical) by dry weight (e.g. less than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight). In embodiments, the oleaginous organism (e.g. yeast cell, oleaginous yeast cell, *Yarrowia lipolytica*, algae, or plant cell) does not sediment to the bottom of a column of liquid (e.g. water, buffer, growth media, minimal media) that is about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, or 99 mm tall due to gravitation force alone. The term "about" when used in connection with a defined amount refers to an amount up to and including greater than and/or less than 10% of the associated value and includes the associated value. In embodiments, the oleaginous organism (e.g. yeast cell, oleaginous yeast cell, *Yarrowia lipolytica*, algae, or plant cell) does not sediment to the bottom of a column of liquid (e.g. water, buffer, growth media, minimal media) that is 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, or 99 mm tall due to gravitation force alone. In embodiments, the yeast cell includes a greater buoyancy (i.e. greater tendency to float, lower density) than a yeast cell that does not include the same recombinant nucleic acid or combination of recombinant nucleic acids as the buoyant yeast cell. In embodiments, the yeast cell is buoyant following centrifugation (e.g. at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950. 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500, or 10000×g).

In embodiments of the oleaginous organism (e.g. yeast cell, oleaginous yeast cell, *Yarrowia lipolytica*, algae, or plant cell) including more than about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight (e.g. more than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight), included are lipids, lipid precursors, and/or oleochemicals (e.g., lipid, lipids, lipid precursors, lipid precursor, oleochemicals, or oleochemical) selected from the group consisting of a fatty acid, wax, sterol, vitamin, monoglyceride, diglyceride, triglyceride, phospholipid, glycerolipid, glycerophospholipid, sphingolipid, saccharolipid, polyketide, sterol lipid, triacylglyceride, wax ester, fatty acid ethyl ester, fatty acid methyl ester, component of biodiesel, saturated hydrocarbon, unsaturated hydrocarbon, branched hydrocarbon, and a prenol lipid. In embodiments, the majority lipid, lipid precursor, or oleochemical in the oleaginous organism (e.g. yeast cell, oleaginous yeast cell, *Yarrowia lipolytica*, algae, or plant cell) is a fatty acid. In embodiments, the majority lipid, lipid precursor, or oleochemical in the oleaginous organism (e.g. yeast cell, oleaginous yeast cell, *Yarrowia lipolytica*, algae, or plant cell) is a wax. In embodiments, the majority lipid, lipid precursor, or oleochemical in the oleaginous organism (e.g. yeast cell, oleaginous yeast cell, *Yarrowia lipolytica*, algae, or plant cell) is a sterol. In embodiments, the majority lipid, lipid precursor, or oleochemical in the oleaginous organism (e.g. yeast cell, oleaginous yeast cell, *Yarrowia lipolytica*, algae, or plant cell) is a vitamin. In embodiments, the majority lipid, lipid precursor, or oleochemical in the oleaginous organism (e.g. yeast cell, oleaginous yeast cell, *Yarrowia lipolytica*, algae, or plant cell) is a monoglyceride. In embodiments, the majority lipid, lipid precursor, or oleochemical in the oleaginous organism (e.g. yeast cell, oleaginous yeast cell, *Yarrowia lipolytica*, algae, or plant cell) is a diglyceride. In embodiments, the majority lipid, lipid precursor, or oleochemical in the oleaginous organism (e.g. yeast cell, oleaginous yeast cell, *Yarrowia lipolytica*, algae, or plant cell) is a triglyceride. In embodiments, the majority lipid, lipid precursor, or oleochemical in the oleaginous organism (e.g. yeast cell, oleaginous yeast cell, *Yarrowia lipolytica*, algae, or plant cell) is a phospholipid. In embodiments, the majority lipid, lipid precursor, or oleochemical in the oleaginous organism (e.g. yeast cell, oleaginous yeast cell, *Yarrowia lipolytica*, algae, or plant cell) is a glycerolipid. In embodiments, the majority lipid, lipid precursor, or oleochemical in the oleaginous organism (e.g. yeast cell, oleaginous yeast cell, *Yarrowia lipolytica*, algae, or plant cell) is a glycerophospholipid. In embodiments, the majority lipid, lipid precursor, or oleochemical in the oleaginous organism (e.g. yeast cell, oleaginous yeast cell, *Yarrowia lipolytica*, algae, or plant cell) is a sphingolipid. In embodiments, the majority lipid, lipid precursor, or oleochemical in the oleaginous organism (e.g. yeast cell, oleaginous yeast cell, *Yarrowia lipolytica*, algae, or plant cell) is a saccharolipid. In embodiments, the majority lipid, lipid precursor, or oleochemical in the oleaginous organism (e.g. yeast cell, oleaginous yeast cell, *Yarrowia lipolytica*, algae, or plant cell) is a polyketide.

In embodiments, the majority lipid, lipid precursor, or oleochemical in the oleaginous organism (e.g. yeast cell, oleaginous yeast cell, *Yarrowia lipolytica*, algae, or plant cell) is a sterol lipid. In embodiments, the majority lipid, lipid precursor, or oleochemical in the oleaginous organism (e.g. yeast cell, oleaginous yeast cell, *Yarrowia lipolytica*, algae, or plant cell) is a triacylglyceride. In embodiments, the majority lipid, lipid precursor, or oleochemical in the oleaginous organism (e.g. yeast cell, oleaginous yeast cell, *Yarrowia lipolytica*, algae, or plant cell) is a prenol lipid. In embodiments, the majority lipid, lipid precursor, or oleochemical in the oleaginous organism (e.g. yeast cell, oleaginous yeast cell, *Yarrowia lipolytica*, algae, or plant cell) is a wax ester. In embodiments, the majority lipid, lipid precursor, or oleochemical in the oleaginous organism (e.g. yeast cell, oleaginous yeast cell, *Yarrowia lipolytica*, algae, or plant cell) is a fatty acid ethyl ester. In embodiments, the majority lipid, lipid precursor, or oleochemical in the oleaginous organism (e.g. yeast cell, oleaginous yeast cell, *Yarrowia lipolytica*, algae, or plant cell) is a fatty acid methyl ester. In embodiments, the majority lipid, lipid precursor, or oleochemical in the oleaginous organism (e.g. yeast cell, oleaginous yeast cell, *Yarrowia lipolytica*, algae, or plant cell) is a component of biodiesel. In embodiments, the majority lipid, lipid precursor, or oleochemical in the oleaginous organism (e.g. yeast cell, oleaginous yeast cell, *Yarrowia lipolytica*, algae, or plant cell) is a saturated hydrocarbon. In embodiments, the majority lipid, lipid precursor, or oleochemical in the oleaginous organism (e.g. yeast cell, oleaginous yeast cell, *Yarrowia lipolytica*, algae, or plant cell) is an unsaturated hydrocarbon. In embodiments, the majority lipid, lipid precursor, or oleochemical in the oleaginous organism (e.g. yeast cell, oleaginous yeast cell, *Yarrowia lipolytica*, algae, or plant cell) is a branched hydrocarbon. In embodiments, the majority lipid, lipid precursor, or oleochemical in the oleaginous organism (e.g. yeast cell, oleaginous yeast cell, *Yarrowia lipolytica*, algae, or plant cell) is a lipid. In embodiments, the majority lipid, lipid precursor, or oleochemical in the oleaginous organism (e.g. yeast cell, oleaginous yeast cell, *Yarrowia lipolytica*, algae, or plant cell) is a lipid precursor. In embodiments, the majority lipid, lipid precursor, or oleochemical in the oleaginous organism (e.g. yeast cell, oleaginous yeast cell, *Yarrowia lipolytica*, algae, or plant cell) is an oleochemical.

In embodiments, the oleaginous organism (e.g. yeast cell, oleaginous yeast cell, *Yarrowia lipolytica*, algae, or plant cell) produces C5:0 fatty acid. In embodiments, the oleaginous organism (e.g. yeast cell, oleaginous yeast cell, *Yarrowia lipolytica*, algae, or plant cell) produces C5:1 fatty acid. In embodiments, the oleaginous organism (e.g. yeast cell, oleaginous yeast cell, *Yarrowia lipolytica*, algae, or plant cell) produces C5:2 fatty acid. In embodiments, the oleaginous organism (e.g. yeast cell, oleaginous yeast cell, *Yarrowia lipolytica*, algae, or plant cell) produces C5:3 fatty acid. In embodiments, the oleaginous organism (e.g. yeast cell, oleaginous yeast cell, *Yarrowia lipolytica*, algae, or plant cell) produces C6:0 fatty acid. In embodiments, the oleaginous organism (e.g. yeast cell, oleaginous yeast cell, *Yarrowia lipolytica*, algae, or plant cell) produces C6:1 fatty acid. In embodiments, the oleaginous organism (e.g. yeast cell, oleaginous yeast cell, *Yarrowia lipolytica*, algae, or plant cell) produces C6:2 fatty acid. In embodiments, the oleaginous organism (e.g. yeast cell, oleaginous yeast cell, *Yarrowia lipolytica*, algae, or plant cell) produces C6:3 fatty acid. In embodiments, the oleaginous organism (e.g. yeast cell, oleaginous yeast cell, *Yarrowia lipolytica*, algae, or plant cell) produces C7:0 fatty acid. In embodiments, the oleaginous organism (e.g. yeast cell, oleaginous yeast cell, *Yarrowia lipolytica*, algae, or plant cell) produces C7:1 fatty acid. In embodiments, the oleaginous organism (e.g. yeast cell, oleaginous yeast cell, *Yarrowia lipolytica*, algae, or plant cell) produces C7:2 fatty acid. In embodiments, the oleaginous organism (e.g. yeast cell, oleaginous yeast cell, *Yarrowia lipolytica*, algae, or plant cell) produces C7:3 fatty acid. In embodiments, the oleaginous organism (e.g. yeast cell, oleaginous yeast cell, *Yarrowia lipolytica*, algae, or plant cell) produces C8:0 fatty acid. In embodiments, the oleaginous organism (e.g. yeast cell, oleaginous yeast cell, *Yarrowia lipolytica*, algae, or plant cell) produces C8:1 fatty acid. In embodiments, the oleaginous organism (e.g. yeast cell, oleaginous yeast cell, *Yarrowia lipolytica*, algae, or plant cell) produces C8:2 fatty acid. In embodiments, the oleaginous organism (e.g. yeast cell, oleaginous yeast cell, *Yarrowia lipolytica*, algae, or plant cell) produces C8:3 fatty acid. In embodiments, the oleaginous organism (e.g. yeast cell, oleaginous yeast cell, *Yarrowia lipolytica*, algae, or plant cell) produces C9:0 fatty acid. In embodiments, the oleaginous organism (e.g. yeast cell, oleaginous yeast cell, *Yarrowia lipolytica*, algae, or plant cell) produces C9:1 fatty acid. In embodiments, the oleaginous organism (e.g. yeast cell, oleaginous yeast cell, *Yarrowia lipolytica*, algae, or plant cell) produces C9:2 fatty acid. In embodiments, the oleaginous organism (e.g. yeast cell, oleaginous yeast cell, *Yarrowia lipolytica*, algae, or plant cell) produces C9:3 fatty acid. In embodiments, the oleaginous organism (e.g. yeast cell, oleaginous yeast cell, *Yarrowia lipolytica*, algae, or plant cell) produces C10:0 fatty acid. In embodiments, the oleaginous organism (e.g. yeast cell, oleaginous yeast cell, *Yarrowia lipolytica*, algae, or plant cell) produces C10:1 fatty acid. In embodiments, the oleaginous organism (e.g. yeast cell, oleaginous yeast cell, *Yarrowia lipolytica*, algae, or plant cell) produces C10:2 fatty acid. In embodiments, the oleaginous organism (e.g. yeast cell, oleaginous yeast cell, *Yarrowia lipolytica*, algae, or plant cell) produces C10:3 fatty acid. In embodiments, the oleaginous organism (e.g. yeast cell, oleaginous yeast cell, *Yarrowia lipolytica*, algae, or plant cell) produces C11:0 fatty acid. In embodiments, the oleaginous organism (e.g. yeast cell, oleaginous yeast cell, *Yarrowia lipolytica*, algae, or plant cell) produces C11:1 fatty acid. In embodiments, the oleaginous organism (e.g. yeast cell, oleaginous yeast cell, *Yarrowia lipolytica*, algae, or plant cell) produces C11:2 fatty acid. In embodiments, the oleaginous organism (e.g. yeast cell, oleaginous yeast cell, *Yarrowia lipolytica*, algae, or plant cell) produces C11:3 fatty acid. In embodiments, the oleaginous organism (e.g. yeast cell, oleaginous yeast cell, *Yarrowia lipolytica*, algae, or plant cell) produces C12:0 fatty acid. In embodiments, the oleaginous organism (e.g. yeast cell, oleaginous yeast cell, *Yarrowia lipolytica*, algae, or plant cell) produces C12:1 fatty acid. In embodiments, the oleaginous organism (e.g. yeast cell, oleaginous yeast cell, *Yarrowia lipolytica*, algae, or plant cell) produces C12:2 fatty acid. In embodiments, the oleaginous organism (e.g. yeast cell, oleaginous yeast cell, *Yarrowia lipolytica*, algae, or plant cell) produces C12:3 fatty acid. In embodiments, the oleaginous organism (e.g. yeast cell, oleaginous yeast cell, *Yarrowia lipolytica*, algae, or plant cell) produces C13:0 fatty acid. In embodiments, the oleaginous organism (e.g. yeast cell, oleaginous yeast cell, *Yarrowia lipolytica*, algae, or plant cell) produces C13:1 fatty acid. In embodiments, the oleaginous organism (e.g. yeast cell, oleaginous yeast cell, *Yarrowia lipolytica*, algae, or plant cell) produces C13:2 fatty acid. In embodiments, the oleaginous organism (e.g. yeast cell, oleaginous yeast cell,

*Yarrowia lipolytica*, algae, or plant cell) produces C13:3 fatty acid. In embodiments, the oleaginous organism (e.g. yeast cell, oleaginous yeast cell, *Yarrowia lipolytica*, algae, or plant cell) produces C14:0 fatty acid. In embodiments, the oleaginous organism (e.g. yeast cell, oleaginous yeast cell, *Yarrowia lipolytica*, algae, or plant cell) produces C14:1 fatty acid. In embodiments, the oleaginous organism (e.g. yeast cell, oleaginous yeast cell, *Yarrowia lipolytica*, algae, or plant cell) produces C14:2 fatty acid. In embodiments, the oleaginous organism (e.g. yeast cell, oleaginous yeast cell, *Yarrowia lipolytica*, algae, or plant cell) produces C14:3 fatty acid. In embodiments, the oleaginous organism (e.g. yeast cell, oleaginous yeast cell, *Yarrowia lipolytica*, algae, or plant cell) produces C15:0 fatty acid. In embodiments, the oleaginous organism (e.g. yeast cell, oleaginous yeast cell, *Yarrowia lipolytica*, algae, or plant cell) produces C15:1 fatty acid. In embodiments, the oleaginous organism (e.g. yeast cell, oleaginous yeast cell, *Yarrowia lipolytica*, algae, or plant cell) produces C15:2 fatty acid. In embodiments, the oleaginous organism (e.g. yeast cell, oleaginous yeast cell, *Yarrowia lipolytica*, algae, or plant cell) produces C15:3 fatty acid. In embodiments, the oleaginous organism (e.g. yeast cell, oleaginous yeast cell, *Yarrowia lipolytica*, algae, or plant cell) produces C16:0 fatty acid. In embodiments, the oleaginous organism (e.g. yeast cell, oleaginous yeast cell, *Yarrowia lipolytica*, algae, or plant cell) produces C16:1 fatty acid. In embodiments, the oleaginous organism (e.g. yeast cell, oleaginous yeast cell, *Yarrowia lipolytica*, algae, or plant cell) produces C16:2 fatty acid. In embodiments, the oleaginous organism (e.g. yeast cell, oleaginous yeast cell, *Yarrowia lipolytica*, algae, or plant cell) produces C16:3 fatty acid. In embodiments, the oleaginous organism (e.g. yeast cell, oleaginous yeast cell, *Yarrowia lipolytica*, algae, or plant cell) produces C17:0 fatty acid. In embodiments, the oleaginous organism (e.g. yeast cell, oleaginous yeast cell, *Yarrowia lipolytica*, algae, or plant cell) produces C17:1 fatty acid. In embodiments, the oleaginous organism (e.g. yeast cell, oleaginous yeast cell, *Yarrowia lipolytica*, algae, or plant cell) produces C17:2 fatty acid. In embodiments, the oleaginous organism (e.g. yeast cell, oleaginous yeast cell, *Yarrowia lipolytica*, algae, or plant cell) produces C17:3 fatty acid. In embodiments, the oleaginous organism (e.g. yeast cell, oleaginous yeast cell, *Yarrowia lipolytica*, algae, or plant cell) produces C18:0 fatty acid. In embodiments, the oleaginous organism (e.g. yeast cell, oleaginous yeast cell, *Yarrowia lipolytica*, algae, or plant cell) produces C18:1 fatty acid. In embodiments, the oleaginous organism (e.g. yeast cell, oleaginous yeast cell, *Yarrowia lipolytica*, algae, or plant cell) produces C18:2 fatty acid. In embodiments, the oleaginous organism (e.g. yeast cell, oleaginous yeast cell, *Yarrowia lipolytica*, algae, or plant cell) produces C18:3 fatty acid. In embodiments, the oleaginous organism (e.g. yeast cell, oleaginous yeast cell, *Yarrowia lipolytica*, algae, or plant cell) produces C19:0 fatty acid. In embodiments, the oleaginous organism (e.g. yeast cell, oleaginous yeast cell, *Yarrowia lipolytica*, algae, or plant cell) produces C19:1 fatty acid. In embodiments, the oleaginous organism (e.g. yeast cell, oleaginous yeast cell, *Yarrowia lipolytica*, algae, or plant cell) produces C19:2 fatty acid. In embodiments, the oleaginous organism (e.g. yeast cell, oleaginous yeast cell, *Yarrowia lipolytica*, algae, or plant cell) produces C19:3 fatty acid. In embodiments, the oleaginous organism (e.g. yeast cell, oleaginous yeast cell, *Yarrowia lipolytica*, algae, or plant cell) produces C20:0 fatty acid. In embodiments, the oleaginous organism (e.g. yeast cell, oleaginous yeast cell, *Yarrowia lipolytica*, algae, or plant cell) produces C20:1 fatty acid. In embodiments, the oleaginous organism (e.g. yeast cell, oleaginous yeast cell, *Yarrowia lipolytica*, algae, or plant cell) produces C20:2 fatty acid. In embodiments, the oleaginous organism (e.g. yeast cell, oleaginous yeast cell, *Yarrowia lipolytica*, algae, or plant cell) produces C20:3 fatty acid. In embodiments, the oleaginous organism (e.g. yeast cell, oleaginous yeast cell, *Yarrowia lipolytica*, algae, or plant cell) produces C21:0 fatty acid. In embodiments, the oleaginous organism (e.g. yeast cell, oleaginous yeast cell, *Yarrowia lipolytica*, algae, or plant cell) produces C21:1 fatty acid. In embodiments, the oleaginous organism (e.g. yeast cell, oleaginous yeast cell, *Yarrowia lipolytica*, algae, or plant cell) produces C21:2 fatty acid. In embodiments, the oleaginous organism (e.g. yeast cell, oleaginous yeast cell, *Yarrowia lipolytica*, algae, or plant cell) produces C21:3 fatty acid. In embodiments, the oleaginous organism (e.g. yeast cell, oleaginous yeast cell, *Yarrowia lipolytica*, algae, or plant cell) produces C22:0 fatty acid. In embodiments, the oleaginous organism (e.g. yeast cell, oleaginous yeast cell, *Yarrowia lipolytica*, algae, or plant cell) produces C22:1 fatty acid. In embodiments, the oleaginous organism (e.g. yeast cell, oleaginous yeast cell, *Yarrowia lipolytica*, algae, or plant cell) produces C22:2 fatty acid. In embodiments, the oleaginous organism (e.g. yeast cell, oleaginous yeast cell, *Yarrowia lipolytica*, algae, or plant cell) produces C22:3 fatty acid. In embodiments, the oleaginous organism (e.g. yeast cell, oleaginous yeast cell, *Yarrowia lipolytica*, algae, or plant cell) produces C23:0 fatty acid. In embodiments, the oleaginous organism (e.g. yeast cell, oleaginous yeast cell, *Yarrowia lipolytica*, algae, or plant cell) produces C23:1 fatty acid. In embodiments, the oleaginous organism (e.g. yeast cell, oleaginous yeast cell, *Yarrowia lipolytica*, algae, or plant cell) produces C23:2 fatty acid. In embodiments, the oleaginous organism (e.g. yeast cell, oleaginous yeast cell, *Yarrowia lipolytica*, algae, or plant cell) produces C23:3 fatty acid. In embodiments, the oleaginous organism (e.g. yeast cell, oleaginous yeast cell, *Yarrowia lipolytica*, algae, or plant cell) produces a fatty acid described herein above at a greater level (e.g. 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 100000, 1000000 fold) compared to the same oleaginous organism lacking the genetic modification. In embodiments, the oleaginous organism (e.g. yeast cell, oleaginous yeast cell, *Yarrowia lipolytica*, algae, or plant cell) produces a lipid including a fatty acid selected from the group consisting of C5:0, C5:1, C5:2, C5:3, C6:0, C6:1, C6:2, C6:3, C7:0, C7:1, C7:2, C7:3, C8:0, C8:1, C8:2, C8:3, C9:0, C9:1, C9:2, C9:3, C10:0, C10:1, C10:2, C10:3, C11:0, C11:1, C11:2, C11:3, C12:0, C12:1, C12:2, C12:3, C13:0, C13:1, C13:2, C13:3, C14:0, C14:1, C14:2, C14:3, C15:0, C15:1, C15:2, C15:3, C16:0, C16:1, C16:2, C16:3, C17:0, C17:1, C17:2, C17:3, C18:0, C18:1, C18:2, C18:3, C19:0, C19:1, C19:2, C19:3, C20:0, C20:1, C20:2, C20:3, C21:0, C21:1, C21:2, C21:3, C22:0, C22:1, C22:2, C22:3, C23:0, C23:1, C23:2, and C23:3. In embodiments, the oleaginous organism (e.g. yeast cell, oleaginous yeast cell, *Yarrowia lipolytica*, algae, or plant cell) produces a lipid derived from an endogenously produced fatty acid selected from the group consisting of C5:0, C5:1, C5:2, C5:3, C6:0, C6:1, C6:2, C6:3, C7:0, C7:1, C7:2, C7:3, C8:0, C8:1, C8:2, C8:3, C9:0, C9:1, C9:2, C9:3, C10:0, C10:1, C10:2, C10:3, C11:0, C11:1, C11:2, C11:3, C12:0, C12:1, C12:2, C12:3, C13:0, C13:1, C13:2, C13:3, C14:0, C14:1, C14:2, C14:3, C15:0, C15:1, C15:2, C15:3, C16:0, C16:1, C16:2, C16:3, C17:0, C17:1, C17:2, C17:3, C18:0, C18:1, C18:2, C18:3, C19:0, C19:1, C19:2, C19:3, C20:0, C20:1, C20:2, C20:3, C21:0, C21:1, C21:2, C21:3, C22:0, C22:1, C22:2, C22:3, C23:0, C23:1, C23:2, and C23:3. In embodiments, the oleaginous organism (e.g. yeast cell, oleaginous yeast cell, *Yarrowia lipolytica*, algae, or plant cell) produces a lipid, lipid precursor, or oleochemical (e.g. fatty acid) described herein at a greater level (e.g. 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 100000, 1000000 fold) compared to the same oleaginous organism lacking the genetic modification.

In embodiments, the oleaginous organism (e.g. yeast cell, oleaginous yeast cell, *Yarrowia lipolytica*, algae, or plant cell) includes a recombinant nucleic acid, wherein the recombinant nucleic acid modulates the level of activity of a protein in the oleaginous organism (e.g. yeast cell, oleaginous yeast cell, *Yarrowia lipolytica*, algae, or plant cell) relative to the absence of the recombinant nucleic acid. In embodiments, the protein is selected from the group consisting of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA:diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), and IRC20 E3 ubiquitin-protein ligase and helicase (IRC20). In embodiments, the protein is Leucine Biosynthesis Gene (LEU2). In embodiments, the protein is Uracil Biosynthesis gene (URA3). In embodiments, the protein is multifunctional enzyme (MFE1). In embodiments, the protein is Transcription Factor (PEX10). In embodiments, the protein is AMP Deaminase (AMPD). In embodiments, the protein is ATP-Citrate Lyase (ACL) (e.g. ACL subunit 1, ACL subunit 2, or subunit 1 and 2). In embodiments, the protein is Malic Enzyme (MAE). In embodiments, the protein is Acetyl-CoA Carboxylase (ACC). In embodiments, the protein is acyl-CoA: diacylglycerol acyltransferase (DGA1). In embodiments, the protein is acyl-CoA:diacylglycerol acyltransferases (DGA2). In embodiments, the protein is Mitochondrial 2' O-ribose methyltransferase (MRM2). In embodiments, the protein is Lipid synthesis regulator (MGA2). In embodiments, the protein is Chromatin assembly gene (RLF2 subunit p90). In embodiments, the protein is O-6-methylguanine-DNA methyltransferase (MGMT). In embodiments, the protein is Aconitase (ACO1). In embodiments, the protein is Citrate Synthase (CIT1). In embodiments, the protein is RME1 zinc-finger transcription factor (RME1). In embodiments, the protein is YOX1 homeodomain protein (YOX1). In embodiments, the protein is UGA2 succinate semialdehyde dehydrogenase (UGA2). In embodiments, the protein is OSH6 oxysterol-binding protein homolog 6 (OSH6). In embodiments, the protein is IRC20 E3 ubiquitin-protein ligase and helicase (IRC20). In embodiments, modulating the level of activity of a protein in an oleaginous organism (e.g. yeast cell, oleaginous yeast cell, *Yarrowia lipolytica*, algae, or plant cell) is modulating the function of the protein. In embodiments, modulating the level of activity of a protein in an oleaginous organism (e.g. yeast cell, oleaginous yeast cell, *Yarrowia lipolytica*, algae, or plant cell) is modulating the amount of the protein. In embodiments, modulating the level of activity of a protein in an oleaginous organism (e.g. yeast cell, oleaginous yeast cell, *Yarrowia lipolytica*, algae, or plant cell) is modulating the transcription of the mRNA encoding the protein. In embodiments, modulating the level of activity of a protein in an oleaginous organism (e.g. yeast cell, oleaginous yeast cell, *Yarrowia lipolytica*, algae, or plant cell) is modulating the translation of the protein. In embodiments, modulating the level of activity of a protein in an oleaginous organism (e.g. yeast cell, oleaginous yeast cell, *Yarrowia lipolytica*, algae, or plant cell) is modulating the coding sequence of the gene encoding the protein (e.g. mutating (e.g. point mutant or missense mutant), truncating, inserting into, or deleting). In embodiments, modulating the level of activity of a protein in an oleaginous organism (e.g. yeast cell, oleaginous yeast cell, *Yarrowia lipolytica*, algae, or plant cell) is modulating the regulatory elements (e.g. promoter) of the gene encoding the protein. In embodiments, modulating the level of activity of a protein in an oleaginous organism (e.g. yeast cell, oleaginous yeast cell, *Yarrowia lipolytica*, algae, or plant cell) is modulating the stability of the protein. In embodiments, modulating the level of activity of a protein in an oleaginous organism (e.g. yeast cell, oleaginous yeast cell, *Yarrowia lipolytica*, algae, or plant cell) is modulating the stability of the transcript encoding the protein. In embodiments, modulating the level of activity of a protein in an oleaginous organism (e.g. yeast cell, oleaginous yeast cell, *Yarrowia lipolytica*, algae, or plant cell) is reducing the level of activity of the protein. In embodiments, modulating the level of activity of a protein in an oleaginous organism (e.g. yeast cell, oleaginous yeast cell, *Yarrowia lipolytica*, algae, or plant cell) is increasing the level of activity of the protein.

In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein in the citric acid cycle in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in the Kennedy Pathway in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in fatty acid synthesis in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in fatty acid storage (e.g. accumulation) in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that that modulates (e.g. reduces or increases) the level of activity of a protein involved in lipid synthesis in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in lipid storage (e.g. accumulation) in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in triacylglyceride storage (e.g. accumulation) in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in triacylglyceride synthesis in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in peroxisomal biogenesis in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in the beta-oxidation cycle in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in fatty acid degradation in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in lipid degradation in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in triacylglyceride degradation in the oleaginous organism relative to the absence of the genetic modification (e.g. recombinant nucleic acid). In embodiments, the oleaginous organism (e.g. yeast cell, oleaginous yeast cell, *Yarrowia lipolytica*, algae, or plant cell) includes a genetic modification (e.g. recombinant nucleic acid) that modulates (e.g. reduces or increases) the level of activity of a protein involved in central carbon metabolism in the oleaginous organism relative to the absence of the genetic modification (e.g. recombinant nucleic acid).

In embodiments, the recombinant nucleic acid increases the level of activity of a protein in the oleaginous organism (e.g. yeast cell, oleaginous yeast cell, *Yarrowia lipolytica*, algae, or plant cell). In embodiments, the protein is selected from the group consisting of Leucine Biosynthesis Gene (LEU2), Uracil Biosynthesis gene (URA3), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), and IRC20 E3 ubiquitin-protein ligase and helicase (IRC20). In embodiments, the protein is selected from the group consisting of Leucine Biosynthesis Gene (LEU2), Uracil Biosynthesis gene (URA3), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), 0-6-methylguanine-DNA methyltransferase (MGMT), and Citrate Synthase (CIT1). In embodiments, the protein is Leucine Biosynthesis Gene (LEU2). In embodiments, the protein is Uracil Biosynthesis gene (URA3). In embodiments, the protein is AMP Deaminase (AMPD). In embodiments, the protein is ATP-Citrate Lyase (ACL) (e.g. ACL subunit 1, ACL subunit 2, or subunit 1 and 2). In embodiments, the protein is Malic Enzyme (MAE). In embodiments, the protein is Acetyl-CoA Carboxylase (ACC). In embodiments, the protein is acyl-CoA:diacylglycerol acyltransferase (DGA1). In embodiments, the protein is acyl-CoA:diacylglycerol acyltransferases (DGA2). In embodiments, the protein is Mitochondrial 2' O-ribose methyltransferase (MRM2). In embodiments, the protein is Lipid synthesis regulator (MGA2). In embodiments, the protein is Chromatin assembly gene (RLF2 subunit p90). In embodiments, the protein is O-6-methylguanine-DNA methyltransferase (MGMT). In embodiments, the protein is Citrate Synthase (CIT1). In embodiments, the protein is RME1 zinc-finger transcription factor (RME1). In embodiments, the protein is YOX1 homeodomain protein (YOX1). In embodiments, the protein is UGA2 succinate semialdehyde dehydrogenase (UGA2). In embodiments, the protein is OSH6 oxysterol-binding protein homolog 6 (OSH6). In embodiments, the protein is IRC20 E3 ubiquitin-protein ligase and helicase (IRC20). In embodiments, the protein is selected from the group consisting of Leucine Biosynthesis Gene (LEU2), Uracil Biosynthesis gene (URA3), Malic Enzyme (MAE), Mitochondrial 2' O-ribose methyltransferase (MRM2), Lipid synthesis regulator (MGA2), and O-6-methylguanine-DNA methyltransferase (MGMT) or said nucleic acid decreases the level of activity of Lipid synthesis regulator (MGA2).

In embodiments, the genetic modification (e.g. recombinant nucleic acid) decreases the level of activity of a protein in the oleaginous organism (e.g. yeast cell, oleaginous yeast cell, Yarrowia lipolytica, algae, or plant cell). In embodiments, the protein is selected from the group consisting of multifunctional enzyme (MFE1), Lipid synthesis regulator (MGA2), Chromatin assembly gene (RLF2 subunit p90), Transcription Factor (PEX10), and Aconitase (ACO1). In embodiments, the protein is multifunctional enzyme (MFE1). In embodiments, the protein is Lipid synthesis regulator (MGA2). In embodiments, the protein is Chromatin assembly gene (RLF2 subunit p90). In embodiments, the protein is Transcription Factor (PEX10). In embodiments, the protein is Aconitase (ACO1). In embodiments, the protein is RME1 zinc-finger transcription factor (RME1). In embodiments, the protein is YOX1 homeodomain protein (YOX1). In embodiments, the protein is UGA2 succinate semialdehyde dehydrogenase (UGA2). In embodiments, the protein is OSH6 oxysterol-binding protein homolog 6 (OSH6). In embodiments, the protein is IRC20 E3 ubiquitin-protein ligase and helicase (IRC20).

In embodiments, the oleaginous organism (e.g. yeast cell, oleaginous yeast cell, Yarrowia lipolytica, algae, or plant cell) includes a plurality of genetic modifications (e.g. recombinant nucleic acids) that collectively modulate one, two, three, four, five, six, seven, eight, nine, ten, or more of the group of proteins consisting of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), and IRC20 E3 ubiquitin-protein ligase and helicase (IRC20).

In embodiments, the recombinant nucleic acid encodes a protein comprising a mutation relative to the wildtype protein. In embodiments, the mutation is a point mutation. In embodiments, the mutation is a deletion. In embodiments, the mutation is an insertion. In embodiments, the mutation is a fusion with a second protein. In embodiments, the recombinant nucleic acid encodes a mutant of a protein selected from the group consisting of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20).

In embodiments, the recombinant nucleic acid encodes a mutant of a protein selected from the group consisting of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), or IRC20 E3 ubiquitin-protein ligase and helicase (IRC20).

In embodiments, the recombinant nucleic acid is an AMP Deaminase (AMPD) having the nucleotide sequence of SEQ ID NO.:33. In embodiments, the recombinant nucleic acid is an AMP Deaminase (AMPD) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, or the entire sequence) with SEQ ID NO.:33, (e.g. using the same length of nucleotides for comparison or the entirety of both nucleic acids).

In embodiments, the recombinant nucleic acid is a Leucine Biosynthesis Gene (LEU2) having the nucleotide sequence of SEQ ID NO.:35. In embodiments, the recombinant nucleic acid is a Leucine Biosynthesis Gene (LEU2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, or the entire sequence) with SEQ ID NO.:35, (e.g. using the same length of nucleotides for comparison or the entirety of both nucleic acids).

In embodiments, the recombinant nucleic acid is a Uracil Biosynthesis gene (URA3) having the nucleotide sequence of SEQ ID NO.:37. In embodiments, the recombinant nucleic acid is a Uracil Biosynthesis gene (URA3) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, or the entire sequence) with SEQ ID NO.:37, (e.g. using the same length of nucleotides for comparison or the entirety of both nucleic acids).

In embodiments, the recombinant nucleic acid is an ATP-Citrate Lyase (ACL) (subunit 1) having the nucleotide sequence of SEQ ID NO.:39. In embodiments, the recombinant nucleic acid is an ATP-Citrate Lyase (ACL) (subunit 1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, or the entire sequence) with SEQ ID NO.:39, (e.g. using the same length of nucleotides for comparison or the entirety of both nucleic acids).

In embodiments, the recombinant nucleic acid is an ATP-Citrate Lyase (ACL) (subunit 2) having the nucleotide sequence of SEQ ID NO.:41. In embodiments, the recombinant nucleic acid is an ATP-Citrate Lyase (ACL) (subunit 2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, or the entire sequence) with SEQ ID NO.:41, (e.g. using the same length of nucleotides for comparison or the entirety of both nucleic acids).

In embodiments, the recombinant nucleic acid is a Malic Enzyme (MEA, MAE, MEA1) having the nucleotide sequence of SEQ ID NO.:43. In embodiments, the recombinant nucleic acid is a Malic Enzyme (MEA, MAE, MEA1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, or the entire sequence) with SEQ ID NO.:43, (e.g. using the same length of nucleotides for comparison or the entirety of both nucleic acids).

In embodiments, the recombinant nucleic acid is a acyl-CoA:diacylglycerol acyltransferase (DGA1) having the nucleotide sequence of SEQ ID NO.:45. In embodiments, the recombinant nucleic acid is a acyl-CoA: diacylglycerol acyltransferase (DGA1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, or the entire sequence) with SEQ ID NO.:45, (e.g. using the same length of nucleotides for comparison or the entirety of both nucleic acids).

In embodiments, the recombinant nucleic acid is a acyl-CoA:diacylglycerol acyltransferase (DGA2) having the nucleotide sequence of SEQ ID NO.:47. In embodiments, the recombinant nucleic acid is a acyl-CoA:diacylglycerol acyltransferase (DGA2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, or the entire sequence) with SEQ ID NO.:47, (e.g. using the same length of nucleotides for comparison or the entirety of both nucleic acids).

In embodiments, the recombinant nucleic acid is a Lipid synthesis regulator (MGA2) having the nucleotide sequence of SEQ ID NO.:49. In embodiments, the recombinant nucleic acid is a Lipid synthesis regulator (MGA2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, or the entire sequence) with SEQ ID NO.:49, (e.g. using the same length of nucleotides for comparison or the entirety of both nucleic acids).

In embodiments, the recombinant nucleic acid is a mutant Lipid synthesis regulator (MGA2-L36 mutant) having the nucleotide sequence of SEQ ID NO.:51. In embodiments, the recombinant nucleic acid is a mutant Lipid synthesis regulator (MGA2-L36 mutant) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, or the entire sequence) with SEQ ID NO.:51, (e.g. using the same length of nucleotides for comparison or the entirety of both nucleic acids).

In embodiments, the recombinant nucleic acid is a truncated Lipid synthesis regulator (MGA2-truncated) having the nucleotide sequence of SEQ ID NO.:53. In embodiments, the recombinant nucleic acid is a truncated Lipid synthesis regulator (MGA2-truncated) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, or the entire sequence) with SEQ ID NO.:53, (e.g. using the same length of nucleotides for comparison or the entirety of both nucleic acids).

In embodiments, the recombinant nucleic acid is a Chromatin assembly gene (RLF2 subunit p90) having the nucleotide sequence of SEQ ID NO.:58. In embodiments, the recombinant nucleic acid is a Chromatin assembly gene (RLF2 subunit p90) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, or the entire sequence) with SEQ ID NO.:58, (e.g. using the same length of nucleotides for comparison or the entirety of both nucleic acids).

In embodiments, the recombinant nucleic acid is a Mitochondrial 2' O-ribose methyltransferase (MRM2) having the nucleotide sequence of SEQ ID NO.:63. In embodiments, the recombinant nucleic acid is a Mitochondrial 2' O-ribose methyltransferase (MRM2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, or the entire sequence) with SEQ ID NO.:63, (e.g. using the same length of nucleotides for comparison or the entirety of both nucleic acids).

In embodiments, the recombinant nucleic acid is a Citrate Synthase (CIT1) having the nucleotide sequence of SEQ ID NO.:67. In embodiments, the recombinant nucleic acid is a Citrate Synthase (CIT1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, or the entire sequence) with SEQ ID NO.:67, (e.g. using the same length of nucleotides for comparison or the entirety of both nucleic acids).

In embodiments, the recombinant nucleic acid is a Acetyl-CoA Carboxylase (ACC) having the nucleotide sequence of SEQ ID NO.:69. In embodiments, the recombinant nucleic acid is a Acetyl-CoA Carboxylase (ACC) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 3000, 4000, 5000, 6000, 7000, or the entire sequence) with SEQ ID NO.:69, (e.g. using the same length of nucleotides for comparison or the entirety of both nucleic acids).

In embodiments, the recombinant nucleic acid is a Transcription Factor (PEX10) having the nucleotide sequence of SEQ ID NO.:71. In embodiments, the recombinant nucleic acid is a Transcription Factor (PEX10) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, or the entire sequence) with SEQ ID NO.:71, (e.g. using the same length of nucleotides for comparison or the entirety of both nucleic acids).

In embodiments, the recombinant nucleic acid is a multifunctional enzyme (MFE1) having the nucleotide sequence of SEQ ID NO.:73. In embodiments, the recombinant nucleic acid is a multifunctional enzyme (MFE1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 2100, 2200, 2300, or the entire sequence) with SEQ ID NO.:73, (e.g. using the same length of nucleotides for comparison or the entirety of both nucleic acids).

In embodiments, the recombinant nucleic acid is a Aconitase (ACO1) having the nucleotide sequence of SEQ ID NO.:75. In embodiments, the recombinant nucleic acid is a Aconitase (ACO1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, or the entire sequence) with SEQ ID NO.:75, (e.g. using the same length of nucleotides for comparison or the entirety of both nucleic acids).

In embodiments, the recombinant nucleic acid is a YOX1 homeodomain protein (YOX1) having the nucleotide sequence of SEQ ID NO.:77. In embodiments, the recombinant nucleic acid is a YOX1 homeodomain protein (YOX1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, or the entire sequence) with SEQ ID NO.:77, (e.g. using the same length of nucleotides for comparison or the entirety of both nucleic acids).

In embodiments, the recombinant nucleic acid is a UGA2 succinate semialdehyde dehydrogenase (UGA2) having the nucleotide sequence of SEQ ID NO.:78. In embodiments, the recombinant nucleic acid is a UGA2 succinate semialdehyde dehydrogenase (UGA2) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, or the entire sequence) with SEQ ID NO.:78, (e.g. using the same length of nucleotides for comparison or the entirety of both nucleic acids).

In embodiments, the recombinant nucleic acid is a RME1 zinc-finger transcription factor (RME1) having the nucleotide sequence of SEQ ID NO.:79. In embodiments, the recombinant nucleic acid is a RME1 zinc-finger transcription factor (RME1) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, or the entire sequence) with SEQ ID NO.:79, (e.g. using the same length of nucleotides for comparison or the entirety of both nucleic acids).

In embodiments, the recombinant nucleic acid is a OSH6 oxysterol-binding protein homolog 6 (OSH6) having the nucleotide sequence of SEQ ID NO.:80. In embodiments, the recombinant nucleic acid is a OSH6 oxysterol-binding protein homolog 6 (OSH6) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, or the entire sequence) with SEQ ID NO.:80, (e.g. using the same length of nucleotides for comparison or the entirety of both nucleic acids).

In embodiments, the recombinant nucleic acid is a IRC20 E3 ubiquitin-protein ligase and helicase (IRC20) having the nucleotide sequence of SEQ ID NO.:81. In embodiments, the recombinant nucleic acid is a IRC20 E3 ubiquitin-protein ligase and helicase (IRC20) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, 1600, 1700, 1800, 1900, 2000, 3000, 4000, 5000, or the entire sequence) with SEQ ID NO.:81, (e.g. using the same length of nucleotides for comparison or the entirety of both nucleic acids).

In embodiments, the recombinant nucleic acid is a O-6-methylguanine-DNA methyltransferase (MGMT) having the nucleotide sequence of SEQ ID NO.:65. In embodiments, the recombinant nucleic acid is a O-6-methylguanine-DNA methyltransferase (MGMT) having at least 60% identity (e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) over a region of at least 100 nucleotides (e.g. at least 200, 300, 400, 500, 600, 700, 800, 900, 1000, 1100, 1200, 1300, 1400, 1500, or the entire sequence) with SEQ ID NO.:65, (e.g. using the same length of nucleotides for comparison or the entirety of both nucleic acids).

In embodiments, the oleaginous organism (e.g. yeast cell, oleaginous yeast cell, *Yarrowia lipolytica*, algae, or plant cell) includes a recombinant nucleic acid that decreases the level of activity of multifunctional enzyme (MFE1) protein and Transcription Factor (PEX10) protein, increases the level of activity of acyl-CoA: diacylglycerol acyltransferase (DGA1) protein, or increases the level of activity of Leucine Biosynthesis Gene (LEU2) protein relative to a oleaginous organism (e.g. yeast cell, oleaginous yeast cell, *Yarrowia lipolytica*, algae, or plant cell) that does not include the recombinant nucleic acid. In embodiments, the oleaginous organism (e.g. yeast cell, oleaginous yeast cell, *Yarrowia lipolytica*, algae, or plant cell) includes recombinant nucleic acids that decrease the level of activity of multifunctional enzyme (MFE1) protein and Transcription Factor (PEX10) protein, increase the level of activity of acyl-CoA:diacylglycerol acyltransferase (DGA1) protein, and increase the level of activity of Leucine Biosynthesis Gene (LEU2) protein relative to a oleaginous organism (e.g. yeast cell, oleaginous yeast cell, *Yarrowia lipolytica*, algae, or plant cell) that does not include the recombinant nucleic acids. In embodiments, the level of activity is the level of expression of the protein.

In embodiments, the oleaginous organism (e.g. yeast cell, oleaginous yeast cell, *Yarrowia lipolytica*, algae, or plant cell) includes an extra-chromosomal recombinant nucleic acid. In embodiments, the oleaginous organism (e.g. yeast cell, oleaginous yeast cell, *Yarrowia lipolytica*, algae, or plant cell) includes a recombinant nucleic acid integrated into the oleaginous organism (e.g. yeast cell, oleaginous yeast cell, *Yarrowia lipolytica*, algae, or plant cell) genome. In embodiments, the extra-chromosomal recombinant nucleic acid includes a gene that is also included in the genome of the yeast cell oleaginous organism (e.g. yeast cell, oleaginous yeast cell, *Yarrowia lipolytica*, algae, or plant cell) (e.g. Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA:diacylglycerol acyltransferase (DGA1), acyl-CoA:diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Aconitase (ACO1), Citrate Synthase (CIT1), RME1 zinc-finger transcription factor (RME1), YOX1 homeodomain protein (YOX1), UGA2 succinate semialdehyde dehydrogenase (UGA2), OSH6 oxysterol-binding protein homolog 6 (OSH6), IRC20 E3 ubiquitin-protein ligase and helicase (IRC20), a wildtype version thereof, or a mutant version thereof). In embodiments, the extra-chromosomal recombinant nucleic acid includes a gene that is also included in the genome of the oleaginous organism (e.g. yeast cell, oleaginous yeast cell, *Yarrowia lipolytica*, algae, or plant cell) (e.g. Leucine Biosynthesis Gene (LEU2), Uracil Biosynthesis gene (URA3), AMP Deaminase (AMPD), ATP-Citrate Lyase (ACL) (e.g. ACL subunit 1, ACL subunit 2, or subunit 1 and 2), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), O-6-methylguanine-DNA methyltransferase (MGMT), Citrate Synthase (CIT1), RME1 zinc-finger transcription factor (RME1), YOX1 homeodomain protein (YOX1), UGA2 succinate semialdehyde dehydrogenase (UGA2), OSH6-oxysterol-binding protein homolog 6 (OSH6), IRC20 E3 ubiquitin-protein ligase and helicase (IRC20), a wildtype version thereof, or a mutant version thereof). In embodiments, a recombinant nucleic acid integrated into the oleaginous organism (e.g. yeast cell, oleaginous yeast cell, *Yarrowia lipolytica*, algae, or plant cell) genome replaces (e.g. partially or completely) a promoter included in the oleaginous organism (e.g. yeast cell, oleaginous yeast cell, *Yarrowia lipolytica*, algae, or plant cell) genome pror to integration of the recombinant nucleic acid.

In embodiments, the yeast cell is a yeast cell including one or more genetic modifications (e.g. recombinant nucleic acids), as described herein (including in the Examples section below, the tables, the figures, and the claims herein). In embodiments, the yeast cell is a yeast cell described herein, including in an example, table, figure, or claim. In embodiments, the oleaginous yeast cell is L36 as described herein (e.g. examples, tables, and figures). In embodiments, the oleaginous yeast cell is derived from L36 as described herein (e.g. examples, tables, and figures). In embodiments, the oleaginous yeast cell is E26 as described herein (e.g. examples, tables, and figures). In embodiments, the oleaginous yeast cell is E13 as described herein (e.g. examples, tables, and figures). In embodiments, the oleaginous yeast cell is derived from E26 or E13.

In embodiments, the dry weight of the genetically modified yeast cell described herein includes greater than about 20% wt/wt lipids, lipid precursors, and/or oleochemicals (e.g., greater than about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%; greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%; of lipid; lipids; lipid precursors; lipid precursor, oleochemical, and/or oleochemicals).

In embodiments, the genetically modified yeast cell described herein includes a recombinant Leucine Biosynthesis Gene (LEU2). In embodiments, the genetic modification increases the level of activity of the Leucine Biosynthesis Gene (LEU2) protein relative to an otherwise identical yeast cell lacking the genetic modification. In embodiments, the genetically modified yeast cell described herein is capable of de novo synthesis of leucine (e.g. at sufficient levels to meet the leucine requirements of the yeast cell). In embodiments, the genetically modified yeast cell described herein is capable of de novo synthesis of leucine independent of the genetic modification. In embodiments, the genetically modified yeast cell described herein includes a recombinant Uracil Biosynthesis gene (URA3). In embodiments, the genetic modification increases the level of activity of the Uracil Biosynthesis gene (URA3) protein relative to an otherwise identical yeast cell lacking the genetic modification. In embodiments, the genetically modified yeast cell described herein is capable of de novo synthesis of uracil (e.g. at sufficient levels to meet the uracil requirements of the yeast cell). In embodiments, the genetically modified yeast cell described herein is capable of de novo synthesis of uracil independent of the genetic modification. In embodiments, the genetically modified yeast cell described herein includes a genetically modified multifunctional enzyme (MFE1) gene. In embodiments, the genetic modification decreases the level of activity of the multifunctional enzyme (MFE1) protein relative to an otherwise identical yeast cell lacking the genetic modification. In embodiments, the genetically modified yeast cell described herein includes a genetically modified PEX10 Transcription Factor (PEX10) gene. In embodiments, the genetic modification decreases the level of activity of the PEX10 Transcription Factor (PEX10) protein relative to an otherwise identical yeast cell lacking the genetic modification. In embodiments, the genetically modified yeast cell described herein includes a recombinant AMP Deaminase (AMPD) protein. In embodiments, the genetic modification increases the level of activity of the AMP Deaminase (AMPD) protein relative to an otherwise identical yeast cell lacking the genetic modification. In embodiments, the genetically modified yeast cell described herein includes a recombinant ATP-Citrate Lyase 1 (ACL1) protein. In embodiments, the genetic modification increases the level of activity of the ATP-Citrate Lyase 1 (ACL1) protein relative to an otherwise identical yeast cell lacking the genetic modification. In embodiments, the genetically modified yeast cell described herein includes a recombinant ATP-Citrate Lyase 2 (ACL2) protein. In embodiments, the genetic modification increases the level of activity of the ATP-Citrate Lyase 2 (ACL2) protein relative to an otherwise identical yeast cell lacking the genetic modification. In embodiments, the genetically modified yeast cell described herein includes a recombinant ATP-Citrate Lyase 1 (ACL1) protein and ATP-Citrate Lyase 2 (ACL2) protein. In embodiments, the genetic modification increases the level of activity of the ATP-Citrate Lyase 1 (ACL1) protein and ATP-Citrate Lyase 2 (ACL2) protein relative to an otherwise identical yeast cell lacking the genetic modification. In embodiments, the genetically modified yeast cell described herein includes a recombinant Malic Enzyme (MAE) protein. In embodiments, the genetic modification increases the level of activity of the Malic Enzyme (MAE) protein relative to an otherwise identical yeast cell lacking the genetic modification. In embodiments, the genetically modified yeast cell described herein includes a recombinant Acetyl-CoA Carboxylase (ACC) protein. In embodiments, the genetic modification increases the level of activity of the Acetyl-CoA Carboxylase (ACC) protein relative to an otherwise identical yeast cell lacking the genetic modification. In embodiments, the genetically modified yeast cell described herein includes a recombinant acyl-CoA:diacylglycerol acyltransferase 1 (DGA1) protein. In embodiments, the genetic modification increases the level of activity of the acyl-CoA:diacylglycerol acyltransferase 1 (DGA1) protein relative to an otherwise identical yeast cell lacking the genetic modification. In embodiments, the genetically modified yeast cell described herein includes a recombinant acyl-CoA:diacylglycerol acyltransferase 2 (DGA2) protein. In embodiments, the genetic modification increases the level of activity of the acyl-CoA:diacylglycerol acyltransferase 2 (DGA2) protein relative to an otherwise identical yeast cell lacking the genetic modification. In embodiments, the genetically modified yeast cell described herein includes a recombinant Mitochondrial 2' O-ribose methyltransferase (MRM2) protein. In embodiments, the genetic modification increases the level of activity of the Mitochondrial 2' O-ribose methyltransferase (MRM2) protein relative to an otherwise identical yeast cell lacking the genetic modification. In embodiments, the genetically modified yeast cell described herein includes a recombinant Lipid synthesis regulator (MGA2) protein. In embodiments, the genetically modified yeast cell described herein includes a genetically modified Lipid synthesis regulator (MGA2) gene. In embodiments, the genetically modified yeast cell described herein includes at least one nucleotide deletion in the genomic Lipid synthesis regulator (MGA2) gene and expression of a Lipid synthesis regulator (MGA2) protein including a mutation corresponding to G643R in *Yarrowia lipolytica* Lipid synthesis regulator (MGA2) In embodiments, the genetic modification decreases the level of activity of the Lipid synthesis regulator (MGA2) protein relative to an otherwise identical yeast cell lacking the genetic modification. In embodiments, the genetically modified yeast cell described herein includes a genetically modified Chromatin assembly gene (RLF2 subunit p90) gene. In embodiments, the genetic modification decreases the level of activity of the Chromatin assembly gene (RLF2 subunit p90) protein relative to an otherwise identical yeast cell lacking the genetic modification. In embodiments, the genetically modified yeast cell described herein includes a recombinant O-6-methylguanine-DNA methyltransferase (MGMT) protein. In embodiments, the genetic modification increases the level of activity of the O-6-methylguanine-DNA methyltransferase (MGMT) protein relative to an otherwise identical yeast cell lacking the genetic modification. In embodiments, the genetically modified yeast cell described herein includes a genetically modified Aconitase (ACO1) gene. In embodiments, the genetic modification decreases the level of activity of the Aconitase (ACO1) protein relative to an otherwise identical yeast cell lacking the genetic modification. In embodiments, the genetically modified yeast cell described herein includes a recombinant Citrate Synthase (CIT1) gene. In embodiments, the genetic modification increases the level of activity of the Citrate Synthase (CIT1) protein relative to an otherwise identical yeast cell lacking the genetic modification. In embodiments, the genetically modified yeast cell described herein includes a genetically modified RME1 zinc-finger transcription factor (RME1) gene. In embodiments, the genetic modification decreases the level of activity of the RME1 zinc-finger transcription factor (RME1) protein relative to an otherwise identical yeast cell lacking the genetic modification. In embodiments, the genetically modified yeast cell described herein includes a genetically modified YOX1 homeodomain protein (YOX1) gene. In embodiments, the genetic modification decreases the level of activity of the YOX1 homeodomain protein (YOX1) protein relative to an otherwise identical yeast cell lacking the genetic modification. In embodiments, the genetically modified yeast cell described herein includes a genetically modified UGA2 succinate semialdehyde dehydrogenase (UGA2) gene. In embodiments, the genetic modification decreases the level of activity of the UGA2 succinate semialdehyde dehydrogenase (UGA2) protein relative to an otherwise identical yeast cell lacking the genetic modification. In embodiments, the genetically modified yeast cell described herein includes a genetically modified OSH6 oxysterol-binding protein homolog 6 (OSH6) gene. In embodiments, the genetic modification decreases the level of activity of the OSH6 oxysterol-binding protein homolog 6 (OSH6) protein relative to an otherwise identical yeast cell lacking the genetic modification. In embodiments, the genetically modified yeast cell described herein includes a genetically modified IRC20 E3 ubiquitin-protein ligase and helicase (IRC20) gene. In embodiments, the genetic modification decreases the level of activity of the IRC20 E3 ubiquitin-protein ligase and helicase (IRC20) protein relative to an otherwise identical yeast cell lacking the genetic modification. In embodiments, the gene or protein described herein is a *Yarrowia lipolytica* gene or protein. In embodiments, the gene or protein is a yeast gene or protein corresponding to the *Yarrowia lipolytica* gene or protein. In embodiments, the gene or protein is a gene or protein from an oleaginous organism corresponding to the *Yarrowia lipolytica* gene or protein. In embodiments, the gene or protein is the *Yarrowia lipolytica* gene or protein identified by sequence herein. In embodiments, the gene or protein is a mutant gene or protein of a wildtype gene or protein corresponding to the *Yarrowia lipolytica* gene or protein. In embodiments, the gene or protein is a mutant gene or protein of a wildtype yeast gene or protein corresponding to the *Yarrowia lipolytica* gene or protein. In embodiments, the gene or protein is a homolog of the *Yarrowia lipolytica* gene or protein. In embodiments, the gene or protein is a homolog of the *Yarrowia lipolytica* gene or protein identified by sequence herein. In embodiments, the gene or protein is a mutant of the *Yarrowia lipolytica* gene or protein. In embodiments, the gene or protein described in this paragraph is LEU2, URA3, MFE1, PEX10, AMPD, ACL, ACL1, ACL2, MAE, ACC, DGA, DGA1, DGA2, MRM2, MGA2, RLF2 subunit p90, MGMT, ACO1, CIT1, RME1, YOX1, UGA2, OSH6, or IRC20). In embodiments, the gene or protein described in this paragraph is LEU2, URA3, MFE1, PEX10, AMPD, ACL, ACL1, ACL2, MAE, ACC, DGA, DGA1, DGA2, MRM2, MGA2, RLF2 subunit p90, MGMT, ACO1, CIT1, RME1, YOX1, UGA2, OSH6, or IRC20), having the sequence identified herein.

In embodiments, the genetic modification modulates the level of activity of a component of a lipid biosynthetic pathway. In embodiments, the genetic modification modulates the level of activity of a component of a lipid precursor biosynthetic pathway. In embodiments, the genetic modification modulates the level of activity of a component of an oleochemical biosynthetic pathway. In embodiments, the genetic modification modulates the level of activity of a component of a pathway incorporating Acetyl-CoA into a lipid, lipid precursor, or oleochemical. In embodiments, the genetic modification modulates the level of activity of a component of a pathway incorporating malonyl-CoA into a lipid, lipid precursor, or oleochemical. In embodiments, the genetic modification increases the level of activity of a component of a lipid biosynthetic pathway. In embodiments, the genetic modification increases the level of activity of a component of a lipid precursor biosynthetic pathway. In embodiments, the genetic modification increases the level of activity of a component of an oleochemical biosynthetic pathway. In embodiments, the genetic modification increases the level of activity of a component of a pathway incorporating acetyl-CoA into a lipid, lipid precursor, or oleochemical. In embodiments, the genetic modification increases the level of activity of a component of a pathway incorporating malonyl-CoA into a lipid, lipid precursor, or oleochemical. In embodiments, the genetic modification modulates the level of activity of a component of a lipid, or lipid precursor, metabolic pathway. In embodiments, the genetic modification decreases the level of activity of a component of a lipid, or lipid precursor, metabolic pathway. In embodiments, the genetic modification decreases the level of activity of a component of a lipid, or lipid precursor, metabolic pathway. In embodiments, the genetic modification increases the level of acetyl-CoA in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification increases the level of malonyl-CoA in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification increases the level of triglyceride production in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification decreases the level of beta-oxidation activity in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification decreases the level of fatty acid catabolism in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification decreases the level of peroxisome biogenesis activity in the genetically modified oleaginous organism (e.g. yeast cell, oleaginous yeast cell, *Yarrowia lipolytica*, algae, or plant cell) relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification produces a lipid, lipid precursor, or oleochemical at a higher level than by a genetically unmodified oleaginous organism (e.g. yeast cell, oleaginous yeast cell, *Yarrowia lipolytica*, algae, or plant cell) that is otherwise identical to the genetically modified oleaginous organism (e.g. yeast cell, oleaginous yeast cell, *Yarrowia lipolytica*, algae, or plant cell). In embodiments, the genetically modified oleaginous organism (e.g. yeast cell, oleaginous yeast cell, *Yarrowia lipolytica*, algae, or plant cell) produces a lipid, lipid precursor, or oleochemical at a higher level than by a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the genetic modification modulates the level of activity of a component of the citric acid cycle. In embodiments, the genetic modification modulates the level of activity of a component of the TCA cycle. In embodiments, the genetic modification modulates the level of activity of a component of the Kennedy pathway. In embodiments, the genetic modification reduces the level of activity of the TCA cycle. In embodiments, the genetic modification increases the level of activity of the Kennedy pathway.

In embodiments, the lipid, lipid precursor, or oleochemical produced at a higher level by the genetically modified oleaginous organism (e.g. yeast cell, oleaginous yeast cell, *Yarrowia lipolytica*, algae, or plant cell) is a fatty acid, wax, sterol, vitamin, monoglyceride, diglyceride, triglyceride, phospholipid, glycerolipid, glycerophospholipid, sphingolipid, saccharolipid, polyketide, sterol lipid, triacylglyceride, prenol lipid, fatty acid ester, fatty acid methyl ester, fatty acid ethyl ester, fatty acid propyl ester, fatty acid butyl ester, fatty alcohol, fatty amine, glycerol, alcohol ethoxylate, alcohol sulfate, or alcohol ether sulfate. In embodiments, the genetic modification includes a mutation relative to the wild type gene. In embodiments, the genetic modification includes a deletion of a portion of a gene. In embodiments, the genetically modified oleaginous organism (e.g. yeast cell, oleaginous yeast cell, *Yarrowia lipolytica*, algae, or plant cell) includes an increased level of a fatty acid selected from the group consisting of C5:0, C5:1, C5:2, C5:3, C6:0, C6:1, C6:2, C6:3, C7:0, C7:1, C7:2, C7:3, C8:0, C8:1, C8:2, C8:3, C9:0, C9:1, C9:2, C9:3, C10:0, C10:1, C10:2, C10:3, C11:0, C11:1, C11:2, C11:3, C12:0, C12:1, C12:2, C12:3, C13:0, C13:1, C13:2, C13:3, C14:0, C14:1, C14:2, C14:3, C15:0, C15:1, C15:2, C15:3, C16:0, C16:1, C16:2, C16:3, C17:0, C17:1, C17:2, C17:3, C18:0, C18:1, C18:2, C18:3, C19:0, C19:1, C19:2, C19:3, C20:0, C20:1, C20:2, C20:3, C21:0, C21:1, C21:2, C21:3, C22:0, C22:1, C22:2, C22:3, C23:0, C23:1, C23:2, and C23:3, relative to a genetically unmodified oleaginous organism (e.g. yeast cell, oleaginous yeast cell, *Yarrowia lipolytica*, algae, or plant cell) that is otherwise identical (e.g. genetically) to the genetically modified oleaginous organism (e.g. yeast cell, oleaginous yeast cell, *Yarrowia lipolytica*, algae, or plant cell). In embodiments, the fatty acid is C17:0 C17:1. In embodiments, the fatty acid is C16:1n9.

In embodiments, the genetic modification is an engineered genetic modification. In embodiments, the engineered genetic modification includes modulated expression of a protein. In embodiments, the engineered genetic modification includes increased expression of a protein. In embodiments, the engineered genetic modification includes decreased expression of a protein. In embodiments, the genetic modification is associated with exposure to a mutagen. In embodiments, the genetic modification includes modulated expression of a protein in a lipid, or lipid precursor, or oleochemical biosynthetic pathway.

III. METHODS OF MAKING AND PURIFYING LIPIDS, LIPID PRECURSORS, AND/OR OLEOCHEMICALS

Lipids, lipid precursors, and/or oleochemicals (e.g., lipid, lipids, lipid precursors, lipid precursor, oleochemicals, or oleochemical) produced by cells of the invention can be harvested, or otherwise collected, by any convenient method (e.g. centrifugation of extracellular secreted lipids, exposure to solvent, whole cell extraction (e.g. cell disruption and collection), hydrophobic solvent extraction (e.g. hexane), liquefaction, supercritical carbon dioxide extraction, freeze drying, mechanical pulverization, secretion (e.g. by addition of effective exporter proteins), or combinations thereof).

In embodiments, reduced nitrogen conditions promote accumulation of lipids, lipid precursors, and/or oleochemicals (e.g., lipid, lipids, lipid precursors, lipid precursor, oleochemicals, or oleochemical). In embodiments, cells (e.g. oleaginous organisms or oleaginous yeast) are first cultured in standard conditions and then cultured in low nitrogen conditions where harvesting is desired. In embodiments, oleaginous yeast species are grown in a medium including a carbon substrate and/or nitrogen source, optionally in the absence of light, optionally in an aerobic environment. In embodiments, media for culturing oleaginous yeast may include a carbon substrate, a fixed nitrogen source, trace elements, a buffer for pH maintenance, phosphate, or a combination thereof.

In embodiments, the carbon substrate may be selected from the group consisting of monosaccharides, oligosaccharides, polysaccharides, alkanes, fatty acids, esters of fatty acids, monoglycerides, carbon dioxide, methanol, formaldehyde, formate, carbon-containing amines, glucose, fructose, sucrose, lactose, galactose, xylose, mannose, rhamnose, arabinose, glycerol, acetate, depolymerized sugar beet pulp, black liquor, corn starch, depolymerized cellulosic material, corn stover, sugar beet pulp, switchgrass, milk whey, molasses, potato, rice, sorghum, sugar cane, wheat, thick cane juice, sugar beet juice, wheat, lignocellulosic biomass, and combinations thereof.

Examples of cellulosic material that may be depolymerized and used as a carbon substrate (e.g. fixed carbon source) include sugarcane bagasse, rice hulls, corn fiber (including stalks, leaves, husks, and cobs), wheat straw, rice straw, sugar beet pulp, citrus pulp, citrus peels; hardwood and softwood thinnings; hardwood and softwood residues; saw mill wastes (wood chips, sawdust) and pulp mill waste; paper fractions of municipal solid waste; municipal grass clippings; wood construction waste; and cellulosic crops such as switchgrass, hybrid poplar wood, and *miscanthus*, fiber cane, and fiber sorghum.

Oleaginous yeast cultures may yield oleaginous yeast biomass in fermentation media. To extract lipids, lipid precursors, and/or oleochemicals (e.g., lipid, lipids, lipid precursors, lipid precursor, oleochemicals, or oleochemical)

from the biomass, the biomass may be harvested, concentrated, dewatered (i.e. separation of the biomass from the liquid medium) (e.g. through centrifugation, filtration, use of mechanical pressure, simple sedimentation, or sedimentation), or combinations thereof. Centrifugation does not always remove significant amounts of intracellular water from the oleaginous yeast and so is often considered a dewatering, not a drying, step. The biomass can optionally be dried (oven dried, lyophilized, and the like) and conditioned prior to cell disruption (lysis).

In a second aspect is provided a method of producing a lipid, lipid precursor, or oleochemical (e.g., lipid, lipid precursor, oleochemical) including: 1) culturing a yeast cell as described herein (including embodiments or as described in the examples, tables, figures, and/or claims) in a growth medium; and 2) isolating the lipid, lipid precursor, or oleochemical (e.g., lipid, lipid precursor, oleochemical) (e.g. from the medium or yeast cell).

In embodiments, the lipid, lipid precursor, or oleochemical (e.g., lipid, lipid precursor, oleochemical) is isolated from the yeast cell. In embodiments, the lipid, lipid precursor, or oleochemical (e.g., lipid, lipid precursor, oleochemical) is isolated from the medium. In embodiments, the growth medium includes a majority carbon source selected from the group consisting of glucose, glycerol, xylose, fructose, mannose, ribose, sucrose, and lignocellulosic biomass. In embodiments, the majority carbon source is glucose. In embodiments, the majority carbon source is glycerol. In embodiments, the majority carbon source is xylose. In embodiments, the majority carbon source is fructose. In embodiments, the majority carbon source is mannose. In embodiments, the majority carbon source is ribose. In embodiments, the majority carbon source is sucrose. In embodiments, the majority carbon source is lignocellulosic biomass. In embodiments, the carbon source is glucose. In embodiments, the carbon source is glycerol. In embodiments, the carbon source is xylose. In embodiments, the carbon source is fructose. In embodiments, the carbon source is mannose. In embodiments, the carbon source is ribose. In embodiments, the carbon source is sucrose. In embodiments, the carbon source is lignocellulosic biomass. In embodiments, the majority carbon source is not glucose. In embodiments, the majority nitrogen source is ammonium sulfate (($NH_4$)$_2SO_4$).

In embodiments, the growth medium includes a carbon source and a nitrogen source wherein the carbon source is at a concentration at least 2-fold greater than the concentration of the nitrogen source. In embodiments, the carbon source is at a concentration at least 3-fold greater than the concentration of the nitrogen source. In embodiments, the carbon source is at a concentration at least 4-fold greater than the concentration of the nitrogen source. In embodiments, the carbon source is at a concentration at least 5-fold greater than the concentration of the nitrogen source. In embodiments, the carbon source is at a concentration at least 6-fold greater than the concentration of the nitrogen source. In embodiments, the carbon source is at a concentration at least 7-fold greater than the concentration of the nitrogen source. In embodiments, the carbon source is at a concentration at least 8-fold greater than the concentration of the nitrogen source. In embodiments, the carbon source is at a concentration at least 9-fold greater than the concentration of the nitrogen source. In embodiments, the carbon source is at a concentration at least 10-fold greater than the concentration of the nitrogen source. In embodiments, the carbon source is at a concentration at least 11-fold greater than the concentration of the nitrogen source. In embodiments, the carbon source is at a concentration at least 12-fold greater than the concentration of the nitrogen source. In embodiments, the carbon source is at a concentration at least 13-fold greater than the concentration of the nitrogen source. In embodiments, the carbon source is at a concentration at least 14-fold greater than the concentration of the nitrogen source. In embodiments, the carbon source is at a concentration at least 15-fold greater than the concentration of the nitrogen source. In embodiments, the carbon source is at a concentration at least 16-fold greater than the concentration of the nitrogen source. In embodiments, the carbon source is at a concentration at least 17-fold greater than the concentration of the nitrogen source. In embodiments, the carbon source is at a concentration at least 18-fold greater than the concentration of the nitrogen source. In embodiments, the carbon source is at a concentration at least 19-fold greater than the concentration of the nitrogen source. In embodiments, the carbon source is at a concentration at least 20-fold greater than the concentration of the nitrogen source. In embodiments, the ratio of the carbon source to the nitrogen source (wt/wt) is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In embodiments, the ratio of the carbon source to the nitrogen source (wt/wt) is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In embodiments, the ratio of the carbon source to the nitrogen source (wt/wt) is about 0.03125, 0.0625, 0.125, 0.25, 0.5, 1.0, 2.0, 4.0, 8.0, 16, 32, 64, 128, 256, 512, 1024, 1600, 2048, 4096, 8192, or 16284. In embodiments, the ratio of the carbon source to the nitrogen source (wt/wt) is about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, or 10000. In embodiments, the ratio of the carbon source to the nitrogen source (wt/wt) is 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, or 10000. In embodiments, the ratio of the carbon source to the nitrogen source (wt/wt) is at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 500, 550, 600, 650, 700, 750, 800, 850, 900, 950, 1000, 2000, 3000, 4000, 5000, 6000, 7000, 8000, 9000, or 10000. In embodiments, the carbon source to nitrogen source ratio corresponds to a ratio calculated from one or more of the ratios described above when the ratios described above are for a carbon source of glucose (g/L) and a nitrogen source of ammonium sulfate (g/L) for a carbon source that may not be glucose and a nitrogen source that may not be ammonium sulfate. In embodiments, the ratio of the concentration of the carbon source to the concentration of the nitrogen source is as described herein, including in embodiments, examples, tables, figures, and claims. In embodiments, the amount and ratio of the carbon source to the nitrogen source (wt/wt) is equivalent to 160:0.2 glucose:ammonium sulfate. In embodiments, the amount and ratio of the carbon source to the nitrogen source (wt/wt) is equivalent to 80:5 glucose: ammonium sulfate.

In embodiments, the carbon source is at a concentration (g/L) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 100, 410, 420, 430, 440, 450, 460, 470, 480, 490, or 500. In embodiments, the carbon source is at a concentration (g/L) of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 100, 410, 420, 430, 440, 450, 460, 470, 480, 490, or 500. In embodiments, the carbon source, which is optionally not glucose, is at a concentration for the carbon source that would provide an equal amount of carbon as one of the amounts described above where the amount described above is for glucose.

In embodiments, the nitrogen source is at a concentration (g/L) of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100. In embodiments, the nitrogen source is at a concentration (g/L) of 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100. In embodiments, the nitrogen source, which is optionally not ammonium sulfate, is at a concentration for the nitrogen source that would provide an equal amount of nitrogen as one of the amounts described above where the amount described above is for ammonium sulfate.

In embodiments, the growth medium includes a micronutrient. In embodiments, the growth medium includes a plurality of micronutrients. In embodiments, the growth medium includes cobalt, iron, magnesium, potassium, zinc, nickel, molybdenum, manganese, copper, and/or boron. In embodiments, the growth medium includes iron and copper or molybdenum. In embodiments, the growth medium includes copper and nickel. In embodiments, the growth medium includes copper, iron, and either molybdenum or nickel. In embodiments, the growth medium includes copper, iron, molybdenum, and nickel. In embodiments, the growth medium includes cobalt. In embodiments, the growth medium includes iron. In embodiments, the growth medium includes magnesium. In embodiments, the growth medium includes potassium. In embodiments, the growth medium includes zinc. In embodiments, the growth medium includes nickel. In embodiments, the growth medium includes molybdenum. In embodiments, the growth medium includes manganese. In embodiments, the growth medium includes copper. In embodiments, the growth medium includes boron. In embodiments, the growth medium is supplemented with cobalt, iron, magnesium, potassium, zinc, nickel, molybdenum, manganese, copper, and/or boron. In embodiments, the growth medium is supplemented with iron and copper or molybdenum. In embodiments, the growth medium is supplemented with copper and nickel. In embodiments, the growth medium is supplemented with copper, iron, and either molybdenum or nickel. In embodiments, the growth medium is supplemented with copper, iron, molybdenum, and nickel. In embodiments, the growth medium is supplemented with cobalt. In embodiments, the growth medium is supplemented with iron. In embodiments, the growth medium is supplemented with magnesium. In embodiments, the growth medium is supplemented with potassium. In embodiments, the growth medium is supplemented with zinc. In embodiments, the growth medium is supplemented with nickel. In embodiments, the growth medium is supplemented with molybdenum. In embodiments, the growth medium is supplemented with manganese. In embodiments, the growth medium is supplemented with copper. In embodiments, the growth medium is supplemented with boron. In embodiments, the growth medium includes $CoCl_2$ at a concentration of about 15 mg/L. In embodiments, the growth medium includes $MgSO_4$ at a concentration of about 250 mg/L. In embodiments, the growth medium includes KI at a concentration of about 15 mg/L. In embodiments, the growth medium includes $ZnSO_4.7H_2O$ at a concentration of about 20 mg/L. In embodiments, the growth medium includes $MnSO_4.H_2O$ at a concentration of about 12.5 mg/L. In embodiments, the growth medium includes Boric acid at a concentration of about 12.5 mg/L. In embodiments, the growth medium includes $(NH_4)_2Mo.4H_2O$ at a concentration of about 15 mg/L. In embodiments, the growth medium includes $NiSO_4.6H_2O$ at a concentration of about 12.5 mg/L. In embodiments, the growth medium includes $FeSO_4.7H_2O$ at a concentration of about 20 mg/L. In embodiments, the growth medium includes $CuSO_4$ at a concentration of about 15 mg/L. In embodiments, the growth medium includes $CoCl_2$ at a concentration of 15 mg/L. In embodiments, the growth medium includes $MgSO_4$ at a concentration of 250 mg/L. In embodiments, the growth medium includes KI at a concentration of 15 mg/L. In embodiments, the growth medium includes $ZnSO_4.7H_2O$ at a concentration of 20 mg/L. In embodiments, the growth medium includes $MnSO_4.H_2O$ at a concentration of 12.5 mg/L. In embodiments, the growth medium includes Boric acid at a concentration of 12.5 mg/L. In embodiments, the growth medium includes $(NH_4)_2Mo.4H_2O$ at a concentration of 15 mg/L. In embodiments, the growth medium includes $NiSO_4.6H_2O$ at a concentration of 12.5 mg/L. In embodiments, the growth medium includes $FeSO_4.7H_2O$ at a concentration of 20 mg/L. In embodiments, the growth medium includes $CuSO_4$ at a concentration of 15 mg/L. In embodiments, the growth medium is supplemented with $CoCl_2$ at a concentration of about 15 mg/L. In embodiments, the growth medium is supplemented with $MgSO_4$ at a concentration of about 250 mg/L. In embodiments, the growth medium is supplemented with KI at a concentration of about 15 mg/L. In embodiments, the growth medium is supplemented with $ZnSO_4.7H_2O$ at a concentration of about 20 mg/L. In embodiments, the growth medium is supplemented with $MnSO_4.H_2O$ at a concentration of about 12.5 mg/L. In embodiments, the growth medium is supplemented with Boric acid at a concentration of about 12.5 mg/L. In embodiments, the growth medium is supplemented with $(NH_4)_2Mo.4H_2O$ at a concentration of about 15 mg/L. In embodiments, the growth medium is supplemented with $NiSO_4.6H_2O$ at a concentration of about 12.5 mg/L. In embodiments, the growth medium is supplemented with $FeSO_4.7H_2O$ at a concentration of about 20 mg/L. In embodiments, the growth medium is supplemented with $CuSO_4$ at a concentration of about 15 mg/L. In embodiments, the growth medium is supplemented with $CoCl_2$ at a concentration of 15 mg/L. In embodiments, the growth medium is supplemented with $MgSO_4$ at a concentration of 250 mg/L. In embodiments, the growth medium is supplemented with KI at a concentration of 15 mg/L. In embodiments, the growth medium is supplemented with $ZnSO_4.7H_2O$ at a concentration of 20 mg/L. In embodiments, the growth medium is supplemented with $MnSO_4.H_2O$ at a concentration of 12.5 mg/L. In embodiments, the growth medium is supplemented with Boric acid at a concentration of 12.5 mg/L. In embodiments, the growth medium is supplemented with $(NH_4)_2Mo.4H_2O$ at a concentration of 15 mg/L. In embodiments, the growth medium is supplemented with $NiSO_4.6H_2O$ at a concentration of 12.5 mg/L. In embodiments, the growth medium is supplemented with $FeSO_4.7H_2O$ at a concentration of 20 mg/L. In embodiments, the growth medium is supplemented with $CuSO_4$ at a concentration of 15 mg/L. In embodiments, the growth medium includes $CoCl_2$ at a concentration of about 7.5 to 22.5 mg/L. In embodiments, the growth medium includes $MgSO_4$ at a concentration of about 125 to 375 mg/L. In embodiments, the growth medium includes KI at a concentration of about 7.5 to 22.5 mg/L. In embodiments, the growth medium includes $ZnSO_4.7H_2O$ at a concentration of about 10 to 30 mg/L. In embodiments, the growth medium includes $MnSO_4.H_2O$ at a concentration of about 6 to 18 mg/L. In embodiments, the growth medium includes Boric acid at a concentration of about 6 to 18 mg/L. In embodiments, the growth medium includes $(NH_4)_2Mo.4H_2O$ at a concentration of about 7.5 to 22.5 mg/L. In embodiments, the growth medium includes $NiSO_4.6H_2O$ at a concentration of about 6 to 18 mg/L. In embodiments, the growth medium includes $FeSO_4.7H_2O$ at a concentration of about 10 to 30 mg/L. In embodiments, the growth medium includes $CuSO_4$ at a concentration of about 7.5 to 22.5 mg/L. In embodiments, the growth medium includes $CoCl_2$ at a concentration of 7.5 to 22.5 mg/L. In embodiments, the growth medium includes $MgSO_4$ at a concentration of 125 to 375 mg/L. In embodiments, the growth medium includes KI at a concentration of 7.5 to 22.5 mg/L. In embodiments, the growth medium includes $ZnSO_4.7H_2O$ at a concentration of 10 to 30 mg/L. In embodiments, the growth medium includes $MnSO_4.H_2O$ at a concentration of 6 to 18 mg/L. In embodiments, the growth medium includes Boric acid at a concentration of 6 to 18 mg/L. In embodiments, the growth medium includes $(NH_4)_2Mo.4H_2O$ at a concentration of 7.5 to 22.5 mg/L. In embodiments, the growth medium includes $NiSO_4.6H_2O$ at a concentration of 6 to 18 mg/L. In embodiments, the growth medium includes $FeSO_4.7H_2O$ at a concentration of 10 to 30 mg/L. In embodiments, the growth medium includes $CuSO_4$ at a concentration of 7.5 to 22.5 mg/L. In embodiments, the growth medium is supplemented with $CoCl_2$ at a concentration of about 7.5 to 22.5 mg/L. In embodiments, the growth medium is supplemented with $MgSO_4$ at a concentration of about 125 to 375 mg/L. In embodiments, the growth medium is supplemented with KI at a concentration of about 7.5 to 22.5 mg/L. In embodiments, the growth medium is supplemented with $ZnSO_4.7H_2O$ at a concentration of about 10 to 30 mg/L. In embodiments, the growth medium is supplemented with $MnSO_4.H_2O$ at a concentration of about 6 to 18 mg/L. In embodiments, the growth medium is supplemented with Boric acid at a concentration of about 6 to 18 mg/L. In embodiments, the growth medium is supplemented with $(NH_4)_2Mo.4H_2O$ at a concentration of about 7.5 to 22.5 mg/L. In embodiments, the growth medium is supplemented with $NiSO_4.6H_2O$ at a concentration of about 6 to 18 mg/L. In embodiments, the growth medium is supplemented with $FeSO_4.7H_2O$ at a concentration of about 10 to 30 mg/L. In embodiments, the growth medium is supplemented with $CuSO_4$ at a concentration of about 7.5 to 22.5 mg/L. In embodiments, the growth medium is supplemented with $CoCl_2$ at a concentration of 7.5 to 22.5 mg/L. In embodiments, the growth medium is supplemented with $MgSO_4$ at a concentration of 125 to 375 mg/L. In embodiments, the growth medium is supplemented with KI at a concentration of 7.5 to 22.5 mg/L. In embodiments, the growth medium is supplemented with $ZnSO_4.7H_2O$ at a concentration of 10 to 30 mg/L. In embodiments, the growth medium is supplemented with $MnSO_4.H_2O$ at a concentration of 6 to 18 mg/L. In embodiments, the growth medium is supplemented with Boric acid at a concentration of 6 to 18 mg/L. In embodiments, the growth medium is supplemented with $(NH_4)_2Mo.4H_2O$ at a concentration of 7.5 to 22.5 mg/L. In embodiments, the growth medium is supplemented with $NiSO_4.6H_2O$ at a concentration of 6 to 18 mg/L. In embodiments, the growth medium is supplemented with $FeSO_4.7H_2O$ at a concentration of 10 to 30 mg/L. In embodiments, the growth medium is supplemented with $CuSO_4$ at a concentration of 7.5 to 22.5 mg/L.

In embodiments, the method does not include nitrogen starvation of the oleaginous organism (e.g. oleaginous yeast cell).

In embodiments, the oleaginous yeast is cultured for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, or 500 hours. In embodiments, the oleaginous yeast is cultured for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, or 500 hours. In embodiments, the oleaginous yeast is cultured for about 48, 96, 144, or 192 hours. In embodiments, the oleaginous yeast is cultured for 48, 96, 144, or 192 hours. In embodiments, the oleaginous yeast is cultured for about 0.5, 1, 1.5, 2, 2.5, 3, 3.5, 4, 4.5, 5, 5.5, 6, 6.5, 7, 7.5, 8, 8.5, 9, 9.5, or 10 days. In embodiments, the oleaginous yeast is cultured for 0.5, 1, 1.5, 2, 2.5, 3, 3.5, 4, 4.5, 5, 5.5, 6, 6.5, 7, 7.5, 8, 8.5, 9, 9.5, or 10 days.

In an aspect is provided a method of producing a lipid, lipid precursor, or oleochemical including culturing a yeast cell described herein in a growth medium; and isolating the lipid, lipid precursor, or oleochemical.

In embodiments, the lipid, lipid precursor, or oleochemical is isolated from the yeast cell. In embodiments, the lipid, lipid precursor, or oleochemical is isolated from the growth medium. In embodiments, the growth medium includes a majority carbon source selected from the group consisting of glucose, glycerol, xylose, fructose, mannose, ribose, sucrose, and lignocellulosic biomass. In embodiments, the growth medium includes lignocellulosic biomass as the majority carbon source. In embodiments, the growth medium includes a carbon source and a nitrogen source wherein the carbon source is at a concentration at least 10-fold greater than the concentration of the nitrogen source (wt/wt). In embodiments, the growth medium includes a carbon source and a nitrogen source wherein the carbon source is at a concentration at least 16-fold greater than the concentration of the nitrogen source (wt/wt). In embodiments, the growth medium includes a carbon source and a nitrogen source wherein the carbon source is at a concentration at least 320-fold greater than the concentration of the nitrogen source (wt/wt).

In embodiments, the growth medium includes cobalt, iron, magnesium, potassium, zinc, nickel, molybdenum, manganese, copper, or boron. In embodiments, the growth medium includes any combination of two or more of cobalt, iron, magnesium, potassium, zinc, nickel, molybdenum, manganese, copper, or boron. In embodiments, the growth medium includes cobalt in an amount equivalent to 7.5 to 22.5 mg/L $CoCl_2$, magnesium in an amount equivalent to 125 to 375 mg/L $MgSO_4$, potassium in an amount equivalent to 7.5 to 22.5 mg/L KI, zinc in an amount equivalent to 10 to 30 mg/L $ZnSO_4.7H_2O$, manganese in an amount equivalent to 6 to 18 mg/L $MnSO_4.H_2O$, boron in an amount equivalent to 6 to 18 mg/L Boric acid, molybdenum in an amount equivalent to 7.5 to 22.5 mg/L $(NH_4)_2Mo.4H_2O$, nickel in an amount equivalent to 6 to 18 mg/L $NiSO_4.6H_2O$, iron in an amount equivalent to 10 to 30 mg/L $FeSO_4.7H_2O$, or copper in an amount equivalent to 7.5 to 22.5 mg/L $CuSO_4$. In embodiments, the growth medium includes about $5.77 \times 10^{-5}$ M to $1.73 \times 10^{-4}$ M cobalt, about 0.001 M to 0.003 M magnesium, about $4.52 \times 10^{-5}$ M to $1.35 \times 10^{-4}$ M potassium, about $4.05 \times 10^{-5}$ M to $1.22 \times 10^{-4}$ M zinc, about $3.55 \times 10^{-5}$ to $1.06 \times 10^{-4}$ M manganese, about $9.07 \times 10^{-5}$ M to $2.91 \times 10^{-4}$ M boron, about $3.76 \times 10^{-5}$ M to $1.10 \times 10^{-4}$ M molybdenum, about $2.28 \times 10^{-5}$ M to $6.84 \times 10^{-5}$ M nickel, about $3.60 \times 10^{-5}$ M to $1.08 \times 10^{-4}$ M iron, or about $4.70 \times 10^{-5}$ M to $1.41 \times 10^{-4}$ M copper. In embodiments, the growth medium includes $5.77 \times 10^{-5}$ M to $1.73 \times 10^{-4}$ M cobalt, 0.001 M to 0.003 M magnesium, $4.52 \times 10^{-5}$ M to $1.35 \times 10^{-4}$ M potassium, $4.05 \times 10^{-5}$ M to $1.22 \times 10^{-4}$ M zinc, $3.55 \times 10^{-5}$ to $1.06 \times 10^{-4}$ M manganese, $9.07 \times 10^{-5}$ M to $2.91 \times 10^{-4}$ M boron, $3.76 \times 10^{-5}$ M to $1.10 \times 10^{-4}$ M molybdenum, $2.28 \times 10^{-5}$ M to $6.84 \times 10^{-5}$ M nickel, $3.60 \times 10^{-5}$ M to $1.08 \times 10^{-4}$ M iron, or $4.70 \times 10^{-5}$ M to $1.41 \times 10^{-4}$ M copper. In embodiments, the growth medium includes about $5.77 \times 10^{-5}$ M to $1.73 \times 10^{-4}$ M cobalt. In embodiments, the growth medium includes about 0.001 M to 0.003 M magnesium. In embodiments, the growth medium includes about $4.52 \times 10^{-5}$ M to $1.35 \times 10^{-4}$ M potassium. In embodiments, the growth medium includes about $4.05 \times 10^{-5}$ M to $1.22 \times 10^{-4}$ M zinc. In embodiments, the growth medium includes about $3.55 \times 10^{-5}$ to $1.06 \times 10^{-4}$ M manganese. In embodiments, the growth medium includes about $9.07 \times 10^{-5}$ M to $2.91 \times 10^{-4}$ M boron. In embodiments, the growth medium includes about $3.76 \times 10^{-5}$ M to $1.10 \times 10^{-4}$ M molybdenum. In embodiments, the growth medium includes about $2.28 \times 10^{-5}$ M to $6.84 \times 10^{-5}$ M nickel. In embodiments, the growth medium includes about $3.60 \times 10^{-5}$ M to $1.08 \times 10^{-4}$ M iron. In embodiments, the growth medium includes about $4.70 \times 10^{-5}$ M to $1.41 \times 10^{-4}$ M copper. In embodiments, the growth medium includes $5.77 \times 10^{-5}$ M to $1.73 \times 10^{-4}$ M cobalt. In embodiments, the growth medium includes 0.001 M to 0.003 M magnesium. In embodiments, the growth medium includes $4.52 \times 10^{-5}$ M to $1.35 \times 10^{-4}$ M potassium. In embodiments, the growth medium includes $4.05 \times 10^{-5}$ M to $1.22 \times 10^{-4}$ M zinc. In embodiments, the growth medium includes $3.55 \times 10^{-5}$ to $1.06 \times 10^{-4}$ M manganese. In embodiments, the growth medium includes $9.07 \times 10^{-5}$ M to $2.91 \times 10^{-4}$ M boron. In embodiments, the growth medium includes $3.76 \times 10^{-5}$ M to $1.10 \times 10^{-4}$ M molybdenum. In embodiments, the growth medium includes $2.28 \times 10^{-5}$ M to $6.84 \times 10^{-5}$ M nickel. In embodiments, the growth medium includes $3.60 \times 10^{-5}$ M to $1.08 \times 10^{-4}$ M iron. In embodiments, the growth medium includes $4.70 \times 10^{-5}$ M to $1.41 \times 10^{-4}$ M copper. In embodiments, the growth medium includes iron, copper, and molybdenum. In embodiments, the growth medium includes molybdenum in an amount equivalent to 7.5 to 22.5 mg/L $(NH_4)_2Mo.4H_2O$, iron in an amount equivalent to 10 to 30 mg/L $FeSO_4.7H_2O$, or copper in an amount equivalent to 7.5 to 22.5 mg/L $CuSO_4$. In embodiments, the growth medium includes $3.76 \times 10^{-5}$ M to $1.10 \times 10^{-4}$ M molybdenum, $3.60 \times 10^{-5}$ M to $1.08 \times 10^{-4}$ M iron, or $4.70 \times 10^{-5}$ M to $1.41 \times 10^{-4}$ M copper. In embodiments, the growth medium includes copper and nickel. In embodiments, the growth medium includes nickel in an amount equivalent to 6 to 18 mg/L $NiSO_4.6H_2O$ or copper in an amount equivalent to 7.5 to 22.5 mg/L $CuSO_4$. In embodiments, the growth medium includes $2.28 \times 10^{-5}$ M to $6.84 \times 10^{-5}$ M nickel or $4.70 \times 10^{-5}$ M to $1.41 \times 10^{-4}$ M copper. In embodiments, the growth medium includes copper, iron, and either molybdenum or nickel. In embodiments, the growth medium includes molybdenum in an amount equivalent to 7.5 to 22.5 mg/L $(NH_4)_2Mo.4H_2O$, nickel in an amount equivalent to 6 to 18 mg/L $NiSO_4.6H_2O$, iron in an amount equivalent to 10 to 30 mg/L $FeSO_4.7H_2O$, or copper in an amount equivalent to 7.5 to 22.5 mg/L $CuSO_4$. In embodiments, the growth medium includes $3.76 \times 10^{-5}$ M to $1.10 \times 10^{-4}$ M molybdenum, $2.28 \times 10^{-5}$ M to $6.84 \times 10^{-5}$ M nickel, $3.60 \times 10^{-5}$ M to $1.08 \times 10^{-4}$ M iron, or $4.70 \times 10^{-5}$ M to $1.41 \times 10^{-4}$ M copper. In embodiments, the growth medium includes copper, iron, molybdenum, and nickel.

In another aspect is provided a method of isolating a yeast cell including greater than 20% wt/wt lipids, lipid precursors, and/or oleochemicals (e.g., lipid, lipids, lipid precursors, lipid precursor, oleochemicals, or oleochemical) in dry weight from a plurality of yeast cells, including allowing a yeast cell including greater than 20% wt/wt lipids, lipid precursors, and/or oleochemicals (e.g., lipid, lipids, lipid precursors, lipid precursor, oleochemicals, or oleochemical) to separate from a population of yeast cells within the plurality of yeast cells by floating above the population of yeast cells within an aqueous medium thereby isolating the yeast cell including greater than 20% wt/wt lipids, lipid precursors, and/or oleochemicals (e.g., lipid, lipids, lipid precursors, lipid precursor, oleochemicals, or oleochemical), wherein the population of yeast cells includes a lower percentage wt/wt of lipids, lipid precursors, and/or oleochemicals (e.g., lipid, lipids, lipid precursors, lipid precursor, oleochemicals, or oleochemical) than the yeast cell including greater than 20% wt/wt lipids, lipid precursors, and/or oleochemicals (e.g., lipid, lipids, lipid precursors, lipid precursor, oleochemicals, or oleochemical). In another aspect is provided a method of isolating a genetically modified yeast cell from a plurality of yeast cells including greater than 20% wt/wt lipids, lipid precursors, and/or oleochemicals (e.g., lipid, lipids, lipid precursors, lipid precursor, oleochemicals, or oleochemical) in dry weight, including allowing a genetically modified yeast cell to separate from a population of yeast cells within the plurality of yeast cells by floating above the population of yeast cells within an aqueous medium thereby isolating the genetically modified yeast cell, wherein the population of yeast cells includes a lower percentage wt/wt of lipids, lipid precursors, and/or oleochemicals (e.g., lipid, lipids, lipid precursors, lipid precursor, oleochemicals, or oleochemical) than the genetically modified yeast cell.

In embodiments is a method of isolating a yeast cell (e.g. genetically modified yeast cell), including greater than 20% wt/wt lipids, lipid precursors, and/or oleochemicals (e.g., lipid, lipids, lipid precursors, lipid precursor, oleochemicals, or oleochemical) in dry weight, from a plurality of yeast cells, including allowing a yeast cell (e.g. genetically modified yeast cell) to separate from a population of yeast cells within the plurality of yeast cells by floating above the population of yeast cells within an aqueous medium thereby isolating the yeast cell (e.g. genetically modified yeast cell), wherein the population of yeast cells includes a lower percentage wt/wt of lipids, lipid precursors, and/or oleochemicals (e.g., lipid, lipids, lipid precursors, lipid precursor, oleochemicals, or oleochemical) than the genetically modified yeast cell.

In embodiments, the yeast cell (e.g. genetically modified yeast cell) includes greater than 30% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 40% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 50% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 60% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 70% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 80% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) includes greater than 90% wt/wt lipids, lipid precursors, and/or oleochemicals (e.g., lipid, lipids, lipid precursors, lipid precursor, oleochemicals, or oleochemical) in dry weight. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) is floating on the top surface of the aqueous medium. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) is above the bottom of a vessel containing the aqueous medium. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) is floating above the population of yeast cells including a lower percentage wt/wt of lipids, lipid precursors, and/or oleochemicals (e.g., lipid, lipids, lipid precursors, lipid precursor, oleochemicals, or oleochemical) than the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight by about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, or 99 mm in the aqueous medium. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) is floating above the population of yeast cells including a lower percentage wt/wt of lipids, lipid precursors, and/or oleochemicals (e.g., lipid, lipids, lipid precursors, lipid precursor, oleochemicals, or oleochemical) than the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight by at least 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, or 99 mm in the aqueous medium. In embodiments, the genetically modified yeast cell including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) floating above the population of yeast cells including a lower percentage wt/wt of lipids, lipid precursors, and/or oleochemicals (e.g., lipid, lipids, lipid precursors, lipid precursor, oleochemicals, or oleochemical) than the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight has a buoyant density greater than the buoyant density of the population of yeast cells including a lower percentage wt/wt of lipids, lipid precursors, and/or oleochemicals (e.g., lipid, lipids, lipid precursors, lipid precursor, oleochemicals, or oleochemical) than yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight by about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, g/mL. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight (e.g. greater than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% lipids, lipid precursors, and/or oleochemicals (e.g., lipid, lipids, lipid precursors, lipid precursor, oleochemicals, or oleochemical) in dry weight) floating above the population of yeast cells including a lower percentage wt/wt of lipids, lipid precursors, and/or oleochemicals (e.g., lipid, lipids, lipid precursors, lipid precursor, oleochemicals, or oleochemical) than the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight has a buoyant density greater than the buoyant density of the population of yeast cells including a lower percentage wt/wt of lipids, lipid precursors, and/or oleochemicals (e.g., lipid, lipids, lipid precursors, lipid precursor, oleochemicals, or oleochemical) than the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight by 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, g/mL. In embodiments, the yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical), includes a mutation created by natural genetic drift.

In embodiments of the method, the plurality of yeast cells are in a bioreactor with agitation and aeration rates of about 0.5 vvm (volume per volume per minute). In embodiments of the method, the plurality of yeast cells are in a bioreactor with agitation and aeration rates of about 1.0 vvm (volume per volume per minute). In embodiments of the method, the plurality of yeast cells are in a bioreactor with agitation and aeration rates of about 2.0 vvm (volume per volume per minute). In embodiments of the method, the plurality of yeast cells are in a bioreactor with agitation and aeration rates of about 2.5 vvm (volume per volume per minute). In embodiments of the method, the plurality of yeast cells are in a bioreactor with agitation and aeration rates of about 3.0 vvm (volume per volume per minute). In embodiments of the method, the plurality of yeast cells are in a bioreactor with agitation and aeration rates of about 4.0 vvm (volume per volume per minute). In embodiments of the method, the plurality of yeast cells are in a bioreactor with agitation and aeration rates of 0.5 vvm (volume per volume per minute). In embodiments of the method, the plurality of yeast cells are in a bioreactor with agitation and aeration rates of 1.0 vvm (volume per volume per minute). In embodiments of the method, the plurality of yeast cells are in a bioreactor with agitation and aeration rates of 2.0 vvm (volume per volume per minute). In embodiments of the method, the plurality of yeast cells are in a bioreactor with agitation and aeration rates of 2.5 vvm (volume per volume per minute). In embodiments of the method, the plurality of yeast cells are in a bioreactor with agitation and aeration rates of 3.0 vvm (volume per volume per minute). In embodiments of the method, the plurality of yeast cells are in a bioreactor with agitation and aeration rates of 4.0 vvm (volume per volume per minute).

In embodiments of the method, the aqueous medium includes a yeast growth medium, minimal media, complete supplement media, or greater than 50 g/L carbon source (e.g. glucose) and less than 5 g/L of a nitrogen source (e.g. ammonium sulfate). In embodiments of the method, the aqueous medium includes a yeast growth medium. In embodiments of the method, the aqueous medium includes a minimal media. In embodiments of the method, the aqueous medium includes a complete supplement media. In embodiments of the method, the aqueous medium includes greater than 50 g/L carbon source (e.g. glucose) and less than 5 g/L of a nitrogen source (e.g. ammonium sulfate). In embodiments of the method, the aqueous medium is a yeast growth medium. In embodiments of the method, the aqueous medium is a minimal media. In embodiments of the method, the aqueous medium is a complete supplement media.

In embodiments of the method of isolating a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight, including allowing a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight to separate from a population of yeast cells within the plurality of yeast cells by floating above the population of yeast cells within an aqueous medium, the allowing is performed by centrifugation or simple sedimentation. In embodiments of the method of isolating a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight, including allowing a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight to separate from a population of yeast cells within the plurality of yeast cells by floating above the population of yeast cells within an aqueous medium, the allowing is performed by centrifugation. In embodiments of the method of isolating a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight, including allowing a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight to separate from a population of yeast cells within the plurality of yeast cells by floating above the population of yeast cells within an aqueous medium, the allowing is performed by simple sedimentation. In embodiments of the method of isolating a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight, including allowing a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight to separate from a population of yeast cells within the plurality of yeast cells by floating above the population of yeast cells within an aqueous medium, the allowing is performed by sedimentation. In embodiments of the method of isolating a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight, including allowing a yeast cell (e.g. genetically modified yeast cell) including greater than 20% wt/wt lipids, lipid precursors, and/or oleochemicals (e.g., lipid, lipids, lipid precursors, lipid precursor, oleochemicals, or oleochemical) in dry weight to separate from a population of yeast cells within the plurality of yeast cells by floating above the population of yeast cells within an aqueous medium, the allowing is performed by sedimentation due to gravity.

In embodiments of the method, the genetically modified yeast cell is formed by transforming a yeast cell with a recombinant nucleic acid (e.g. as described herein, including in embodiments, examples, tables, figures, and/or claims). In embodiments, the genetically modified yeast cell is formed by mutagenizing a yeast cell. In embodiments, the yeast cell (e.g. genetically modified yeast cell includes a mutation created by natural genetic drift.

In embodiments, the method is a method described herein, including in embodiments, examples, tables, figures, and claims.

IV. ADDITIONAL EMBODIMENTS

1p. A genetically modified yeast cell wherein the dry weight of said yeast cell comprises greater than 20% wt/wt lipid.
2p. The yeast cell of embodiment 1p comprising greater than 30% wt/wt lipid.
3p. The yeast cell of embodiment 1p comprising greater than 40% wt/wt lipid.
4p. The yeast cell of embodiment 1p comprising greater than 50% wt/wt lipid.
5p. The yeast cell of embodiment 1p comprising greater than 60% wt/wt lipid.
6p. The yeast cell of embodiment 1p comprising greater than 70% wt/wt lipid.
7p. The yeast cell of embodiment 1p comprising greater than 80% wt/wt lipid.
8p. The yeast cell of embodiment 1p comprising greater than 90% wt/wt lipid.
9p. The yeast cell of any one of embodiments 1p to 8p, selected from the group consisting of the genera *Yarrowia, Candida, Rhodotorula, Rhodosporidium, Cryptococcus, Trichosporon* and *Lipomyces*.
10p. The yeast cell of any one of embodiments 1p to 8p, selected from the group consisting of *Rhodosporidium toruloides, Lipomyces starkeyii, Lipomyces lipoferus, Apiotrichum curvatum, Candida curvata, Cryptococcus curvatus, Trichosporon fermentans, Candida revkaufi, Candida pulcherrima, Candida tropicalis, Candida utilis, Trichosporon pullans, Trichosporon cutaneum, Rhodotorula glutinus, Rhodotorula graminis* and *Yarrowia lipolytica*.
11p. The yeast cell of any one of embodiments 1p to 8p, selected from the group consisting of *Lipomyces starkeyii, Rhodosporidium toruloides, Apiotrichum curvatum, Candida curvata, Cryptococcus curvatus, Trichosporon fermentans, Rhodotorula glutinis*, and *Yarrowia lipolytica*.
12p. The yeast cell of any one of embodiments 1p to 8p, wherein said yeast cell is *Yarrowia lipolytica*.
13p. The yeast cell of any one of embodiments 1p to 12p, wherein said yeast cell is buoyant in an aqueous medium.
14p. The yeast cell of any one of embodiments 1p to 13p, wherein said lipid is selected from the group consisting of a fatty acid, wax, sterol, vitamin, monoglyceride, diglyceride, triglyceride, phospholipid, glycerolipid, glycerophospholipid, sphingolipid, saccharolipid, polyketide, sterol lipid, triacylglyceride, and a prenol lipid.
15p. A yeast cell comprising a recombinant nucleic acid, wherein said recombinant nucleic acid modulates the level of activity of a protein in said yeast cell relative to the absence of the recombinant nucleic acid, and wherein said protein is selected from the group consisting of Leucine Biosynthesis Gene (LEU2), Uracil Biosynthesis gene (URA3), multifunctional enzyme (MFE1), Transcription Factor (PEX10), AMP Deaminase (AMPD), ATP-Citrate Lyase (ACL), Malic Enzyme (MAE), Acetyl-CoA Carboxylase (ACC), acyl-CoA:diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), and O-6-methylguanine-DNA methyltransferase (MGMT).
16p. The yeast cell of embodiment 15p, wherein said recombinant nucleic acid increases the level of activity of a protein in said yeast cell selected from the group consisting of Leucine Biosynthesis Gene (LEU2), Uracil Biosynthesis gene (URA3), AMP Deaminase (AMPD), ATP-Citrate Lyase (ACL), Malic Enzyme (MAE), Acetyl-CoA Carboxylase (ACC), acyl-CoA: diacylglycerol acyltransferase (DGA1), acyl-CoA: diacylglycerol acyltransferases (DGA2), Mitochondrial 2' O-ribose methyltransferase (MRM2), Lipid synthesis regulator (MGA2), Chromatin assembly gene (RLF2 subunit p90), and O-6-methylguanine-DNA methyltransferase (MGMT).
17p. The yeast cell of any one of embodiments 15p to 16p, wherein said recombinant nucleic acid decreases the level of activity of a protein in said yeast cell selected from the group consisting of multifunctional enzyme (MFE1), Lipid synthesis regulator (MGA2), Chromatin assembly gene (RLF2 subunit p90), and Transcription Factor (PEX10).

18p. The yeast cell of any one of embodiments 15p to 17p, wherein said recombinant nucleic acid increases the level of activity of a protein in said yeast cell selected from the group consisting of Leucine Biosynthesis Gene (LEU2), Uracil Biosynthesis gene (URA3), Malic Enzyme (MAE), Mitochondrial 2' O-ribose methyltransferase (MRM2), Lipid synthesis regulator (MGA2), and O-6-methylguanine-DNA methyltransferase (MGMT) or said nucleic acid decrease the level of activity of Lipid synthesis regulator (MGA2).

19p. The yeast cell of any one of embodiments 15p to 18p, wherein said recombinant nucleic acid encodes a protein comprising a mutation relative to the wildtype protein.

20p. The yeast cell of any one of embodiments 15p to 18p, wherein said nucleic acid modulates the level of expression of a protein.

21p. The yeast cell of embodiment 15p, wherein said yeast cell comprises a recombinant nucleic acid that decreases the level of activity of multifunctional enzyme (MFE1) protein and Transcription Factor (PEX10) protein, increases the level of activity of acyl-CoA:diacylglycerol acyltransferase (DGA1) protein, or increases the level of activity of Leucine Biosynthesis Gene (LEU2) protein relative to a yeast cell that does not comprise said recombinant nucleic acids.

22p. The yeast cell of any one of embodiments 1p to 21p, wherein said yeast cell comprises a fatty acid selected from the group consisting of C5:0, C5:1, C5:2, C5:3, C6:0, C6:1, C6:2, C6:3, C7:0, C7:1, C7:2, C7:3, C8:0, C8:1, C8:2, C8:3, C9:0, C9:1, C9:2, C9:3, C10:0, C10:1, C10:2, C10:3, C11:0, C11:1, C11:2, C11:3, C12:0, C12:1, C12:2, C12:3, C13:0, C13:1, C13:2, C13:3, C14:0, C14:1, C14:2, C14:3, C15:0, C15:1, C15:2, C15:3, C16:0, C16:1, C16:2, C16:3, C17:0, C17:1, C17:2, C17:3, C18:0, C18:1, C18:2, C18:3, C19:0, C19:1, C19:2, C19:3, C20:0, C20:1, C20:2, C20:3, C21:0, C21:1, C21:2, C21:3, C22:0, C22:1, C22:2, C22:3, C23:0, C23:1, C23:2, and C23:3.

23p. The yeast cell of any one of embodiments 1p to 21p, wherein said yeast cell comprises a fatty acid selected from the group consisting of C17:0 and C17:1.

24p. A method of producing a lipid comprising:
1) culturing a yeast cell of any one of embodiments 1p to 23p in a growth medium;
2) isolating said lipid.

25p. The method of embodiment 24p, wherein said lipid is isolated from said yeast cell. 26p. The method of embodiment 24p, wherein said lipid is isolated from the medium.

27p. The method of any one of embodiments 24p to 26p, wherein said growth medium comprises a majority carbon source selected from the group consisting of glucose, glycerol, xylose, fructose, mannose, ribose, sucrose, and lignocellulosic biomass.

28p. The method of any one of embodiments 24p to 26p, wherein said growth medium comprises lignocellulosic biomass as the majority carbon source.

29p. The method of any one of embodiments 24p to 28p, wherein said growth medium comprises a carbon source and a nitrogen source wherein said carbon source is at a concentration at least 10-fold greater than the concentration of the nitrogen source.

30p. The method of any one of embodiments 24p to 29p, wherein said growth medium comprises cobalt, iron, magnesium, potassium, zinc, nickel, molybdenum, manganese, copper, or boron.

31p. The method of embodiment 30p, wherein the growth medium comprises iron, copper, and molybdenum.

32p. The method of embodiment 30p, wherein the growth medium comprises copper and nickel.

33p. The method of embodiment 30p, wherein the growth medium comprises copper, iron, and either molybdenum or nickel.

34p. The method of embodiment 30p, wherein the growth medium comprises copper, iron, molybdenum, and nickel.

35p. A method of isolating a genetically modified yeast cell from a plurality of yeast cells comprising greater than 20% wt/wt lipids in dry weight, comprising allowing a genetically modified yeast cell to separate from a population of yeast cells within said plurality of yeast cells by floating above said population of yeast cells within an aqueous medium thereby isolating said genetically modified yeast cell, wherein said population of yeast cells comprises a lower percentage wt/wt of lipids than said genetically modified yeast cell.

36p. The method of any embodiment 35p, wherein said genetically modified yeast cell comprises greater than 30% wt/wt lipids in dry weight.

37p. The method of embodiment 35p, wherein said genetically modified yeast cell comprises greater than 40% wt/wt lipids in dry weight.

38p. The method of embodiment 35p, wherein said genetically modified yeast cell comprises greater than 50% wt/wt lipids in dry weight.

39p. The method of embodiment 35p, wherein said genetically modified yeast cell comprises greater than 60% wt/wt lipids in dry weight.

40p. The method of any one of embodiments 35p to 39p, wherein said plurality of yeast cells are in a bioreactor with agitation and aeration rates of about 0.5 vvm (volume per volume per minute).

41p. The method of any one of embodiments 35p to 39p, wherein said plurality of yeast cells are in a bioreactor with agitation and aeration rates of about 1.0 vvm (volume per volume per minute).

42p. The method of any one of embodiments 35p to 39p, wherein said plurality of yeast cells are in a bioreactor with agitation and aeration rates of about 2.0 vvm (volume per volume per minute).

43p. The method of any one of embodiments 35p to 39p, wherein said plurality of yeast cells are in a bioreactor with agitation and aeration rates of about 3.0 vvm (volume per volume per minute).

44p. The method of any one of embodiments 35p to 39p, wherein said plurality of yeast cells are in a bioreactor with agitation and aeration rates of about 4.0 vvm (volume per volume per minute).

45p. The method of any one of embodiments 35p to 44p, wherein said aqueous medium comprises a yeast growth medium, minimal media, complete supplement media, or greater than 50 g/L glucose and less than 5 g/L of a nitrogen source.

46p. The method of any one of embodiments 35p to 45p, wherein said allowing is performed by centrifugation or simple sedimentation.

47p. The method of any one of embodiments 35p to 46p, wherein said genetically modified yeast cell was formed by transforming a yeast cell with a recombinant nucleic acid.

48p. The method of any one of embodiments 35p to 4'7p, wherein said genetically modified yeast cell was formed by mutagenizing a yeast cell.

1. A genetically modified yeast cell wherein the dry weight of said yeast cell comprises greater than 20% wt/wt lipids, lipid precursors, and/or oleochemicals (e.g., lipid, lipids, lipid precursors, lipid precursor, oleochemicals, or oleochemical).

2. The genetically modified yeast cell of embodiment 1 comprising greater than 30% wt/wt lipids, lipid precursors, and/or oleochemicals (e.g., lipid, lipids, lipid precursors, lipid precursor, oleochemicals, or oleochemical).

3. The genetically modified yeast cell of embodiment 1 comprising greater than 40% wt/wt lipids, lipid precursors, and/or oleochemicals (e.g., lipid, lipids, lipid precursors, lipid precursor, oleochemicals, or oleochemical).

4. The genetically modified yeast cell of embodiment 1 comprising greater than 50% wt/wt lipids, lipid precursors, and/or oleochemicals (e.g., lipid, lipids, lipid precursors, lipid precursor, oleochemicals, or oleochemical).

5. The genetically modified yeast cell of embodiment 1 comprising greater than 60% wt/wt lipids, lipid precursors, and/or oleochemicals (e.g., lipid, lipids, lipid precursors, lipid precursor, oleochemicals, or oleochemical).

6. The genetically modified yeast cell of embodiment 1 comprising greater than 70% wt/wt lipids, lipid precursors, and/or oleochemicals (e.g., lipid, lipids, lipid precursors, lipid precursor, oleochemicals, or oleochemical).

7. The genetically modified yeast cell of embodiment 1 comprising greater than 80% wt/wt lipids, lipid precursors, and/or oleochemicals (e.g., lipid, lipids, lipid precursors, lipid precursor, oleochemicals, or oleochemical).

8. The genetically modified yeast cell of embodiment 1 comprising greater than 90% wt/wt lipids, lipid precursors, and/or oleochemicals (e.g., lipid, lipids, lipid precursors, lipid precursor, oleochemicals, or oleochemical).

9. The genetically modified yeast cell of any one of embodiments 1 to 8, selected from the group consisting of the genera *Yarrowia, Candida, Rhodotorula, Rhodosporidium, Cryptococcus, Trichosporon* and *Lipomyces*.

10. The genetically modified yeast cell of any one of embodiments 1 to 8, selected from the group consisting of *Rhodosporidium toruloides, Lipomyces starkeyii, Lipomyces lipoferus, Apiotrichum curvatum, Candida curvata, Cryptococcus curvatus, Trichosporon fermentans, Candida revkaufi, Candida pulcherrima, Candida tropicalis, Candida utilis, Trichosporon pullans, Trichosporon cutaneum, Rhodotorula glutinus, Rhodotorula graminis* and *Yarrowia lipolytica*.

11. The genetically modified yeast cell of any one of embodiments 1 to 8, selected from the group consisting of *Lipomyces starkeyii, Rhodosporidium toruloides, Apiotrichum curvatum, Candida curvata, Cryptococcus curvatus, Trichosporon fermentans, Rhodotorula glutinis*, and *Yarrowia lipolytica*.

12. The genetically modified yeast cell of any one of embodiments 1 to 8, wherein said yeast cell is *Yarrowia lipolytica*.

13. The genetically modified yeast cell of any one of embodiments 1 to 12, wherein said yeast cell is buoyant in an aqueous medium.

14. The genetically modified yeast cell of one of embodiments 1 to 13, comprising a recombinant Leucine Biosynthesis Gene (LEU2).

15. The genetically modified yeast cell of one of embodiments 1 to 13, wherein said genetic modification increases the level of activity of the Leucine Biosynthesis Gene (LEU2) protein relative to an otherwise identical yeast cell lacking said genetic modification.

16. The genetically modified yeast cell of one of embodiments 1 to 15, comprising a recombinant Uracil Biosynthesis gene (URA3).

17. The genetically modified yeast cell of one of embodiments 1 to 15, wherein said genetic modification increases the level of activity of the Uracil Biosynthesis gene (URA3) protein relative to an otherwise identical yeast cell lacking said genetic modification.

18. The genetically modified yeast cell of one of embodiments 1 to 17, comprising a genetically modified multifunctional enzyme (MFE1) gene.

19. The genetically modified yeast cell of one of embodiments 1 to 17, wherein said genetic modification decreases the level of activity of the multifunctional enzyme (MFE1) protein relative to an otherwise identical yeast cell lacking said genetic modification.

20. The genetically modified yeast cell of one of embodiments 1 to 19, comprising a genetically modified PEX10 Transcription Factor (PEX10) gene.

21. The genetically modified yeast cell of one of embodiments 1 to 19, wherein said genetic modification decreases the level of activity of the PEX10 Transcription Factor (PEX10) protein relative to an otherwise identical yeast cell lacking said genetic modification.

22. The genetically modified yeast cell of one of embodiments 1 to 21, comprising a recombinant AMP Deaminase (AMPD) protein.

23. The genetically modified yeast cell of one of embodiments 1 to 21, wherein said genetic modification increases the level of activity of the AMP Deaminase (AMPD) protein relative to an otherwise identical yeast cell lacking said genetic modification.

24. The genetically modified yeast cell of one of embodiments 1 to 23, comprising a recombinant ATP-Citrate Lyase (ACL1) protein.

25. The genetically modified yeast cell of one of embodiments 1 to 23, wherein said genetic modification increases the level of activity of the ATP-Citrate Lyase (ACL1) protein relative to an otherwise identical yeast cell lacking said genetic modification.

26. The genetically modified yeast cell of one of embodiments 1 to 25, comprising a recombinant ATP-Citrate Lyase (ACL2) protein.

27. The genetically modified yeast cell of one of embodiments 1 to 25, wherein said genetic modification increases the level of activity of the ATP-Citrate Lyase (ACL2) protein relative to an otherwise identical yeast cell lacking said genetic modification.

28. The genetically modified yeast cell of one of embodiments 1 to 27, comprising a recombinant Malic Enzyme (MAE) protein.

29. The genetically modified yeast cell of one of embodiments 1 to 27, wherein said genetic modification increases the level of activity of the Malic Enzyme (MAE) protein relative to an otherwise identical yeast cell lacking said genetic modification.

30. The genetically modified yeast cell of one of embodiments 1 to 29, comprising a recombinant Acetyl-CoA Carboxylase (ACC) protein.

31. The genetically modified yeast cell of one of embodiments 1 to 29, wherein said genetic modification increases the level of activity of the Acetyl-CoA Carboxylase (ACC) protein relative to an otherwise identical yeast cell lacking said genetic modification.

32. The genetically modified yeast cell of one of embodiments 1 to 31, comprising a recombinant acyl-CoA: diacylglycerol acyltransferase 1 (DGA1) protein.

33. The genetically modified yeast cell of one of embodiments 1 to 31, wherein said genetic modification increases the level of activity of the acyl-CoA:diacylglycerol acyltransferase 1 (DGA1) protein relative to an otherwise identical yeast cell lacking said genetic modification.

34. The genetically modified yeast cell of one of embodiments 1 to 33, comprising a recombinant acyl-CoA: diacylglycerol acyltransferase 2 (DGA2) protein.

35. The genetically modified yeast cell of one of embodiments 1 to 33, wherein said genetic modification increases the level of activity of the acyl-CoA:diacylglycerol acyltransferase 2 (DGA2) protein relative to an otherwise identical yeast cell lacking said genetic modification.

36. The genetically modified yeast cell of one of embodiments 1 to 35, comprising a recombinant Mitochondrial 2' O-ribose methyltransferase (MRM2) protein.

37. The genetically modified yeast cell of one of embodiments 1 to 35, wherein said genetic modification increases the level of activity of the Mitochondrial 2' O-ribose methyltransferase (MRM2) protein relative to an otherwise identical yeast cell lacking said genetic modification.

38. The genetically modified yeast cell of one of embodiments 1 to 37, comprising a recombinant Lipid synthesis regulator (MGA2) protein.

39. The genetically modified yeast cell of one of embodiments 1 to 37, comprising a genetically modified Lipid synthesis regulator (MGA2) gene.

40. The genetically modified yeast cell of one of embodiments 1 to 37, comprising at least one nucleotide deletion in the genomic Lipid synthesis regulator (MGA2) gene and expression of a Lipid synthesis regulator (MGA2) protein comprising a mutation corresponding to G643R in *Yarrowia lipolytica*. Lipid synthesis regulator (MGA2)

41. The genetically modified yeast cell of one of embodiments 1 to 37, wherein said genetic modification decreases the level of activity of the Lipid synthesis regulator (MGA2) protein relative to an otherwise identical yeast cell lacking said genetic modification.

42. The genetically modified yeast cell of one of embodiments 1 to 41, comprising a genetically modified Chromatin assembly gene (RLF2 subunit p90) gene.

43. The genetically modified yeast cell of one of embodiments 1 to 41, wherein said genetic modification decreases the level of activity of the Chromatin assembly gene (RLF2 subunit p90) protein relative to an otherwise identical yeast cell lacking said genetic modification.

44. The genetically modified yeast cell of one of embodiments 1 to 43, comprising a recombinant O-6-methylguanine-DNA methyltransferase (MGMT) protein.

45. The genetically modified yeast cell of one of embodiments 1 to 43, wherein said genetic modification increases the level of activity of the O-6-methylguanine-DNA methyltransferase (MGMT) protein relative to an otherwise identical yeast cell lacking said genetic modification.

46. The genetically modified yeast cell of one of embodiments 1 to 45, comprising a genetically modified Aconitase (ACO1) gene.

47. The genetically modified yeast cell of one of embodiments 1 to 45, wherein said genetic modification decreases the level of activity of the Aconitase (ACO1) protein relative to an otherwise identical yeast cell lacking said genetic modification.

48. The genetically modified yeast cell of one of embodiments 1 to 47, comprising a recombinant Citrate Synthase (CIT1) gene.

49. The genetically modified yeast cell of one of embodiments 1 to 47, wherein said genetic modification increases the level of activity of the Citrate Synthase (CIT1) protein relative to an otherwise identical yeast cell lacking said genetic modification.

50. The genetically modified yeast cell of one of embodiments 1 to 49, comprising a genetically modified RME1 zinc-finger transcription factor (RME1) gene.

51. The genetically modified yeast cell of one of embodiments 1 to 49, wherein said genetic modification decreases the level of activity of the RME1 zinc-finger transcription factor (RME1) protein relative to an otherwise identical yeast cell lacking said genetic modification.

52. The genetically modified yeast cell of one of embodiments 1 to 51, comprising a genetically modified YOX1 homeodomain protein (YOX1) gene.

53. The genetically modified yeast cell of one of embodiments 1 to 51, wherein said genetic modification decreases the level of activity of the YOX1 homeodomain protein (YOX1) protein relative to an otherwise identical yeast cell lacking said genetic modification.

54. The genetically modified yeast cell of one of embodiments 1 to 53, comprising a genetically modified UGA2 succinate semialdehyde dehydrogenase (UGA2) gene.

55. The genetically modified yeast cell of one of embodiments 1 to 53, wherein said genetic modification decreases the level of activity of the UGA2 succinate semialdehyde dehydrogenase (UGA2) protein relative to an otherwise identical yeast cell lacking said genetic modification.

56. The genetically modified yeast cell of one of embodiments 1 to 55, comprising a genetically modified OSH6 oxysterol-binding protein homolog 6 (OSH6) gene.

57. The genetically modified yeast cell of one of embodiments 1 to 55, wherein said genetic modification decreases the level of activity of the OSH6 oxysterol-binding protein homolog 6 (OSH6) protein relative to an otherwise identical yeast cell lacking said genetic modification.

58. The genetically modified yeast cell of one of embodiments 1 to 57, comprising a genetically modified IRC20 E3 ubiquitin-protein ligase and helicase (IRC20) gene.

59. The genetically modified yeast cell of one of embodiments 1 to 57, wherein said genetic modification decreases the level of activity of the IRC20 E3 ubiquitin-protein ligase and helicase (IRC20) protein relative to an otherwise identical yeast cell lacking said genetic modification.

60. The genetically modified yeast cell of any one of embodiments 1 to 59, wherein said genetic modification modulates the level of activity of a component of a lipid biosynthetic pathway.

61. The genetically modified yeast cell of any one of embodiments 1 to 59, wherein said genetic modification modulates the level of activity of a component of a pathway incorporating Acetyl-CoA into a lipid, lipid precursor, or oleochemical.

62. The genetically modified yeast cell of any one of embodiments 1 to 59, wherein said genetic modification modulates the level of activity of a component of a pathway incorporating malonyl-CoA into a lipid, lipid precursor, or oleochemical.

63. The genetically modified yeast cell of any one of embodiments 1 to 59, wherein said genetic modification increases the level of activity of a component of a lipid biosynthetic pathway.

64. The genetically modified yeast cell of any one of embodiments 1 to 59, wherein said genetic modification increases the level of activity of a component of a pathway incorporating acetyl-CoA into a lipid, lipid precursor, or oleochemical.

65. The genetically modified yeast cell of any one of embodiments 1 to 59, wherein said genetic modification increases the level of activity of a component of a pathway incorporating malonyl-CoA into a lipid, lipid precursor, or oleochemical.

66. The genetically modified yeast cell of any one of embodiments 1 to 59, wherein said genetic modification modulates the level of activity of a component of a lipid, lipid precursor, or oleochemical, metabolic pathway.

67. The genetically modified yeast cell of any one of embodiments 1 to 59, wherein said genetic modification decreases the level of activity of a component of a lipid, lipid precursor, or oleochemical, metabolic pathway.

68. The genetically modified yeast cell of any one of embodiments 1 to 59, wherein said genetic modification decreases the level of activity of a component of a lipid, lipid precursor, or oleochemical, metabolic pathway.

69. The genetically modified yeast cell of any one of embodiments 1 to 59, wherein said genetic modification increases the level of acetyl-CoA in the genetically modified yeast cell relative to a genetically unmodified yeast cell that is otherwise identical to said genetically modified yeast cell.

70. The genetically modified yeast cell of any one of embodiments 1 to 59, wherein said genetic modification increases the level of malonyl-CoA in the genetically modified yeast cell relative to a genetically unmodified yeast cell that is otherwise identical to said genetically modified yeast cell.

71. The genetically modified yeast cell of any one of embodiments 1 to 59, wherein said genetic modification increases the level of triglyceride production in the genetically modified yeast cell relative to a genetically unmodified yeast cell that is otherwise identical to said genetically modified yeast cell.

72. The genetically modified yeast cell of any one of embodiments 1 to 59, wherein said genetic modification decreases the level of beta-oxidation activity in the genetically modified yeast cell relative to a genetically unmodified yeast cell that is otherwise identical to said genetically modified yeast cell.

73. The genetically modified yeast cell of any one of embodiments 1 to 59, wherein said genetic modification decreases the level of fatty acid catabolism in the genetically modified yeast cell relative to a genetically unmodified yeast cell that is otherwise identical to said genetically modified yeast cell.

74. The genetically modified yeast cell of any one of embodiments 1 to 59, wherein said genetic modification decreases the level of peroxisome biogenesis activity in the genetically modified yeast cell relative to a genetically unmodified yeast cell that is otherwise identical to said genetically modified yeast cell.

75. The genetically modified yeast cell of any one of embodiments 1 to 59, wherein said genetic modification produces a lipid, lipid precursor, or oleochemical at a higher level than by a genetically unmodified yeast cell that is otherwise identical to said genetically modified yeast cell.

76. The genetically modified yeast cell of embodiment 75, wherein said lipid, lipid precursor, or oleochemical produced at a higher level by said genetically modified yeast cell is a fatty acid, wax, sterol, vitamin, monoglyceride, diglyceride, triglyceride, phospholipid, glycerolipid, glycerophospholipid, sphingolipid, saccharolipid, polyketide, sterol lipid, triacylglyceride, prenol lipid, fatty acid ester, fatty acid methyl ester, fatty acid ethyl ester, fatty acid propyl ester, fatty acid butyl ester, fatty alcohol, fatty amine, glycerol, alcohol ethoxylate, alcohol sulfate, or alcohol ether sulfate.

77. The genetically modified yeast cell of any one of embodiments 1 to 76, wherein said genetic modification comprises a mutation relative to the wild type gene.

78. The genetically modified yeast cell of any one of embodiments 1 to 76, wherein said genetic modification comprises a deletion of a portion of a gene.

79. The genetically modified yeast cell of one of embodiments 1 to 78, wherein said yeast cell comprises an increased level of a fatty acid selected from the group consisting of C5:0, C5:1, C5:2, C5:3, C6:0, C6:1, C6:2, C6:3, C7:0, C7:1, C7:2, C7:3, C8:0, C8:1, C8:2, C8:3, C9:0, C9:1, C9:2, C9:3, C10:0, C10:1, C10:2, C10:3, C11:0, C11:1, C11:2, C11:3, C12:0, C12:1, C12:2, C12:3, C13:0, C13:1, C13:2, C13:3, C14:0, C14:1, C14:2, C14:3, C15:0, C15:1, C15:2, C15:3, C16:0, C16:1, C16:2, C16:3, C17:0, C17:1, C17:2, C17:3, C18:0, C18:1, C18:2, C18:3, C19:0, C19:1, C19:2, C19:3, C20:0, C20:1, C20:2, C20:3, C21:0, C21:1, C21:2, C21:3, C22:0, C22:1, C22:2, C22:3, C23:0, C23:1, C23:2, and C23:3, relative to a genetically unmodified yeast cell that is otherwise identical to said genetically modified yeast cell.

80. The genetically modified yeast cell of embodiment 79, wherein said fatty acid is C17:0 C17:1.

81. The genetically modified yeast cell of embodiment 79, wherein said fatty acid is C16:1n9.

82. The genetically modified yeast cell of one of embodiments 1 to 81, wherein said genetic modification is an engineered genetic modification.

83. The genetically modified yeast cell of embodiment 82, wherein said engineered genetic modification comprises modulated expression of a protein.

84. The genetically modified yeast cell of embodiment 82, wherein said engineered genetic modification comprises increased expression of a protein.

85. The genetically modified yeast cell of embodiment 82, wherein said engineered genetic modification comprises decreased expression of a protein.

86. The genetically modified yeast cell of one of embodiments 1 to 81, wherein said genetic modification is associated with exposure to a mutagen.

87. The genetically modified yeast cell of one of embodiments 1 to 86, wherein said genetic modification comprises modulated expression of a protein in a lipid, or lipid precursor, biosynthetic pathway.

88. A method of producing a lipid, lipid precursor, or oleochemical comprising:
1) culturing a yeast cell of any one of embodiments 1 to 87 in a growth medium; and
2) isolating said lipid, lipid precursor, or oleochemical.

89. The method of embodiment 88, wherein said lipid, lipid precursor, or oleochemicalis isolated from said yeast cell.

90. The method of embodiment 88, wherein said lipid, lipid precursor, or oleochemical is isolated from the growth medium.

91. The method of any one of embodiments 88 to 90, wherein said growth medium comprises a majority carbon source selected from the group consisting of glucose, glycerol, xylose, fructose, mannose, ribose, sucrose, and lignocellulosic biomass.

92. The method of any one of embodiments 88 to 90, wherein said growth medium comprises lignocellulosic biomass as the majority carbon source.

93. The method of any one of embodiments 88 to 92, wherein said growth medium comprises a carbon source and a nitrogen source wherein said carbon source is at a concentration at least 10-fold greater than the concentration of the nitrogen source (wt/wt).

94. The method of any one of embodiments 88 to 92, wherein said growth medium comprises a carbon source and a nitrogen source wherein said carbon source is at a concentration at least 16-fold greater than the concentration of the nitrogen source (wt/wt).

95. The method of any one of embodiments 88 to 92, wherein said growth medium comprises a carbon source and a nitrogen source wherein said carbon source is at a concentration at least 320-fold greater than the concentration of the nitrogen source (wt/wt).

96. The method of any one of embodiments 88 to 95, wherein said growth medium comprises micronutrients (e.g. cobalt, iron, magnesium, potassium, zinc, nickel, molybdenum, manganese, copper, or boron).

97. The method of any one of embodiments 88 to 95, wherein said growth medium comprises cobalt in an amount equivalent to 7.5 to 22.5 mg/L $CoCl_2$, magnesium in an amount equivalent to 125 to 375 mg/L $MgSO_4$, potassium in an amount equivalent to 7.5 to 22.5 mg/L KI, zinc in an amount equivalent to 10 to 30 mg/L $ZnSO_4.7H_2O$, manganese in an amount equivalent to 6 to 18 mg/L $MnSO_4.H_2O$, boron in an amount equivalent to 6 to 18 mg/L Boric acid, molybdenum in an amount equivalent to 7.5 to 22.5 mg/L $(NH_4)_2Mo.4H_2O$, nickel in an amount equivalent to 6 to 18 mg/L $NiSO_4.6H_2O$, iron in an amount equivalent to 10 to 30 mg/L $FeSO_4.7H_2O$, or copper in an amount equivalent to 7.5 to 22.5 mg/L $CuSO_4$.

98. The method of any one of embodiments 88 to 95, wherein said growth medium comprises $5.77 \times 10^{-5}$ M to $1.73 \times 10^{-4}$ M cobalt, 0.001 M to 0.003 M magnesium, $4.52 \times 10^{-5}$ M to $1.35 \times 10^{-4}$ M potassium, $4.05 \times 10^{-5}$ M to $1.22 \times 10^{-4}$ M zinc, $3.55 \times 10^{-5}$ M to $1.06 \times 10^{-4}$ M manganese, $9.07 \times 10^{-5}$ M to $2.91 \times 10^{-4}$ M boron, $3.76 \times 10^{-5}$ M to $1.10 \times 10^{-4}$ M molybdenum, $2.28 \times 10^{-5}$ M to $6.84 \times 10^{-5}$ M nickel, $3.60 \times 10^{-5}$ M to $1.08 \times 10^{-4}$ M iron, or $4.70 \times 10^{-5}$ M to $1.41 \times 10^{-4}$ M copper.

99. The method of any one of embodiments 88 to 95, wherein the growth medium comprises iron, copper, and molybdenum.

100. The method of any one of embodiments 88 to 95, wherein said growth medium comprises molybdenum in an amount equivalent to 7.5 to 22.5 mg/L $(NH_4)_2Mo.4H_2O$, iron in an amount equivalent to 10 to 30 mg/L $FeSO_4.7H_2O$, or copper in an amount equivalent to 7.5 to 22.5 mg/L $CuSO_4$.

101. The method of any one of embodiments 88 to 95, wherein said growth medium comprises $3.76 \times 10^{-5}$ M to $1.10 \times 10^{-4}$ M molybdenum, $3.60 \times 10^{-5}$ M to $1.08 \times 10^{-4}$ M iron, or $4.70 \times 10^{-5}$ M to $1.41 \times 10^{-4}$ M copper.

102. The method of any one of embodiments 88 to 95, wherein the growth medium comprises copper and nickel.

103. The method of any one of embodiments 88 to 95, wherein said growth medium comprises nickel in an amount equivalent to 6 to 18 mg/L $NiSO_4.6H_2O$ or copper in an amount equivalent to 7.5 to 22.5 mg/L $CuSO_4$.

104. The method of any one of embodiments 88 to 95, wherein said growth medium comprises $2.28 \times 10^{-5}$ M to $6.84 \times 10^{-5}$ M nickel or $4.70 \times 10^{-5}$ M to $1.41 \times 10^{-4}$ M copper.

105. The method of any one of embodiments 88 to 95, wherein the growth medium comprises copper, iron, and either molybdenum or nickel.

106. The method of any one of embodiments 88 to 95, wherein said growth medium comprises molybdenum in an amount equivalent to 7.5 to 22.5 mg/L $(NH_4)_2Mo.4H_2O$, nickel in an amount equivalent to 6 to 18 mg/L $NiSO_4.6H_2O$, iron in an amount equivalent to 10 to 30 mg/L $FeSO_4.7H_2O$, or copper in an amount equivalent to 7.5 to 22.5 mg/L $CuSO_4$.

107. The method of any one of embodiments 88 to 95, wherein said growth medium comprises $3.76 \times 10^{-5}$ M to $1.10 \times 10^{-4}$ M molybdenum, $2.28 \times 10^{-5}$ M to $6.84 \times 10^{-5}$ M nickel, $3.60 \times 10^{-5}$ M to $1.08 \times 10^{-4}$ M iron, or $4.70 \times 10^{-5}$ M to $1.41 \times 10^{-4}$ M copper.

108. The method of any one of embodiments 88 to 95, wherein the growth medium comprises copper, iron, molybdenum, and nickel.

109. A method of isolating a genetically modified yeast cell from a plurality of yeast cells, comprising greater than 20% wt/wt lipids, lipid precursors, and/or oleochemicals (e.g., lipid, lipids, lipid precursors, lipid precursor, oleochemicals, or oleochemical) in dry weight, comprising allowing a genetically modified yeast cell to separate from a population of yeast cells within said plurality of yeast cells by floating above said population of yeast cells within an aqueous medium thereby isolating said genetically modified yeast cell, wherein said population of yeast cells comprises a lower percentage wt/wt of lipids, lipid precursors, and/or oleochemicals (e.g., lipid, lipids, lipid precursors, lipid precursor, oleochemicals, or oleochemical) than said genetically modified yeast cell.

110. The method of embodiment 109, wherein said genetically modified yeast cell comprises greater than 30% wt/wt lipids, lipid precursors, and/or oleochemicals (e.g., lipid, lipids, lipid precursors, lipid precursor, oleochemicals, or oleochemical) in dry weight.

111. The method of embodiment 109, wherein said genetically modified yeast cell comprises greater than 40% wt/wt lipids, lipid precursors, and/or oleochemicals (e.g., lipid, lipids, lipid precursors, lipid precursor, oleochemicals, or oleochemical) in dry weight.

112. The method of embodiment 109, wherein said genetically modified yeast cell comprises greater than 50% wt/wt lipids, lipid precursors, and/or oleochemicals (e.g., lipid, lipids, lipid precursors, lipid precursor, oleochemicals, or oleochemical) in dry weight.

113. The method of embodiment 109, wherein said genetically modified yeast cell comprises greater than 60% wt/wt lipids, lipid precursors, and/or oleochemicals (e.g., lipid, lipids, lipid precursors, lipid precursor, oleochemicals, or oleochemical) in dry weight.

114. The method of any one of embodiments 109 to 113, wherein said plurality of yeast cells are in a bioreactor with agitation and aeration rates of about 0.5 vvm (volume per volume per minute).

115. The method of any one of embodiments 109 to 113, wherein said plurality of yeast cells are in a bioreactor with agitation and aeration rates of about 1.0 vvm (volume per volume per minute).

116. The method of any one of embodiments 109 to 113, wherein said plurality of yeast cells are in a bioreactor with agitation and aeration rates of about 2.0 vvm (volume per volume per minute).

117. The method of any one of embodiments 109 to 113, wherein said plurality of yeast cells are in a bioreactor with agitation and aeration rates of about 3.0 vvm (volume per volume per minute).

118. The method of any one of embodiments 109 to 113, wherein said plurality of yeast cells are in a bioreactor with agitation and aeration rates of about 4.0 vvm (volume per volume per minute).

119. The method of any one of embodiments 109 to 118, wherein said aqueous medium comprises a yeast growth medium, minimal media, complete supplement media, or greater than 50 g/L glucose and less than 5 g/L of a nitrogen source.

120. The method of any one of embodiments 109 to 119, wherein said allowing is performed by centrifugation or simple sedimentation.

121. The method of any one of embodiments 109 to 120, wherein said genetically modified yeast cell was formed by transforming a yeast cell with a recombinant nucleic acid.

122. The method of any one of embodiments 109 to 120, wherein said genetically modified yeast cell was formed by mutagenizing a yeast cell.

123. The method of any one of embodiments 109 to 120, wherein said genetically modified yeast cell is created by first exposing a yeast cell to a mutagen (e.g. a chemical mutagen, radiation, UV, or a biological mutagen).

124. The method of any one of embodiments 109 to 120, wherein said genetically modified yeast cell was formed by mutagenizing a yeast cell.

125. A method of isolating a yeast cell comprising greater than 20% wt/wt lipids, lipid precursors, and/or oleochemicals (e.g., lipid, lipids, lipid precursors, lipid precursor, oleochemicals, or oleochemical) in dry weight from a plurality of yeast cells, comprising allowing a yeast cell comprising greater than 20% wt/wt lipids, lipid precursors, and/or oleochemicals (e.g., lipid, lipids, lipid precursors, lipid precursor, oleochemicals, or oleochemical) to separate from a population of yeast cells within said plurality of yeast cells by floating above said population of yeast cells within an aqueous medium thereby isolating said yeast cell comprising greater than 20% wt/wt lipids, lipid precursors, and/or oleochemicals (e.g., lipid, lipids, lipid precursors, lipid precursor, oleochemicals, or oleochemical), wherein said population of yeast cells comprises a lower percentage wt/wt of lipids, lipid precursors, and/or oleochemicals (e.g., lipid, lipids, lipid precursors, lipid precursor, oleochemicals, or oleochemical) than said yeast cell comprising greater than 20% wt/wt lipids, lipid precursors, and/or oleochemicals (e.g., lipid, lipids, lipid precursors, lipid precursor, oleochemicals, or oleochemical).

126. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 30% wt/wt lipids, lipid precursors, and/or oleochemicals (e.g., lipid, lipids, lipid precursors, lipid precursor, oleochemicals, or oleochemical) in dry weight.

127. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 40% wt/wt lipids, lipid precursors, and/or oleochemicals (e.g., lipid, lipids, lipid precursors, lipid precursor, oleochemicals, or oleochemical) in dry weight.

128. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 50% wt/wt lipids, lipid precursors, and/or oleochemicals (e.g., lipid, lipids, lipid precursors, lipid precursor, oleochemicals, or oleochemical) in dry weight.

129. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 60% wt/wt lipids, lipid precursors, and/or oleochemicals (e.g., lipid, lipids, lipid precursors, lipid precursor, oleochemicals, or oleochemical) in dry weight.

130. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 70% wt/wt lipids, lipid precursors, and/or oleochemicals (e.g., lipid, lipids, lipid precursors, lipid precursor, oleochemicals, or oleochemical) in dry weight.

131. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 80% wt/wt lipids, lipid precursors, and/or oleochemicals (e.g., lipid, lipids, lipid precursors, lipid precursor, oleochemicals, or oleochemical) in dry weight.

132. The method of embodiment 125, wherein said yeast cell comprising greater than 20% wt/wt lipids, lipid precursors, and/or oleochemicals (e.g., lipid, lipids, lipid precursors, lipid precursor, oleochemicals, or oleochemical) comprises greater than 90% wt/wt lipids, lipid precursors, and/or oleochemicals (e.g., lipid, lipids, lipid precursors, lipid precursor, oleochemicals, or oleochemical) in dry weight.

133. The method of one of embodiments 125 to 132, wherein said yeast cell comprising greater than 20% wt/wt lipids, lipid precursors, and/or oleochemicals (e.g., lipid, lipids, lipid precursors, lipid precursor, oleochemicals, or oleochemical) comprises a mutation created by natural genetic drift.

134. The method of any one of embodiments 88 to 95, wherein said growth medium comprises cobalt.

135. The method of any one of embodiments 88 to 95 and 134, wherein said growth medium comprises iron.

136. The method of any one of embodiments 88 to 95 and 134 to 135, wherein said growth medium comprises magnesium.

137. The method of any one of embodiments 88 to 95 and 134 to 136, wherein said growth medium comprises potassium.

138. The method of any one of embodiments 88 to 95 and 134 to 137, wherein said growth medium comprises zinc.

139. The method of any one of embodiments 88 to 95 and 134 to 138, wherein said growth medium comprises nickel.

140. The method of any one of embodiments 88 to 95 and 134 to 139, wherein said growth medium comprises molybdenum.

141. The method of any one of embodiments 88 to 95 and 134 to 140, wherein said growth medium comprises manganese.

142. The method of any one of embodiments 88 to 95 and 134 to 141, wherein said growth medium comprises copper.

143. The method of any one of embodiments 88 to 95 and 134 to 142, wherein said growth medium comprises boron.

V. EXAMPLES

The following examples are meant to illustrate certain embodiments of the invention and not to limit the scope of the invention described herein.

A. MATERIALS AND METHODS

Base Strains and Media.

*E. coli* strain DH10B was used for cloning and plasmid propagation. DH10B was grown at 37° C. with constant shaking in Luria-Bertani Broth (Teknova) supplemented with 50 μg/ml of ampicillin for plasmid propagation. *Yar-* rowia lipolytica strain PO1f (ATCC #MYA-2613), a leucine and uracil auxotroph devoid of any secreted protease activity (Madzak et al., 2000), was used as the base strain for all studies. Table 1 contains a list of PO1f derivatives produced in this study. *Y. lipolytica* was cultivated at 30° C. with constant agitation. 2 mL cultures of *Y. lipolytica* used in large-scale screens were grown in a rotary drum (CT-7, New Brunswick Scientific) at speed seven, and larger culture volumes were shaken in flasks at 225 rpm.

YSC media consisted of 20 g/L glucose (Fisher Scientific), 0.79 g/L CSM supplement (MP Biomedicals), and 6.7 g/L Yeast Nitrogen Base w/o amino acids (Becton, Dickinson, and Company). YSC-URA, YSC-LEU, and YSC-LEU-URA media contained 0.77 g/L CSM-Uracil, 0.69 g/L CSM-Leucine, or 0.67 g/L CSM-Leucine-Uracil in place of CSM, respectively. YPD media contained 10 g/L yeast extract (Fisher Scientific), 20 g/L peptone (Fisher Scientific) and 20 g/L glucose, and was often supplemented with 300 μg/ml Hygromycin B (Invitrogen) for knockout selection. Lipid accumulation response towards media formulation was investigated by cultivation in varying concentrations of glucose and nitrogen. These media formulations contained 0.79 g/L CSM, 1.7 g/L Yeast Nitrogen Base w/o amino acid and w/o $(NH_4)_2SO_4$ (Becton, Dickinson, and Company), between 10 g/L and 320 g/L glucose, and between 0.04 g/L and 10 g/L ammonium sulfate—$(NH_4)_2SO_4$ (Fisher Scientific). These media are routinely referred to by their ratio of carbon content (glucose) to nitrogen content (ammonium sulfate). For instance, media containing 80 g/L glucose and 5 g/L ammonium sulfate is called $C_{80}:N_5$ media. When utilizing alternative carbon sources, glucose was replaced by 80 g/L arabinose, 80 g/L fructose, 80 g/L galactose, 80 g/L glycerol (Fisher Scientific), 80 g/L mannose, 80 g/L maltose 80 g/L ribose, 80 g/L sucrose (Acros Organics), 80 g/L Xylose, or 80 g/L of a saccharide mix resembling the composition of lignocellulosic biomass (57% Glucose, 32% Xylose, 5% Arabinose, 3% Mannose, and 3% Galactose by weight). Solid media for *E. coli* and *Yarrowia lipolytica* was prepared by adding 20 g/L agar (Teknova) to liquid media formulations.

When analyzing the effect of micronutrient supplementation, $CoCl_2$ (15 mg/L), $MgSO_4$ (250 mg/L), KI (15 mg/L), $ZnSO_4.7H_2O$ (20 mg/L), $MnSO_4.H_2O$ (12.5 mg/L), Boric acid (12.5 mg/L), $(NH_4)_2Mo.4H_2O$ (15 mg/L), $NiSO_4.6H_2O$ (12.5 mg/L), $FeSO_4.7H_2O$ (20 mg/L), or $CuSO_4$ (15 mg/L) were added to the stated media formulation. Concentrations given are the final concentrations of the metal ion.

Initial Optimization of Media Formulation for Wildtype and Engineered Strains.

Figure 2:
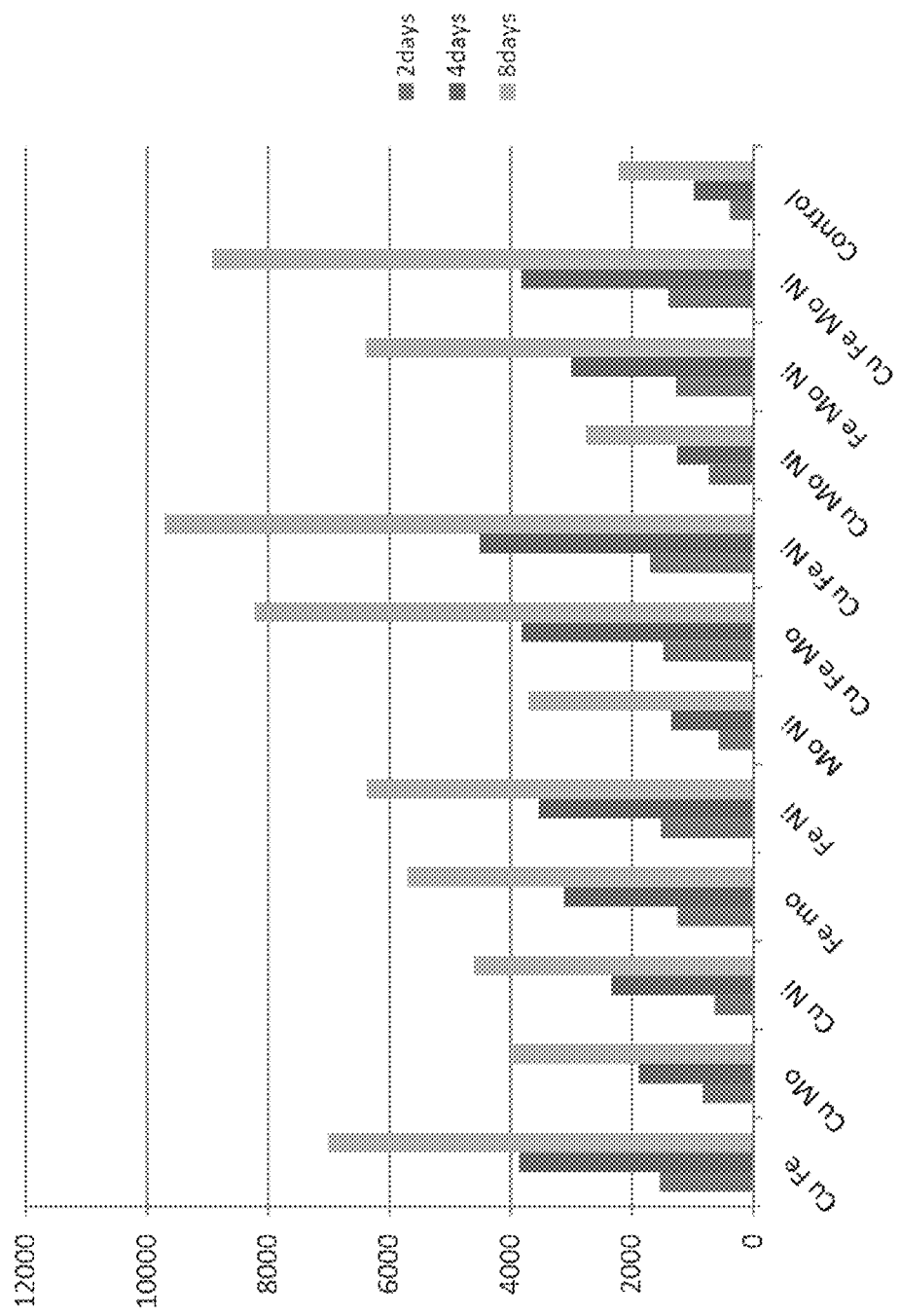
FIG. 2. Nile Red assay quantifying lipid content of PO1f WT strain in C160N0.2 media supplemented with multiple micronutrients after 2, 4, and 8 days of cultivation.

Nitrogen starvation is the accepted impetus for effecting a state of lipid accumulation in oleaginous organisms (Ratledge 2002). As a preliminary analysis of this induction potential, we selected seven media variations wildly variant in their ratios' of carbon content (glucose) to nitrogen content (ammonium sulfate) to assay for their ability to induce lipid accumulation. These media formulations are routinely referred to by this carbon to nitrogen ratio (C:N ratio), i.e., media containing 160 g/L glucose and 0.2 g/L ammonium sulfate is called $C_{160}:N_{0.2}$ media. We cultivated wildtype *Y. lipolytica* strain PO1f in these seven media formulations and assayed for relative lipid (e.g. triacylglyceride) accumulation using nile red fluorescence flow cytometry after 2, 4, 6, and 8 days. We observed a strong correlation between increasing carbon to nitrogen ratio and increased lipid (e.g. triacylglyceride) accumulation that spanned a 10-fold range, and we were able to increase nile red fluorescence levels by three-fold compared to levels induced in standard minimal (YSC) media. Thus, we confirmed the beneficial effect of increasing C:N ratio towards lipid (e.g. triacylglyceride) accumulation in non-engineered *Y. lipolytica*, so we sought to further improve oleo-content with additional media supplementation. In particular, $FeSO_4$ supplementation has been implicated in enabling increased citric acid accumulation in *Y. lipolytica* (Kamzolova et al. 2003), specifically under oxygen limiting conditions. Citric acid and fatty acid accumulation are closely linked in *Y. lipolytica*, so we hypothesized that this iron-responsive citric acid accumulation could also increase downstream lipid (e.g. triacylglyceride) accumulation. To fully analyze the potential benefits of micronutrient addition towards lipid (e.g. triacylglyceride) accumulation (Song et al. 2012; Zhao et al. 2008), we cultivated PO1f in minimal media supplemented with cobalt, magnesium, potassium, zinc, manganese, boric acid, molybdenum, nickel, iron, and copper (FIG. 1), and saw increased lipid (e.g. triacylglyceride) accumulation with iron, nickel, copper, molybdenum, and zinc. We performed a combinatorial screening of iron, nickel, copper, and molybdenum supplementation to detect cumulative beneficial effects towards increasing cellular lipid content. Triple supplementation with copper, nickel, and iron increased lipid accumulation levels to the highest observed at that time (FIG. 2).

Thus, manipulating media formulation effectively increased lipid formulation in a wildtype strain, however, the relationship between strain genotype and this effect has yet to be explored. We sought to determine if a strain rationally engineered for increased lipid accumulation would benefit in the same manner from increasing C:N ratio. In our initial attempts to engineer a *Y. lipolytica* strain for increased lipid accumulation, we overexpressed the AMPDp in a ΔPEX10 background to create a strain with a 17-fold increase in nile red fluorescence levels. To determine if genomic modifications could affect differential responses towards media-induced lipid accumulation, we cultivated unmodified PO1f and our engineered high lipid producer in twenty media formulations that varied in carbon and nitrogen levels (Table 3) and analyzed for lipid content with nile red fluorescence flow cytometry after two days, four days, and eight days. Two days was insufficient time to induce lipid accumulation, while lipid accumulation is evident a majority of media formulation for the PO1f ΔPEX10 AMPDp overexpression strain after eight days. Heat graphs of relative fluorescent values illustrate that the PO1f ΔPEX10 AMPDp overexpression strain accumulates lipids efficiently at an optimum value of 80 g/L glucose after 4 days, while PO1f is only slight induced in any condition, most noticeably after six to eight days in $C_{160}N_{0.2}$ media. In general, the 320 g/L glucose condition is too high to induce lipid accumulation effectively, most likely because the high sugar content prevents cell growth. Likewise, formulations 0.04 and 0.2 g/L ammonium sulfate tend to poorly induce lipid accumulation, especially within four days or less. Finally, an optimum C:N ratio of ~10 to 40 can be observed when discounting these highest glucose and lowest ammonium sulfate.

B. CLONING AND TRANSFORMATION PROCEDURES

All restriction enzymes were purchased from New England Biolabs and all digestions were performed according to standard protocols. PCR reactions were set up with recommended conditions using Phusion high fidelity DNA polymerase (Finnzymes), or LongAmp Taq DNA polymerase (New England Biolabs). Ligation reactions were performed overnight at room temperature using T4 DNA Ligase (Fermentas). Gel extractions were performed using the Fermentas GeneJET extraction kit purchased from Fisher Thermo-Scientific. *E. coli* minipreps were performed using the Zyppy Plasmid Miniprep Kit (Zymo Research Corporation). *E. coli* maxipreps were performed using the Qiagen HiSpeed Plasmid Maxi Kit. Transformation of *E. coli* strains was performed using standard electroporator protocols (Sambrook and Russell, 2001). Large amounts of linearized DNA (>20n), necessary for *Y. lipolytica* PO1f transformation were cleaned and precipitated using a standard phenol:chloroform extraction followed by an ethanol precipitation (Kirby, 1956).

Genomic DNA (gDNA) was extracted from *Y. lipolytica* using the Wizard Genomic DNA Purification kit (Promega). Transformation of *Y. lipolytica* with replicative plasmids was performed using the Zymogen Frozen EZ Yeast Transformation Kit II (Zymo Research Corporation), with plating on YSC-LEU plates. Transformation of *Y. lipolytica* PO1f with linearized cassettes was performed as described previously (Blazeck et al. 2013a), with selection on appropriate plates. All auxotrophic or antibiotic selection markers were flanked with LoxP sites to allow for retrieval of integrated markers the pMCS-UAS1B$_{16}$-TEF-Cre replicative vector (Blazeck et al. 2013a).

Plasmid Construction.

Primer sequences can be found in the Table 2. All *Y. lipolytica* episomal plasmids were centromeric, replicative vectors derived from plasmid pS116-Cen1-1(227) (Yamane et al. 2008) after it had been modified to include a multi-cloning site, a hrGFP green fluorescent reporter gene (pIRES-hrGFP, Agilent) driven by the strong UAS1B$_{16}$-TEF promoter (Blazeck et al. 2011), and a cyc1 terminator (Mumberg et al. 1995) to create plasmid pMCS-UAS1B$_{16}$-TEF-hrGFP. Integrative plasmids were derived from plasmids pUC-S1-UAS1B$_{16}$-Leum or pUC-S1-UAS1B$_{16}$-TEF (Blazeck et al. 2013a) that contained 5' and 3' rDNA integrative sequences surrounding the following elements— (from 5' to 3') a uracil section marker surrounded by LoxP sites for marker retrieval, the strong UAS1B$_{16}$-Leum or UAS1B$_{16}$-TEF promoter, AscI and PacI restriction enzyme sites for gene insertion, and a XPR2 minimal terminator. These integrative plasmids were also designed to contain two identical NotI restriction enzyme sites directly outside of the rDNA regions so that plasmid linearization would simultaneously remove *E. coli* pUC19-based DNA. All plasmids containing expression cassettes were sequenced confirmed before transformation into *Y. lipolytica*.

Construction of Episomal Expression Cassettes:

The following genes were PCR amplified from *Y. lipolytica* PO1f gDNA and inserted into vector pMCS-UAS1B$_{16}$-TEF-hrGFP in place of hrGFP with an AscI/PacI digest: AMPD, ACL subunit 1 (ACL1), ACL subunit 2 (ACL2), MEA1, DGA1, DGA2, the Tup1 general transcriptional repressor (Morin et al. 2011), and the HAC1 basic leucine zipper transcription factor involved in unfolded protein response (Morin et al. 2011) with primers, respectively. This formed plasmids pMCS-UAS1B$_{16}$-TEF-AMPD, pMCS-UAS1B$_{16}$-TEF-ACL1, pMCS-UAS1B$_{16}$-TEF-ACL2, pMCS-UAS1B$_{16}$-TEF-MEA, pMCS-UAS1B$_{16}$-TEF-DGA1, pMCS-UAS1B$_{16}$-TEF-DGA2, pMCS-UAS1B$_{16}$-TEF-TUP1, and pMCS-UAS1B$_{16}$-TEF-HAC1.

Construction of Integrative Expression Cassettes:

The following genes were gel extracted from the previously constructed episomal expression vectors and inserted into vector pUC-S1-UAS1B$_{16}$-TEF with an AscI/PacI digest: AMPD, ACL subunit 1 (ACL1), ACL subunit 2 (ACL2), MEA1, DGA1, and DGA2. This formed plasmids pUC-S1-UAS1B$_{16}$-TEF-AMPD, pUC-S1-UAS1B$_{16}$-TEF-ACL1, pUC-S1-UAS1B$_{16}$-TEF-ACL2, pUC-S1-UAS1B$_{16}$-TEF-MEA1, and pUC-S1-UAS1B$_{16}$-TEF-DGA1, and pUC-S1-UAS1B$_{16}$-TEF-DGA2. The loxP-surrounded uracil marker of these integrative plasmids was replaced with a loxP-surrounded leucine marker to enable integrative selection with leucine auxotrophy and co-expression of two enzymes without marker retrieval. These leucine marker integrative plasmids were dubbed plasmids pUC-S2-UAS1B$_{16}$-TEF-AMPD, pUC-S2-UAS1B$_{16}$-TEF-ACL1, pUC-S2-UAS1B$_{16}$-TEF-ACL2, pUC-S2-UAS1B$_{16}$-TEF-MEA1, and pUC-S2-UAS1B$_{16}$-TEF-DGA1, and pUC-S2-UAS1B$_{16}$-TEF-DGA2.

ACL1 and ACL2 were similarly inserted into pUC-S1-UAS1B$_{16}$-Leum with primers, respectively, to form plasmids pUC-S1-UAS1B$_{16}$-Leum-ACL1 and pUC-S1-UAS1B$_{16}$-Leum-ACL2.

Strain Construction.

All strains were confirmed through gDNA extraction and PCR confirmation and are listed in Table 1. We previously constructed two markerless single-gene deletion strains in the *Y. lipolytica* PO1f background, PO1f-Δmfe1 and PO1f-Δpex10, deficient in their β-oxidation and peroxisomal biogenesis capacity, respectively (Blazeck et al. 2013a). Following our previous protocol, the PEX10 gene was deleted from strain PO1f-Δmfe1 to form the markerless double mutant PO1f-Δmfe1-Δpex10. These four strains, PO1f, PO1f-Δmfe1, PO1f-Δpex10, and PO1f-Δmfe1-Δpex10 were utilized as backgrounds for single and double overexpression of the AMPD, ACL1, ACL2, MEA, DGA1, and DGA2 genes, including variation in selective marker utilized, i.e., leucine (S2 integrative cassette or pMCS episomal cassette) vs. uracil (S1 integrative cassette). S2 and S1 integrative cassettes were linearized, transformed into our four background strains, and selected for on appropriate dropout plates. Table 1 contains a list of rationally engineered strains derived in this manner. ORF-less plasmids pUC-S1-UAS1B$_{16}$-TEF and pUC-S1-UAS1B$_{16}$-TEF were utilized to create strains lacking leucine, uracil, or both leucine and uracil auxotrophies, dubbed S1-Ø, S2-Ø, and S1-S2-Ø (Table 1).

Combinatorial Genome Engineering.

Prior engineering efforts have successfully increased lipid accumulation in *Y. lipolytica* by manipulating fatty acid, lipid, or central carbon metabolism, but no attempt has been made to simultaneously alter these metabolic functionalities (Beopoulos et al. 2008; Dulermo and Nicaud 2011; Tai and Stephanopoulos 2013). We sought to concurrently control these aspects of lipid synthesis by overexpressing three enzymes that control metabolic flux from central carbon metabolism into fatty acid synthesis (AMPDp, ACLp, and MEA1p) or two isozymes that control lipid synthesis (DGA1p and DGA2p) in four genomic backgrounds with altered fatty acid catabolic ability. These four genomic backgrounds included the PO1f (WT) strain, a PO1f MFE1 deletion strain (ΔMFE1), a PO1f PEX10 deletion strain (ΔPEX10), and a MFE1 PEX10 double knockout strain (ΔPEX10ΔMFE1). The majority of enzymatic overexpressions were driven by the high strength UAS1B$_{16}$-TEF constitutive promoter (Blazeck et al. 2011), were integrated into *Y. lipolytica*'s genomic rDNA repeats (Blazeck et al. 2013a; Ledall et al. 1994), and alleviated either PO1f s uracil or leucine auxotrophy. In our previous work, we noticed that alleviation of the leucine auxotrophy tended to increase lipid (e.g. triacylglyceride) accumulation far more than alleviation of the uracil auxotrophy. Therefore, nearly identical strains were routinely created differing only in the marker utilized to integrate an enzymatic overexpression cassette, enabling either uracil synthesis (S1) or leucine synthesis (S2). Initial overexpressions of the DGA1p and DGA2p enzymes occurred episomally with an identical UAS1B$_{16}$-TEF promoter on a leucine-marker containing plasmid, though final strain construction entailed integrating these cassettes. Strain names included background (WT, ΔMFE1, ΔPEX10, or ΔPEX10ΔMFE1), markers used (S1, S2, S1-S2, or pMCS), and enzymes overexpressed (AMPD, MEA, ACL1, ACL2, DGA1, DGA2) so a strain overexpressing the AMPDp enzyme with a leucine marker in the ΔPEX10ΔMFE1 background is called ΔPEX10ΔMFE1 S2-AMPD. S1-Ø, S2-Ø, and S1, 2-Ø refer to strains without protein overexpressions but with uracil, leucine, or uracil+leucine auxotrophies alleviated. ACL1p and ACL2p form a heterodimer in vivo so were tested as concurrent overexpressions.

Figure 3:
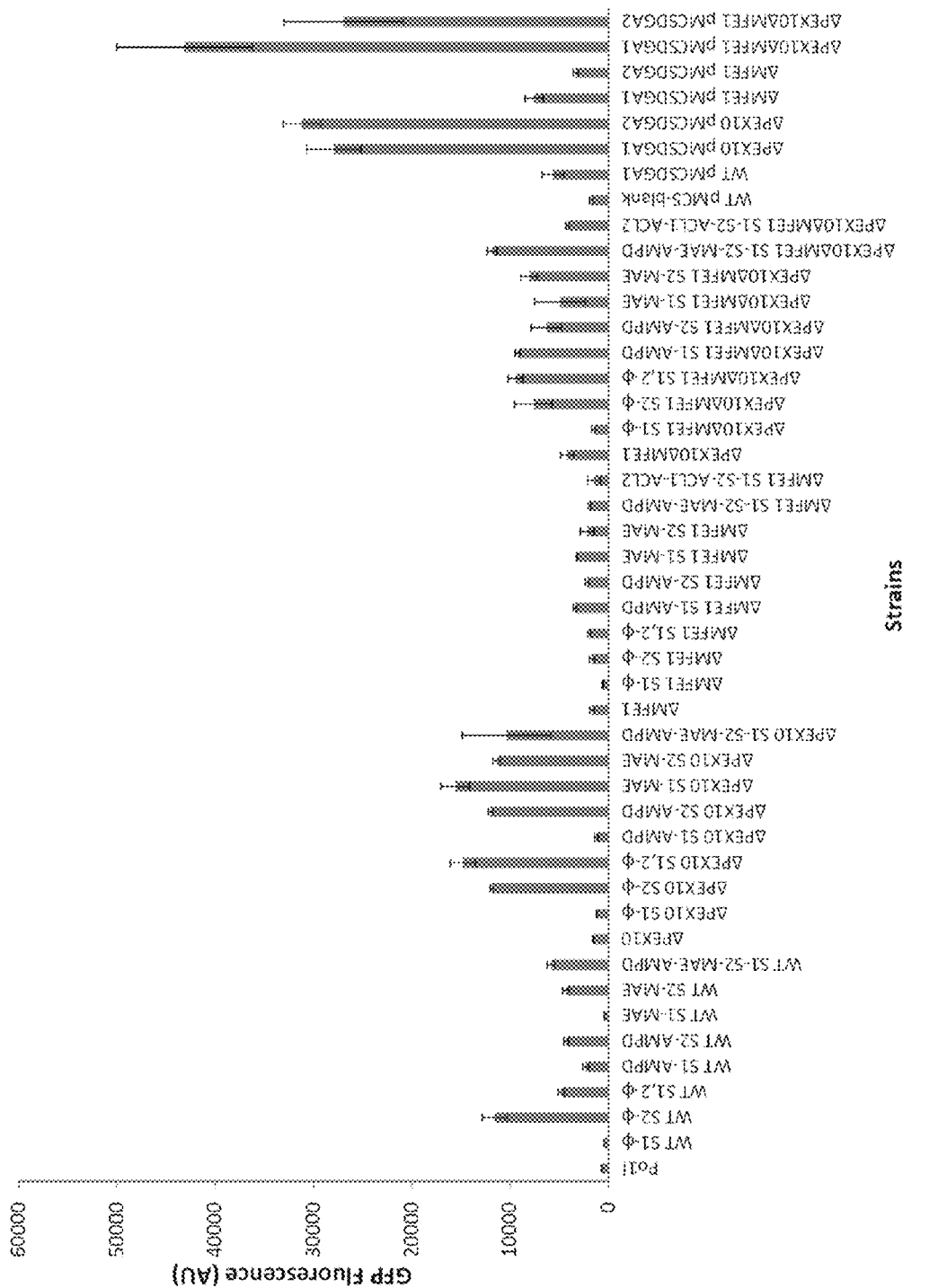
FIG. 3. Nile Red assay quantify lipid content of 46 rationally constructed genetically modified PO1f derivatives.
Figure 4:
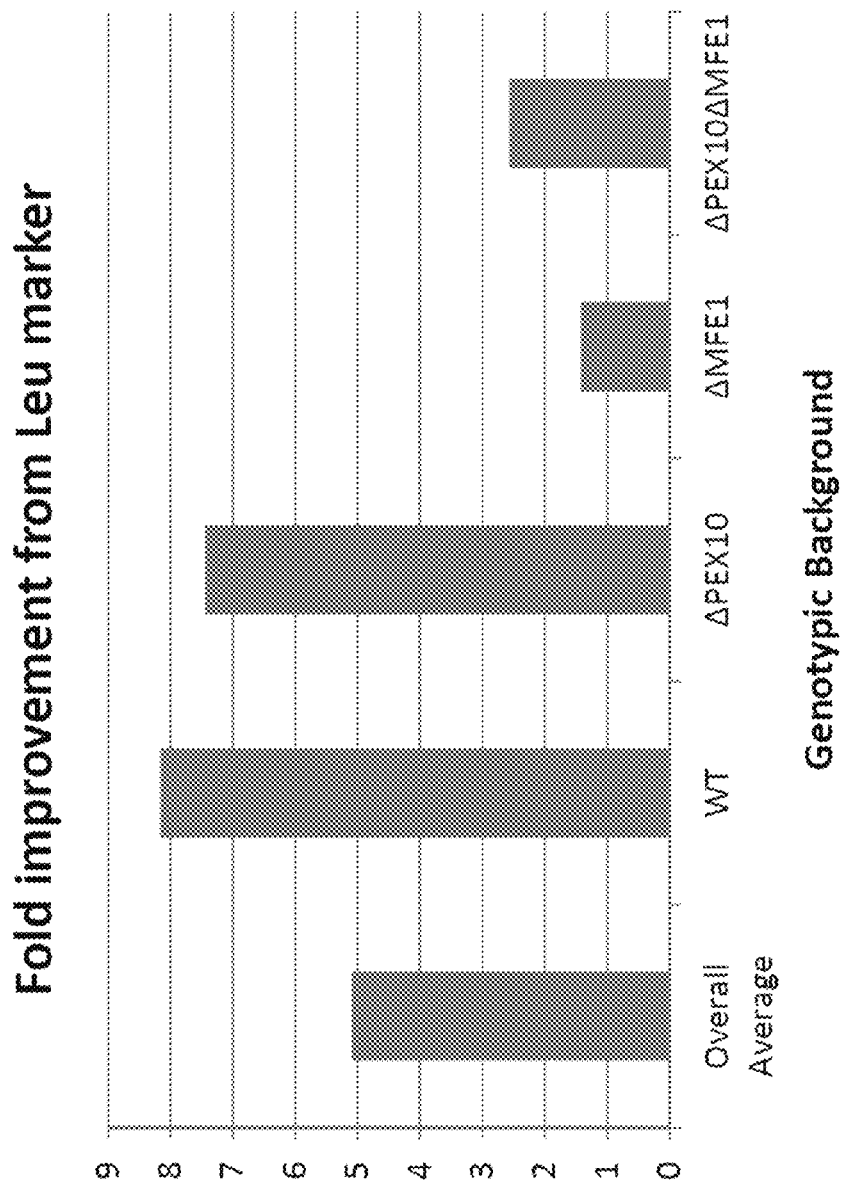
FIG. 4. Fold improvement of lipid accumulation (from Nile Red assay signal (RFU)) by enabling the capacity to synthesis leucine through incorporation of the LEU2 marker to different genotypic background. LEU2 expression can be from an episomal or an integrated sequence.
Figure 5:
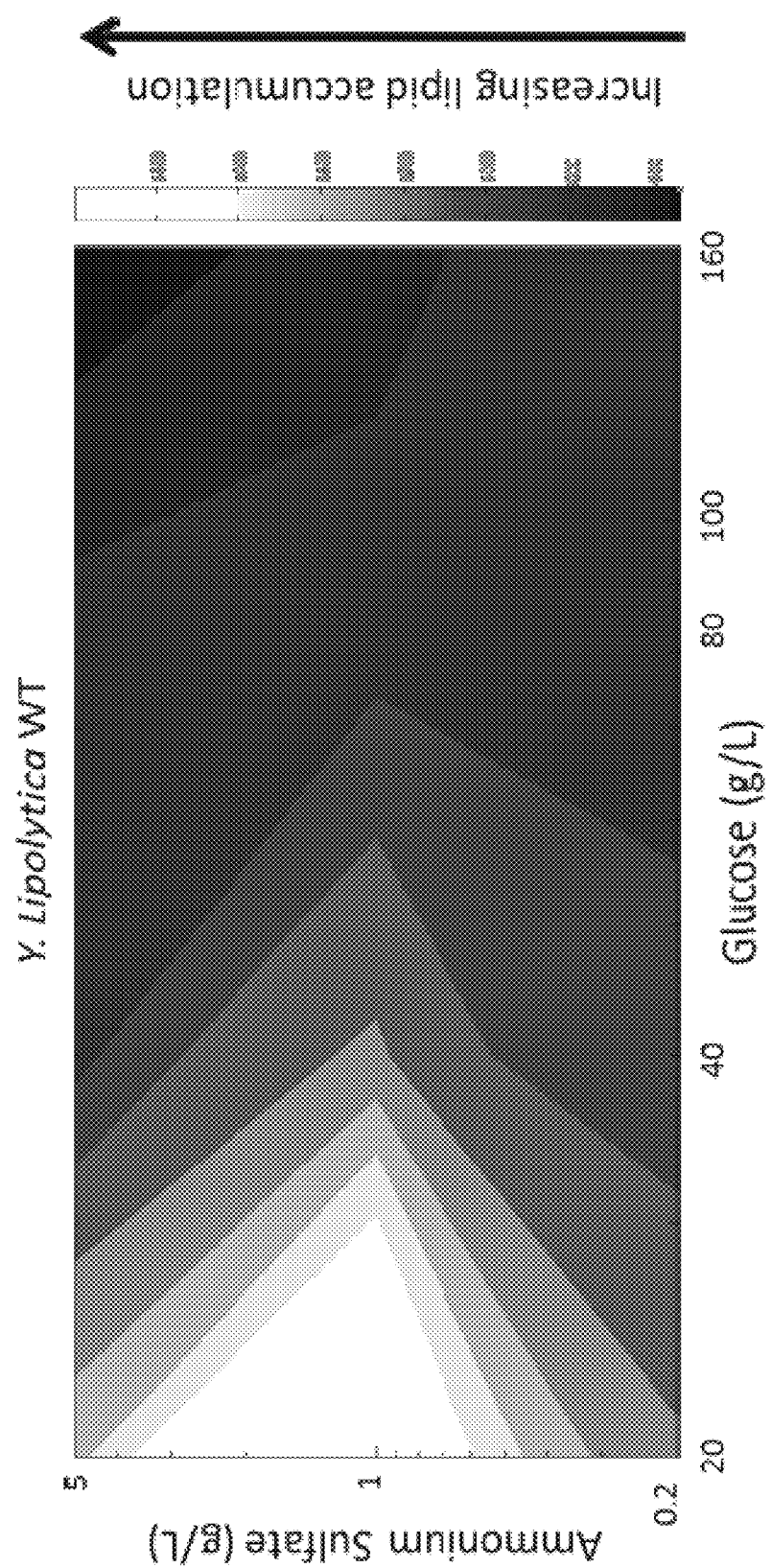
FIG. 5. Heat map of lipid content based on Nile Red signal of PO1f WT cultured in media formulations with different carbon to nitrogen ratios after 4 days.
Figure 6:
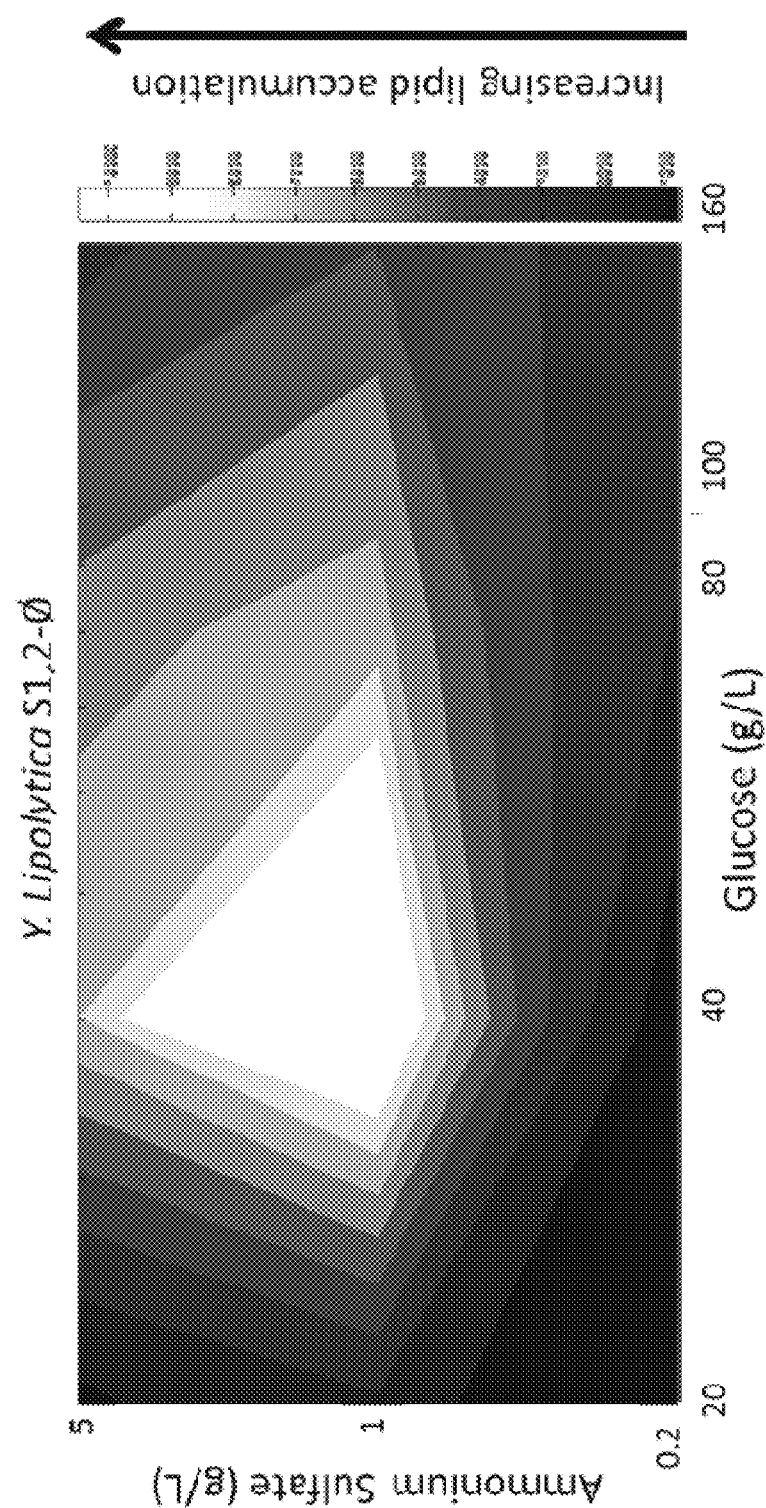
FIG. 6. Heat map of lipid content based on Nile Red signal of PO1f-S1-S2-φ cultured in media formulations with different carbon to nitrogen ratios after 4 days.
Figure 7:
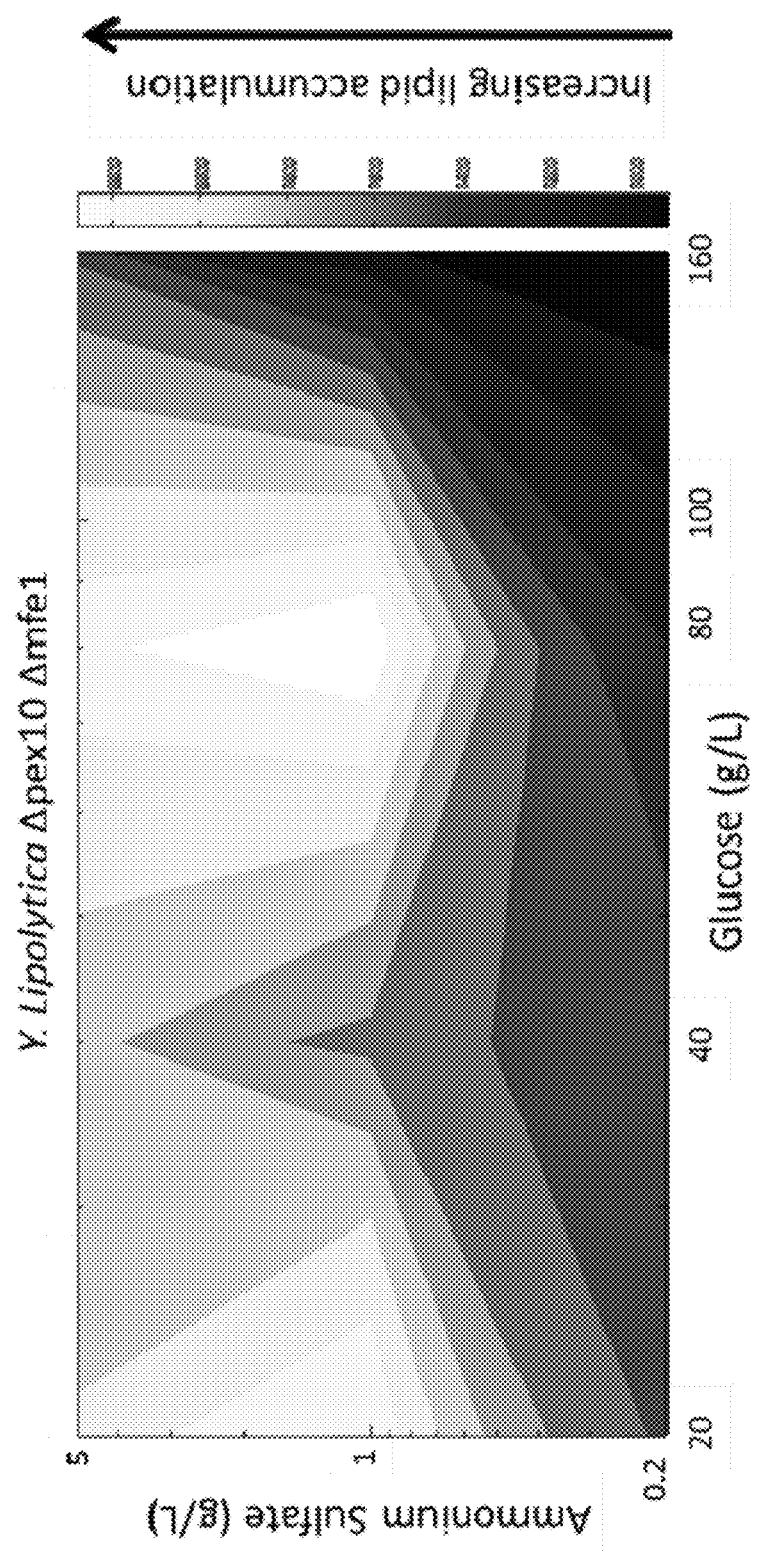
FIG. 7. Heat map of lipid content based on Nile Red signal of ΔPEX10ΔMFE1 cultured in media formulations with different carbon to nitrogen ratios after 4 days.
Figure 8:
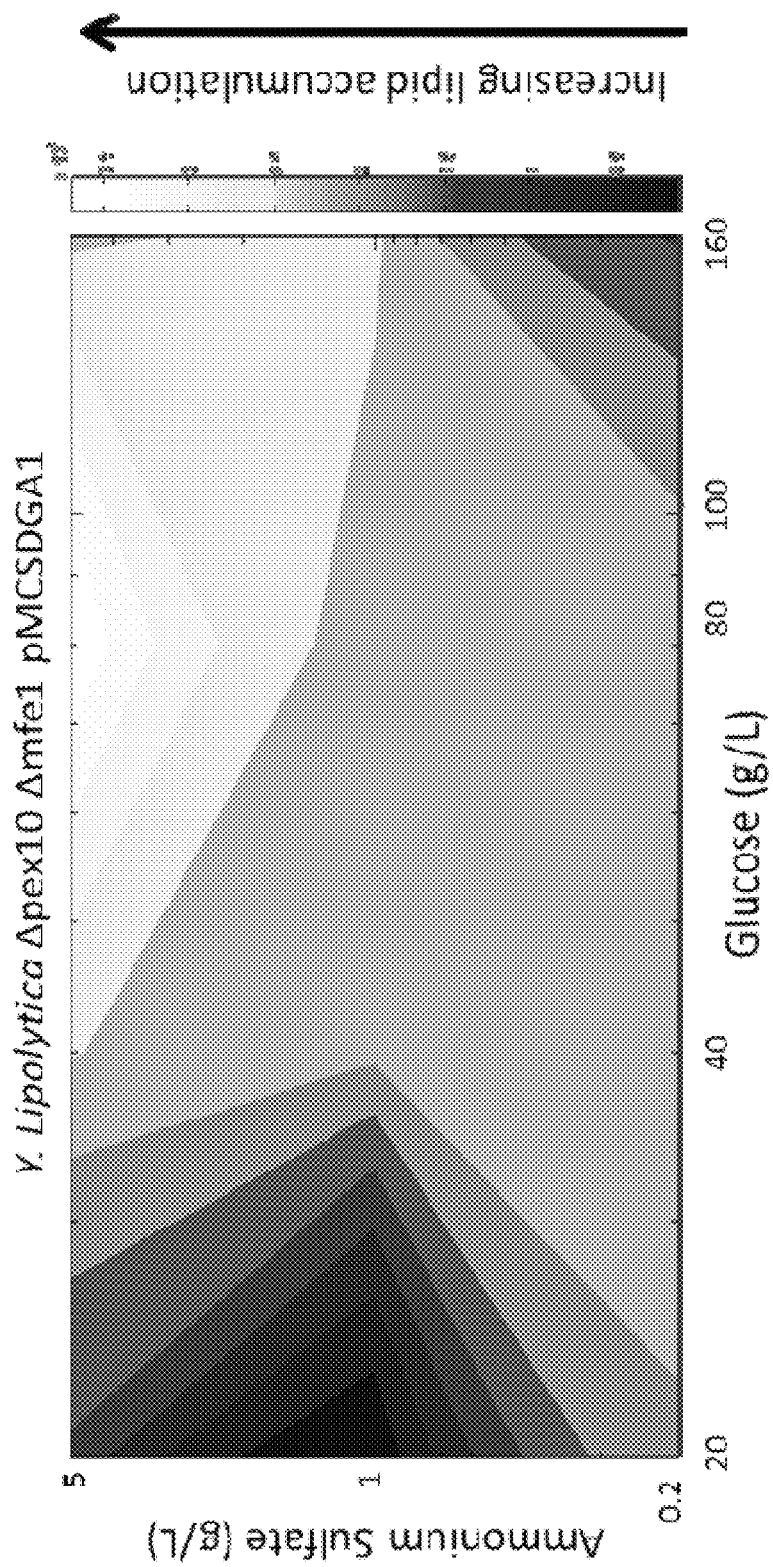
FIG. 8. Heat map of lipid content based on Nile Red signal of ΔPEX10ΔMFE1-pMCS-DGA1 cultured in media formulations with different carbon to nitrogen ratios after 4 days.

Our combinatorial approach generated over 46 distinct genotypes that were analyzed for lipid (e.g. triacylglyceride) accumulation with nile red fluorescence flow cytometry after four days growth in $C_{80}N_5$ media and produced a large range in lipid (e.g. triacylglyceride) accumulation ability, culminating in a 60-fold improvement over PO1f WT control (FIG. 3). We saw that the deletion of the pex10 peroxisomal biogenesis transcription factor combined with overexpression of a acyl-CoA:diacylglycerol acyltransferase (DGA1 or DGA2) are essential for the highest lipid (e.g. triacylglyceride) production (FIG. 3). When comparing ammonia depletion in PO1f WT and our highest lipid producer, ΔPEX10ΔMFE1 pMCSDGA1, we observed a pronounced reduction in steady state nitrogen concentration in the ΔPEX10ΔMFE1 pMCSDGA1 strain. We saw a very noticeable correlation between the ability to synthesize leucine and lipid (e.g. triacylglyceride) accumulation ability, with an average increase of five fold in lipid content between comparable strains with and without a leucine marker present (FIG. 4). Deletion of mfe1 drastically reduced this increase in lipid (e.g. triacylglyceride) content. ΔMFE1 and ΔPEX10ΔMFE1 saw only a 1.42 fold and 2.58 fold increases in lipid (e.g. triacylglyceride) content granted from the capacity to synthesize leucine compared to 8.16 and 7.45 fold increases in WT and ΔPEX10 backgrounds (FIG. 4). In three of our four backgrounds, DGA1p outperformed DGA2p (FIG. 3); WT pMCSDGA2 was not included, but subsequent testing showed WT pMCSDGA1 to give higher lipid (e.g. triacylglyceride) levels than WT pMCSDGA2. Overall, fluorescence levels were highest in the ΔPEX10 and ΔPEX10ΔMFE1 backgrounds (~3-fold WT), and lowest in the ΔMFE1 background (~65% of WT), although mfe1 deletion has been shown to increase lipid (e.g. triacylglyceride) accumulation in media containing higher C:N ratio in eight day cultivation periods (Blazeck et al. 2013a). Because mfe1 deletion should further inhibit fatty acid degradation in the ΔPEX10ΔMFE1 background in long-scale fermentations, the DGA1p was integrated into the ΔPEX10ΔMFE1 background with S2 cassette and a S1-Ø to form our final fully heterotrophic rationally engineered strain. This ΔPEX10ΔMFE1 S1-S2-DGA1 strain displayed similar lipid (e.g. triacylglyceride) content to strains containing episomally expressed DGA1p and could accumulate lipids (e.g. triacylglyceride) effectively without any amino acid supplementation (Table 4) and yielded are highest % lipid (e.g. triacylglyceride) content of 32% dry cell weight for a total of 1.32 g/L. Furthermore, we saw no significant difference in LEU3 or DGA1 mRNA levels between these two strains.

Figure 15:
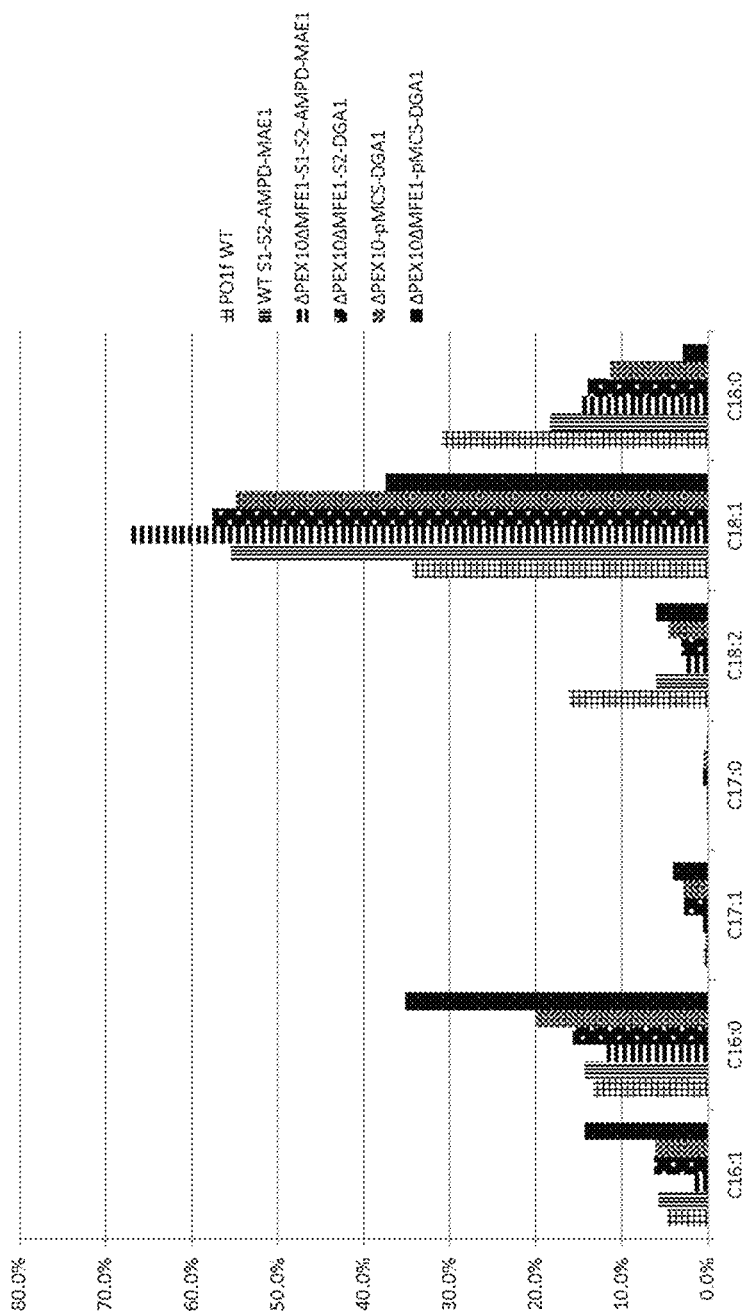
FIG. 15. Fatty acid profiles for different strains.
Figure 16:
FIG. 16. Lipid accumulation in strain PO1f and PO1fΔaco1 DGA1 leu+ ura+ characterized with flow cytometry using cells stained with Nile Red on 48 hour and 96 hour time point. The starting OD of the culture is 2.5 and the cells were cultivated in yeast synthetic medium with 80 g/L glucose.
Figure 17:
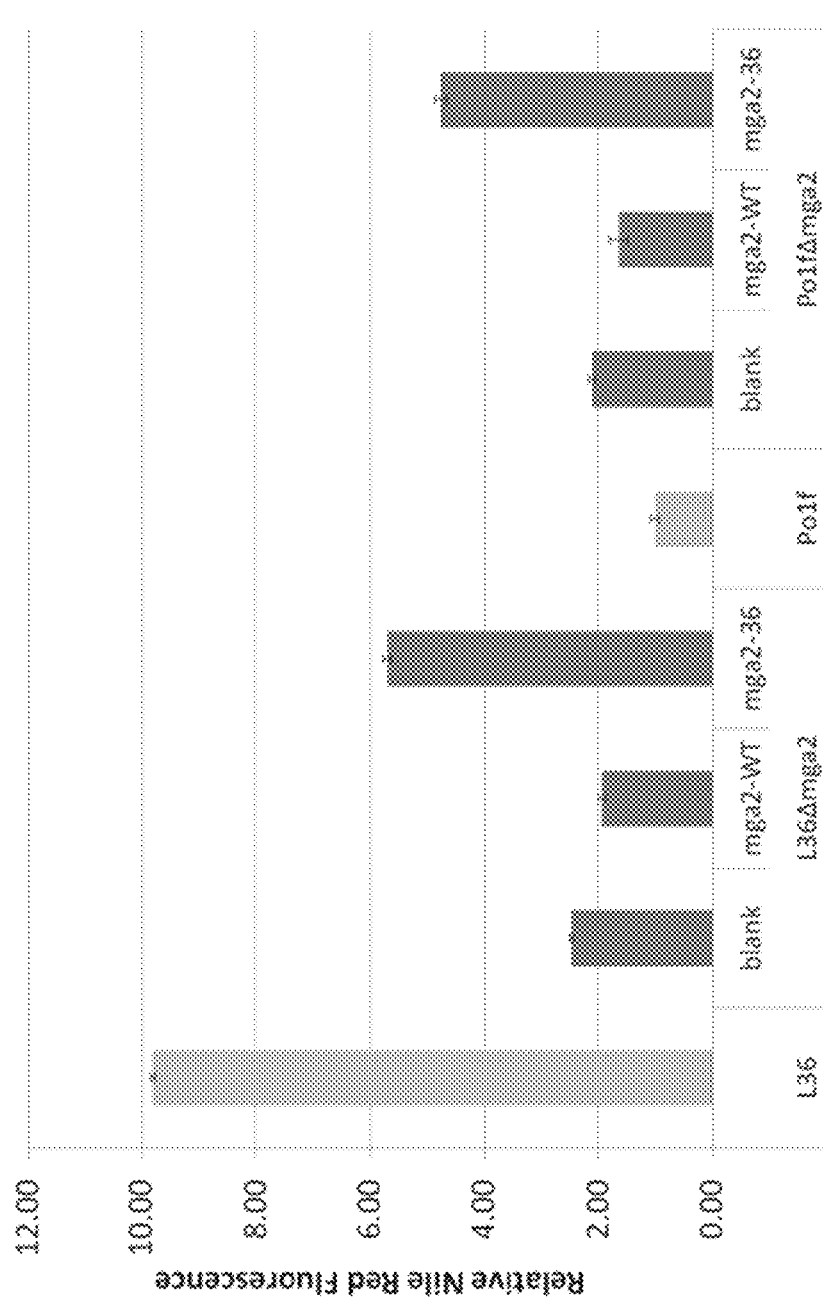
FIG. 17. Lipid accumulation characterized with flow cytometry using cells stained with Nile Red on 192 h time point. The starting OD of the culture is 5 and the cells were cultivated in yeast synthetic medium with 160 g/L glucose and 0.2 g/L ammonium sulfate. Illustrated in the bar graph, L36Δmga2 presented a significantly reduced lipid level comparing to L36 and L36Δmga2 MGA2-36 presented an elevated level of lipid accumulation comparing to L36Δmga2, indicating that mga2-36 is the reason of the high lipid accumulation phenotype in L36 strain. Combining the data with Δmga2 and Δmga2 MGA2-36 in PO1f, this set of data proves that Δmga2 can lead to improved lipid accumulation and further introduce the mutant transcriptional factor MGA2-36 can further elevate the level of lipid accumulation. (All strains in the set contain an episomal plasmid with LEU2). Lipid accumulation characterized with flow cytometry using cells stained with Nile Red on 192 h time point with yeast synthetic medium containing 160 g/L glucose and 0.2 g/L ammonium sulfate and 96 h time point with yeast synthetic medium containing 80 g/L glucose and 5 g/L ammonium sulfate. Introducing MGA2-36 to the engineered strain leads to elevated level of lipid accumulation, suggesting MGA2-36 can be used a lipid enhancer in the rationally engineered lipid production strain. Lipid accumulation characterized with flow cytometry using cells stained with Nile Red on 192 h time point with yeast synthetic medium containing 160 g/L glucose and 0.2 g/L ammonium sulfate. PO1fΔmga2 leu+ showed improved level of lipid accumulation comparing to PO1f leu+ indicating mga2 knockout could improve lipid accumulation. Introducing a transmembrane domain truncated MGA2-36 in PO1f could elevate the lipid level inside the cell.
Figure 18:
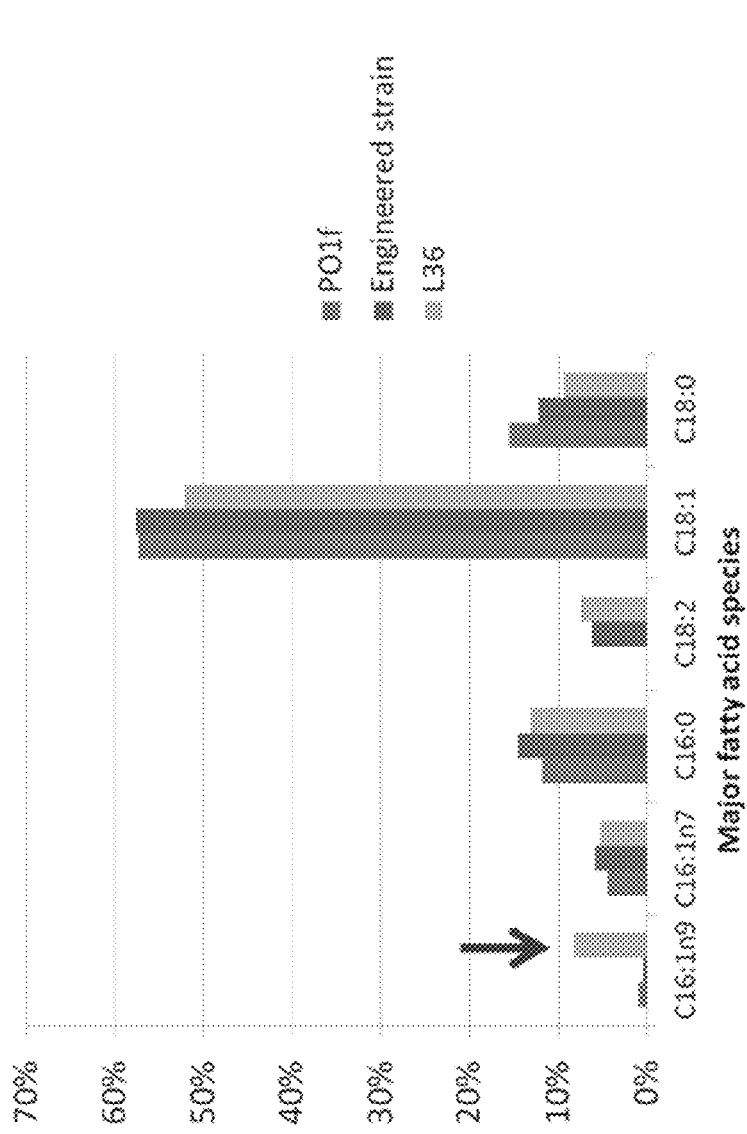
FIG. 18. Gas chromatography characterization of major fatty acid species profile in PO1f, Engineered strain and L36. L36 overproduced C16:1n9 fatty acid which could be linked with the mutant of MGA2 gene, which plays an important function on activating/regulating delta9 desaturase expression.
Figure 19:
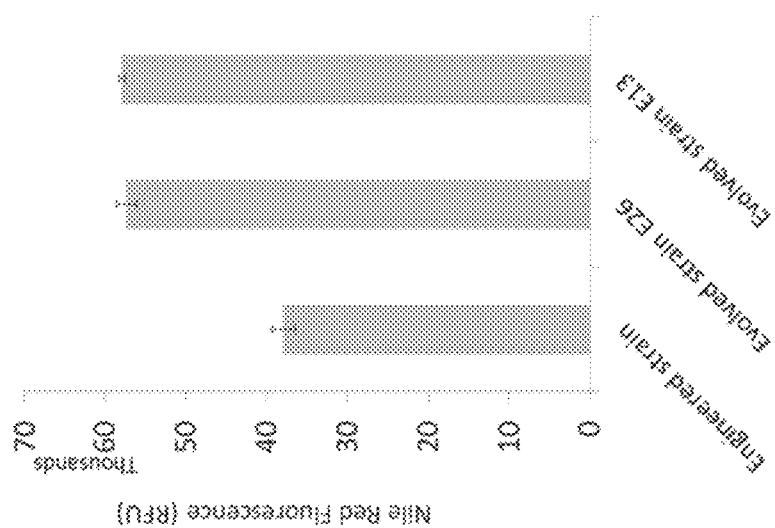
FIG. 19. Lipid accumulation characterized with flow cytometry using cells stained with Nile Red on 96 h time point with yeast synthetic medium containing 80 g/L glucose and 5 g/L ammonium sulfate. $1^{st}$ round EMS mutagenesis and floating cell transfer method selected strain E26 and E13 using final engineered strain PO1f Δpex10,mfe DGA1 leu+ ura+ presented a higher lipid accumulation level comparing to the engineered strain.
Figure 20:
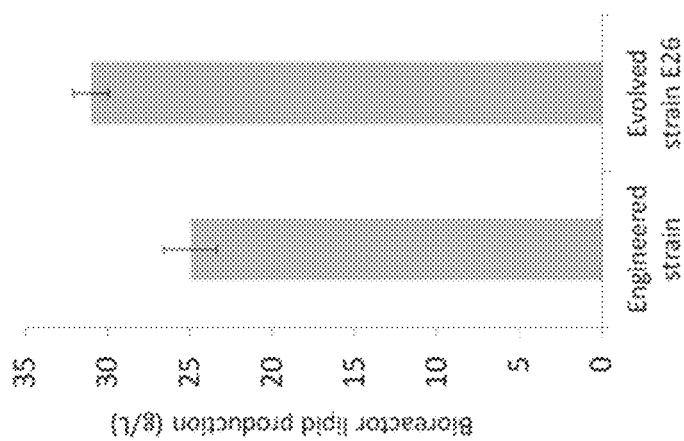
FIG. 20. Lipid production (g/L) in bioreaction with 160 g/L glucose and 13.4 g/L YNB with ammonium sulfate without amino acid (set control DO at 50% and pH=3.5) with engineered strain and evolved strain E26.
Figure 22:
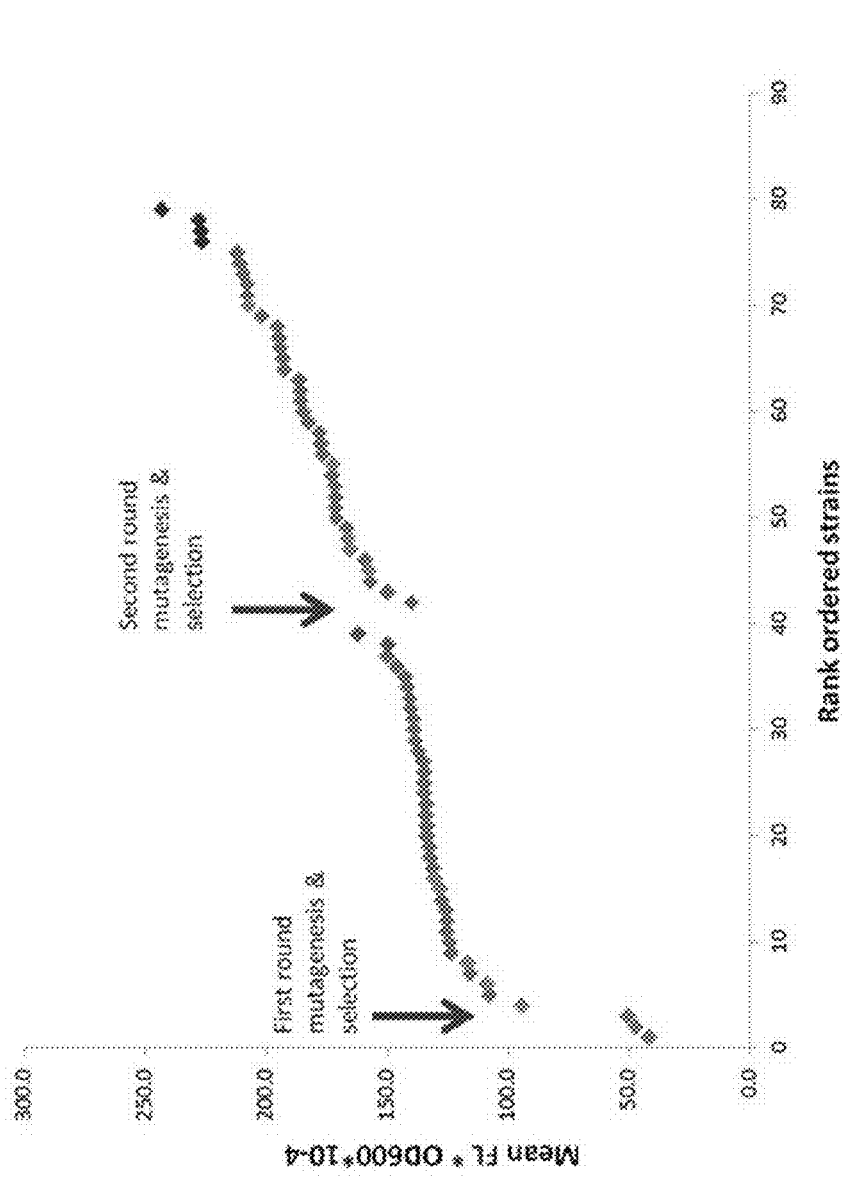
FIG. 22. Summary illustration of $1^{st}$ and $2^{nd}$ round of EMS mutagenesis and floating cells transfer selection with final engineered strain PO1f Δpex10,mfe DGA1 leu+ ura+ as starting strain for evolving and selecting high lipid production strain. Green indicating the final engineering strain, blue indicating the non-EMS treated control stains and red indicating the selected high lipid production strains. Strains were rank ordered based on the value cultured OD600*Nile Red mean fluorescence intensity*10−4.
Figure 23:
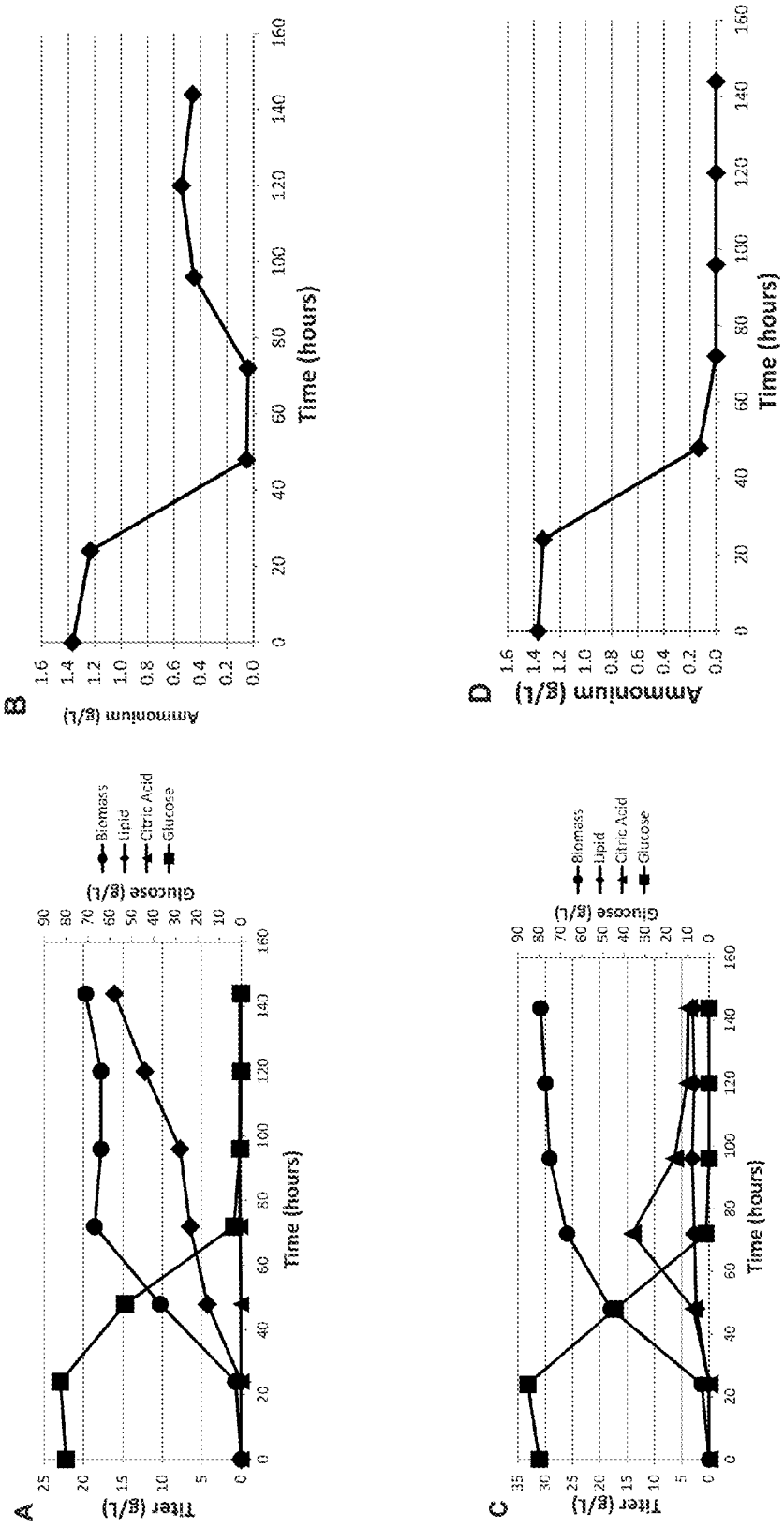
FIG. 23. Fermentation profiles of pex10 mfe1 leucine$^+$ uracil$^+$ DGA1 and PO1f leucine$^+$ uracil$^+$. Time courses of the 1.5 L scale batch fermentation of the pex10 mfe1 leucine$^+$ uracil$^+$ DGA1 (a,b) and PO1f leucine$^+$ uracil$^+$ (c,d) strains in 80 g/L glucose, 6.7 g/L YNB (no amino acids, 1.365 g/L ammonium) are shown, including production of biomass, lipids, and citric acid (left axis a,c), consumption of glucose (right axis a,c), and ammonium level (b,d). (a) During the pex10 mfe1 leucine$^+$ uracil$^+$ DGA1 fermentation, negligible citric acid was produced, and lipid product accumulated during and after biomass production phases. This fermentation was run three times in identical conditions, reaching final yields of 15.25 g/L lipids and 20.3 g/L biomass (75% lipid content), 14.96 g/L lipids and 20.6 g/L biomass (73% lipid content), and 16.9 g/L lipids and 19.21 g/L biomass (88% lipid content). Most time points show average values from the former two fermentations (75% and 73% final lipid content), while endpoints represent averages from all three final values. Glucose and ammonium substrate were fully consumed after 72 hours, but surprisingly, (b) ammonium level was replenished to a steady state level of ~0.5 g/L, almost 40% of the original starting level. (c) During the PO1f leucine$^+$ uracil$^+$ fermentation, citric acid accumulated to more than 14 g/L after 72 hours before quickly reducing to 4 g/L. Lipid production did not trend with biomass production, reaching a final yield of only 3 g/L lipids, compared to 30 g/L biomass, and glucose was again consumed within 72 hours. (d) Ammonium was fully consumed after 72 hours with no replenishment as observed in the mutant strain.

During bioreactor runs, these strains are able to produce significant amounts of lipids and cells exhibit 88% by dry cell weight lipids. Improved lipid production with one of the highest producing strains, ΔPEX10ΔMFE1-S1-S2-DGA1 in a bioreactor. Lipid levels have reached 22 g/L in media containing only 80 g/L glucose, 5 g/L ammonium sulfate, and 1.7 g/L Yeast Nitrogen Base (without amino acids or ammonium sulfate). Increasing dissolved oxygen content and maintaining pH at or above 5.0 enabled this yield. This represents ~86% of the theoretical yield. Furthermore, in these strains, we identify the presence of unique C17 fatty acids (FIG. 15).

Complex control of cellular processes, like lipid accumulation, is coordinated by transcription factors that regulate gene networks. In particular, the TupI general transcriptional repressor and the Had leucine zipper transcription factor involved in unfolded protein response have been shown to be upregulated in lipid (e.g. triacylglyceride) accumulation cell states (Morin et al. 2011). However, overexpression of these two proteins decreased lipid (e.g. triacylglyceride) accumulation in the PO1f WT background.

Dissection of Genotype-Dependence Towards Media Induction.

We more fully examined how C:N ratio and genotype interacted towards enabling lipid (e.g. triacylglyceride) accumulate on a larger scale by examining the response of twelve strains grown in thirteen different C:N ratios (Table 5). We were pleased to observe a strong tendency towards high lipid (e.g. triacylglyceride) levels in most high producers at a single media formulation—$C_{80}N_5$ (FIG. 5-8), allowing us to pinpoint a formulation for later use. Two trends stand out—(1) The 0.2 g/L ammonium sulfate formulations rarely enable lipid (e.g. triacylglyceride) accumulation, so that (2) the difference in induction from media containing 1 g/L and 5 g/L is slight, making glucose concentration seem more important towards increasing content than nitrogen content (after a certain threshold is reached).

Lipid Accumulation on Multiple Carbon Sources.

Figure 9:
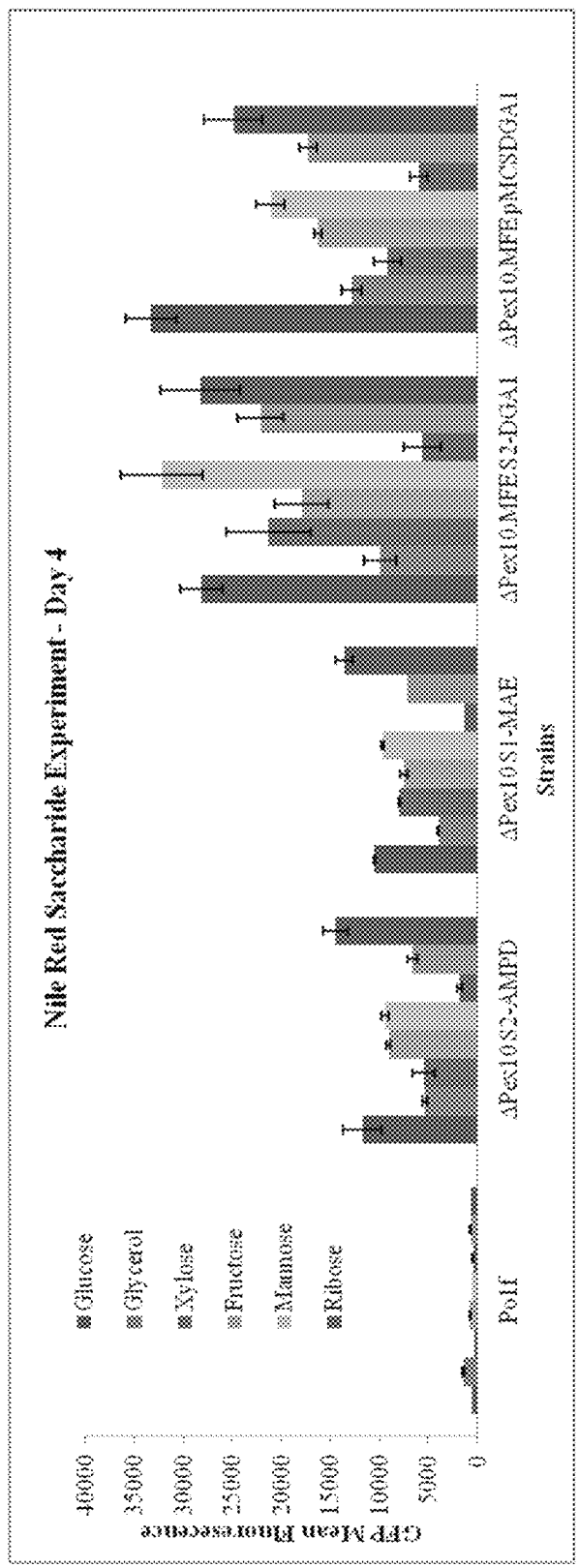
FIG. 9. Nile Red assay quantify lipid content on Day 4 with different strains growing on different saccharides as carbon sources. Saccharide initial concentration was set at 80 g/L with 5 g/L ammonium sulfate.

Viability of lipid (e.g. triacylglyceride) production depends on the capacity to fully convert all sugars from lignocellulosic biomass to lipids or to use carbon from industrial waste streams for lipid production. We analyzed the ability PO1f WT, ΔPEX10 S1-MEA, ΔPEX10 S2-AMPD, ΔPEX10ΔMFE1 S2-DGA1, and ΔPEX10ΔMFE pMCSDGA1 to generate lipids (e.g. triacylglyceride) when utilizing glucose, glycerol, xylose, fructose, mannose, ribose, sucrose, or a lignocellulosic sugar blend as their carbon source (FIG. 9). ΔPEX10ΔMFE1 S2-DGA1 and ΔPEX10ΔMFE1 pMCSDGA1 generated the highest lipid (e.g. triacylglyceride) content across the board under conditions tested, and all engineered strains demonstrated the capacity to utilize each carbon source for lipid (e.g. triacylglyceride) production. Glucose, mannose, and the lignocellulosic saccharide blend were utilized easiest while ribose utilizations generated the least lipid (e.g. triacylglyceride) content of the conditions tested. The PO1f WT and ΔPEX10ΔMFE1 S2-DGA1 strain were tested to determine if decreasing carbon content or increasing initial inoculum amount could increase xylose-generate lipid (e.g. triacylglyceride) accumulation. Increasing xylose concentration and decreasing inoculum amount increased lipid (e.g. triacylglyceride) content in the ΔPEX10ΔMFE1 S2-DGA1 strain, while little difference was noticeable in the PO1f WT strain. However, PO1f WT demonstrated a surprising capacity to utilize pure glycerol for lipid (e.g. triacylglyceride) generation.

Isolation of a Novel MGA2 Mutation with Whole Genome Sequencing.

Figure 10:
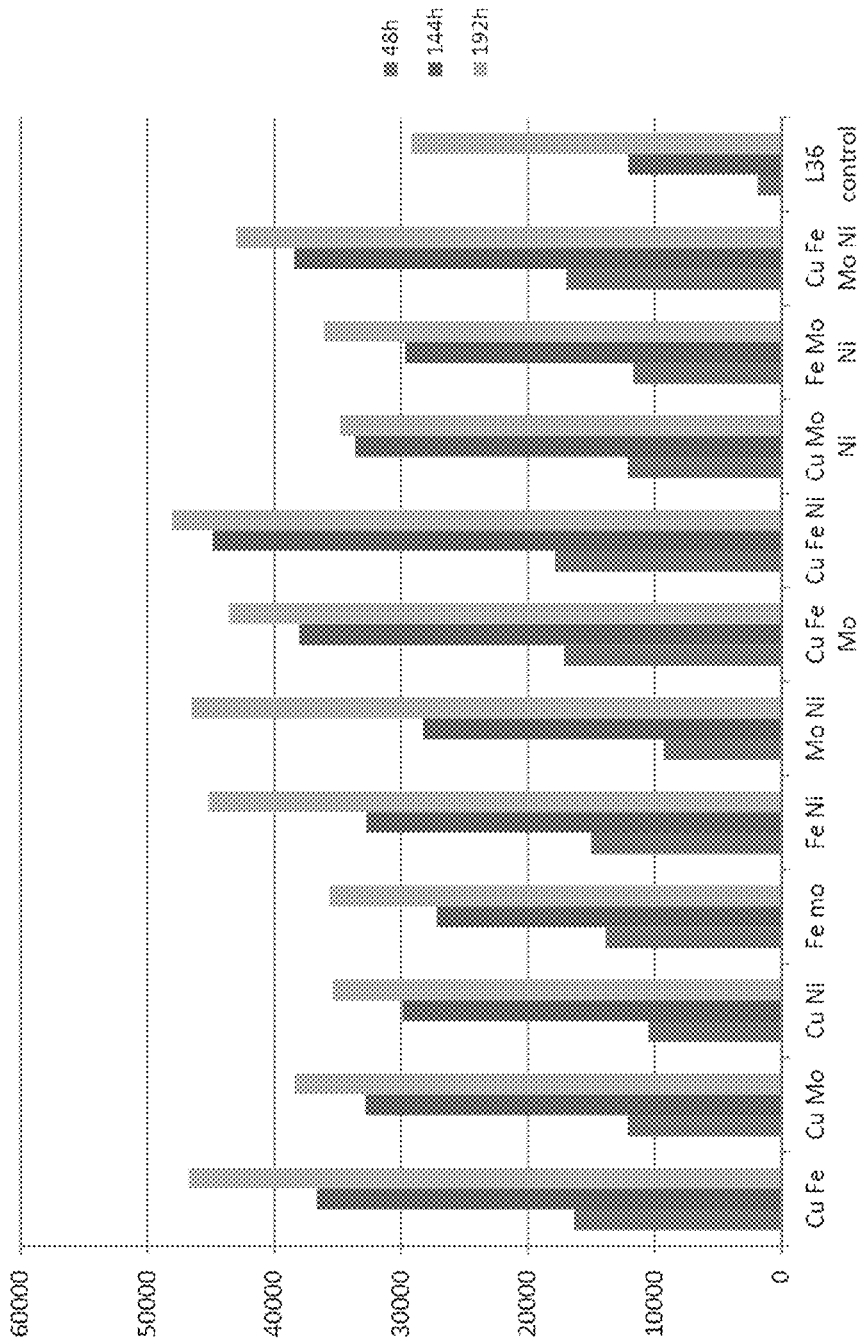
FIG. 10. Nile Red assay quantify lipid content of isolated L36 strain cultured in C160N0.2 media supplemented with multiple micronutrients after 2, 4, and 8 days of cultivation.

During the screening of a gDNA overexpression library intended to increase *Y. lipolytica*'s lipid (e.g. triacylglyceride) production, we isolated a strain, dubbed L36, with incredible lipid (e.g. triacylglyceride) accumulation ability (FIG. 10). L36's lipid (e.g. triacylglyceride) production could be enhanced with micronutrient supplementation (FIG. 10). Complete sequencing of the L36 genome revealed a missense mutation in the MGA2 lipid synthesis regulator (MGA2G643R) as the most likely potential cause for L36's lipid (e.g. triacylglyceride) production capacity. Overexpression of a truncated MGA2p in a PO1f WT background reconstituted 58% of the observed L36 phenotype.

Directed Evolution with EMS Mutagenesis to Increase Lipid Accumulation

Figure 11:
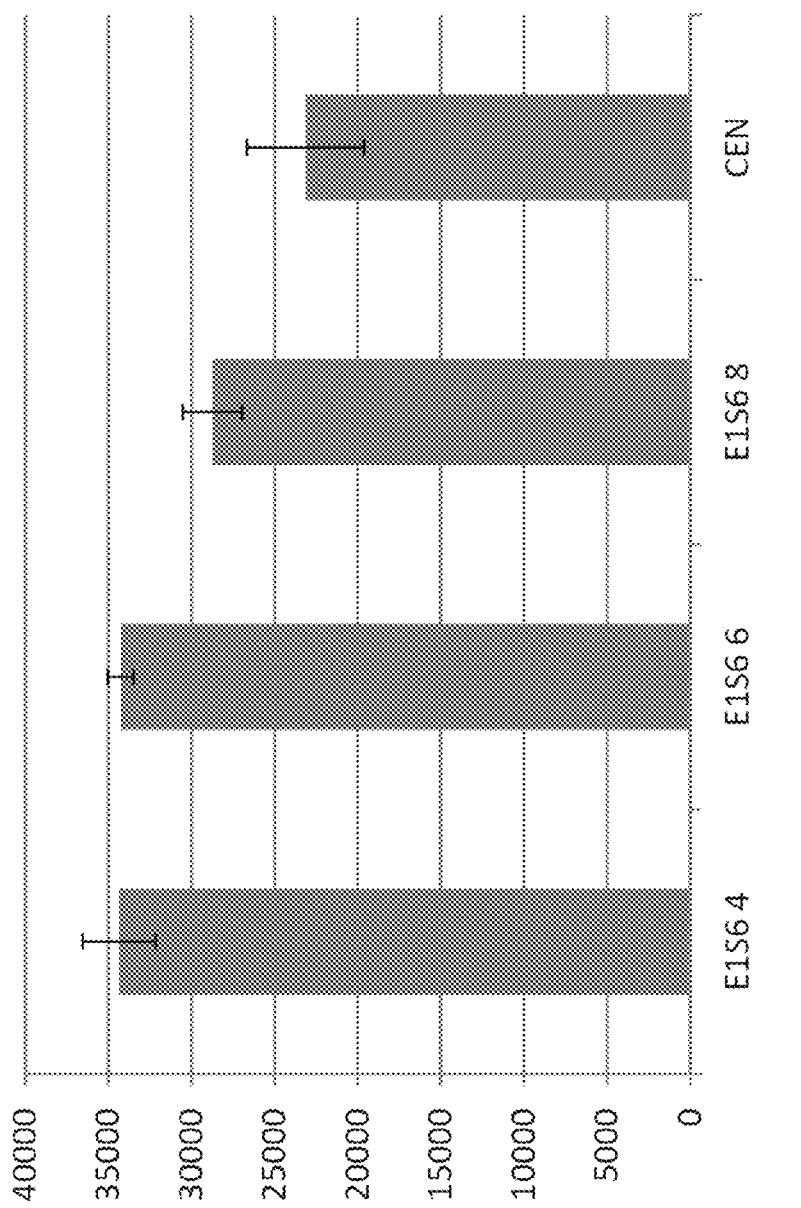
FIG. 11. Nile Red assay quantify lipid content with EMS mutagenesis in evolved L36 strains and L36.
Figure 12:
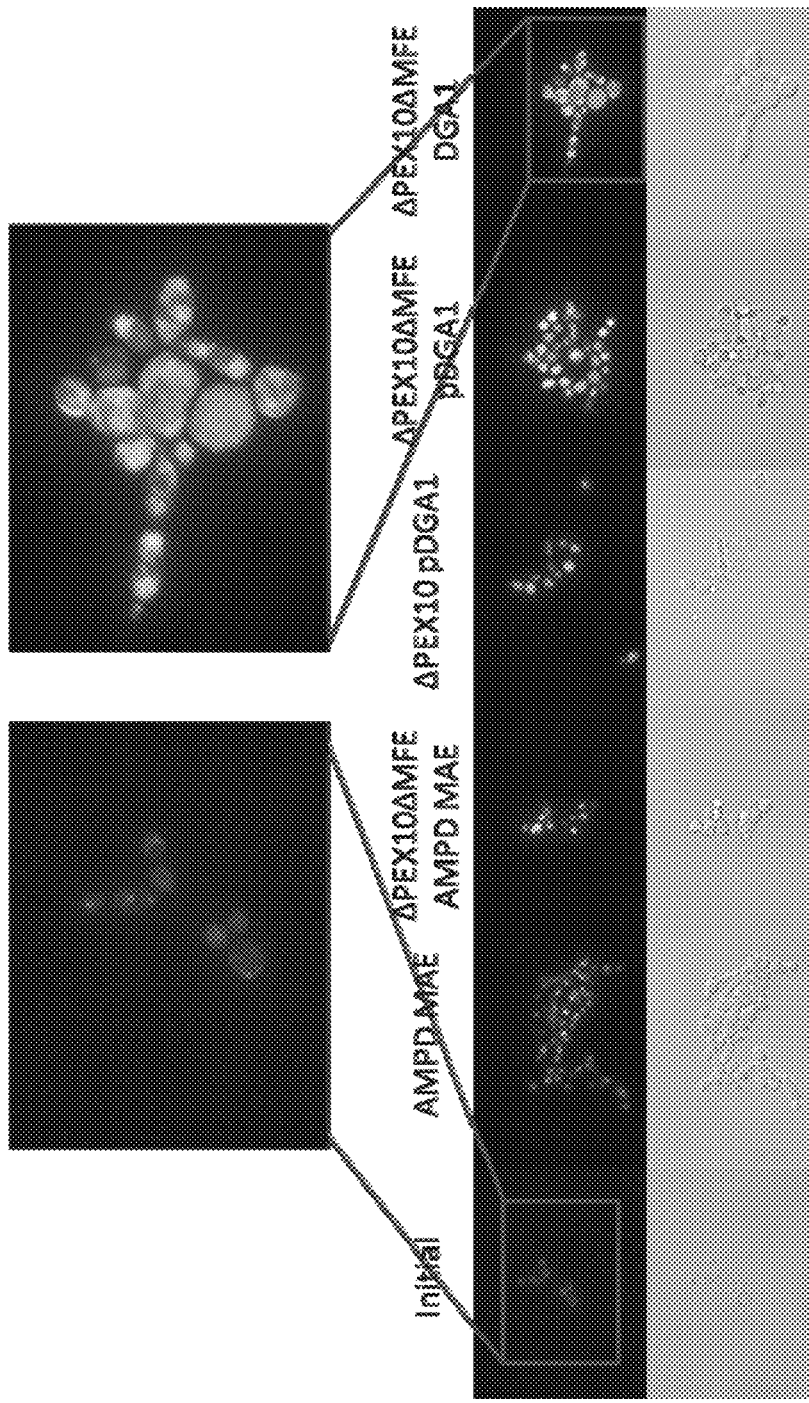
FIG. 12. Fluorescence light microscopy pictures of lipid accumulation in selected strains. Lipids were stained with Nile Red as usual. Strain ΔPEX10ΔMFE1-pMCS-DGA1 shows almost total lipid content while PO1f WT has very little.
Figure 13:
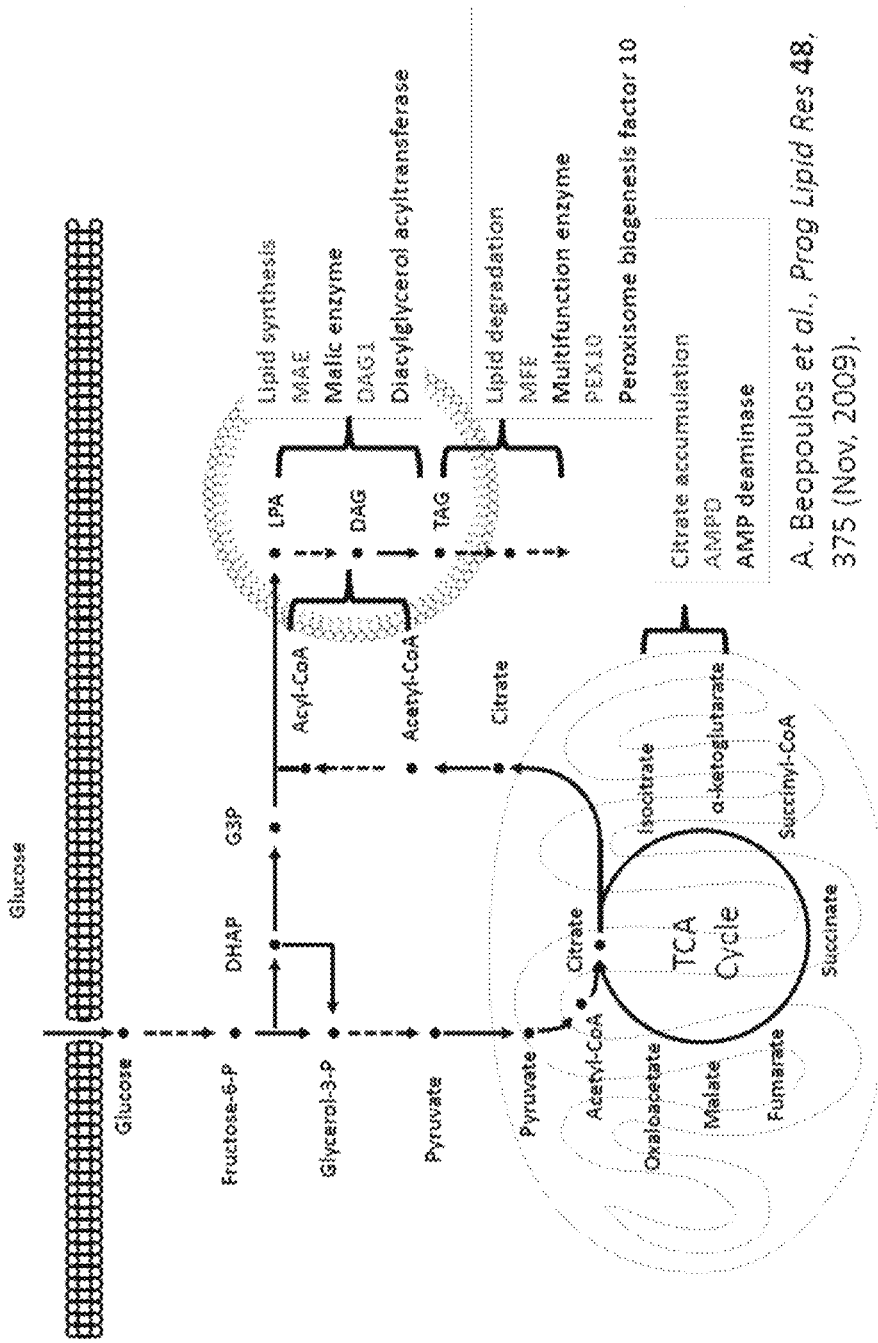
FIG. 13. General lipid metabolism in yeast and a portion of selected targets to engineering lipid metabolism.
Figure 14:
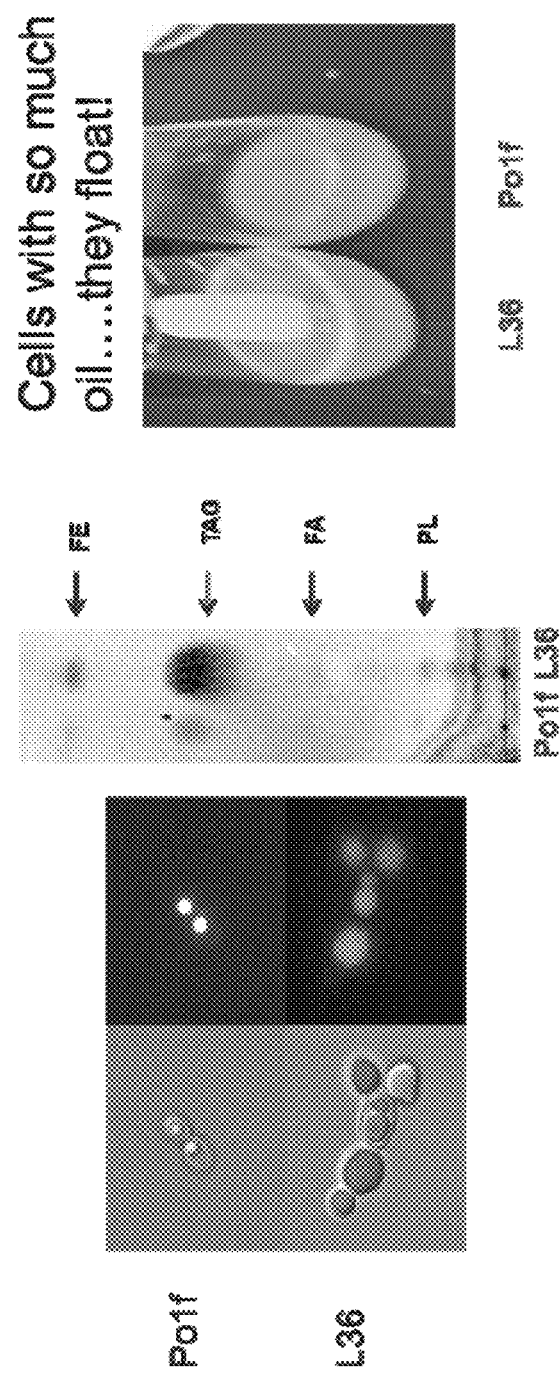
FIG. 14. The isolation and characterization of superior lipid production strain L36.

Direct evolution is commonly utilized to increase growth rate or to decrease sensitivity to a toxic metabolite. However, directed evolution has never been evaluated as a tool to increase lipid (e.g. triacylglyceride) production in oleaginous organisms. As evidenced by the isolation of strain L36, it is likely that *Y. lipolytica* is amenable to this approach. We subjected both L36 (FIG. 11) and ΔPEX10ΔMFE1 S2-DGA1 to EMS mutagenesis followed by serial selection via subculturing and then nile red staining. Both backgrounds proved highly responsive towards the directed evolution approach, and an increase in fluorescence with a large increase in final cell concentration (Table 6).

Besides the minerals, during the experiments, we also observed a critical phenotype for lipid (e.g. triacylglyceride) production in *Yarrowia lipolytica*: the lipid (e.g. triacylglyceride) de novo lipid (e.g. triacylglyceride) accumulation is close related to leucine biosynthesis pathway. A 5 fold lipid (e.g. triacylglyceride) level increase was achieved with strain harboring complete LEU biosynthesis pathway comparing to the one without complete pathway. Although this phenotype has been reported with engineered *Saccharomyces cerevisiae* (Kamisaka et al. 2007), this is the first observation in oleaginous yeast to our best knowledge. Understanding of this phenotype could be essential to understand the basic differences between oleaginous microbes and normal ones. However, to the date, the fundamental reason is still missing. Two possible routes may contribute to this, one is through TOR pathway (Kim and Guan 2011; Laplante and Sabatini 2009) and the other one is through leucine degradation and ketone body generation (Endemann et al. 1982). Either pathway heavily interacts with the whole cell metabolism which requires deep analysis to reveal the true mechanism behind.

Engineering with Known: Biosynthesis pathways and basic regulations. Rational systematic engineering *Yarrowia lipolytica* for high lipid production. Engineering with Unknown: Pathway interactions and complex regulation networks. Engineering lipid production in *Yarrowia lipolytica* through Inverse combinatorial metabolic Engineering. Confirmed lipid enhancers include DGA1 (Diacylglycerol acyltransferase) 300% improvement, MRM2 (Mitochondrial 2' O-ribose methyltransferase) 25% improvement, MGMT (O-6-methylguanine-DNA methyltransferase) 15% improvement.

C. FATTY ACID CHARACTERIZATION BY NILE RED STAINING COUPLE WITH FLOW CYTOMETRY OR FLUORESCENCE MICROSCOPY

Nile Red is commonly utilized to stain oleaginous cellular material, and can be coupled with fluorescence flow cytometry to gauge relative lipid content (Greenspan et al. 1985). *Y. lipolytica* strains were routinely inoculated from glycerol stock in biological triplicate in appropriate media for 72 hours at 30° C. with shaking Cell concentrations were normalized to a specific $OD_{600}$ for reinoculation in fresh media and further incubation. In general, 2 mL cultures were inoculated to an $OD_{600}$=2.5, and larger volume cultures were inoculated to an $OD_{600}$=0.1. Cultures were incubated for two to eight days at 30° C. with constant agitation. 2 mL cultures were incubated in a rotary drum (CT-7, New Brunswick Scientific) at speed seven and flasks were shaken at 225 rpm in a standing incubator. To harvest, one $OD_{600}$ unit of each cultures was spun down at 1000 g for three minutes and resuspended in 500 µL Phosphate Buffered Saline solution (PBS) (Sigma Aldrich). 6 µL of 1 mM Nile Red (dissolved in DMSO) was added, and then cells were incubated in the dark at room temperature for 15 minutes. Cells were spun down at 1000 g for three minutes, resuspended in 800 µL ice cold water, spun down again, and resuspended again in 800 µL ice cold water. 300 µL of stained cells were added to 1 ml ice cold water and tested with a FACS Fortessa (BD Biosciences), a voltage of 350, a 10,000 cell count, a forward scatter of 125, a side scatter of 125, and the 535LP and 585/42BP filters for fluorescence detection using the GFP fluorochrome. Samples were kept on ice and in the dark during the test and the data was analyzed using FlowJo software (Tree Star Inc., Ashland, Oreg.) to compute mean fluorescence values. Day-to-day variability was mitigated by analyzing all comparable strains on the same day. An average fluorescence and standard deviation were calculated from the mean values of biological replicates. Stained cells were routinely examined with fluorescence microscopy under a 100× oil immersion objective using the FITC channel on an Axiovert 200M microscope (Zeiss).

D. LIPID QUANTIFICATION AND FATTY ACID PROFILE ANALYSIS

Lipids from ~20-30 $OD_{600}$ equivalents were extracted following the procedure described by (Folch et al. 1957) and modified for yeast (Schneiter and Daum 2006). Dried lipids were transesterified with N-tert-Butyldimethylsilyl-N-methyltrifluoroacetamide (Sigma-Aldrich) following the procedure of (Paik et al., 2009), and 2 µL samples were injected into a GC-FID (Agilent Technologies 6890 Network GC System) equipped with an Agilent HP-5 column (5% phenyl-95% methylsiloxane—product number 19091J-413) to analyze fatty acid fractions. Briefly, the following settings were used: Detector Temp=300° C., He Flow=1.0 mL/min, Oven Temp=80° C. for 2 min, increased at 30° C./min to 200° C., increased at 2° C./min to 229° C., increased at 1° C./min to 232° C., increased at 50° C./min to 325° C. Fatty acid standards for C16:0 palmitic acid, C16:1(n-7) palmitoleic acid, C18:0 stearic acid, C18:1 (n-9) oleic acid, and C18:2 (n-6) linoleic acid were purchased from Sigma-Aldrich, transesterified, and analyzed by GC to identify fatty acid peaks.

E. CITRIC ACID QUANTIFICATION

A 2 mL culture sample was pelleted down for 5 minutes at 3000×g, and the supernatant was filtered using a 0.2 mm syringe filter (Corning Incorporated). Filtered supernatant was analyzed with a HPLC Ultimate 3000 (Dionex) and a Zorbax SB-Aq column (Agilent Technologies). A 2.0 µL injection volume was used in a mobile phase composed of a 99.5:0.5 ratio of 25 mM potassium phosphate buffer (pH=2.0) to acetonitrile with a flow rate of 1.25 mL/min.

The column temperature was maintained at 30° C. and UV-Vis absorption was measured at 210 nm. A citric acid standard (Sigma-Aldrich) was used to detect and quantify citric acid production.

F. EMS MUTAGENESIS AND ISOLATION OF HIGH LIPID PRODUCING STRAINS

10 OD units from cultures grown overnight were spun down in sterile microcentrifuge tubes at 5000 g for 10 seconds. Cell pellets were resuspended in 1 mL $H_2O$, repelleted, and resuspended in 1 mL PBS. Two samples were spun down from each culture, one for EMS mutagenesis (30 µl of EMS added) and one as a control to determine the prevalence of spontaneous beneficial mutation (no EMS added). Cells were incubated for 1 hr at 30° C., with agitation, pelleted and resuspended in 200 µl of 5% sodium thiosulfate, transferred to fresh microcentrifuge tubes, washed twice in 200 µl of 5% sodium thiosulfate, and resuspended in 1 mL $H_2O$. Cells were then grown to stationary phase in YSC media, and then reinoculated at an $OD_{600}$=2.5 in 1 mL $C_{80}N_5$ media and grown for four days. Three to six serial transfers of the cell cultures followed in which the 1 mL cultures were spun down at 1000 g for two minutes, and the top 200 µL of the supernatant was transferred to 1 mL of fresh YSC media and allowed to grow to stationary phase before again spinning down and transferring. Final cultures (top 200 µL after spin down) were plated on YSC plates containing 0.01 mM Nile Red. After four days, high lipid producers were selected by viewing plates under a blue fluorescent light and picking colonies with brighter pink fluorescent color. Lipid amount was determined by coupling Nile Red staining with flow cytometry as described above.

The EMS mutagenesis procedures were performed following the protocol described by Winston (Winston 2001). Briefly, an overnight culture was cultivated to OD about 10. Cells were then harvested, washed and resuspended with 0.1 M sodium phosphate buffer (pH 7). 30 µl of EMS were added and incubated with unmutagenized control for 1 hr at 30° C., with agitation. The cells were then washed with 5% sodium thiosulfate and ready for serial transfer experiments to enrich the high lipid population. The EMS treated cells and unmutagenized cells were first cultured YSC media for 72 hours and then cultured in high glucose media with starting OD at 2.5 for 96 hours. The cells were centrifuged down with 100 g, the unclear supernatant, which contains high lipid accumulation strains, was used as seed for another round of cultivation. After five rounds of transfer, the cells were plated on Nile Red YSC plate to facilitate the isolation of high lipid production strains. Individual colonies were picked from the EMS treated cells as well as unmutagenized cells for characterization.

Characterization of EMS mutagenesis and floating cell transfer selection procedure selected strain E13 and E26. Second generation sequencing platform illumina paired ended sequencing PE 2×100 were performed with genomic DNA extracted from strain E26, E13 as well as PO1f by Genomic Sequencing and Analysis Facility in The University of Texas at Austin. 6424381 reads for strain E26 and 6565093 reads for strain E13 were collected from illumina HiSeq, which lead to a coverage approximately 65×. The Illumina reads were mapped to the CLIB122 genome using BWA (Li and Durbin 2009) and analyzed with Samtools (Beopoulos, Cescut et al. 2009) and BEDTools (Quinlan and Hall 2010). The SNPs identified were then filtered with SnpSift with QUAL>=30 (Pablo, Viral et al. 2012) The SNPs identified from PO1f, EMS26 and EMS13 were compared to extract the authentic SNPs in EMS26 and EMS13. The identified SNPs were then visualized in the IGV genome visualization software to validate as well as study the location of the SNPs in the genome due to the high false error rate in SNP calling process (Liu, Guo et al. 2012).

Information on identified targets in E26 and E13 strains following mutagenesis. Succinate semialdehyde dehydrogenase (SSADH), which coverts succinate semialdehyde to succinate after UGA1,4-aminobutyrate aminotransferase, deaminates GABA to succinate (Ramos, El Guezzar et al. 1985). Higher levels of accumulation of α-ketoglutarate were found in uga2 mutants in *Saccharomyces cerevisiae* (Cao, Barbosa et al. 2013) (3VZ1; 3VZ3). In the same time, lower levels of succinic acid (more than 5 fold decrease) were also identified in the yeast (Kamei, Tamura et al. 2011). The identified mutation in UGA2 in sequenced strains of Proline 209 is a highly conserved residual and close to a hydrogen bond forming Serine (Yuan, Yin et al. 2013). GABA metabolism is closely related to nitrogen assimilation in yeast and nitrogen limitation has been studied as a key function for triggering lipogenesis in *Yarrowia lipolytica* (Beopoulos, Cescut et al. 2009). Nitrogen sources have also been proven as an important factor for lipid accumulation inside cells (Evans and Ratledge 1984). A relationship between GABA metabolism and the TOR pathway, an important signaling pathway for lipid accumulation (Blazeck, Hill et al. 2014), has also been suggested (Cardenas, Cutler et al. 1999; Staschke, Dey et al. 2010). YALI0E17215 g codes for a protein with similarity to *Saccharomyces cerevisiae* RME1, which is a zinc finger protein involved in the control of meiosis (Covitz, Herskowitz et al. 1991). A similar protein has shown significant levels of increase in mRNA levels in a lipid accumulation-improved snf1 mutant in *Yarrowia lipolytica* (Xue, Sharpe et al. 2013). YALI0E20449p shows limited similarity to known protein sequences except the homeodomain, a DNA binding domain involved in the transcriptional regulation of key eukaryotic developmental processes, which shows similarities. Mutation V289G in YALI0E20449p exists outside of the homeodomain. *S. cerevisiae* homeodomain protein yox1 is able to bind leucine-tRNA (Kaufmann 1993) and leucine-tRNA synthase plays an important role (Han, Jeong et al. 2012) in the TOR pathway. Leucine has been suggested to be a critical lipid production enhancer (Blazeck, Hill et al. 2014). Recently, IRC20 containing a Snf2/Swi2 family ATPase/helicase and a RING finger domain, has been shown to be an E3 ubiquitin ligase (Richardson, Gardner et al. 2013) as well as a putative helicase. OSH6 overexpression has shown lifespan extension effect on yeast by increasing vacuole fusion and may relate to TORC (Gebre, Connor et al. 2012).

G. REFERENCES

Alper H, Stephanopoulos G. 2009. Engineering for biofuels: exploiting innate microbial capacity or importing biosynthetic potential? Nature Reviews Microbiology 7(10): 715-723. Andre A, Chatzifragkou A, Diamantopoulou P, Sarris D, Philippoussis A, Galiotou-Panayotou M, Komaitis M, Papanikolaou S. 2009. Biotechnological conversions of bio-diesel-derived crude glycerol by *Yarrowia lipolytica* strains. Engineering in Life Sciences 9(6):468-478. Barth G, Gaillardin C. 1996. *Yarrowia lipolytica*. In: Wolf K, editor. Nonconventional Yeasts in Biotechnology: A Handbook: Springer. p 313-388. Beopoulos A, Cescut J, Haddouche R, Uribelarrea J L, Molina-Jouve C, Nicaud J M. 2009a.

*Yarrowia lipolytica* as a model for bio-oil production. Progress in Lipid Research 48(6):375-387. Beopoulos A, Chardot T, Nicaud J M. 2009b. *Yarrowia lipolytica*: A model and a tool to understand the mechanisms implicated in lipid accumulation. Biochimie 91(6):692-696. Beopoulos A, Haddouche R, Kabran P, Dulermo T, Chardot T, Nicaud J M. 2012. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. Applied Microbiology and Biotechnology 93(4):1523-1537. Beopoulos A, Mrozova Z, Thevenieau F, Le Dall M T, Hapala I, Papanikolaou S, Chardot T, Nicaud J M. 2008. Control of Lipid Accumulation in the Yeast *Yarrowia lipolytica*. Applied and Environmental Microbiology 74(24):7779-7789. Beopoulos A, Nicaud J M, Gaillardin C. 2011. An overview of lipid metabolism in yeasts and its impact on biotechnological processes. Applied Microbiology and Biotechnology 90(4):1193-1206. Blazeck J, Liu L, Knight R, Alper H. 2013a. Heterologous production of pentane in the oleaginous yeast *Yarrowia lipolytica*. Journal of Biotechnology. Blazeck J, Liu L, Redden H, Alper H. 2011. Tuning Gene Expression in *Yarrowia lipolytica* by a Hybrid Promoter Approach. Applied and Environmental Microbiology 77(22):7905-7914 Blazeck J, Reed B, Garg R, Gerstner R, Pan A, Agarwala V, Alper H. 2013b. Generalizing a hybrid synthetic promoter approach in *Yarrowia lipolytica*. Appl Microbiol Biotechnol 97(7): 3037-3052. Christophe G, Kumar V, Nouaille R, Gaudet G, Fontanille P, Pandey A, Soccol C R, Larroche C. 2012. Recent Developments in Microbial Oils Production: a Possible Alternative to Vegetable Oils for Biodiesel Without Competition with Human Food? Brazilian Archives of Biology and Technology 55(1):29-46. Chuang L T, Chen D C, Nicaud J M, Madzak C, Chen Y H, Huang Y S. 2010. Co-expression of heterologous desaturase genes in *Yarrowia lipolytica*. New Biotechnology 27(4):277-282. Curran K A, Leavitt J, Karim A, Alper H S. 2013. Metabolic engineering of muconic acid production in *Saccharomyces cerevisiae*. Metabolic Engineering 15:55-66. Dujon B, Sherman D, Fischer G, Durrens P, Casaregola S, Lafontaine I, de Montigny J, Marck C, Neuveglise C, Talla E and others. 2004. Genome evolution in yeasts. Nature 430(6995):35-44. Dulermo T, Nicaud J M. 2011. Involvement of the G3P shuttle and beta-oxidation pathway in the control of TAG synthesis and lipid accumulation in *Yarrowia lipolytica*. Metabolic Engineering 13(5):482-491. Elshahed M S. 2010. Microbiological aspects of biofuel production: Current status and future directions. Journal of Advanced Research 1(103-111). Endemann G, Goetz P G, Edmond J, Brunengraber H. 1982. Lipogenesis from ketone bodies in the isolated perfused rat liver. Evidence for the cytosolic activation of acetoacetate. Journal of Biological Chemistry 257(7):3434-3440. Fickers P, Benetti P H, Wache Y, Marty A, Mauersberger S, Smit M S, Nicaud J M. 2005. Hydrophobic substrate utilisation by the yeast *Yarrowia lipolytica*, and its potential applications. Fems Yeast Research 5(6-7):527-543. Fickers P, Le Dall M T, Gaillardin C, Thonart P, Nicaud J M. 2003. New disruption cassettes for rapid gene disruption and marker rescue in the yeast *Yarrowia lipolytica*. Journal of Microbiological Methods 55(3):727-737. Folch J, Lees M, Stanley G H S. 1957. A simple method for the isolation and purification of total lipids from animal tissues. Journal of Biological Chemistry 226(1):497-509. Greenspan P, Mayer E P, Fowler S D. 1985. Nile red: a selective fluorescent stain for intracelluluar lipid droplets. Journal of Cell Biology 100(3):965-973. Groenewald M, Boekhout T, Neuveglise C, Gaillardin C, van Dijck P W M, Wyss M. 2013. *Yarrowia lipolytica*: Safety assessment of an oleaginous yeast with a great industrial potential. Critical Reviews in Microbiology:1-20. Gruzdienė D, Anelauskaitė E. 2011. Chemical composition and stability of rapeseed oil produced from various cultivars grown in Lithuania. 1 lth International Congress on Engineering and Food (ICEF) Athens, Greece. Hammond E G, Johnson L A, Su C, Wang T, White P J. 2005. Soybean Oil. In: Shahidi F, editor. Bailey's Industrial Oil and Fat Products. 6 ed: John Wiley & Sons, Inc. p 577-653. Hill J, Nelson E, Tilman D, Polasky S, Tiffany D. 2006. Environmental, economic, and energetic costs and benefits of biodiesel and ethanol biofuels. Proceedings of the National Academy of Sciences of the United States of America 103(30):11206-11210. Hong S, Sharpe P, Xue Z, Yadav N, Zhu Q; E. I. du Pont de Nemours and Company (Wilmington, Del.), assignee. 2012. Peroxisome biogenesis factor protein (pex) disruptions for altering the content of polyunsaturated fatty acids and the total lipid content in oleaginous eukaryotic organisms. USA. Juretzek T, Le Dall M T, Mauersberger S, Gaillardin C, Barth G, Nicaud J M. 2001. Vectors for gene expression and amplification in the yeast *Yarrowia lipolytica*. Yeast 18(2):97-113. Kamisaka Y, Tomita N, Kimura K, Kainou K, Uemura H. 2007. DGA1 (diacylglycerol acyltransferase gene) overexpression and leucine biosynthesis significantly increase lipid accumulation in the delta snf2 disruptant of *Saccharomyces cerevisiae*. Biochemical Journal 408:61-68. Kamzolova S V, Shishkanova N V, Morgunov I G, Finogenova T V. 2003. Oxygen requirements for growth and citric acid production of *Yarrowia lipolytica*. Fems Yeast Research 3(2):217-222. Kennedy E P. 1961. Biosynthesis of Complex Lipids. Federation Proceedings 20(4):934-940. Kim J, Guan K L. 2011. Amino Acid Signaling in TOR Activation. In: Kornberg R D, Raetz C R H, Rothman J E, Thorner J W, editors Annual Review of Biochemistry, Vol 80. p 1001-1032. Kirstine W V, Galbally I E. 2012. Ethanol in the Environment: A Critical Review of Its Roles as a Natural Product, a Biofuel, and a Potential Environmental Pollutant. Critical Reviews in Environmental Science and Technology 42(16):1735-1779. Laplante M, Sabatini D M. 2009. An Emerging Role of mTOR in Lipid Biosynthesis. Current Biology 19(22):R1046-R1052. Ledall M T, Nicaud J M, Gaillardin C. 1994. Multiple-copy integration in the yeast *Yarrowia lipolytica*. Current Genetics 26(1):38-44. Li Q, Du W, Liu D H. 2008. Perspectives of microbial oils for biodiesel production. Applied Microbiology and Biotechnology 80(5):749-756. Madzak C, Gaillardin C, Beckerich J M. 2004. Heterologous protein expression and secretion in the non-conventional yeast *Yarrowia lipolytica*: a review. Journal of Biotechnology 109(1-2):63-81. Makri A, Fakas S, Aggelis G. 2010. Metabolic activities of biotechnological interest in *Yarrowia lipolytica* grown on glycerol in repeated batch cultures. Bioresource Technology 101(7):2351-2358. Matsuoka M, Matsubara M, Daidoh H, Imanaka T, Uchida K, Aiba S. 1993. Analysis of regions essential for the function of chromosomal replicator sequences from *Yarrowia lipolytica*. Molecular & General Genetics 237(3):327-333. Morin N, Cescut J, Beopoulos A, Lelandais G, Le Berre V, Uribelarrea J L, Molina-Jouve C, Nicaud J M. 2011. Transcriptomic Analyses during the Transition from Biomass Production to Lipid Accumulation in the Oleaginous Yeast *Yarrowia lipolytica*. Plos One 6(11): 13. Mumberg D, Muller R, Funk M. 1995. Yeast vectors for the controlled expression of heterologous proteins in different genetic backgrounds. Gene 156(1):119-22. Papanikolaou S, Aggelis G. 2002. Lipid production by *Yarrowia lipolytica* growing on industrial glycerol in a single-stage continuous culture. Bioresource Technology 82(1):43-49. Ratledge C. 2002. Regulation of lipid accumulation in oleaginous micro-organisms. Biochemical Society Transactions 30:1047-1050. Rywinska A, Juszczyk P, Wojtatowicz M, Robak M, Lazar Z, Tomaszewska L, Rymowicz W. 2013. Glycerol as a promising substrate for *Yarrowia lipolytica* biotechnological applications. Biomass & Bioenergy 48:148-166. Rywinska A, Musial I, Rymowicz W, Zarowska B, Boruczkowski T. 2012. Effect of agitation and aeration on the citric acid production by *Yarrowia lipolytica* grown on glycerol. Preparative Biochemistry & Biotechnology 42(3): 279-291. Schirmer A, Rude M A, Li X Z, Popova E, del Cardayre S B. 2010. Microbial Biosynthesis of Alkanes. Science 329(5991):559-562. Schneiter R, Daum G. 2006. Extraction of yeast lipids. Methods in Molecular Biology 313:41-45. Shi S B, Valle-Rodriguez J O, Khoomrung S, Siewers V, Nielsen J. 2012. Functional expression and characterization of five wax ester synthases in *Saccharomyces cerevisiae* and their utility for biodiesel production. Biotechnology for Biofuels 5(7):1-10. Song L, Qin J G, Su S Q, Xu J H, Clarke S, Shan Y C. 2012. Micronutrient Requirements for Growth and Hydrocarbon Production in the Oil Producing Green Alga *Botryococcus braunii* (Chlorophyta). Plos One 7(7). Subramaniam R, Dufreche S, Zappi M, Bajpai R. 2010. Microbial lipids from renewable resources: production and characterization. Journal of Industrial Microbiology & Biotechnology 37(12):1271-1287. Tai M, Stephanopoulos G. 2013. Engineering the push and pull of lipid biosynthesis in oleaginous yeast *Yarrowia lipolytica* for biofuel production. Metabolic Engineering 15:1-9. Thevenieau F, Nicaud J M, Gaillardin C. 2009. Applications of the Non-Conventional Yeast *Yarrowia lipolytca*. In: Satyanarayana T, Kunze G, editors. Yeast biotechnology: diversity and applications. Dordrecht: Springer Science and Business Media. p 589-613. Xu J Y, Du W, Zhao X B, Zhang G L, Liu D H. 2013. Microbial oil production from various carbon sources and its use for biodiesel preparation. Biofuels Bioproducts & Biorefining-Biofpr 7(1):65-77. Yamane T, Sakai H, Nagahama K, Ogawa T, Matsuoka M. 2008. Dissection of centromeric DNA from yeast *Yarrowia lipolytica* and identification of protein-binding site required for plasmid transmission. J Biosci Bioeng 105(6):571-8. Yim H, Haselbeck R, Niu W, Pujol-Baxley C, Burgard A, Boldt J, Khandurina J, Trawick J D, Osterhout R E, Stephen R and others. 2011. Metabolic engineering of *Escherichia coli* for direct production of 1,4-butanediol. Nature Chemical Biology 7(7):445-452. Zhao X, Kong X L, Hua Y Y, Feng B, Zhao Z B. 2008. Medium optimization for lipid production through co-fermentation of glucose and xylose by the oleaginous yeast *Lipomyces starkeyi*. European Journal of Lipid Science and Technology 110(5):405-412. Zhu Q, Xue Z, Yadav N, Sharpe P, Fan X, Tyreus B, Short D, Xie D, Boonyaratanakornkit B, Dellomonaco C and others. 2012. Production of omega-3 fatty acids from *Yarrowia lipolytica*: factors affecting lipid accumulation SIMB Annual Meeting & Exhbition. Washington, D.C. Beopoulos, A., Haddouche, R., Kabran, P., Dulermo, T., Chardot, T., Nicaud, J. M., (2012) Identification and characterization of DGA2, an acyl transferase of the DGAT1 acyl-CoA: diacylglycerol acyltransferase family in the oleaginous yeast *Yarrowia lipolytica*. New insights into the storage lipid metabolism of oleaginous yeasts. Applied Microbiology and Biotechnology 93, 1523-1537. Mlicknva, K., Roux, E., Athenstaedt, K., d'Andrea, S., Daum, G., Chardot, T., Nicaud, J. M., (2004) Lipid accumulation, lipid body formation, and acyl coenzyme A oxidases of the yeast *Yarrowia lipolytica*. Appl Environ Microbiol 70, 3918-3924. Thierry, D., Nicaud, J. M., (2011) Involvement of the G3P shuttle and beta-oxidation pathway in the control of TAG synthesis and lipid accumulation in *Yarrowia lipolytica*. Metab. Eng. 13, 482-491. Wang, H. J. J., Le Dall, M. T., Wache, Y., Laroche, C., Belin, J. M., Gaillardin, C., Nicaud, J. M., (1999) Evaluation of acyl coenzyme A oxidase (Aox) isozyme function in the n-alkane-assimilating yeast *Yarrowia lipolytica*. Journal of Bacteriology 181, 5140-5148. Tai, Stephanopoulos (2013), Engineering the push and pull of lipid biosynthesis in oleaginous yeast *Yarrowia lipolytica* for biofuel production, Metabolic Engineering, doi: 10.1016/j.ymben.2012.08.007. Beopoulos, A., J. Cescut, et al. (2009). Progress in Lipid Research 48(6): 375-387. Beopoulos, A., J. Cescut, et al. (2009). Progress in Lipid Research 48(6): 375-387. Blazeck, J., A. Hill, et al. (2014). Nat Commun 5. Cao, J., J. M. Barbosa, et al. (2013). Yeast 30(4): 129-144. Cardenas, M. E., N. S. Cutler, et al. (1999). "Genes & Development 13(24): 3271-3279. Covitz, P. A., I. Herskowitz, et al. (1991). Genes & *Development* 5(11): 1982-1989. EVANS, C. T. and C. RATLEDGE (1984). Journal of General Microbiology 130(7): 1693-1704. Gebre, S., R. Connor, et al. (2012). Cell Cycle 11(11): 2176-2188. Han, Jung M., Seung J. Jeong, et al. (2012). *Cell* 149(2): 410-424. Kamei, Y., T. Tamura, et al. (2011). Biochemical and Biophysical Research Communications 407(1): 185-190. Kaufmann, E. (1993). Chromosoma 102(3): 174-179. Li, H. and R. Durbin (2009). Bioinformatics 25(14): 1754-1760. Liu, Q., Y. Guo, et al. (2012). BMC Genomics 13(Suppl 8): S8. Pablo, C., M. P. Viral, et al. (2012). Frontiers in Genetics 3. Quinlan, A. R. and I. M. Hall (2010). Bioinformatics 26(6): 841-842. Ramos, F., M. El Guezzar, et al. (1985). European Journal of Biochemistry 149(2): 401-404. Richardson, A., R. G. Gardner, et al. (2013). PLoS ONE 8(10): e76424. Staschke, K. A., S. Dey, et al. (2010). Journal of Biological Chemistry 285(22): 16893-16911. Winston, F. (2001). EMS and UV Mutagenesis in Yeast. Current Protocols in Molecular Biology, John Wiley & Sons, Inc. Xue, Z., P. L. Sharpe, et al. (2013). Nature Biotechnology 31(8): 734-740. Yuan, Z., B. Yin, et al. (2013). Journal of Structural Biology 182(2): 125-135.

TABLE 1

List of select strains used in this study

| Host Strain Name | Genotype | Reference or Source |
|---|---|---|
| *Escherichia coli* strains | | |
| DH10B | F⁻ mcrA Δ(mrr-hsdRMS-mcrBC) φ80d/acZΔM15 ΔlacX74 endA1 recA1 deoR Δ(ara, leu)7697 araD139 galU galK nupG rpsL λ | Open Biosystems |

TABLE 1-continued

List of select strains used in this study

| Host Strain Name | Genotype | Reference or Source |
|---|---|---|
| *Yarrowia lipolytica* base strains | | |
| WT (PO1f) | MatA, leu2-270, ura3-302, xpr2-322, axp1-2 | Madzak et al. 2000 |
| ΔMFE1 (PO1f-Δmfe1) | MatA, leu2-270, ura3-302, xpr2-322, axp1-2, Δmfe1 | Blazeck et al. 2013 |
| ΔPEX10 (PO1f-Δpex10) | MatA, leu2-270, ura3-302, xpr2-322, axp1-2, Δpex10 | Blazeck et al. 2013 |
| ΔPEX10ΔMFE1 (PO1f-Δpex10-Δmfe1) | MatA, leu2-270, ura3-302, xpr2-322, axp1-2, Δpex10, Δmfe1 | This work |
| ΔACO1 (PO1f-Δaco1) | MatA, leu2-270, ura3-302, xpr2-322, axp1-2, Δaco1 | This work |
| Selected *Yarrowia lipolytica* overexpression strains | | |
| WT-S1-Ø | MatA, leu2-270, ura3-302, xpr2-322, axp1-2, URA3 (S1) | This work |
| WT-S2-Ø | MatA, leu2-270, ura3-302, xpr2-322, axp1-2, LEU2 (S2) | This work |
| WT-S1-S2-Ø | MatA, leu2-270, ura3-302, xpr2-322, axp1-2, URA3, LEU2 (S1, S2) | This work |
| WT-pMCS | MatA, leu2-270, ura3-302, xpr2-322, axp1-2, LEU2 (pMCS) | This work |
| WT-pMCS-TUP1 | MatA, leu2-270, ura3-302, xpr2-322, axp1-2, LEU2 (pMCS), UAS1B16-TEF-TUP1 | This work |
| WT-pMCS-HAC1 | MatA, leu2-270, ura3-302, xpr2-322, axp1-2, LEU2 (pMCS), UAS1B16-TEF-HAC1 | This work |
| WT-S1-AMPD | MatA, leu2-270, ura3-302, xpr2-322, axp1-2, URA3 (S1), UAS1B$_{16}$-TEF-AMPD | This work |
| WT-S2-AMPD | MatA, leu2-270, ura3-302, xpr2-322, axp1-2, LEU2 (S2), UAS1B$_{16}$-TEF-AMPD | This work |
| WT-S1-MEA1 | MatA, leu2-270, ura3-302, xpr2-322, axp1-2, URA3 (S1), UAS1B$_{16}$-TEF-MEA1 | This work |
| WT-S2-MEA1 | MatA, leu2-270, ura3-302, xpr2-322, axp1-2, LEU2 (S2), UAS1B$_{16}$-TEF-MEA1 | This work |
| WT-S1-S2-AMPD-MEA1 | MatA, leu2-270, ura3-302, xpr2-322, axp1-2, URA3, LEU2 (S1, S2), UAS1B16-TEF-AMPD, UAS1B16-TEF-MEA1 | This work |
| WT-pMCS-DGA1 | MatA, leu2-270, ura3-302, xpr2-322, axp1-2, LEU2 (pMCS), UAS1B$_{16}$-TEF-DGA1 | This work |
| ΔMFE1-S1-Ø | MatA, leu2-270, ura3-302, xpr2-322, axp1-2, Δmfe1, URA3 (S1) | This work |
| ΔMFE1-S2-Ø | MatA, leu2-270, ura3-302, xpr2-322, axp1-2, Δmfe1, LEU2 (S2) | This work |
| ΔMFE1-S1-S2-Ø | MatA, leu2-270, ura3-302, xpr2-322, axp1-2, Δmfe1, URA3, LEU2 (S1, S2) | This work |
| ΔMFE1-S1-AMPD | MatA, leu2-270, ura3-302, xpr2-322, axp1-2, Δmfe1, URA3 (S1), UAS1B16-TEF-AMPD | This work |
| ΔMFE1-S2-AMPD | MatA, leu2-270, ura3-302, xpr2-322, axp1-2, Δmfe1, LEU2 (S2), UAS1B16-TEF-AMPD | This work |
| ΔMFE1-S1-MEA1 | MatA, leu2-270, ura3-302, xpr2-322, axp1-2, Δmfe1, URA3 (S1), UAS1B16-TEFMEA1 | This work |
| ΔMFE1-S2-MEA1 | MatA, leu2-270, ura3-302, xpr2-322, axp1-2, Δmfe1, LEU2 (S2), UAS1B16-TEF-MEA1 | This work |
| ΔMFE1-S1-S2-AMPD-MEA1 | MatA, leu2-270, ura3-302, xpr2-322, axp1-2, Δmfe1, URA3, LEU2 (S1, S2), UAS1B16-TEF-AMPD, UAS1B16-TEF-MEA1 | This work |
| ΔMFE1-S1-S2-ACL1-ACL2 | MatA, leu2-270, ura3-302, xpr2-322, axp1-2, Δmfe1, URA3, LEU2 (S1, S2), UAS1B16-TEF-ACL1, UAS1B16-TEF-ACL2 | This work |
| ΔMFE1-pMCS-DGA1 | MatA, leu2-270, ura3-302, xpr2-322, axp1-2, Δmfe1, LEU2 (pMCS), UAS1B$_{16}$-TEF-DGA1 | This work |
| ΔMFE1-pMCS-DGA2 | MatA, leu2-270, ura3-302, xpr2-322, axp1-2, Δmfe1, LEU2 (pMCS), UAS1B$_{16}$-TEF-DGA2 | This work |
| ΔPEX10-S1-Ø | MatA, leu2-270, ura3-302, xpr2-322, axp1-2, Δpex10, URA3 (S1) | This work |
| ΔPEX10-S2-Ø | MatA, leu2-270, ura3-302, xpr2-322, axp1-2, Δpex10, LEU2 (S2) | This work |
| ΔPEX10-S1-S2-Ø | MatA, leu2-270, ura3-302, xpr2-322, axp1-2, Δpex10, URA3, LEU2 (S1, S2) | This work |
| ΔPEX10-S1-AMPD | MatA, leu2-270, ura3-302, xpr2-322, axp1-2, Δpex10, URA3 (S1), UAS1B16-TEF-AMPD | This work |
| ΔPEX10-S2-AMPD | MatA, leu2-270, ura3-302, xpr2-322, axp1-2, Δpex10, LEU2 (S2), UAS1B16-TEF-AMPD | This work |
| ΔPEX10-S1-MEA1 | MatA, leu2-270, ura3-302, xpr2-322, axp1-2, Δpex10, URA3 (S1), UAS1B16-TEFMEA1 | This work |

TABLE 1-continued

List of select strains used in this study

| Host Strain Name | Genotype | Reference or Source |
|---|---|---|
| ΔPEX10-S2-MEA1 | MatA, leu2-270, ura3-302, xpr2-322, axp1-2, Δpex10, LEU2 (S2), UAS1B16-TEF-MEA1 | This work |
| ΔPEX10-S1-S2-AMPD-MEA1 | MatA, leu2-270, ura3-302, xpr2-322, axp1-2, Δpex10, URA3, LEU2 (S1, S2), UAS1B16-TEF-AMPD, UAS1B16-TEF-MEA1 | This work |
| ΔPEX10-pMCS-DGA1 | MatA, leu2-270, ura3-302, xpr2-322, axp1-2, Δpex10, LEU2 (pMCS), UAS1B$_{16}$-TEF-DGA1 | This work |
| ΔPEX10-pMCS-DGA2 | MatA, leu2-270, ura3-302, xpr2-322, axp1-2, Δpex10, LEU2 (pMCS), UAS1B$_{16}$-TEF-DGA2 | This work |
| ΔPEX10ΔMFE1-S1-Ø | MatA, leu2-270, ura3-302, xpr2-322, axp1-2, Δpex10, Δmfe1, URA3 (S1) | This work |
| ΔPEX10ΔMFE1-S2-Ø | MatA, leu2-270, ura3-302, xpr2-322, axp1-2, Δpex10, Δmfe1, LEU2 (S2) | This work |
| ΔPEX10ΔMFE1-S1-S2-Ø | MatA, leu2-270, ura3-302, xpr2-322, axp1-2, Δpex10, Δmfe1, URA3, LEU2 (S1, S2) | This work |
| ΔPEX10ΔMFE1-S1-AMPD | MatA, leu2-270, ura3-302, xpr2-322, axp1-2, Δpex10, Δmfe1, URA3 (S1), UAS1B16-TEF-AMPD | This work |
| ΔPEX10ΔMFE1-S2-AMPD | MatA, leu2-270, ura3-302, xpr2-322, axp1-2, Δpex10, Δmfe1, LEU2 (S2), UAS1B16-TEF-AMPD | This work |
| ΔPEX10ΔMFE1-S1-MEA1 | MatA, leu2-270, ura3-302, xpr2-322, axp1-2, Δpex10, Δmfe1, URA3 (S1), UAS1B16-TEFMEA1 | This work |
| ΔPEX10ΔMFE1-S2-MEA1 | MatA, leu2-270, ura3-302, xpr2-322, axp1-2, Δpex10, Δmfe1, LEU2 (S2), UAS1B16-TEF-MEA1 | This work |
| ΔPEX10ΔMFE1-S1-S2-AMPD-MEA1 | MatA, leu2-270, ura3-302, xpr2-322, axp1-2, Δpex10, Δmfe1, URA3, LEU2 (S1, S2), UAS1B16-TEF-AMPD, UAS1B16-TEF-MEA1 | This work |
| ΔPEX10ΔMFE1-S1-S2-ACL1-ACL2 | MatA, leu2-270, ura3-302, xpr2-322, axp1-2, Δpex10, Δmfe1, URA3, LEU2 (S1, S2), UAS1B16-TEF-ACL1, UAS1B16-TEF-ACL2 | This work |
| ΔPEX10ΔMFE1-pMCS-DGA1 | MatA, leu2-270, ura3-302, xpr2-322, axp1-2, Δpex10, Δmfe1, LEU2 (pMCS), UAS1B$_{16}$-TEF-DGA1 | This work |
| ΔPEX10ΔMFE1-pMCS-DGA2 | MatA, leu2-270, ura3-302, xpr2-322, axp1-2, Δpex10, Δmfe1, LEU2 (pMCS), UAS1B$_{16}$-TEF-DGA2 | This work |
| ΔPEX10ΔMFE1-S2-DGA1 | MatA, leu2-270, ura3-302, xpr2-322, axp1-2, Δpex10, Δmfe1, LEU2 (S2), UAS1B$_{16}$-TEF-DGA1 | This work |
| ΔPEX10ΔMFE1-S1-Ø-S2-DGA1 | MatA, leu2-270, ura3-302, xpr2-322, axp1-2, Δpex10, Δmfe1, URA3 (S1), LEU2 (S2), UAS1B$_{16}$-TEF-DGA1 | This work |
| ΔPEX10ΔMFE1-S1-AMPD-S2-DGA1 | MatA, leu2-270, ura3-302, xpr2-322, axp1-2, Δpex10, Δmfe1, URA3 (S1), LEU2 (S2), UAS1B16-TEF-AMPD, UAS1B$_{16}$-TEF-DGA1 | This work |
| ΔPEX10ΔMFE1-S1-MEA1-S2-DGA1 | MatA, leu2-270, ura3-302, xpr2-322, axp1-2, Δpex10, Δmfe1, URA3 (S1), LEU2 (S2), UAS1B16-TEF-MEA1, UAS1B$_{16}$-TEF-DGA1 | This work |
| ΔPEX10ΔMFE1-S1-DGA1 | MatA, leu2-270, ura3-302, xpr2-322, axp1-2, Δpex10, Δmfe1, URA3 (S1), UAS1B$_{16}$-TEF-DGA1 | This work |
| WT-S2-DGA1 | MatA, leu2-270, ura3-302, xpr2-322, axp1-2, Leu2 (S2), UAS1B$_{16}$-TEF-DGA1 | This work |
| ΔPEX10ΔMFE1-S1-DGA1 | MatA, leu2-270, ura3-302, xpr2-322, axp1-2, Δpex10, Δmfe1, URA3 (S1), UAS1B$_{16}$-TEF-DGA1 | This work |
| ΔPEX10-S2-DGA1 | MatA, leu2-270, ura3-302, xpr2-322, axp1-2, Δpex10, LEU2 (S2), UAS1B$_{16}$-TEF-DGA1 | This work |
| WT-pMCS-DGA2 | MatA, leu2-270, ura3-302, xpr2-322, axp1-2, LEU2 (pMCS), UAS1B$_{16}$-TEF-DGA1 | This work |
| ΔPEX10ΔMFE1-S1-DGA1 | MatA, leu2-270, ura3-302, xpr2-322, axp1-2, Δpex10, Δmfe1, URA3, UAS1B$_{16}$-TEF-DGA1 | This work |
| ΔMFE1-S2-DGA1 | MatA, leu2-270, ura3-302, xpr2-322, axp1-2, Δmfe1, LEU2(S2), UAS1B$_{16}$-TEF-DGA1 | This work |
| ΔMFE1-S2-DGA2 | MatA, leu2-270, ura3-302, xpr2-322, axp1-2, Δmfe1, LEU2 (S2), UAS1B$_{16}$-TEF-DGA2 | This work |
| ΔPEX10ΔMFE1-S1-Ø-pMCS-DGA1 | MatA, leu2-270, ura3-302, xpr2-322, axp1-2, Δpex10, Δmfe1, URA3 (S1), LEU2 (pMCS), UAS1B$_{16}$-TEF-DGA1 | This work |
| Po1f pMCSmga2 | MatA, leu2-270, ura3-302, xpr2-322, axp1-2 LEU2 (pMCS), UAS1B16-TEF-Mga2 | This work |
| Po1f pMCSmga2dTM | MatA, leu2-270, ura3-302, xpr2-322, axp1-2 LEU2 (pMCS), UAS1B16-TEF-Mga2dTM (truncated of transmembrane span) | This work |

TABLE 1-continued

List of select strains used in this study

| Host Strain Name | Genotype | Reference or Source |
|---|---|---|
| Po1f pMCSMga2L36 | MatA, leu2-270, ura3-302, xpr2-322, axp1-2 LEU2 (pMCS), UAS1B16-TEF-Mga2L36 (has SNP found in L36 strain) | This work |
| Po1f pMCSMRM2 | MatA, leu2-270, ura3-302, xpr2-322, axp1-2, LEU2 (pMCS), UAS1B$_{16}$-TEF-MRM2 | This work |
| Po1f pMCSO6M | MatA, leu2-270, ura3-302, xpr2-322, axp1-2, LEU2 (pMCS), UAS1B$_{16}$-TEF-O6M | This work |
| ΔACO1-DGA1 | MatA, leu2-270, ura3-302, xpr2-322, axp1-2, Δaco1, URA3 (S1), LEU2 (S2), UAS1B$_{16}$-TEF-DGA1 | This work |
| L36 and EMS derived strains | | |
| L36 | MatA, leu2-270, ura3-302, xpr2-322, axp1-2, LEU2 (pMCS) - isolated and fully sequenced to determine source of high lipid accumulation - most likely from mutation in MGA2 ORF. | This work |
| L36 E1S6-4 | L36 strain mutagenized further with EMS | This work |
| L36 E1S6-5 | L36 strain mutagenized further with EMS | This work |
| L36 E1S6-6 | L36 strain mutagenized further with EMS | This work |
| ΔPEX10ΔMFE1-S2-DGA1 E1 | ΔPEX10ΔMFE1-S2-DGA1 strain mutagenized with EMS | This work |
| ΔPEX10ΔMFE1-S2-DGA1 E6 | ΔPEX10ΔMFE1-S2-DGA1 strain mutagenized with EMS | This work |
| ΔPEX10ΔMFE1-S2-DGA1 E12 | ΔPEX10ΔMFE1-S2-DGA1 strain mutagenized with EMS | This work |
| E13 | MatA, leu2-270, ura3-302, xpr2-322, axp1-2, Δpex10, Δmfe1, URA3 (S1), LEU2 (S2), UAS1B$_{16}$-TEF-DGA1 strain mutagenized with EMS and selected | This work |
| E26 | MatA, leu2-270, ura3-302, xpr2-322, axp1-2, Δpex10, Δmfe1, URA3 (S1), LEU2 (S2), UAS1B$_{16}$-TEF-DGA1 strain mutagenized with EMS and selected | This work |

TABLE 2

List of primers used in this study

| | |
|---|---|
| JB387 YL AMPD 5' AscI | TTGGCGCGCCatgccgcagcaagcaatgg (SEQ ID NO.: 1) |
| JB388 YL AMPD 3' PacI | CCTTAATTAAttaaccatgcagccgctcaaac (SEQ ID NO.: 2) |
| JB402 YL ACL1 5' AscI | TTGGCGCGCCatgtctgccaacgagaacat (SEQ ID NO.: 3) |
| JB403 YL ACL1 + 4 5' AscI | TTGGCGCGCCtctgccaacgagaacatctc (SEQ ID NO.: 4) |
| JB404 YL ACL1 3' PacI | CCTTAATTAActatgatcgagtcttggccttg (SEQ ID NO.: 5) |
| JB405 YL ACL2 5' AscI | TTGGCGCGCCATGTCAGCGAAATCCATTCACG (SEQ ID NO.: 6) |
| JB406 YL ACL2 + 4 5' AscI | TTGGCGCGCCTCAGCGAAATCCATTCACGAG (SEQ ID NO.: 7) |
| JB407 YL ACL2 3' PacI | CCTTAATTAATTAAACTCCGAGAGGAGTGGAA (SEQ ID NO.: 8) |
| JB862 Loxleu 5' SacII | CCAccgcggataacttcgtataatgtatgctatacgaagttatgagtctttattggtgatgggaaga (SEQ ID NO.: 9) |
| JB863 Loxleu 3' Bstb1 | CGGTTCGAAataacttcgtatagcatacattatacgaagttatcagtcgccagcttaaagatatcta (SEQ ID NO.: 10) |
| JB865 hygR 3' bglII | GgaacggtAGATCtCGAGCGTCCCAAAACCTTCTC (SEQ ID NO.: 11) |

TABLE 2-continued

List of primers used in this study

| | |
|---|---|
| JB883 hygR 5' Nae | GtggacGGgccggcgtttggcgcccgttttttcg (SEQ ID NO.: 12) |
| JB911 DGA1 5' AscI | CattcaaaGGCGCGCCatgactatcgactcacaatactaca (SEQ ID NO.: 13) |
| JB912 DGA1 3' PacI | GcGGATCCTTAATTAAttactcaatcattcggaactctgg (SEQ ID NO.: 14) |
| JB913 DGA2 5' AscI | CattcaaaGGCGCGCCATGGAAGTCCGACGACGAAA (SEQ ID NO.: 15) |
| JB914 DGA2 3' PacI | GcGGATCCTTAATTAACTACTGGTTCTGCTTGTAGTTGT (SEQ ID NO.: 16) |
| AH011 Tup1 5' Asc | GACTGGCGCGCATGAGCTTCCCCCAACAAGTA (SEQ ID NO.: 17) |
| AH012 Tup1 3' PacI | GTCCTTAATTAATTATCTGTTGACAGGAAAGTATCGC (SEQ ID NO.: 18) |
| AH007 HacI 5' AscI | GACTGGCGCGCATGTCTATCAAGCGAGAAGAGT (SEQ ID NO.: 19) |
| AH008 HacI 3' PacI | GTCCTTAATTAACTAGATCAGCAATAAAGTCGTGCT (SEQ ID NO.: 20) |
| AH020 MAE 5' AscI | GACTGGCGCGCCATGTTACGACTACGAACCATGC (SEQ ID NO.: 21) |
| AH021 MAE 3' PacI | GTCCTTAATTAACTAGTCGTAATCCCGCACATG (SEQ ID NO.: 22) |
| LQ310 Mga2 5' AscI | ACTGGGCGCGCC atggctaaagacaaggaaatcgactttgac (SEQ ID NO.: 23) |
| LQ303 Mga2TM 3' PacI | ACTGTTAATTAA tcagtaaatgtaagccagaacatcgt (SEQ ID NO.: 24) |
| LQ309 Mga2 3' PacI | ACTGTTAATTAA tcatgcagcctgggcctgg (SEQ ID NO.: 25) |
| LQ294 O6M 5' AscI | ACTGGGCGCGCC atgttttacaccaagcccgacccg (SEQ ID NO.: 26) |
| LQ295 O6M 3' PacI | ACTGTTAATTAA ttagagagtcccccacatgtcaccc (SEQ ID NO.: 27) |
| LQ259 MRM2 5' AscI | ACTGGGCGCGCC Atgcgccaaaagctgccgttcaac (SEQ ID NO.: 28) |
| LQ260 MRM2 3' PacI | ACTGTTAATTAA ttatggcttcccttctgccacatc (SEQ ID NO.: 29) |
| LQ261 DGA1 5' AscI | ACTGGGCGCGCC Atgactatcgactcacaatactac (SEQ ID NO.: 30) |
| LQ262 DGA1 3' PacI | ACTGTTAATTAA ttactcaatcattcggaactctgg (SEQ ID NO.: 31) |

TABLE 3

Media formulations used for two strain testing

| Media Name | Carbon Source Glucose (g/L) | Nitrogen Source Ammonium Sulfate (g/L) |
|---|---|---|
| $C_{10}N_5$ | 10 | 5 |
| $C_{20}N_{0.04}$ | 20 | 0.04 |
| $C_{20}N_{0.2}$ | 20 | 0.2 |
| $C_{20}N_1$ | 20 | 1 |
| $C_{20}N_5$ (YSC) | 20 | 5 |
| $C_{20}N_{10}$ | 20 | 10 |
| $C_{40}N_{0.2}$ | 40 | 0.2 |
| $C_{40}N_1$ | 40 | 1 |
| $C_{40}N_5$ | 40 | 5 |
| $C_{80}N_{0.04}$ | 80 | 0.04 |
| $C_{80}N_{0.2}$ | 80 | 0.2 |
| $C_{80}N_1$ | 80 | 1 |

TABLE 3-continued

Media formulations used for two strain testing

| Media Name | Carbon Source Glucose (g/L) | Nitrogen Source Ammonium Sulfate (g/L) |
|---|---|---|
| $C_{80}N_5$ | 80 | 5 |
| $C_{80}N_{10}$ | 80 | 10 |
| $C_{160}N_{0.2}$ | 160 | 0.2 |
| $C_{160}N_1$ | 160 | 1 |
| $C_{160}N_5$ | 160 | 5 |
| $C_{320}N_{0.2}$ | 320 | 0.2 |
| $C_{320}N_1$ | 320 | 1 |
| $C_{320}N_5$ | 320 | 5 |

TABLE 4

ΔPex10, Mfe S1Ø, S2-DGA1 CSM vs Minimal Media (-CSM) Comparison
ΔPex10, Mfe S1Ø, S2-DGA1 CSM vs Minimal Media (-CSM) Comparison
Strain: ΔPex10, Mfe S1-φ, S2-DGA1

| Media | Sample | Day 4 OD | Day 4 GFP Fluorescence |
|---|---|---|---|
| CSM - C80N5 | A | 16.83 | 36696 |
| CSM - C80N5 | B | 16.76 | 34397 |
| CSM - C80N5 | C | 16.31 | 39166 |
| Minimal Media - C80N5 | A | 11.7 | 29365 |
| Minimal Media - C80N5 | B | 11.46 | 52520 |
| Minimal Media - C80N5 | C | 11.87 | 32427 |

TABLE 5

Media Formulations used for 12 strain testing

| Media Name | Carbon Source Glucose (g/L) | Nitrogen Source Ammonium Sulfate (g/L) |
|---|---|---|
| $C_{20}N_{0.2}$ | 20 | 0.2 |
| $C_{20}N_1$ | 20 | 1 |
| $C_{20}N_5$ (YSC) | 20 | 5 |
| $C_{40}N_{0.2}$ | 40 | 0.2 |
| $C_{40}N_1$ | 40 | 1 |
| $C_{40}N_5$ | 40 | 5 |
| $C_{80}N_{0.2}$ | 80 | 0.2 |
| $C_{80}N_1$ | 80 | 1 |
| $C_{80}N_5$ | 80 | 5 |
| $C_{80}N_{10}$ | 80 | 10 |
| $C_{160}N_{0.2}$ | 160 | 0.2 |
| $C_{160}N_1$ | 160 | 1 |
| $C_{160}N_5$ | 160 | 5 |

TABLE 6

RFU and OD for EMS data

|  | RFU | OD |
|---|---|---|
| ΔPEX10ΔMFE1 S2-DGA1 Control | 23750 | 8.81 |
| E1 | 31800 | 21.91 |
| E6 | 35400 | 18.86 |
| E12 | 37100 | 22.5 |
| L36 Control | 23133.33 | 11.83 |
| E1S6 4 | 34350 | 20.61 |
| E1S6 6 | 34250 | 20.58 |
| E1S6 8 | 28750 | 18.31 |

TABLE 7

List of genes and genetic changes

| Gene | Type of Modification |
|---|---|
| Leucine Biosynthesis Gene (LEU2) - Note may also be able to include rest of genes of leucine biosynthetic pathway, have yet to test these additional ones | Over-expression |
| Uracil Biosynthesis gene (URA3) | Over-expression |
| multifunctional enzyme (MFE1) in b-oxidation pathway | Deletion |
| Transcription Factor (PEX10) | Deletion |
| AMP Deaminase (AMPD) | Over-expression |
| ATP-Citrate Lyase (ACL1 and/or ACL2) | Over-expression |
| Malic Enzyme (MAE/MEA) | Over-expression |
| Acetyl-CoA Carboxylase (ACC) | Over-expression |
| acyl-CoA:diacylglycerol acyltransferases (DGA1 and/or DGA2) | Over-expression |
| Mitochondrial 2' O-ribose methyltransferase(MRM2) | Over-expression |
| O-6-methylguanine-DNA methyltransferase (MGMT) | Over-expression |
| Aconitase (ACO1) | Deletion |
| Citrate Synthase (CIT1) | Over-expression |

TABLE 8

Strain L36 important SNP list

| Chromosome | Position | Mutation type | sequence | Gene | Accession numbers |
|---|---|---|---|---|---|
| B | 1644655 | SNP | C > T | mga2 | 12342g |
| D | 2401168 | Insertion | A > AG | sorbitol utilization protein SOU2 | 18964g |
| E | 1837892 | SNP | C > A | CEN0E | 15444s |
|   | 1837894 | SNP | T > A | CEN0E | 15444s |
|   | 4025540 | SNP | C > A | DEHA0A1298g IPF 95.1 | 33891g |
|   | 4025542 | SNP | G > C | DEHA0A1298g IPF 95.1 | 33891g |
| F | 2861334 | Insertion | A > AGAGGGCTAGAGAGAGGGAGAA (SEQ ID NO.: 32) | RLF2 chromatin asembly complex subunit p90 | 21637g |

Gene Targets: The reference number given for each name corresponds to the Genolevures database: http://www.genolevures.org/. YALI0 stands for *Yarrowia lipolytica*. A,B, C,D,E,F specifies chromosome, and the following number specifies location. Note: Leu2 and Ura3 given as GenBank Accession numbers

```
AMPD - YALI0E11495
                                                     (SEQ ID NO.: 33)
Nucleotide =
atgccgcagcaagcaatggatatcaagggcaaggccaagtctgtgcccatgcccgaagaagacgacctgg actcgcattttgtgggtcccatctctccccgacctcacggagcagacgagattgctggctacgtgggctg cgaagacgacgaagacgagcttgaagaactgggaatgctgggccgatctgcgtccacccacttctcttac gcggaagaacgccacctcatcgaggttgatgccaagtacagagctcttcatggccatctgcctcatcagc actctcagagtcccgtgtccagatcttcgtcatttgtgcgggccgaaatgaaccacccccctcccccacc ctccagccacacccaccaacagccagaggacgatgacgcatcttccactcgatctcgatcgtcgtctcga gcttctggacgcaagttcaacagaaacagaaccaagtctggatcttcgctgagcaagggtctccagcagc tcaacatgaccggatcgctcgaagaagagccctacgagagcgatgacgatgcccgactatctgcggaaga cgacattgtctatgatgctacccagaaagacacctgcaagcccatatctcctactctcaaacgcacccgc accaaggacgacatgaagaacatgtccatcaacgacgtcaaaatcaccaccaccacagaagatcctcttg tggcccaggagctgtccatgatgttcgaaaaggtgcagtactgccgagacctccgagacaagtaccaaac cgtgtcgctacagaaggacggagacaaccccaaggatgacaagacacactggaaaatttaccccgagcct ccaccaccctcctggcacgagaccgaaaagcgattccgaggctcgtccaaaaaggagcaccaaaagaaag acccgacaatggatgaattcaaattcgaggactgcgaaatccccgacccaacgacatggtcttcaagcg agatcctacctgtgtctatcaggtctatgaggatgaaagctctctcaacgaaaataagccgtttgttgcc atcccctcaatccgagattactacatggatctggaggatctcattgtggcttcgtctgacggacctgcca agtcttttgctttccgacgactgcaatatctagaagccaagtggaacctctactacctgctcaacgagta cacggagacaaccgagtccaagaccaaccccatcgagacttttacaacgtacgaaaggtcgacacccac gttcaccactctgcctgcatgaaccagaagcatctgctgcgattcatcaaatacaagatgaagaactgcc ctgatgaagttgtcatccaccgagacggtcgggagctgacactctcccaggtgtttgagtcacttaactt gactgcctacgacctgtctatcgatacccttgatatgcatgctcacaaggactcgttccatcgatttgac
```

-continued aagttcaacctcaagtacaaccctgtcggtgagtctcgactgcgagaaatcttcctaaagaccgacaact
acatccagggtcgatacctagctgagatcacaaaggaggtgttccaggatctcgagaactcgaagtacca
gatggcggagtaccgtatttccatctacggtcggtccaaggacgagtgggacaagctggctgcctgggtg
ctggacaacaaactgttttcgcccaatgttcggtggttgatccaggtgcctcgactgtacgacatttaca
agaaggctggtctggttaacacctttgccgacattgtgcagaacgtctttgagcctcttttcgaggtcac
caaggatcccagtaccatcccaagctgcacgtgttcctgcagcgagttgtgggctttgactctgtcgat
gacgagtcgaagctggaccgacgtttccaccgaaagttcccaactgcagcatactgggacagcgcacaga
accctccctactcgtactggcagtactatctatacgccaacatggcctccatcaacacctggagacagcg
tttgggctataatacttttgagttgcgaccccatgctggagaggctggtgacccagagcatcttctgtgc
acttatctggttgctcagggtatcaaccacggtattctgttgcgaaaggtgcccttcattcagtaccttt
actacctggaccagatccccattgccatgtctcctgtgtccaacaatgcgctgttcctcacgttcgacaa
gaaccccttctactcatacttcaagcggggtctcaacgtgtccttgtcatcggatgatcctctgcagttt
gcttacactaaggaggctctgattgaggagtactctgtggctgcgctcatttacaagctttccaacgtgg
atatgtgtgagcttgctcgaaactcggtactgcaatctggctttgagcgaatcatcaaggagcattggat
cggcgaaaaactacgagatccatggccccgagggcaacaccatccagaagacaaacgtgcccaatgtgcgt
ctggccttccgagacgagactttgacccacgagcttgctctggtggacaagtacaccaatcttgaggagt
ttgagcggctgcatggtta (SEQ ID NO.: 34)

Amino Acid =
MPQQAMDIKGKAKSVPMPEEDDLDSHFVGPISPRPHGADEIAGYVGCEDDEDELEELGMLGRSASTHFSY
AEERHLIEVDAKYRALHGHLPHQHSQSPVSRSSSFVRAEMNHPPPPPSSHTHQQPEDDDASSTRSRSSSR
ASGRKFNRNRTKSGSSLSKGLQQLNMTGSLEEEPYESDDDARLSAEDDIVYDATQKDTCKPISPTLKRTR
TKDDMKNMSINDVKITTTTEDPLVAQELSMMFEKVQYCRDLRDKYQTVSLQKDGDNPKDDKTHWKIYPEP
PPPSWHETEKRFRGSSKKEHQKKDPTMDEFKFEDCEIPGPNDMVFKRDPTCVYQVYEDESSLNENKPFVA
IPSIRDYYMDLEDLIVASSDGPAKSFAFRRLQYLEAKWNLYYLLNEYTETTESKTNPHRDFYNVRKVDTH
VHHSACMNQKHLLRFIKYKMKNCPDEVVIHRDGRELTLSQVFESLNLTAYDLSIDTLDMHAHKDSFHRFD
KFNLKYNPVGESRLREIFLKTDNYIQGRYLAEITKEVFQDLENSKYQMAEYRISIYGRSKDEWDKLAAWV
LDNKLFSPNVRWLIQVPRLYDIYKKAGLVNTFADIVQNVFEPLFEVTKDPSTHPKLHVFLQRVVGFDSVD
DESKLDRRFHRKFPTAAYWDSAQNPPYSYWQYYLYANMASINTWRQRLGYNTFELRPHAGEAGDPEHLLC
TYLVAQGINHGILLRKVPFIQYLYYLDQIPIAMSPVSNNALFLTFDKNPFYSYFKRGLNVSLSSDDPLQF
AYTKEALIEEYSVAALIYKLSNVDMCELARNSVLQSGFERIIKEHWIGENYEIHGPEGNTIQKTNVPNVR
LAFRDETLTHELALVDKYTNLEEFERLHG*

Leu2 - AF260230

(SEQ ID NO.: 35)

Nucleotide =
atggaacccgaaactaagaagaccaagactgactccaagaagattgttcttctcggcggcgacttctgtg
gccccgaggtgattgccgaggccgtcaaggtgctcaagtctgttgctgaggcctccggcaccgagtttgt
gtttgaggaccgactcattggaggagctgccattgagaaggagggcgagcccatcaccgacgctactctc
gacatctgccgaaaggctgactctattatgctcggtgctgtcggaggcgctgccaacaccgtatggacca
ctcccgacggacgaaccgacgtgcgacccgagcagggtctcctcaagctgcgaaaggacctgaacctgta
cgccaacctgcgaccctgccagctgctgtcgcccaagctcgccgatctctcccccatccgaaacgttgag
ggcaccgacttcatcattgtccgagagctcgtcggaggtatctacttggagagcgaaaggaggatgacg
gatctggcgtcgcttccgacaccgagacctactccgttcctgaggttgagcgaattgcccgaatggccgc -continued

```
cttcctggcccttcagcacaaccccctcttcccgtgtggtctcttgacaaggccaacgtgctggcctcc tctcgactttggcgaaagactgtcactcgagtcctcaaggacgaattcccccagctcgagctcaaccacc agctgatcgactcggccgccatgatcctcatcaagcagccctccaagatgaatggtatcatcatcaccac caacatgtttggcgatatcatctccgacgaggcctccgtcatccccggttctctgggtctgctgccctcc gcctctctggcttctctgcccgacaccaacgaggcgttcggtctgtacgagccctgtcacggatctgccc ccgatctcggcaagcagaaggtcaaccccattgccaccattctgtctgccgccatgatgctcaagttctc tcttaacatgaagcccgccggtgacgctgttgaggctgccgtcaaggagtccgtcgaggctggtatcact accgccgatatcggaggctcttcctccacctccgaggtcggagacttgttgccaacaaggtcaaggagct gctcaagaaggagtaagtcgtttctacgacgcattgatggaaggagcaaactgacgcgcctgcgggttgg tctaccggcagggtccgctagtgtataa
```

(SEQ ID NO.: 36)
Amino Acid =
MEPETKKTKTDSKKIVLLGGDFCGPEVIAEAVKVLKSVAEASGTEFVFEDRLIGGAAIEKEGEPITDATL

DICRKADSIMLGAVGGAANTVWTTPDGRTDVRPEQGLLKLRKDLNLYANLRPCQLLSPKLADLSPIRNVE

GTDFIIVRELVGGIYFGERKEDDGSGVASDTETYSVPEVERIARMAAFLALQHNPPLPVWSLDKANVLAS

SRLWRKTVTRVLKDEFPQLELNHQLIDSAAMILIKQPSKMNGIITTNMFGDIISDEASVIPGSLGLLPS

ASLASLPDTNEAFGLYEPCHGSAPDLGKQKVNPIATILSAAMMLKFSLNMKPAGDAVEAAVKESVEAGIT

TADIGGSSSTSEVGDLLPTRSRSCSRRSKSFLRRIDGRSKLTRLRVGLPAGSASV*

Ura3 - YLU40564

(SEQ ID NO.: 37)
Nucleotide =
```
atgccctcctacgaagctcgagctaacgtccacaagtccgcctttgccgctcgagtgctcaagctcgtgg cagccaagaaaaccaacctgtgtgcttctctggatgttaccaccaccaaggagctcattgagcttgccga taaggtcggaccttatgtgtgcatgatcaagacccatatcgacatcattgacgacttcacctacgccggc actgtgctccccctcaaggaacttgctcttaagcacggtttcttcctgttcgaggacagaaagttcgcag atattggcaacactgtcaagcaccagtacaagaacggtgtctaccgaatcgccgagtggtccgatatcac caacgcccacggtgtacccggaaccggaatcattgctggcctgcgagctggtgccgaggaaactgtctct gaacagaagaaggaggacgtctctgactacgagaactcccagtacaaggagttcctggtcccctctccca acgagaagctggccagaggtctgctcatgctggccgagctgtcttgcaagggctctctggccactggcga gtactccaagcagaccattgagcttgcccgatccgaccccgagtttgtggttggcttcattgcccagaac cgacctaagggcgactctgaggactggcttattctgaccccggggtgggtcttgacgacaagggagacg ctctcggacagcagtaccgaactgttgaggatgtcatgtctaccggaacggatatcataattgtcggccg aggtctgtacggccagaaccgagatcctattgaggaggccaagcgataccagaaggctggctgggaggct taccagaagattaactgttag
```

(SEQ ID NO.: 38)
Amino Acid =
MPSYEARANVHKSAFAARVLKLVAAKKTNLCASLDVTTTKELIELADKVGPYVCMIKTHIDIIDDFTYAG

TVLPLKELALKHGFFLFEDRKFADIGNTVKHQYKNGVYRIAEWSDITNAHGVPGTGIIAGLRAGAEETVS

EQKKEDVSDYENSQYKEFLVPSPNEKLARGLLMLAELSCKGSLATGEYSKQTIELARSDPEFVVGFIAQN

RPKGDSEDWLILTPGVGLDDKGDALGQQYRTVEDVMSTGTDIIIVGRGLYGQNRDPIEEAKRYQKAGWEA

YQKINC*

ACLsubunit1 - YALI0E34793

(SEQ ID NO.: 39)
Nucleotide =
atgtctgccaacgagaacatctcccgattcgacgcccctgtgggcaaggagcaccccgcctacgagctct tccataaccacacacgatctttcgtctatggtctccagcctcgagcctgccagggtatgctggacttcga
```

-continued

```
cttcatctgtaagcgagagaaccccctccgtggccggtgtcatctatcccttcggcggccagttcgtcacc aagatgtactggggcaccaaggagactcttctccctgtctaccagcaggtcgagaaggccgctgccaagc accccgaggtcgatgtcgtggtcaactttgcctcctctcgatccgtctactcctctaccatggagctgct cgagtaccccagttccgaaccatcgccattattgccgagggtgtccccgagcgacgagcccgagagatc ctccacaaggcccagaagaagggtgtgaccatcattggtcccgctaccgtcggaggtatcaagcccggtt gcttcaaggttggaaacaccggaggtatgatggacaacattgtcgcctccaagctctaccgaccggctc cgttgcctacgtctccaagtccggaggaatgtccaacgagctgaacaacattatctctcacaccaccgac ggtgtctacgagggtattgctattggtggtgaccgatacccggtactaccttcattgaccatatcctgc gatacgaggccgaccccaagtgtaagatcatcgtcctccttggtgaggttggtggtgttgaggagtaccg agtcatcgaggctgttaagaacggccagatcaagaagcccatcgtcgcttgggccattggtacttgtgcc tccatgttcaagactgaggttcagttcggccacgccggctccatggccaactccgacctggagactgcca aggctaagaacgccgccatgaagtctgctggcttctacgtccccgataccttcgaggacatgcccgaggt ccttgccgagctctacgagaagatggtcgccaagggcgagctgtctcgaatctctgagcctgaggtcccc aagatccccattgactactcttgggcccaggagcttggtcttatccgaaagcccgctgctttcatctcca ctatttccgatgaccgaggccaggagcttctgtacgctggcatgcccatttccgaggttttcaaggagga cattggtatcggcggtgtcatgtctctgctgtggttccgacgacgactccccgactacgcctccaagttt cttgagatggttctcatgcttactgctgaccacggtcccgccgtatccggtgccatgaacaccattatca ccacccgagctggtaaggatctcatttcttcccctggttgctggtctcctgaccattggtacccgattcgg aggtgctcttgacggtgctgccaccgagttcaccactgcctacgacaagggtctgtcccccgacagttc gttgataccatgcgaaagcagaacaagctgattcctggtattggccatcgagtcaagtctcgaaacaacc ccgatttccgagtcgagcttgtcaaggactttgttaagaagaacttcccctccacccagctgctcgacta cgccttgctgtcgaggaggtcaccacctccaagaaggacaacctgattctgaacgttgacggtgctatt gctgtttcttttgtcgatctcatgcgatcttgcggtgcctttactgtggaggagactgaggactacctca agaacggtgttctcaacggtctgttcgttctcggtcgatccattggtctcattgcccaccatctcgatca gaagcgactcaagaccggtctgtaccgacatccttgggacgatatccacctacctggttggccaggaggct atccagaagaagcgagtcgagatcagcgccggcgacgtttccaaggccaagactcgatcatag
```

(SEQ ID NO.: 40)

```
Amino Acid =
MSANENISRFDAPVGKEHPAYELFHNHTRSFVYGLQPRACQGMLDFDFICKRENPSVAGVIYPFGGQFVT

KMYWGTKETLLPVYQQVEKAAAKHPEVDVVVNFASSRSVYSSTMELLEYPQFRTIAIIAEGVPERRAREI

LHKAQKKGVTIIGPATVGGIKPGCFKVGNTGGMMDNIVASKLYRPGSVAYVSKSGGMSNELNNIISHTTD

GVYEGIAIGGDRYPGTTFIDHILRYEADPKCKIIVLLGEVGGVEEYRVIEAVKNGQIKKPIVAWAIGTCA

SMFKTEVQFGHAGSMANSDLETAKAKNAAMKSAGFYVPDTFEDMPEVLAELYEKMVAKGELSRISEPEVP

KIPIDYSWAQELGLIRKPAAFISTISDDRGQELLYAGMPISEVFKEDIGIGGVMSLLWFRRRLPDYASKF

LEMVLMLTADHGPAVSGAMNTIITTRAGKDLISSLVAGLLTIGTRFGGALDGAATEFTTAYDKGLSPRQF

VDTMRKQNKLIPGIGHRVKSRNNPDFRVELVKDFVKKNFPSTQLLDYALAVEEVTTSKKDNLILNVDGAI

AVSFVDLMRSCGAFTVEETEDYLKNGVLNGLFVLGRSIGLIAHHLDQKRLKTGLYRHPWDDITYLVGQEA

IQKKRVEISAGDVSKAKTRS*
```

ACLsubunit2 - YALI0D24431

(SEQ ID NO.: 41)

```
Nucleotide =
atgtcagcgaaatccattcacgaggccgacggcaaggccctgctcgcacactttctgtccaaggcgcccg tgtgggccgagcagcagcccatcaacacgtttgaaatgggcacacccaagctggcgtctctgacgttcga
```

```
ggacggcgtggcccccgagcagatcttcgccgccgctgaaaagacctacccctggctgctggagtccggc gccaagtttgtggccaagcccgaccagctcatcaagcgacgaggcaaggccggcctgctggtactcaaca agtcgtgggaggagtgcaagccctggatcgccgagcgggccgccaagcccatcaacgtggagggcattga cggagtgctgcgaacgttcctggtcgagccctttgtgccccacgaccagaagcacgagtactacatcaac atccactccgtgcgagagggcgactggatcctcttctaccacgagggaggagtcgacgtcggcgacgtgg acgccaaggccgccaagatcctcatcccgttgacattgagaacgagtacccctccaacgccacgctcac caaggagctgctggcacacgtgcccgaggaccagcaccagaccctgctcgacttcatcaaccggctctac gccgtctacgtcgatctgcagtttacgtatctggagatcaaccccctggtcgtgatccccaccgcccagg gcgtcgaggtccactacctggatcttgccggcaagctcgaccagaccgcagagtttgagtgcggccccaa gtgggctgctgcgcggtccccgccgctctgggccaggtcgtcaacattgacgccggctccaccaaggtg tccatcgacgccggccccgccatggtcttccccgctcctttcggtcgagagctgtccaaggaggaggcgt acattgcggagctcgattccaagaccggagcttctctgaagctgactgttctcaatgccaagggccgaat ctggaccctttgtggctggtggaggagcctccgtcgtctacgccgacgccattgcgtctgccggctttgct gacgagctcgccaactacggcgagtactctggcgctcccaacgagacccagacctacgagtacgccaaaa ccgtactggatctcatgacccggggcgacgctcaccccgagggcaaggtactgttcattggcggaggaat cgccaacttcacccaggttggatccaccttcaagggcatcatccgggccttccgggactaccagtcttct ctgcacaaccacaaggtgaagatttacgtgcgacgaggcggtcccaactggcaggagggtctgcggttga tcaagtcggctggcgacgagctgaatctgcccatggagatttacggccccgacatgcacgtgtcgggtat tgttcctttggctctgcttggaaagcggcccaagaatgtcaagccttttggcaccggaccttctactgag gcttccactcctctcggagtttaa (SEQ ID NO.: 42)
Amino Acid =
MSAKSIHEADGKALLAHFLSKAPVWAEQQPINTFEMGTPKLASLTFEDGVAPEQIFAAAEKTYPWLLESG

AKFVAKPDQLIKRBGKAGLLVLNKSWEECKPWIAERAAKPINVEGIDGVLRTFLVEPFVPHDQKHEYYIN

IHSVREGDWILFYHEGGVDVGDVDAKAAKILIPVDIENEYPSNATLTKELLAHVPEDQHQTLLDFINRLY

AVYVDLQFTYLEINPLVVIPTAQGVEVHYLDLAGKLDQTAEFECGPKWAAARSPAALGQVVTIDAGSTKV

SIDAGPAMVFPAPFGRELSKEEAYIAELDSKTGASLKLTVLNAKGRIWTLVAGGGASVVYADAIASAGFA

DELANYGEYSGAPNETQTYEYAKTVLDLMTRGDAHPEGKVLFIGGGIANFTQVGSTFKGIIRAFRDYQSS

LHNHKVKIYVRRGGPNWQEGLRLIKSAGDELNLPMEIYGPDMHVSGIVPLALLGKRPKNVKPFGTGPSTE

ASTPLGV*

MEA1 - YALI0E18634
(note: 4 nucleotide difference compared to the reference sequence.
In embodiments, MEA1 is the reference sequence associated with
YALI0E18634. In embodiments, MEA1 is the reference sequence with
the four nucleotide differences from the reference sequence
shown below.)
                                                                 (SEQ ID NO.: 43)
Nucleotide =
atgttacgactacgaaccatgcgacccacacagaccagcgtcagggcggcgcttgggcccaccgctgcgg cccgaaacatgtcctcctccagcccctccagcttcgaatactcgtcctacgtcaagggcacgcgggaaat cggccaccgaaaggcgcccacaacccgtctgtcggttgagggccccatctacgtgggcttcgacggcatt cgtcttctcaacctgccgcatctcaacaagggctcggattcccctcaacgagcgacgggaattcggac tcagtggtcttctgccctctgccgaagccaccctggaggaacaggtcgaccgagcataccaacaattcaa aaagtgtggcactcccttagccaaaaacgggttctgcacctcgctcaagttccaaaacgaggtgctctac tacgccctgctgctcaagcacgttaaggaggtcttccccatcatctatacaccgactcagggagaagcca
```

-continued

```
ttgaacagtactcgcggctgttccggcggcccgaaggctgcttcctcgacatcaccagtccctacgacgt ggaggagcgtctgggagcgtttggagaccatgacgacattgactacattgtcgtgactgactccgagggt attctcggaattggagaccaaggagtgggcggtattggtatttccatcgccaagctggctctcatgactc tatgtgctggagtcaacccctcacgagtcattcctgtggttctggatacgggaaccaacaaccaggagct gctgcacgaccccctgtatctcggccgacgaatgccccgagtgcgaggaaagcagtacgacgacttcatc gacaactttgtgcagtctgcccgaaggctgtatcccaaggcggtgatccatttcgaggactttgggctcg ctaacgcacacaagatcctcgacaagtatcgaccggagatcccctgcttcaacgacgacatccagggcac tggagccgtcactctggcctccatcacggccgctctcaaggtgctgggcaaaaatatcacagatactcga attctcgtgtacggagctggttcggccggcatgggtattgctgaacaggtctatgataacctggttgccc agggtctcgacgacaagactgcgcgacaaaacatctttctcatggaccgaccgggtctactgaccaccgc acttaccgacgagcagatgagcgacgtgcagaagccgtttgccaaggacaaggccaattacgagggagtg gacaccaagactctggagcacgtggttgctgccgtcaagccccatattctcattggatgttccactcagc ccggcgcctttaacgagaaggttgtcaaggagatgcttaaacacacccctcgacccatcattctccctct ttccaaccccacacgtcttcatgaggctgtccctgcagatctgtacaagtggaccgacggcaaggctctg gttgccaccggctcgcccttgacccagtcaacggcaaggagacgtctgagaacaataactgctttgttt cccccggaatcgggctgggagccattctgtctcgatcaaagctcatcaccaacaccatgattgctgctgc catcgagtgcctcgccaacaggcccccattctcaagaaccacgacgagggagtacttcccgacgtagct ctcatccagatcatttcggcccgggtggccactgccgtggttcttcaggccaaggctgagggcctagcca ctgtcgaggaagagctcaagcccggcaccaaggaacatgtgcagattcccgacaactttgacgagtgtct cgcctgggtcgagactcagatgtggcggcccgtctaccggcctctcatccatgtgcgggattacgactag
```

(SEQ ID NO.: 44)

Amino Acid =
MLRLRTMRPTQTSVRAALGPTAAARNMSSSSPSSFEYSSYVKGTREIGHRKAPTTRLSVEGPIYVGFDGI

RLLNLPHLNKGSGFPLNERREFGLSGLLPSAEATLEEQVDRAYQQFKKCGTPLAKNGFCTSLKFQNEVLY

YALLLKHVKEVFPIIYTPTQGEAIEQYSRLFRRPEGCFLDITSPYDVEERLGAFGDHDDIDYIVVTDSEG

ILGIGDQGVGGIGISIAKLALMTLCAGVNPSRVIPVVLDTGTNNQELLHDPLYLGRRMPRVRGKQYDDFI

DNFVQSARRLYPKAVIHFEDFGLANAHKILDKYRPEIPCFNDDIQGTGAVTLASITAALKVLGKNITDTR

ILVYGAGSAGMGIAEQVYDNLVAQGLDDKTARQNIFLMDRPGLLTTALTDEQMSDVQKPFAKDKANYEGV

DTKTLEHVVAAVKPHILIGCSTQPGAFNEKVVKEMLKHTPRPIILPLSNPTRLHEAVPADLYKWTDGKAL

VATGSPFDPVNGKETSENNNCFVFPGIGLGAILSRSKLITNTMIAAAIECLAEQAPILKNHDEGVLPDVA

LIQIISARVATAVVLQAKAEGLATVEEELKPGTKEHVQIPDNFDECLAWVETQMWRPVYRPLIHVRDYD*

DGA1 - YALI0E32769

(SEQ ID NO.: 45)

Nucleotide =
```
atgactatcgactcacaatactacaagtcgcgagacaaaaacgacacggcacccaaaatcgcgggaatcc gatatgccccgctatcgacaccattactcaaccgatgtgagaccttctctctggtctggcacattttcag cattcccactttcctcacaattttcatgctatgctgcgcaattccactgctctggccatttgtgattgcg tatgtagtgtacgctgttaaagacgactcccgtccaacggaggagtggtcaagcgatactcgcctattt caagaaacttcttcatctggaagctctttggccgctacttccccataactctgcacaagacggtggatct ggagcccacgcacacatactaccctctggacgtccaggagtatcacctgattgctgagagatactggccg cagaacaagtacctccgagcaatcatctccaccatcgagtactttctgcccgccttcatgaaacggtctc tttctatcaacgagcaggagcagcctgccgagcgagatcctctcctgtctcccgtttctcccagctctcc gggttctcaacctgacaagtggattaaccacgacagcagatatagccgtggagaatcatctggctccaac
```

-continued

```
ggccacgcctcgggctccgaacttaacggcaacggcaacaatggcaccactaaccgacgacctttgtcgt ccgcctctgctggctccactgcatctgattccacgcttcttaacgggtccctcaactcctacgccaacca gatcattggcgaaaacgacccacagctgtcgcccacaaaactcaagcccactggcagaaaatacatcttc ggctaccaccccacgcattatcggcatgggagcctttggtggaattgccaccgagggagctggatggt ccaagctctttccgggcatccctgtttctcttatgactctcaccaacaacttccgagtgcctctctacag agagtacctcatgagtctgggagtcgcttctgtctccaagaagtcctgcaaggccctcctcaagcgaaac cagtctatctgcattgtcgttggtggagcacaggaaagtcttctggccagacccggtgtcatggacctgg tgctactcaagcgaaagggttttgttcgacttggtatggaggtcggaaatgtcgcccttgttcccatcat ggcctttggtgagaacgacctctatgaccaggttagcaacgacaagtcgtccaagctgtaccgattccag cagtttgtcaagaacttccttggattcacccttcctttgatgcatgcccgaggcgtcttcaactacgatg tcggtcttgtccctacaggcgacccgtcaacattgtggttggttccccattgacttgccttatctccc acacccaccgacgaagaagtgtccgaataccacgaccgatacatcgccgagctgcagcgaatctacaac gagcacaaggatgaatatttcatcgattggaccgaggagggcaaaggagccccagagttccgaatgattg agtaa
```

(SEQ ID NO.: 46)
Amino Acid =
MTIDSQYYKSRDKNDTAPKIAGIRYAPLSTPLLNRCETFSLVWHIFSIPTFLTIFMLCCAIPLLWPFVIA

YVVYAVKDDSPSNGGVVKRYSPISRNFFIWKLFGRYFPITLHKTVDLEPTHTYYPLDVQEYHLIAERYWP

QNKYLRAIISTIEYFLPAFMKRSLSINEQEQPAERDPLLSPVSPSSPGSQPDKWINHDSRYSRGESSGSN

GHASGSELNGNGNNGTTNRRPLSSASAGSTASDSTLLNGSLNSYANQIIGENDPQLSPTKLKPTGRKYIF

GYHPHGIIGMGAFGGIATEGAGWSKLFPGIPVSLMTLTNNFRVPLYREYLMSLGVASVSKKSCKALLKRN

QSICIVVGGAQESLLARPGVMDLVLLKRKGFVRLGMEVGNVALVPIMAFGENDLYDQVSNDKSSKLYRFQ

QFVKNFLGFTLPLMHARGVFNYDVGLVPYRRPVNIVVGSPIDLPYLPHPTDEEVSEYHDRYIAELQRIYN

EHKDEYFIDWTEEGKGAPEFRMIE*

DGA2 - YALI0D07986
                                                          (SEQ ID NO.: 47)
Nucleotide =

```
atggaagtccgacgacgaaaaatcgacgtgctcaaggcccagaaaaacggctacgaatcgggcccaccat ctcgacaatcgtcgcagccctcctcaagagcatcgtccagaacccgcaacaaacactcctcgtccaccct gtcgctcagcggactgaccatgaaagtccagaagaaacctgcgggaccccggcgaactccaaaacgcca ttcctacacatcaagcccgtgcacacgtgctgctccacatcaatgctttcgcgcgattatgacggctcca acccagcttcaagggcttcaaaaacatcggcatgatcattctcattgtgggaaatctacggctcgcatt cgaaaactacctcaaatacggcatttccaacccgttcttcgaccccaaaattactccttccgagtggcag ctctcaggcttgctcatagtcgtggcctacgcacatatcctcatggcctacgctattgagagcgctgcca agctgctgttcctctctagcaaacaccactacatggccgtggggcttctgcataccatgaacactttgtc gtccatctcgttgctgtcctacgtcgtctactactacctgcccaaccccgtggcaggcacaatagtcgag tttgtggccgttattctgtctctcaaactcgcctcatacgccctcactaactcggatctccgaaaagccg caattcatgcccagaagctcgacaagacgcaagacgataacgaaaaggaatccacctcgtcttcctcttc ttcagatgacgcagagactttggcagacattgacgtcattcctgcatactacgcacagctgccctacccc cagaatgtgacgctgtcgaacctgctgtacttctggtttgctcccacactggtctaccagcccgtgtacc ccaagacggagcgtattcgacccaagcacgtgatccgaaacctgttgagctcgtctctctgtgcatgct tattcagtttctcatcttccagtacgcctaccccatcatgcagtcgtgtctggctctgttcttccagccc aagctcgattatgccaacatctccgagcgcctcatgaagttggcctccgtgtctatgatggtctggctca
```

-continued ttggattctacgctttcttccagaacggtctcaatcttattgccgagctcacctgttttggaaacagaac cttctaccagcagtggtggaattcccgctccattggccagtactggactctatggaacaagccagtcaac cagtactttagacaccacgtctacgtgcctcttctcgctcggggcatgtcgcggttcaatgcgtcggtgg tggttttcttttctccgccgtcatccatgaactgcttgtcggcatccccactcacaacatcatcggagc cgccttcttcggcatgatgtcgcaggtgcctctgatcatggctactgagaaccttcagcatattaactcc tctctgggccccttccttggcaactgtgcattctggttcaccttttcctgggacaacccacttgtgcat tcctttattatctggcttacaactacaagcagaaccagtag (SEQ ID NO.: 48)

Amino Acid =
MEVRRRKIDVLKAQKNGYESGPPSRQSSQPSSRASSRTRNKHSSSTLSLSGLTMKVQKKPAGPPANSKTP

FLHIKPVHTCCSTSMLSRDYDGSNPSFKGFKNIGMIILIVGNLRLAFENYLKYGISNPFFDPKITPSEWQ

LSGLLIVVAYAHILMAYAIESAAKLLFLSSKHHYMAVGLLHTMNTLSSISLLSYVVYYYLPNPVAGTIVE

FVAVILSLKLASYALTNSDLRKAAIHAQKLDKTQDDNEKESTSSSSSSDDAETLADIDVIPAYYAQLPYP

QNVTLSNLLYFWFAPTLVYQPVYPKTERIRPKHVIRNLFELVSLCMLIQFLIFQYAYPIMQSCLALFFQP

KLDYANISERLMKLASVSMMVWLIGFYAFFQNGLNLIAELTCFGNRTFYQQWWNSRSIGQYWTLWNKPVN

QYFRHHVYVPLLARGMSRFNASVVVFFFSAVIHELLVGIPTHNIIGAAFFGMMSQVPLIMATENLQHINS

SLGPFLGNCAFWFTFFLGQPTCAFLYYLAYNYKQNQ*

MGA2- YALI0B12342

(SEQ ID NO.: 49)

Nucleotide =
atggctaaagacaaggaaatcgactttgactacacgggagaactggtgatggacgatttcgagttcccca tcgacgacatgctccacaacgacggagatgactttgtcaagaaggaaacgtgggacgagggttttggttt cggaacaaatggcgccgtgggtgcgcagatggacgtccagaccagcccatttagcgaccctgttttggc ggcgtgggagcaggccctgacatgatgggtctcatggatacaaacatgaaccacatcaacggtagtcaca acatgaacagcgtcgtcaagcaggaggactactacacaccgtccatgggcactcccatgaaccccaaca gcaacagtccatgaccccteaacagcagcatcacatgaaccacaaccagccctctcagctccaatctttg catcaacagtcccagaaggctcaaccacagcagcaacaacaacagccacatcagtcgacaggagtcgata gcataatcacaaaggcatacaccagggcagcaggagacctaccgtacggacgaaagtactcacgacaact caacaagtaccccgaggacgtggagtattcatctttcgacccatcgctatggagcaatttgctgaccaac tcggaaactccgtaccaataccagatacatgtccattccatgcccggaaaatcacgtgtggagacccaaa tcaaatgtgcattatcaatctaccctccgcctccacagcagtccgttcgacttccgacagacaccatttc gcgtcccaagttccagctcaagcagggccacattccagactcgtgtctctccttggaagtatacattgtg ggcgagcagaaccccagcaagcccgtcaatttgtgttctagatgcatcaaacgagaacagaagcgagcct gtcgaaagaaactcttttgacgagtcggaggagctgtcgtgggtcgagactcgtcaacgacgtctggctgt cttcaactgctccgaggtgcttgagttcaaggatgtggaacggcgagtatacatccccgagtccggcact acagttaccgccaagcagctggttctgcccctgcgtctggcttgctactgtagacaccacggggagaaaa agggatttcgaatcctcttttgtcttagagacgagggaggccagattgtgggtgtgggccagagtggaac gaccgtcatgatcactgacgaccacaaggttgtgggagacgcggttgccatgccgactacagccactgct cctgccaccgctggctcttcacaacccccacccaggttcctaccccgctgcatcttcgtcgacgagct atcgtcctcgaaactcgcttcctctatcgcctacttccatggaagactcttcgtcggagttcacctcgga ccattctcattactccaactatggttctaaacgacgacgagacggctcttccatcagcgattggagcggc atgatgaacgtgcgaggcatggatagacaggcttccattaccagcattcccgaaatggttggtggcatgt cgaacatgactgtggccagtgcttcgggtagcgccactaatctggctgctcacaacatgaacaaccccgc -continued

```
agacgaaaacctgcccgtcatcaagcgaatcatccctcgcagggttccattcgaggcggcattgaagta
accctgcttggatctggcttcaagtccaatctggtggctgttttcggtgacaacaaggccgtgggcaccc
actgctggtctgattcgaccatcgtgacccatctgccgccttcgaccatcgtgggtcccgttgtggtgtc
tttcgaaggttttgtgctcgacaagcctcagattttacctattttgacgacacagacggccagttgatt
gagttggcgctccaggttgtgggtctcaagatgaacggacggctggaagacgcccgaaacattgccatgc
gaatcgtgggcaacaatggaggcgttgcggcgcacaaggcgccatggcaggcgggaacatgtctaacgg
agacgttggaatggaaagtgctgctgcagacagttcggttcaacccgtatcgcctcccacagaccacgaa
gatgtggttctgcgatgtctggctctcacagacattcctggaggccgaattgccaactggcaactcacca
acgccgagggacagaccatggttcatctggccagtattctgggttactcgcgtgttctggtggctcttgt
ggctcgaggagctcgtgtggatgtttccgacaatggtggattcactcctcttcatttcgctgctctcttt
ggccgtcgaaagattgccaagaaactacttcggtgcaacgctgaccctacaaacgtaaccgaattggcg
aaaccgtgtttgatgttgcttgtcctcacattctcgatcttctggtcggtcctcagggcatgcctatggc
cgttcagacgtcgtatactcccgattaccatcgtcagcgtcgatcttcatcttcttccactctggcttcc
attgcatccatccaggattcgcgtgagtacggtttctatgaccatggaatgatttccaacctgtcgcata
ttccgtccacgtgctccattcgatcatcgacttctcagtttgacgctgaagacgagtgggacgagcgaga
tgaggaggatggagactttgacgacgattcagatgaggactcagacgatgactcagacgcgctcttcatg
tctgttagaaagcacgccaaggccaagtctgtggaatctcctctctctgaggaggaagagcgacttgtgc
gacacattgaggccgaagaccaggctgtggaggcccgtgtggctgccggaatcgtcagtagcaatgtacc
cgacgtggtgtcttccaatgactcggatcacgtgagatctgacacttccactgagaacaagtcctttca
cggtactttgaccgtactctcagcatggcatcttgggacgatgttctggcttacatttacagacccaagc
gagctactgtgcccaacaagcggtcttctggagctcctccttcagtcagatccacaagatcgcctctttc
ggaccatcccatcacgtcttcgggagacgagtccgaccgaaccatttctgcacatgcccttccggcggt
gccggtcgaggccggtctcattcgtccatctcgcgaatgtggcgatacctgaagaactcgtctgccgatg
aggccacccggtctcgatctcgagatgcaaacggagccggtgctcccctgcctacgaagaaatcttccc
tggccatgggggttgtccacgacaagaaggttgtgcagatggccgctgcttctgctgccgagaactcgtct
gggcctgttggagcctcatcttcagcagttgcgtccacttctgcggctgccgctgtggtgccctcccac
tagccccattgtggaggacgaggagcagctggtagaggcctggagacgacagcgacgatccatggctaa
cgatcgcatgttatttgccttctggctgcctgtgctgctcatggctattggttatatggtcatcaaggcg
tttggtctgttccccgaccaggtctctgccgttgagtctgtggctgagactgtgggtgtccactgccgtg
gagcagttgccaagctatggttcaagcagtaccctgttcaccgaggccagccactcaaggacacctgttc
atttgagcccaacagtctggtagagtcagctcttcgtcagatgaatgggtggtccgaccgggaggttccc
attcatcaagcccaggcccaggctgcatga
```

(SEQ ID NO.: 50)

Amino Acid =
MAKDKEIDFDYTGELVMDDFEFPIDDMLHNDGDDFVKKETWDEGFGFGTNGAVGAQMDVQTSPFSDPVFG

GVGAGPDMMGLMDTNMNHINGSHNMNSVVKQEDYYTPSMGTPMNPQQQQSMTPQQQHHMNHNQPSQLQSL

HQQSQKAQPQQQQQQPHQSTGVDSIITKAYTRAAGDLPYGRKYSRQLNKYPEDVEYSSFDPSLWSNLLTN

SETPYQYQIHVHSMPGKSRVETQIKCALSIYPPPPQQSVRLPTDTISRPKFQLKQGHIPDSCLSLEVYIV

GEQNPSKPVNLCSRCIKREQKRACRKKLFDESEELSWVETRQRRLAVFNCSEVLEFKDVERRVYIPESGT

TVTAKQLVLPLRLACYCRHHGEKKGFRILFCLRDEGGQIVGVGQSGTTVMITDDHKVVGDAVAMPTTATA

PATAGSSQPPTQVPTPAASSSTSYRPRNSLPLSPTSMEDSSSEFTSDHSHYSNYGSKRRRDGSSISDWSG

MMNVRGMDRQASITSIPEMVGGMSNMTVASASGSATNLAAHNMNNPADENLPVIKRIIPSQGSIRGGIEV

-continued

```
TLLGSGFKSNLVAVFGDNKAVGTHCWSDSTIVTHLPPSTIVGPVVVSFEGFVLDKPQIFTYFDDTDGQLI

ELALQVVGLKMNGRLEDARNIAMRIVGNNGGVAGAQGAMAGGNMSNGDVGMESAAADSSVQPVSPPTDHE

DVVLRCLALTDIPGGRIANWQLTNAEGQTMVHLASILGYSRVLVALVARGARVDVSDNGGFTPLHFAALF

GRRKIAKKLLRCNADPYKRNRIGETVFDVACPHILDLLVGPQGMPMAVQTSYTPDYHRQRRSSSSSTLAS

IASIQDSREYGFYDHGMISNLSHIPSTCSIRSSTSQFDAEDEWDERDEEDGDFDDDSDEDSDDDSDALFM

SVRKHAKAKSVESPLSEEEERLVRHIEAEDQAVEARVAAGIVSSNVPDVVSSNDSDHVRSDTSTENKSFS

RYFDRTLSMASWDDVLAYIYRPKRATVPNKRSSGAPPSVRSTRSPLSDHPITSSGDESDRTISAHAPSGG

AGRGRSHSSISRMWRYLKNSSADEATRSRSRDANGAGAPPAYEEIFPGHGVVHDKKVVQMAAASAAENSS

GPVGASSSAVASTSAAAAVVPSPLAPIVEDEEQLVEAWRRQRRSMANDRMLFAFWLPVLLMAIGYMVIKA

FGLFPDQVSAVESVAETVGVHCRGAVAKLWFKQYPVHRGQPLKDTCSFEPNSLVESALRQMNGWSDREVP

IHQAQAQAA*
```

Mga2-L36-mutant version (SEQ ID NO.: 51)

Nucleotide =
```
atggctaaagacaaggaaatcgactttgactacacgggagaactggtgatggacgatttcgagttcccca tcgacgacatgctccacaacgacgagatgactttgtcaagaaggaaacgtgggacgagggttttggttt cggaacaaatggcgccgtgggtgcgcagatggacgtccagaccagcccatttagcgaccctgttttggc ggcgtgggagcaggccctgacatgatgggtctcatggatacaaacatgaaccacatcaacgtagtcaca acatgaacagcgtcgtcaagcaggaggactactacacaccgtccatgggcactccatgaaccccaaca gcaacagtccatgacccctcaacagcagcatcacatgaaccacaaccagccctctcagctccaatctttg catcaacagtcccagaaggctcaaccacagcagcaacaacaacagccacatcagtcgacaggagtcgata gcataatcacaaaggcatacaccagggcagcaggagacctaccgtacggacgaaagtactcacgacaact caacaagtaccccgaggacgtggagtattcatctttcgacccatcgctatggagcaatttgctgaccaac tcggaaactccgtaccaataccagatacatgtccattccatgcccggaaaatcacgtgtggagacccaaa tcaaatgtgcattatcaatctaccctccgcctccacagcagtccgttcgacttccgacagacaccatttc gcgtcccaagttccagctcaagcagggccacattccagactcgtgtctctccttggaagtatacattgtg ggcgagcagaaccccagcaagcccgtcaatttgtgttctagatgcatcaaacgagaacagaagcgagcct gtcgaaagaaactcttttgacgagtcggaggagctgtcgtgggtcgagactcgtcaacgacgtctggctgt cttcaactgctccgaggtgcttgagttcaaggatgtggaacggcgagtatacatccccgagtccggcact acagttaccgccaagcagctggttctgcccctgcgtctggcttgctactgtagacaccacggggagaaaa agggatttcgaatcctcttttgtcttagagacgagggaggccagattgtgggtgtgggccagagtggaac gaccgtcatgatcactgacgaccacaaggttgtgggagacgcggttgccatgccgactacagccactgct cctgccaccgctggctcttcacaacccccacccaggttcctaccccgctgcatcttcgtcgacgagct atcgtcctcgaaactcgcttcctctatcgcctacttccatggaagactcttcgtcggagttcacctcgga ccattctcattactccaactatggttctaaacgacgacgagacggctcttccatcagcgattggagcggc atgatgaacgtgcgaggcatggatagacaggcttccattaccagcattcccgaaatggttggtggcatgt cgaacatgactgtggccagtgcttcgggtagcgccactaatctggctgctcacaacatgaacaacccgc agacgaaaacctgcccgtcatcaagcgaatcatcccctcgcagggttccattcgaggcggcattgaagta accctgcttggatctggcttcaagtccaatctggtggctgttttcggtgacaacaaggccgtgggcaccc actgctggtctgattcgaccatcgtgacccatctgccgccttcgaccatcgtgggtcccgttgtggtgtc tttcgaaggttttgtgctcgacaagctcagatttttacctattttgacgacacagacggccagttgatt gagttggcgctccaggttgtgggtctcaagatgaacagacggctggaagacgcccgaaacattgccatgc
```

-continued

```
gaatcgtgggcaacaatggaggcgttgcgggcgcacaaggcgccatggcaggcgggaacatgtctaacgg
agacgttggaatggaaagtgctgctgcagacagttcggttcaacccgtatcgcctcccacagaccacgaa
gatgtggttctgcgatgtctggctctcacagacattcctggaggccgaattgccaactggcaactcacca
acgccgagggacagaccatggttcatctggccagtattctgggttactcgcgtgttctggtggctcttgt
ggctcgaggagctcgtgtggatgtttccgacaatggtggattcactcctcttcatttcgctgctctcttt
ggccgtcgaaagattgccaagaaactacttcggtgcaacgctgaccectacaaacgtaaccgaattggcg
aaaccgtgtttgatgttgcttgtcctcacattctcgatcttctggtcggtcctcagggcatgcctatggc
cgttcagacgtcgtatactcccgattaccatcgtcagcgtcgatcttcatcttcttccactctggcttcc
attgcatccatccaggattcgcgtgagtacggtttctatgaccatggaatgatttccaacctgtcgcata
ttccgtccacgtgctccattcgatcatcgacttctcagtttgacgctgaagacgagtgggacgagcgaga
tgaggaggatggagactttgacgacgattcagatgaggactcagacgatgactcagacgcgctcttcatg
tctgttagaaagcacgccaaggccaagtctgtggaatctcctctctctgaggaggaagagcgacttgtgc
gacacattgaggccgaagaccaggctgtggaggcccgtgtggctgccggaatcgtcagtagcaatgtacc
cgacgtggtgtcttccaatgactcggatcacgtgagatctgacacttccactgagaacaagtccttttca
cggtactttgaccgtactctcagcatggcatcttgggacgatgttctggcttacatttacagacccaagc
gagctactgtgcccaacaagcggtcttctggagctcctccttcagtcagatccacaagatcgcctctttc
ggaccatcccatcacgtcttcgggagacgagtccgaccgaaccatttctgcacatgcccttccggcggt
gccggtcgaggccggtctcattcgtccatctcgcgaatgtggcgatacctgaagaactcgtctgccgatg
aggccacccggtctcgatctcgagatgcaaacggagccggtgctcccectgcctacgaagaaatcttccc
tggccatggggttgtccacgacaagaaggttgtgcagatggccgctgcttctgctgccgagaactcgtct
gggcctgttggagcctcatcttcagcagttgcgtccacttctgcggctgccgctgtggtgccctcccac
tagcccccattgtggaggacgaggagcagctggtagaggcctggagacgacagcgacgatccatggctaa
cgatcgcatgttatttgccttctggctgcctgtgctgctcatggctattggttatatggtcatcaaggcg
tttggtctgttccccgaccaggtctctgccgttgagtctgtggctgagactgtgggtgtccactgccgtg
gagcagttgccaagctatggttcaagcagtaccctgttcaccgaggccagccactcaaggacacctgttc
atttgagcccaacagtctggtagagtcagctcttcgtcagatgaatgggtggtccgaccgggaggttccc
attcatcaagcccaggcccaggctgcatga
```

(SEQ ID NO.: 52)

Amino Acid =
MAKDKEIDFDYTGELVMDDFEFPIDDMLHNDGDDFVKKETWDEGFGFGTNGAVGAQMDVQTSPFSDPVFG
GVGAGPDMMGLMDTNMNHINGSHNMNSVVKQEDYYTPSMGTPMNPQQQQSMTPQQQHHMNHNQPSQLQSL
HQQSQKAQPQQQQQQPHQSTGVDSIITKAYTRAAGDLPYGRKYSRQLNKYPEDVEYSSFDPSLWSNLLTN
SETPYQYQIHVHSMPGKSRVETQIKCALSIYPPPPQQSVRLPTDTISRPKFQLKQGHIPDSCLSLEVYIV
GEQNPSKPVNLCSRCIKREQKRACRKKLFDESEELSWVETRQRRLAVFNCSEVLEFKDVERRVYIPESGT
TVTAKQLVLPLRLACYCRHHGEKKGFRILFCLRDEGGQIVGVGQSGTTVMITDDHKVVGDAVAMPTTATA
PATAGSSQPPTQVPTPAASSSTSYRPRNSLPLSPTSMEDSSSEFTSDHSHSYSNYGSKRRRDGSSISDWSG
MMNVRGMDRQASITSIPEMVGGMSNMTVASASGSATNLAAHNMNNPADENLPVIKRIIPSQGSIRGGIEV
TLLGSGFKSNLVAVFGDNKAVGTHCWSDSTIVTHLPPSTIVGPVVVSFEGFVLDKPQIFTYFDDTDGQLI
ELALQVVGLKMNRRLEDARNIAMRIVGNNGGVAGAQGAMAGGNMSNGDVGMESAAADSSVQPVSPPTDHE
DVVLRCLALTDIPGGRIANWQLTNAEGQTMVHLASILGYSRVLVALVARGARVDVSDNGGFTPLHFAALF
GRRKIAKKLLRCNADPYKRNRIGETVFDVACPHILDLLVGPQGMPMAVQTSYTPDYHRQRRSSSSSTLAS

```
IASIQDSREYGFYDHGMISNLSHIPSTCSIRSSTSQFDAEDEWDERDEEDGDFDDDSDEDSDDDSDALFM

SVRKHAKAKSVESPLSEEEERLVRHIEAEDQAVEARVAAGIVSSNVPDVVSSNDSDHVRSDTSTENKSFS

RYFDRTLSMASWDDVLAYIYRPKRATVPNKRSSGAPPSVRSTRSPLSDHPITSSGDESDRTISAHAPSGG

AGRGRSHSSISRMWRYLKNSSADEATRSRSRDANGAGAPPAYEEIFPGHGVVHDKKVVQMAAASAAENSS

GPVGASSSAVASTSAAAAVVPSPLAPIVEDEEQLVEAWRRQRRSMANDRMLFAFWLPVLLMAIGYMVIKA

FGLFPDQVSAVESVAETVGVHCRGAVAKLWFKQYPVHRGQPLKDTCSFEPNSLVESALRQMNGWSDREVP

IHQAQAQAA*
```

Mga2-truncated version removing of transmembrane span.

(SEQ ID NO.: 53)

```
Nucleotide =
atggctaaagacaaggaaatcgactttgactacacgggagaactggtgatggacgatttcgagttcccca tcgacgacatgctccacaacgacgagatgactttgtcaagaaggaaacgtgggacgagggttttggttt cggaacaaatggcgccgtgggtgcgcagatggacgtccagaccagcccatttagcgaccctgttttggc ggcgtgggagcaggccctgacatgatgggtctcatggatacaaacatgaaccacatcaacgtagtcaca acatgaacagcgtcgtcaagcaggaggactactacacaccgtccatgggcactcccatgaaccccaaca gcaacagtccatgacccctcaacagcagcatcacatgaaccacaaccagccctctcagctccaatctttg catcaacagtcccagaaggctcaaccacagcagcaacaacaacagccacatcagtcgacaggagtcgata gcataatcacaaaggcatacaccagggcagcaggagacctaccgtacggacgaaagtactcacgacaact caacaagtaccccgaggacgtggagtattcatctttcgacccatcgctatggagcaatttgctgaccaac tcggaaactccgtaccaataccagatacgtgtccattccatgcccggaaaatcacgtgtggagacccaaa tcaaatgtgcattatcaatctaccctccgcctccacagcagtccgttcgacttccgacagacaccatttc gcgtcccaagttccagctcaagcagggccacattccagactcgtgtctctccttggaagtatacattgtg ggcgagcagaaccccagcaagcccgtcaatttgtgttctagatgcatcaaacgagaacagaagcgagcct gtcgaaagaaactcttgacgagtcggaggagctgtcgtgggtcgagactcgtcaacgacgtctggctgt cttcaactgctccgaggtgcttgagttcaaggatgtggaacggcgagtatacatcccgagtccggcact acagttaccgccaagcagctggttctgcccctgcgtctggcttgctactgtagacaccacggggagaaaa agggatttcgaatcctcttttgtcttagagacgagggaggccagattgtgggtgtgggccagagtggaac gaccgtcatgatcactgacgaccacaaggttgtgggagacgcggttgccatgccgactacagccactgct cctgccaccgctggctcttcacaaccccccacccaggttcctaccccgctgcatcttcgtcgacgagct atcgtcctcgaaactcgcttcctctatcgcctacttccatggaagactcttcgtcggagttcacctcgga ccattctcattactccaactatggttctaaacgacgacgagacggctcttccatcagcgattggagcggc atgatgaacgtgcgaggcatggatagacaggcttccattaccagcattcccgaaatggttggtggcatgt cgaacatgactgtggccagtgcttcgggtagcgccactaatctggctgctcacaacatgaacaaccccgc agacgaaaacctgcccgtcatcaagcgaatcatcccctcgcagggttccattcgaggcggcattgaagta accctgcttggatctggcttcaagtccaatctggtggctgttttcggtgacaacaaggccgtgggcaccc actgctggtctgattcgaccatcgtgacccatctgccgccttcgaccatcgtgggtcccgttgtggtgtc tttcgaaggttttgtgctcgacaagcctcagattttttacctattttgacgacacagacggccagttgatt gagttggcgctccaggttgtgggtctcaagatgaacggacggctggaagacgcccgaaacattgccatgc gaatcgtgggcaacaatggaggcgttgcgggcgcacaaggcgccatggcaggcgggaacatgtctaacgg agacgttggaatggaaagtgctgctgcagacagttcggttcaacccgtatcgcctcccacagaccacgaa gatgtggttctgcgatgtctggctctcacagacattcctggaggccgaattgccaactggcaactcacca acgccgagggacagaccatggttcatctggccagtattctgggttactcgcgtgttctggtggctcttgt
```

-continued ggctcgaggagctcgtgtggatgtttccgacaatggtggattcactcctcttcatttcgctgctctcttt ggccgtcgaaagattgccaagaaactacttcggtgcaacgctgaccoctacaaacgtaaccgaattggcg aaaccgtgtttgatgttgcttgtcctcacattctcgatcttctggtcggtcctcagggcatgcctatggc cgttcagacgtcgtatactcccgattaccatcgtcagcgtcgatcttcatcttcttccactctggcttcc attgcatccatccaggattcgcgtgagtacggtttctatgaccatggaatgatttccaacctgtcgcata ttccgtccacgtgctccattcgatcatcgacttctcagtttgacgctgaagacgagtgggacgagcgaga tgaggaggatggagactttgacgacgattcagatgaggactcagacgatgactcagacgcgctcttcatg tctgttagaaagcacgccaaggccaagtctgtggaatcctctctctgaggaggaagagcgacttgtgc gacacattgaggccgaagaccaggctgtggaggcccgtgtggctgccggaatcgtcagtagcaatgtacc cgacgtggtgtcttccaatgactcggatcacgtgagatctgacacttccactgagaacaagtccttttca cggtactttgaccgtactctcagcatggcatcttgggacgatgttctggcttacatttactga (SEQ ID NO.: 54)

Amino Acid =
MAKDKEIDFDYTGELVMDDFEFPIDDMLHNDGDDFVKKETWDEGFGFGTNGAVGAQMDVQTSPFSDPVFG

GVGAGPDMMGLMDTNMNHINGSHNMNSVVKQEDYYTPSMGTPMNPQQQQSMTPQQQHHMNHNQPSQLQSL

HQQSQKAQPQQQQQQPHQSTGVDSIITKAYTRAAGDLPYGRKYSRQLNKYPEDVEYSSFDPSLWSNLLTN

SETPYQYQIHVHSMPGKSRVETQIKCALSIYPPPPQQSVRLPTDTISRPKFQLKQGHIPDSCLSLEVYIV

GEQNPSKPVNLCSRCIKREQKRACRKKLFDESEELSWVETRQRRLAVFNCSEVLEFKDVERRVYIPESGT

TVTAKQLVLPLRLACYCRHHGEKKGFRILFCLRDEGGQIVGVGQSGTTVMITDDHKVVGDAVAMPTTATA

PATAGSSQPPTQVPTPAASSSTSYRPRNSLPLSPTSMEDSSSEFTSDHSHYSNYGSKRRRDGSSISDWSG

MMNVRGMDRQASITSIPEMVGGMSNMTVASASGSATNLAAHNMNNPADENLPVIKRIIPSQGSIRGGIEV

TLLGSGFKSNLVAVFGDNKAVGTHCWSDSTIVTHLPPSTIVGPVVVSFEGFVLDKPQIFTYFDDTDGQLI

ELALQVVGLKMNGRLEDARNIAMRIVGNNGGVAGAQGAMAGGNMSNGDVGMESAAADSSVQPVSPPTDHE

DVVLRCLALTDIPGGRIANWQLTNAEGQTMVHLASILGYSRVLVALVARGARVDVSDNGGFTPLHFAALF

GRRKIAKKLLRCNADPYKRNRIGETVFDVACPHILDLLVGPQGMPMAVQTSYTPDYHRQRRSSSSSTLAS

IASIQDSREYGFYDHGMISNLSHIPSTCSIRSSTSQFDAEDEWDERDEEDGDFDDDSDEDSDDDSDALFM

SVRKHAKAKSVESPLSEEEERLVRHIEAEDQAVEARVAAGIVSSNVPDVVSSNDSDHVRSDTSTENKSFS

RYFDRTLSMASWDDVLAYIY*

Sou2L36 YALI0D18964g (SEQ ID NO.: 55)
Nucleotide =
Atgtctggaccttccaccctcgccacgggactgcaccctctccccacagagaccccaaagttccccacca acatcatggaccgattctccctcaagggtaaggttgcctccgtcaccggctcctcgtcaggtatcggcta ctgcgtggccgaggcctacgcccaggccggtgccgacgtggccatctggtacaactccaccccgccgac gcaaaggctgagcacctcgctaagacctacggcgtcaaggccaaggcctacaagtgccctgtcaccgacg ccgccgccgtggagtccaccatccagcagatcgagaaggactttggcaccattgacatcttcgtcgccaa cgctggtgtccctggaccgccggccccatgatcgacgtgcccgacaacaaggagtgggacaaggtcatc aacctggatctcaacggtgcctactactgcgccaagtacgccggccagatcttcaagaagaagggcaagg gatccttcatcttcaccgcctccatgtccggccacattgtcaacatccccagatgcaggcctgctacaa cgccgccaaggccgctctgctgcacctgtctcgatcgctggccgtcgagtgggccggcttttgcccgatgc aacacagtctcccctggctacatggccaccgagatctccgactttgtccccaaggagaccaaggagaagt ggtggcagctcattcccatgggccgagagggagacccctccgagctctagcctacctctaccttgcctct ga -continued CEN0EL36 YALI0D15444s (SEQ ID NO.: 56)

Nucleotide =
Cacaaatattcttgatttactttggttttgccctattcggaaattttattgatatctaatagaagtatta aagtaaaaatgtactaatacttaattgtaatgtcatcagaaataacatttgaggaaaatatttcaaacct aattgatatatatattagagatgtcccgcttctctgtcattaatatattcaagcaatcga DEHA0A1298g IPF 95.1 YALI0E33891g (SEQ ID NO.: 57)

Nucleotide =
Atgaagtccacctccgctactctcctcgcccttgccgcccttgtcgttgccgacaacgccgtcgtctctc agatcaacgatggccagatccaggctcctcccgctggtggtgagggtgccaagcccgcccctgctccttc tggagctgcccccggtgccccggtgctggtgctcccggcgctggtgctcccggcgctggtgcccctggc gctggcgagggtgctaagccctctggagctgcccccggtgccccggcgctggtgctcccggtgctggtg agggtgctaagccttctggcggtgcccccggtgctggcgctcctggtgctggcgagggtgctaagccctc tggtggtgcccctggtgccccggcgctggtgctcccggtgctggtgagggtgctaagccctctggtggt gcccccggtgccccggcgctggtgagggtgccaagccctccggctctgctcccggtgctcctggcgctg gtgagggtgccaagccctccggctctgctcccggtgctcctggcgctggtgagggtgccaagccctctgg ctctgctcccggtgctcctggtgctggtgagggtgccaagccctctggctctgctcccggtgctcctgga gctggtgcaggtgctaagccctccgctggaggtgagcacccgctgctgaggccactggtgtcgtcactc agatccacgacggccagatccaggctcccgagcagacccagcccccgctgccggccctgcccaggctaa cggtgctgccaccctcggtgcccagatcgttgccggtgttgtcgccgctgccggtgtcgctctcttctaa RLF2 chromatin assembly complex subunit p90 YALI0F21637g (SEQ ID NO.: 58)

Nucleotide =
atggccgacaacaagcctctgtgcacgattaccacgcccgaaccgtcacccaagcgtcgaaagatctctg ccgaggagaaagaaaagatgcgacttgaaaaggaacagatcaagaagcagaaagaggaagagcgagagca gcttcgaagacagaaggaagaagagaaagagctactgagaaagcagaaagaggaggagaaggaacaactg aggaaacagaaggaggaggagaagagggctaaagaggaggagagagggctagagagagggagaaaacgac gacgagaagaggaacgaaagaaggctgccgaagagaaggagcttgagcgagccaagattgcagaggagaa ggctaagttggctgaagagaaggaggccaagagacttgaaaaagaagctgaactcaagaagaaggagcaa gaacagactcgaatcatgtctttctttaacaagaagaccaaaaagaagaccaagaaggaagctgttaaca gtgacaagtgtttggactttgataaagacttcctaccctt ccacatcaaagataccgtgtgtatggcaga caagacggagtgtgaagtgatggatcaggatcctgttgactggctcaacagtctcaacctttctgatgac agcaacaccgccgaagcagaagaaccacctgttcccgtcaaaaccatcattactcacatccagaccgctg ccactctgggtctcaatcctgataattacaacggtactcctttagacacgctggtcaatgctcttcctag acgatacttgcagttctatggtgacgagcgacccgcatacctgggcacgtactccaagagctgctcgcgt gatctgttgcagaaccctctcttccaggtgcctggtttggactacgagtacgacagtgaggcagactggg aagatgaaggagaagatattgaagatgatgaaattagtggagacgaggagatggaggacgacgaaatggc cgactttgtgtgttctgatgatgccaagagtcccagcaccatgacttcaaaggtcacgacagcccaggaa cctgttgttgtctggggctgctcagatatggttggtatgacttttggaggactgattgtccaggggcaa ttgacccattcaaagactattggactgttgcaaaagttgagcagaagaccgatactaagagtgacgtgac aatgactagtgcgacatcagcttctggtacagctattaaatctactacaaccaaaaccgaactcagcccg tttgaagtcctctccaaaactctgtcaccttccccagcggttgcttcagccacgaaacagtttctggctg ctgccaagcctcagaagctcattgctgggacgacctgactgctcttttgaagcgagtagatggatccga cgataacaagacgctgttgaccgagctgctttgtaagcagtatcccagtacacacgcaagatggtcacg -continued gccaccattcagcactatgctgagcgacagggtcctaagagcgacaagcggtgggttctgaaggatatct ag

TUP1 - YALI0A14542

(SEQ ID NO.: 59)
Nucleotide =
atgagcttcccccaacaagtaatagcgcgggccaacggctcaacgagcttctggaggccatcaaacagg agttcgactccgtgaccaacgaggcgtccgtctaccggctgcacaaggacgagtttgacgtcaaggtgaa ccagcagacgtcagatctgggccagattcgacagtcggtctacgagctagaaatggcgcaccgaaagatg aaggagcgctacgaggaggaaatcatgcggctcaagagcgagctggaggcccgaggtggacccgctgcga acccccgcacactcccagcagcagcaacagcagcaacagcaacagcagcaacagcagcagcagaaccagca ggcacaggaccaacaagcacgggccgcgcaacaacaggcagcccagcagcaggccctcgcccagcagcag gccgcccagcagcaggctctggcccaacagcaggcccaggctcaacagcaggcccaggcccaggcccacc acatgggtggtgtgcccccttcgcaaggacagccccgtcgctgctgcgtccatcatccaacgtgttcag cggcatcatgtccggtcagcccggcacctcttctctggctccccgcagggacagcccggtcagccccag cctggtcagcccaacctggtcaaccccagccctactccggctacgtgggtgctaacggctacacgtctt cgccacataacggaccccccgtcatcagcgcaatggcctcgcccaacagcaagaagcgacaggtgtcgac ccccgttcccggcaaggcgtctccccaggtggccccccaagagatgcaacagcagcagcaacagcagggc cctccacagcagcagcaacctccccagcagcagcaacagagccccgaagagatgggcaactacctgggcg acatggacattgagcgggtacctccggagctcaaaaaacaaaaggccgactggtttgtcgtttacaacca gcgagccaccggctgctggacgtggatattgtgcagtcgctggaccacaactctgtagtgtgctgtgtg cggttctccgctgacggcaagtacattgccactggctgtaaccgatctgcccagattttcgacgtgcaga ctggccagctcatctgccggctgcaggacgactcggtcgaccgagaaggcgacctgtacatccggtccgt gtgtttctcgccggacggtaagtacctggccaccggcgccgaggacaagcagatccgagtgtgggacatt aaatctcagagcatacggcacgtgttcactggccacgagcaggacatttactcgctggacttttcgcgaa acggccgacacattgcctctggctctggcgaccgcacagtccgaatgtgggatattgagagcggccagtg tactctaaccctgtcgatcgaggacggcgtcaccacggtggccatctcgcccgacggcaagtttgtggct gcaggcagcttggacaagtctgtgcgaatctgggacacctctaccggtttcctggttgagcgtctggagg cccctgatggacacaaggactccgtctatagtgtagctttcaccccaacggtatggatcttgtttccgg ctcgctggacaagacgatcaagctgtgggagctgcaggcctcgaggcattcaggccaaccagcgagga ggcgtctgcgtcaagacgctgtgtggacacaaggactttgttctgagtgtggccagcacgctggatgggc agtggattctttccggctccaaggaccggggtgtgcaattctgggaccctcgaacgggccaggtgcaact catgctgcagggtcatcgaaattcggtcatcagtgtggctcctagtcccatgggcgggttgtttgctact ggaagtggagattgcaaggctcgaatctggcgatactttcctgtcaacagataa (SEQ ID NO.: 60)
Amino Acid =
MSFPQQVIAPGQRLNELLEAIKQEFDSVTNEASVYRLHKDEFDVKVNQQTSDLGQIRQSVYELEMAHRKM

KERYEEEIMRLKSELEARGGPAANPAHSQQQQQQQQQQQQQQQQNQQAQDQQARAAQQQAAQQQALAQQQ

AAQQQALAQQQAQAQQQAQAQAHHMGGVPPSQGQPPSLLRPSSNVFSGIMSGQPGTSSLAPPQGQPGQPQ

PGQPQPGQPQPYSGYVGANGYTSSPHNGPPVISAMASPNSKKRQVSTPVPGKASPQVAPQEMQQQQQQQG

PPQQQQPPQQQQQSPEEMGNYLGDMDIERVPPELKKQKADWFVVYNQRAPRLLDVDIVQSLDHNSVVCCV

RFSADGKYTATGCNRSAQIFDVQTGQLICRLQDDSVDREGDLYIRSVCFSPDGKYLATGAEDKQIRVWDI

KSQSIRHVFTGHEQDIYSLDFSRNGRHIASGSGDRTVRMWDIESGQCTLTLSIEDGVTTVAISPDGKFVA

AGSLDKSVRIWDTSTGFLVERLEAPDGHKDSVYSVAFTPNGMDLVSGSLDKTIKLWELQAPRGIQANQRG

-continued

GVCVKTLCGHKDFVLSVASTLDGQWILSGSKDRGVQFWDPRTGQVQLMLQGHRNSVISVAPSPMGGLFAT

GSGDCKARIWRYFPVNR*

HAC1 - YALI0B12716

(SEQ ID NO.: 61)

Nucleotide =
atgtctatcaagcgagaagagtcctttactcccaccccgaggacctgggatctccctgacagctgatt ctcctggctctcccgagtctggagacaagcgaaagaaggatctcactctgccccttcctgctggtgctct tcccctcgaaagagagctaagacagagaacgaaaaggagcagagacgcatcgagcggatcatgcgaaac cggcaggcggcacatgcgtctcgagagaagaagcgacgacatttggaggacctggagaagaagtgctcgg agttgtcgtccgaaaacaacgatctacaccaccaggtgactgagtccaagaagaccaacatgcacctcat ggaacaacactactcgctggtggccaagctgcagcagctctcgtcgctcgtcaacatggccaagtcttcc ggagctttggccggcgttgatgtccccgacatgagcgatgtgtctatggcccccaagttggagatgccca ccgcggctccttcccagcccatgggtctcgccagcgcgcccaccctcttcaaccacgataatgagaccgt cgtccccgactctcctattgtgaagaccgaggaagtcgactctacaaactttctcctccacacggagtcc tcctccccccccgaactagctgagagcactggctcaggctcgccatcgtcgactctgtcctgcgacgaaa ctgattatcttgtggaccgggcgtcatccagcagtgatgactgtcgcaactactgaccagcagcgtcg gcacaagatttcattttcatcaaggacgagcccgttgacgacgagcttggactgcatggactgtcggatg acttcaccctgtttgaagacaacaagcagcctgcccagcacgactttattgctgatctag (SEQ ID NO.: 62)

Amino Acid =
MSIKREESFTPTPEDLGSPLTADSPGSPESGDKRKKDLTLPLPAGALPPRKRAKTENEKEQRRIERIMRN

RQAAHASREKKRRHLEDLEKKCSELSSENNDLHHQVTESKKTNMHLMEQHYSLVAKLQQLSSLVNMAKSS

GALAGVDVPDMSDVSMAPKLEMPTAAPSQPMGLASAPTLFNHDNETVVPDSPIVKTEEVDSTNFLLHTES

SSPPELAESTGSGSPSSTLSCDETDYLVDRARHPAVMTVATTDQQRRHKISFSSRTSPLTTSLDCMDCRM

TSPCLKTTSSLPSTTLLLI*

MRM2- YALI0E31933

(SEQ ID NO.: 63)

Nucleotide =
Atgcgccaaaagctgccgttcaacccgctccagtcgcttctcccgcgaatctttgtgcggggcaaaaaac acgatgcgcgcagccgctgggaaatgcgccagatgaaagacaagcatgtggccatggccaaggctgacgg attccggtctcgagccgcgtacaagctacaggaactcgactccatgttccggctgttcaagcccggcatg acggtggtggatttgggctttgcgcccggcgcatggagtcaagtggctgctcagcgagtgcggcctggag gcagagttattggagtggatatccttccttgcattcctcctccaggagtgtccagcatccagggaaattt cctgtccaaagaaacacaaaacgagctcaaacgtgtgctggccgtctcggcgatgggagttcccaaggac aaggactctggtggcgccataggcactgctcctccgtcttatctggacactgaacgcgagcttggcagta ttaacagcaacagcaacgaaccccaatttggcgacgactacccggtagatatagtgcttagtgacatgtg cgaaacgttaccccaggaacacggatttttttcaaagaactattaatgacccatactataggatggccaat gtttccggcatagctgtgagggaccatgctgccagtattgtgagtgaaggaaggaagcgcattgggtgtg gtgcagccagcttcgatgtggcagaagggaagccataa (SEQ ID NO.: 64)

Amino Acid =
MRQKLPFNPLQSLLPRIFVRGKKHDARSRWEMRQMKDKHVAMAKADGFRSRAAYKLQELDSMFRLFKPGM

TVVDLGFAPGAWSQVAAQRVRPGGRVIGVDILPCIPPPGVSSIQGNFLSKETQNELKRVLAVSAMGVPKD

KDSGGAIGTAPPSYLDTERELGSINSNSNEPQFGDDYPVDIVLSDMCETLPQEHGFFQRTINDPYYRMAN

VSGIAVRDHAASIVSEGRKRIGCGAASFDVAEGKP*

O6M- YALI0C10010p

-continued

Nucleotide = (SEQ ID NO.: 65)
atgttttacaccaagcccgacccggtggttgattattcccgcctcaaggacatggacatgtatcctgagt acgacaatggccagaacatgggcttttccaacatgaacatgaccgatctttacgacggcggtcttaacat gtcgtcgatggcgcaacccgtggcgttgaaccagatgggcagcatgggccccatgggctcttaagtaac atgcccatgggttttgtgtcccagaaccagcctcaaactcaggctcaggcccaggcccagagccagaacc agaatcagaaccagaaccagaaccagaaccagcctcagaatcacaacacccatgttatgagcgataacca caaccatacccacaccaacaatactcacaacaccaacgtcacccacaacaccccctccatgggtggtcac acaacctctgtcggggccacgacaccaatgactcggcccatgttggggtcacgccagcaatgtcacat ccccgaccccggcaacccctgcctccacatcttccgtacccgcaacctcgcctcagattcccttcacggt cgcgccacccgcaccgtcaggcaaatatgtgaccgatgacgagcgatggcaggcactggtcgaccgagac cccgaggctgacggcgccttcatctactgcgtcaccagcaccaaggtgtactgccggcccacgtgctcgg cccggctcgcgctgcggtccaacattgtgtattttgacaccatgaaggaggctgtggccgccggctaccg ccctgccgacggtgcaaccccgacgtgagcgagatgaactcgcagcgacgcgccgtgggctccgtgtgt aacctcatccactcgctggagcccgacaaggtgccacgtgtcaagaagctagccgagtccgtcggcctca cgctctggcactttcaccgtctcttcaagcggtacacgggcctcacgcctcgacagtacatcactgagtt ccacaagcgaaagcgccttgggctgccgcagttgcaagtcagcaaggtggtaaccaagaagagctatgag cgacagcagcgtcgccagggcagcaacggttccacgccccagcagtctcccaagtcggcgcctcttcgc cagccggcgaggtggaggccatcaagctcgagaccccgtcgaaaccgtccagccgctatactacgacag caacggcgtgactcacaacgctgccaacgtcggggctcacagctccaatgtcactcacaacactagccat gtcggaagcaacgcaacctccgccacgagctccattgccactcctctttccaacacaacgtcacccgaca cctcgacgccgcccaggactcggcatacatcattgcccacggttccaacgccagcaacgccgctcctgt ggttgctccggggcctgccaccggctctggcgacaactggatcaagacggagccctcgatggattttatg cctcggtacgagccgcggtacgaccagtctatctccattgacgcccccatgtttattcctgatggtaacg agtatcatcacaacggggagatgttgggtgacatgtgggggactctctaa Amino Acid = (SEQ ID NO.: 66)
MFYTKPDPVVDYSRLKDMDMYPEYDNGQNMGFSNMNMTDLYDGGLNMSSMAQPVALNQMGSMGPMGSLSN

MPMGFVSQNQPQTQAQAQSQNQNQNQNQNQPQNHNTHVMSDNHNHTHTNNTHNTNVTHNTPSMGGH

TTSVGGHDTNDSAHVGGHASNVTSPTPATPASTSSVPATSPQIPFTVAPPAPSGKYVTDDERWQALVDRD

PEADGAFIYCVTSTKVYCRPTCSARLALRSNIVYFDTMKEAVAAGYRPCRRCNPDVSEMNSQRRAVGSVC

NLIHSLEPDKVPRVKKLAESVGLTLWHFHRLFKRYTGLTPRQYITEFHKRKRLGLPQLQVSKVVTKKSYE

RQQRRQGSNGSTPQQSPQVGASSPAGEVEAIKLETPVETVQPLYYDSNGVTHNAANVGAHSSNVTHNTSH

VGSNATSATSSIATPLSNTTSPDTSTPAQDSAYIIAHGSNASNAAPVVAPGPATGSGDNWIKTEPSMDFM

PRYEPRYDQSISIDAPMFIPDGNEYHHNGEMLGDMWGTL*

CIT1 - YALI0E02684
Nucleotide = (SEQ ID NO.: 67)
atgatttctgctattcgtcccgccgttcgatcttccgttcgtgttgcccctatggccaacaccgccttcc gggcctactctacccaggatgtgagtatttcttttctttcatcaattggttgctgtgcgacggatttcgt tgcgtcagcctgattgcaacagccttaggccccatttttcgacctgttcttgcctcggcaaaagttttcc gaatgcatgtgacacgtcgaatgtggtgcttcaagcagcagcagcagcataaaatatggaatgtgttgt gtgcagaagtcgacattacataacccgcggcaaccatacgagatggcagtcataacaattgcaattgag caatacaaaccacactgcaacccactaaaaagaaacacgactaacaaatagggtcttaaggagcgattcg -continued

```
ccgagctcatccccgagaacgtcgagaagatcaagaagctccgaaaggagaagggtaacaccgtcatcgg cgaggtcatcctcgaccaggcttacggtggtatgcgaggtattaagggtctcgtctgggagggatccgtc ctcgaccccgaggagggtatccgattccgaggtctgactatccccgacctccagaagcagctcccccacg cccctggcggaaaggagcctctccccgagggtcttttctggctcctgctcaccggcgagatccccactga tgctcaggtcaagggtctgtccgctgactgggcctctcgagccgagatccccaagcatgttgaggagctc atcgaccgatgccccccaccctccacccatggctcagctcggtattgccgtcaacgctctggagtccg agtctcagttcaccaaggcttacgagaagggtgttaacaagaaggagtactggcagtacacctacgagga ttccatgaacctcattgccaagctccccgtcattgcttctcgaatctaccgaaacctttcaaggacgga aagattgttggctccattgacaactctcttgactactctgctaacttcgcctctctgctcggctttggcg acaacaaggagttcattgagcttctgcgactctacctcaccatccacgctgaccacgagggaggtaacgt ctctgcccacaccaccaagcttgttggttctgctctctcctctcccttcctctctctgtccgctggtctc aacggtcttgccggtcctctccacggccgagctaaccaggaggtccttgagtggattctcgagatgaagt ccaagattggctctgatgtcaccaaggaggacattgagaagtacctctgggatacccttaaggccggtcg agtcgtccccggttacggacacgccgttctccgaaagaccgatcctcgatacaccgcccagcgagagttc gccctcgagcacatgcccgactacgacctcttccacctcgtttccaccatctacgaggttgcccccaagg ttctcaccgagcacggcaagaccaagaacccctggcccaatgtggactcccactccggtgtcctcctcca gtactacggtctcactgagcagtcttactacactgttctcttcggtgtttcccgagctatcggtgtcctg ccccagctcatcatggaccgagcttacggtgctcccatcgagcgacccaagtccttctctaccgagaagt acgctgagctcgttggcctcaagctctaa
```

(SEQ ID NO.: 68)

Amino acid =
MISAIRPAVRSSVRVAPMANTAFRAYSTQDGLKERFAELIPENVEKIKKLRKEKGNTVIGEVILDQAYGG

MRGIKGLVWEGSVLDPEEGIRFRGLTIPDLQKQLPHAPGGKEPLPEGLFWLLLTGEIPTDAQVKGLSADW

ASRAEIPKHVEELIDRCPPTLHPMAQLGIAVNALESESQFTKAYEKGVNKKEYWQYTYEDSMNLIAKLPV

IASRIYRNLFKDGKIVGSIDNSLDYSANFASLLGFGDNKEFIELLRLYLTIHADHEGGNVSAHTTKLVGS

ALSSPFLSLSAGLNGLAGPLHGRANQEVLEWILEMKSKIGSDVTKEDIEKYLWDTLKAGRVVPGYGHAVL

RKTDPRYTAQREFALEHMPDYDLFHLVSTIYEVAPKVLTEHGKTKNPWPNVDSHSGVLLQYYGLTEQSYY

TVLFGVSRAIGVLPQLIMDRAYGAPIERPKSFSTEKYAELVGLKL*

ACC - YALI0C11407

(SEQ ID NO.: 69)
Nucleotide =
```
atgcgactgcaattgaggacactaacacgtcggtttttcaggtgagtaaacgacggtggccgtggccacg acagccgaggcgtcacgatgggccagacgagcacattctcgccgccacaacctcgccagcacaagaaact aacccagtatggcttcaggatcttcaacgccagatgtggctcccttggtggaccccaacattcacaaagg tctcgcctctcatttctttggactcaattctgtccacacagccaagccctcaaaagtcaaggagtttgtg gcttctcacggaggtcatacagttatcaacaaggtgagtatttgacgtttagactgtataacaggcggcc gcagtgcaacaacgaccaaaaagggtcgaaaagggtcgaaaacggacacaaaagctggaaaacaagagt gtaatacattcttacacgtccaattgttagacaaacacggctgttcggtcccaaaaccaccagtatcacc tattttccacttgtgtctcggatctgatcataatctgatctcaagatgaaatttacgccaccgacatgat attgtgattttcggattctccagaccgagcagattccagcaataccaccacttgcccaccttcagcggcc tctcggcgcgattcgccactttccccaacgagtgttactaacccaggtcctcatcgctaacaacggtatt gccgcagtaaaggagatccgttcagtacgaaaatgggcctacgagacctttggcgacgagcagcaatct cgttcaccgtcatggccaccccgaagatctcgctgccaacgccgactacattagaatggccgatcagta
```

-continued

```
cgtcgaggtgcccggaggaaccaacaacaacaactacgccaacgtcgagctgattgtcgacgtggctgag cgattcggcgtcgatgccgtgtgggccggatggggccatgccagtgaaaatcccctgctcccgagtcgc tagcggcctctccccgcaagattgtcttcatcggccctcccggagctgccatgagatctctgggagacaa aatttcttctaccattgtggcccagcacgcaaaggtcccgtgtatcccgtggtctggaaccggagtggac gaggttgtggttgacaagagcaccaacctcgtgtccgtgtccgaggaggtgtacaccaagggctgcacca ccggtcccaagcagggtctggagaaggctaagcagattggattcccgtgatgatcaaggcttccgaggg aggaggaggaaagggtattcgaaaggttgagcgagaggaggacttcgaggctgcttaccaccaggtcgag ggagagatcccggctcgcccatcttcattatgcagcttgcaggcaatgccggcatttggaggtgcagc ttctggctgatcagtacggcaacaatatttcactgtttggtcgagattgttcggttcagcgacggcatca aaagattattgaggaggctcctgtgactgtggctggccagcagaccttcactgccatggagaaggctgcc gtgcgactcggtaagcttgtcggatatgtctctgcaggtaccgttgaatatctgtattcccatgaggacg acaagttctacttcttggagctgaatcctcgtcttcaggtcgaacatcctaccaccgagatggtcaccgg tgtcaacctgcccgctgcccagcttcagatcgccatgggtatcccctcgatcgaatcaaggacattcgt ctcttttacggtgttaaccctcacaccaccactccaattgatttcgacttctcgggcgaggatgctgata agacacagcgacgtcccgtcccccgaggtcacaccactgcttgccgaatcacatccgaggacctggaga gggtttcaagccctccggaggtactatgcacgagctcaacttccgatcctcgtccaacgtgtggggttac ttctccgttggtaaccaggagagtatccattcgttctcggattcgcagtttggtcacatcttcgccttcg gtgagaaccgaagtgcgtctcgaaagcacatggttgttgctttgaaggaactatctattcgaggtgactt ccgaaccaccgtcgagtacctcatcaagctgctggagacaccggacttcgaggacaacaccatcaccacc ggctggctggatgagcttatctccaacaagctgactgccgagcgacccgactcgttcctcgctgttgttt gtggtgctgctaccaaggcccatcgagcttccgaggactctattgccacctacatggcttcgctagagaa gggccaggtccctgctcgagacattctcaagaccttttccccgttgacttcatctacgagggccagcgg tacaagttcaccgccacccggtcgtctgaggactcttacacgctgttcatcaacggttctcgatgcgaca ttggagttagacctctttctgacggtggtattctgtgtcttgtaggtgggagatcccacaatgtctactg gaaggaggaggttggagccacgcgactgtctgttgactccaagacctgccttctcgaggtggagaacgac cccactcagcttcgatctccctctcccggtaagctggttaagttcctggtcgagaacggcgaccacgtgc gagccaaccagcccatgccgagattgaggtcatgaagatgtacatgactctcactgctcaggaggacgg tattgtccagctgatgaagcagcccggttccaccatcgaggctggcgacatcctcggtatcttggccctt gatgatccttccaaggtcaagcatgccaagcccttgagggccagcttcccgagcttggacccccactc tcagcggtaacaagcctcatcagcgatacgagcactgccagaacgtgctccataacattctgcttggttt cgataaccaggtggtgatgaagtccactcttcaggagatggttggtctgctccgaaaccctgagcttcct tatctccagtgggctcatcaggtgtcttctctgcacacccgaatgagcgccaagctggatgctactcttg ctggtctcattgacaaggccaagcagcgaggtggcgagtttcctgccaagcagcttctgcgagcccttga gaaggaggcgagctctggcgaggtcgatgcgctcttccagcaaactcttgctcctctgtttgaccttgct cgagagtaccaggacggtcttgctatccacgagcttcaggttgctgcaggccttctgcaggcctactacg actctgaggcccggttctgcggacccaacgtacgtgacgaggatgtcattctcaagcttcgagaggagaa ccgagattctcttcgaaaggttgtgatggcccagctgtctcattctcgagtcggagccaagaacaacctt gtgctggcccttctcgatgaatacaaggtggccgaccaggctggcaccgactctcctgcctccaacgtgc acgttgcaaagtacttgcgacctgtgctgcgaaagattgtggagctggaatctcgagcttctgccaaggt atctctgaaagcccgagagattctcatccagtgcgctctgccctctctaaaggagcgaactgaccagctt gagcacattctgcgatcttctgtcgtcgagtctcgatacggagaggttggtctggagcaccgaactcccc
```

-continued

```
gagccgatattctcaaggaggttgtcgactccaagtacattgtctttgatgtgcttgcccagttctttgc ccacgatgatccctggatcgtccttgctgccctggagctgtacatccgacgagcttgcaaggcctactcc atcctggacatcaactaccaccaggactcggacctgcctcccgtcatctcgtggcgatttagactgccta ccatgtcgtctgctttgtacaactcagtagtgtcttctggctccaaaaccccacttccccctcggtgtc tcgagctgattccgtctccgacttttcgtacaccgttgagcgagactctgctcccgctcgaaccggagcg attgttgccgtgcctcatctggatgatctggaggatgctctgactcgtgttctggagaacctgcccaaac ggggcgctggtcttgccatctctgttggtgctagcaacaagagtgccgctgcttctgctcgtgacgctgc tgctgctgccgcttcatccgttgacactggcctgtccaacatttgcaacgttatgattggtcgggttgat gagtctgatgacgacgacactctgattgcccgaatctcccaggtcattgaggactttaaggaggactttg aggcctgttctctgcgacgaatcaccttctccttcggcaactcccgaggtacttatcccaagtatttcac gttccgaggccccgcatacgaggaggaccccactatccgacacattgagcctgctctggccttccagctg gagctcgcccgtctgtccaacttcgacatcaagcctgtccacaccgacaaccgaaacatccacgtgtacg aggctactggcaagaacgctgcttccgacaagcggttcttcacccgaggtatcgtacgacctggtcgtct tcgagagaacatccccacctcggagtatctcatttccgaggctgaccggctcatgagcgatattttggac gctctagaggtgattggaaccaccaactcggatctcaaccacattttcatcaacttctcagccgtctttg ctctgaagcccgaggaggttgaagctgcctttggcggtttcctggagcgatttggccgacgtctgtggcg acttcgagtcaccggtgccgagatccgaatgatggtatccgaccccgaaactggctctgctttccctctg cgagcaatgatcaacaacgtctctggttacgttgtgcagtctgagctgtacgctgaggccaagaacgaca agggccagtggattttcaagtctctgggcaagcccggctccatgcacatgcggtctatcaacactcccta ccccaccaaggagtggctgcagcccaagcggtacaaggcccatctgatgggtaccacctactgctatgac ttccccgagctgttccgacagtccattgagtcggactggaagaagtatgacggcaaggctcccgacgatc tcatgacttgcaacgagctgattctcgatgaggactctggcgagctgcaggaggtgaaccgagagcccgg cgccaacaacgtcggtatggttgcgtggaagtttgaggccaagaccccgagtaccctcgaggccgatct ttcatcgtggtggccaacgatatcaccttccagattggttcgtttggccctgctgaggaccagttcttct tcaaggtgacggagctggctcgaaagctcggtattcctcgaatctatctgtctgccaactctggtgctcg aatcggcattgctgacgagctcgttggcaagtacaaggttgcgtggaacgacgagactgacccctccaag ggcttcaagtacctttacttcacccctgagtctcttgccaccctcaagcccgacactgttgtcaccactg agattgaggaggagggtcccaacggcgtggagaagcgtcatgtgatcgactacattgtcggagagaagga cggtctcggagtcgagtgtctgcggggctctggtctcattgcaggcgccacttctcgagcctacaaggat atcttcactctcactcttgtcacctgtcgatccgttggtatcggtgcttaccttgttcgtcttggtcaac gagccatccagattgagggccagcccatcattctcactggtgcccccgccatcaacaagctgcttggtcg agaggtctactcttccaacttgcagcttggtggtactcagatcatgtacaacaacggtgtgtctcatctg actgcccgagatgatctcaacggtgtccacaagatcatgcagtggctgtcatacatccctgcttctcgag gtcttccagtgcctgttctccctcacaagaccgatgtgtgggatcgagacgtgacgttccagcctgtccg aggcgagcagtacgatgttagatggcttatttctggccgaactctcgaggatggtgctttcgagtctggt ctctttgacaaggactctttccaggagactctgtctggctgggccaagggtgttgttgttggtcgagctc gtcttggcggcattcccttcggtgtcattggtgtcgagactgcgaccgtcgacaatactaccctgccga tcccgccaacccggactctattgagatgagcacctctgaagccggccaggtttggtaccccaactcggcc ttcaagacctctcaggccatcaacgacttcaaccatggtgaggcgcttcctctcatgattcttgctaact ggcgaggcttttctggtggtcagcgagacatgtacaatgaggttctcaagtacggatctttcattgttga
```

-continued

```
tgctctggttgactacaagcagcccatcatggtgtacatccctcccaccggtgagctgcgaggtggttct tgggttgtggttgaccccaccatcaactcggacatgatggagatgtacgctgacgtcgagtctcgaggtg gtgtgctggagcccgagggaatggtcggtatcaagtaccgacgagacaagctactggacaccatggctcg tctggatcccgagtactcctctctcaagaagcagcttgaggagtctcccgattctgaggagctcaaggtc aagctcagcgtgcgagagaagtctctcatgcccatctaccagcagatctccgtgcagtttgccgacttgc atgaccgagctggccgaatggaggccaagggtgtcattcgtgaggctcttgtgtggaaggatgctcgtcg attcttcttctggcgaatccgacgacgattagtcgaggagtacctcattaccaagatcaatagcattctg ccctcttgcactcggcttgagtgtctggctcgaatcaagtcgtggaagcctgccactcttgatcagggct ctgaccgggtgttgccgagtggtttgacgagaactctgatgccgtctctgctcgactcagcgagctcaa gaaggacgcttctgcccagtcgtttgcttctcaactgagaaaggaccgacagggtactctccagggcatg aagcaggctctcgcttctctttctgaggctgagcgggctgagctgctcaaggggttgtga
```

(SEQ ID NO.: 70)

Amino Acid =
MRLQLRTLTRRFFSMASGSSTPDVAPLVDPNIHKGLASHFFGLNSVHTAKPSKVKEFVASHGGHTVINKV

LIANNGIAAVKEIRSVRKWAYETFGDERAISFTVMATPEDLAANADYIRMADQYVEVPGGTNNNNYANVE

LIVDVAERFGVDAVWAGWGHASENPLLPESLAASPRKIVFIGPPGAAMRSLGDKISSTIVAQHAKVPCIP

WSGTGVDEVVVDKSTNLVSVSEEVYTKGCTTGPKQGLEKAKQIGFPVMIKASEGGGGKGIRKVEREEDFE

AAYHQVEGEIPGSPIFIMQLAGNARHLEVQLLADQYGNNISLFGRDCSVQRRHQKIIEEAPVTVAGQQTF

TAMEKAAVRLGKLVGYVSAGTVEYLYSHEDDKFYFLELNPRLQVEHPTTEMVTGVNLPAAQLQIAMGIPL

DRIKDIRLFYGVNPHTTTPIDFDFSGEDADKTQRRPVPRGHTTACRITSEDPGEGFKPSGGTMHELNFRS

SSNVWGYFSVGNQGGIHSFSDSQFGHIFAFGENRSASRKHMVVALKELSIRGDFRTTVEYLIKLLETPDF

EDNTITTGWLDELISNKLTAERPDSFLAVVCGAATKAHRASEDSIATYMASLEKGQVPARDILKTLFPVD

FIYEGQRYKFTATRSSEDSYTLFINGSRCDIGVRPLSDGGILCLVGGRSHNVYWKEEVGATRLSVDSKTC

LLEVENDPTQLRSPSPGKLVKFLVENGDHVRANQPYAEIEVMKMYMTLTAQEDGIVQLMKQPGSTIEAGD

ILGILALDDPSKVKHAKPFEGQLPELGPPTLSGNKPHQRYEHCQNVLHNILLGFDNQVVMKSTLQEMVGL

LRNPELPYLQWAHQVSSLHTRMSAKLDATLAGLIDKAKQRGGEFPAKQLLRALEKEASSGEVDALFQQTL

APLFDLAREYQDGLAIHELQVAAGLLQAYYDSEARFCGPNVRDEDVILKLREENRDSLRKVVMAQLSHSR

VGAKNNLVLALLDEYKVADQAGTDSPASNVHVAKYLRPVLRKIVELESRASAKVSLKAREILIQCALPSL

KERTDQLEHILRSSVVESRYGEVGLEHRTPRADILKEVVDSKYIVFDVLAQFFAHDDPWIVLAALELYIR

RACKAYSILDINYHQDSDLPPVISWRFRLPTMSSALYNSVVSSGSKTPTSPSVSRADSVSDFSYTVERDS

APARTGAIVAVPHLDDLEDALTRVLENLPKRGAGLAISVGASNKSAAASARDAAAAASSVDTGLSNICN

VMIGRVDESDDDDTLIARISQVIEDFKEDFEACSLRRITFSFGNSRGTYPKYFTFRGPAYEEDPTIRHIE

PALAFQLELARLSNFDIKPVHTDNRNIHVYEATGKNAASDKRFFTRGIVRPGRLRENIPTSEYLISEADR

LMSDILDALEVIGTTNSDLNHIFINFSAVFALKPEEVEAAFGGFLERFGRRLWRLRVTGAEIRMMVSDPE

TGSAFPLRAMINNVSGYVVQSELYAEAKNDKGQWIFKSLGKPGSMHMRSINTPYPTKEWLQPKRYKAHLM

GTTYCYDFPELFRQSIESDWKKYDGKAPDDLMTCNELILDEDSGELQEVNREPGANNVGMVAWKFEAKTP

EYPRGRSFIVVANDITFQIGSFGPAEDQFFFKVTELARKLGIPRIYLSANSGARIGIADELVGKYKVAWN

DETDPSKGFKYLYFTPESLATLKPDTVVTTEIEEEGPNGVEKRHVIDYIVGEKDGLGVECLRGSGLIAGA

TSRAYKDIFTLTLVTCRSVGIGAYLVRLGQRAIQIEGQPIILTGAPAINKLLGREVYSSNLQLGGTQIMY

NNGVSHLTARDDLNGVHKIMQWLSYIPASRGLPVPVLPHKTDVWDRDVTFQPVRGEQYDVRWLISGRTLE

DGAFESGLFDKDSFQETLSGWAKGVVVGRARLGGIPFGVIGVETATVDNTTPADPANPDSIEMSTSEAGQ

VWYPNSAFKTSQAINDFNHGEALPLMILANWRGFSGGQRDMYNEVLKYGSFIVDALVDYKQPIMVYIPPT

GELRGGSWVVVDPTINSDMMEMYADVESRGGVLEPEGMVGIKYRRDKLLDTMARLDPEYSSLKKQLEESP

DSEELKVKLSVREKSLMPIYQQISVQFADLHDRAGRMEAKGVIREALVWKDARRFFFWRIRRRLVEEYLI

TKINSILPSCTRLECLARIKSWKPATLDQGSDRGVAEWFDENSDAVSARLSELKKDASAQSFASQLRKDR

QGTLQGMKQALASLSEAERAELLKGL*

Knockouts:
PEX10 - YALI0C01023g (SEQ ID NO.: 71)

Nucleotide =
atgtggggaagttcacatgcattcgctggtgaatctgatctgacactacaactacacaccaggtccaaca tgagcgacaatacgacaatcaaaaagccgatccgacccaaaccgatccggacggaacgcctgccttacgc tggggccgcagaaatcatccgagccaaccagaagaccactactttgagtccgtgcttgaacagcatctc gtcacgtttctgcagaaatggaagggagtacgatttatccaccagtacaaggaggagctggagacggcgt ccaagtttgcatatctcggtttgtgtacgcttgtgggctccaagactctcggagaagagtacaccaatct catgtacactatcagagaccgaacagctctaccggggtggtgagacggtttggctacgtgctttccaac actctgtttccatacctgtttgtgcgctacatgggcaagttgcgcgccaaactgatgcgcgagtatcccc atctggtggagtacgacgaagatgagcctgtgcccagcccggaaacatggaaggagcgggtcatcaagac gtttgtgaacaagtttgacaagttcacggcgctggaggggtttaccgcgatccacttggcgattttctac gtctacggctcgtactaccagctcagtaagcggatctggggcatgcgttatgtatttggacaccgactgg acaagaatgagcctcgaatcggttacgagatgctcggtctgctgattttcgcccggtttgccacgtcatt tgtgcagacgggaagagagtacctcggagcgctgctggaaaagagcgtggagaaagaggcaggggagaag gaagatgaaaaggaagcggttgtgccgaaaaagaagtcgtcaattccgttcattgaggatacagaagggg agacggaagacaagatcgatctggaggaccctcgacagctcaagttcattcctgaggcgtccagagcgtg cactctgtgtctgtcatacattagtgcgccggcatgtacgccatgtggacactttttctgttgggactgt atttccgaatgggtgagagagaagcccgagtgtcccttgtgtcggcagggtgtgagagagcagaacttgt tgcctatcagataa (SEQ ID NO.: 72)

Amino acid =
MWGSSHAFAGESDLTLQLHTRSNMSDNTTIKKPIRPKPIRTERLPYAGAAEIIRANQKDHYFESVLEQHL

VTFLQKWKGVRFIHQYKEELETASKFAYLGLCTLVGSKTLGEEYTNLMYTIRDRTALPGVVRRFGYVLSN

TLFPYLFVRYMGKLRAKLMREYPHLVEYDEDEPVPSPETWKERVIKTFVNKFDKFTALEGFTAIHLAIFY

VYGSYYQLSKRIWGMRYVFGHRLDKNEPRIGYEMLGLLIFARFATSFVQTGREYLGALLEKSVEKEAGEK

EDEKEAVVPKKKSSIPFIEDTEGETEDKIDLEDPRQLKFIPEASRACTLCLSYISAPACTPCGHFFCWDC

ISEWVREKPECPLCRQGVREQNLLPIR*

MFE1 - YALI0E15378

(SEQ ID NO.: 73)

Nucleotide =
atgaccgacaaggactgggatcttgtctacaaggtccacgttttcggtgcctacaaggttacccgagctg cctggccttacttccgaaagcagaagtacggtcgagttatctctacctcttccgctgctggtctttacgg aaacttcggccagaccaactactccgctgccaagctcgccctggttggtttcggtgagactctcgccaag gagggtgccaagtacaacattacttccaacgtcatcgctcctcttgctgcttcccgaatgaccgagacag tcatgcccgaggatatcctcaagctcctcaagcctgagtacgttgttcctctggtcggctacctcaccca cgactctgtcaccgagtcttatggtatttacgaggtcggtgctggttacatggctaaaatccgatgggag cgaggcaacggtgctgttttcaagggcgacgacactttcaccccgtctgctattctgaagcgatgggatg aggtcacctcttttgagagccccacctaccctaacggccctgctgacttcttcaaatacgctgaggagtc tgttaagcgacccgagaaccccagggacccaccgtctcccttcaaggaccaggttgtcattgtcactgga -continued

```
gccggtgctggcattggccgagcttactctcacctccttgctaagcttggtgccaaggtcgttgttaacg atttcggtaaccctcagaaggttgtcgatgaaattaaggccctcggtggtatcgccgtcgctgacaagaa caacgtcatccacggtgagaaggttgttcagaccgctatcgacgccttcggtgctgtccacgccgttgtc aacaacgctggtattctccgagacaagtctttcgccaacatggatgatgagatgtggcagctgatctttg atgtccacctcaacggtacttactccgttaccaaggccgcgtggccccacttccttaagcagaagtacgg ccgtgtcatcaacacccctcaacttctggtatctacggtaacttcggccaggccaactactctgccgcc aaggctggtatcctcggtttctcccgagctcttgctcgagagggtgagaagtacaacattcttgtcaaca ccattgcccctaacgctggtactgccatgactgcttctgtcttcactgaggagatgctcgagctcttcaa gcccgatttcatcgcacccatcaccgtcctgcttgcttccgatcaggctcccgtcaccggtgatctgttt gagactggttctgcttggatcggacagactcgatggcagcgagctggtggtaaggccttcaacaccaaga agggtgtcaccccgaaatggttcgagacagctgggctaagatcgtcgacttcgatgatggtaactccac ccatcccaccactccctccgagtctactactcagattcttgagaacatcttcaacgtgcctgatgaggag gttgaggagactgctctcgttgctggtcccggtggtcccggtatcctcaacaaggagggcgaacctttcg actacacttacacttaccgagacctcattctttacaaccttggtctcggtgccaaggctaatgagctcaa gtatgtcttcgagggtgatgatgacttccagaccgtgcccactttcggtgttatcccttacatgggtggc ctcatcactaccaactatggcgacttcgttcctaacttcaaccctatgatgcttctccacggtgagcagt accttgaaatccgacagtggcctattcctaccaatgctacattggagaacaaggctaaggtcatcgatgt cgttgacaagggcaaggctgccctccttgtcactgctaccaccaccacgaacaaggagactggtgaggag gttttctacaacgagtcttctctcttcatccgaggctctggtggtttcggtggtaagtctaccggtactg accgtggcgctgccactgctgccaacaagccccctgctcgagctcctgacttcgttaaggagatcaagat ccaggaggaccaggctgccatttaccgactttctggtgattacaaccctcttcacatcgaccctgctttt gctgctgttggtaactttgaccgacctattctccacggtctctgctcttttggtgtctccggtaaggctc tttacgatcagtttggtccttttcaagaacgctaaggtccgatttgctggtcacgtcttccctggtgagac cctgaaggttgagggctggaaggagggcaacaaggtcattttccagaccaaggttgttgagcgaggtact accgccatcagcaatgccgccattgagctcttccccaaggatgctaagctctaa
```
(SEQ ID NO.: 74)

Amino Acid =
MTDKDWDLVYKVHVFGAYKVTRAAWPYFRKQKYGRVISTSSAAGLYGNFGQTNYSAAKLALVGFGETLAK

EGAKYNITSNVIAPLAASRMTETVMPEDILKLLKPEYVVPLVGYLTHDSVTESYGIYEVGAGYMAKIRWE

RGNGAVFKGDDTFTPSAILKRWDEVTSFESPTYPNGPADFFKYAEESVKRPENPQGPTVSFKDQVVIVTG

AGAGIGRAYSHLLAKLGAKVVVNDFGNPQKVVDEIKALGGIAVADKNNVIHGEKVVQTAIDAFGAVHAVV

NNAGILRDKSFANMDDEMWQLIFDVHLNGTYSVTKAAWPHFLKQKYGRVINTTSTSGIYGNFGQANYSAA

KAGILGFSRALAREGEKYNILVNTIAPNAGTAMTASVFTEEMLELFKPDFIAPITVLLASDQAPVTGDLF

ETGSAWIGQTRWQRAGGKAFNTKKGVTPEMVRDSWAKIVDFDDGNSTHPTTPSESTTQILENIFNVPDEE

VEETALVAGPGGPGILNKEGEPFDYTYTYRDLILYNLGLGAKANELKYVFEGDDDFQTVPTFGVIPYMGG

LITTNYGDFVPNFNPMMLLHGEQYLEIRQWPIPTNATLENKAKVIDVVDKGKAALLVTATTTTNKETGEE

VFYNESSLFIRGSGGFGGKSTGTDRGAATAANKPPARAPDFVKEIKIQEDQAAIYRLSGDYNPLHIDPAF

AAVGNFDRPILHGLCSFGVSGKALYDQFGPFKNAKVRFAGHVFPGETLKVEGWKEGNKVIFQTKVVERGT

TAISNAAIELFPKDAKL*

ACO1- YALI0D09361

(SEQ ID NO.: 75)

Nucleotide =
atgctggcttctcgagtttccatcaaggctgtgagtatcgatggtgaagaaagacaccgacaatcgccac -continued

```
gttgtgccacagacacagacgcgtttctacacacacacacaagagtcgacgtgtggtttagccgaggt
atttcgacaggaggaaaaacgacaacgaaaggaccgacagataccaaagcaacccaatcaccacctcaa
tcaatgatccccgcccgcgggaatgcggaaaaggcttctgcgacattacaacaaagccaactctgttgat
ttgttgtttgcgacattggctttgtgccggtcccaaaattacctcgaccaaccacacggcggcaattgaa
gacaatgcaaattaaatagcacatactaacccagccccgccttgcacgatctctcgcgactaccactaat
gcctccctcaacttggactccaaggtccgaatgaacaactgggaggccaacaacttcctcaacttcaaga
agcacaccgagaacgtccagattgtcaaggagcgactcaaccgacccctgacctacgctgagaagattct
ctacggccatctcgacaagccccatgagcaggagattgtccgaggtcagtcctacctcaagctgcgaccc
gatcgagccgcctgccaggatgccaccgcccagatggccattctgcagttcatgtctgccggtatcccca
ccgtccagaccccaccaccgtccactgtgaccatcttatccaggcccaggttggtggtgagcaggatct
tgctcgagccatcgacatcaacaaggaggtctacaacttccttggcaccgcctccgccaagtacgacatt
ggtttctggaaggccggatccggtattatccaccagatcattctcgagaactacgccttccccggtgccc
ttctcattggttccgactctcatacccccaacgccggtggtctcggtatgctcgccatcggtgtcggtgg
tgccgatgtcgtcgacgtcatggccggtctcccctgggagcttaaggcccccaagattatcggtgtcaag
ctgaccggtaagctctctggctggacctcccccaaggatattatcctgaaggtcgctggtatcctcaccg
tcaagggtggaaccggtgctatcgtcgagtacttcggtgatggtgtcgataacctgtcctgcactggtat
gggaaccatctgtaacatgggtgccgagattggtgctaccacctccaccttcccctttcaacgagcgaatg
gccgactaccttaacgccactggccgaaaggagattgccgactttgctcgactttacaaccacttcctct
ctgccgatgagggttgtgagtacgatcagctcatcgagattgacctgaacacccttgagccttacgtcaa
cggtcccttcactcccgatcttgccacccccatctccaagctcaaggatgtcgccgtcgagaacggatgg
ccccttgaggtcaaggtcggtcttatcggtcttgcaccaactcctcttacgaggatatggagcgatccg
cctccattgccaaggacgccatggcccacggtcttaagtccaagtccatctacaccgtcaccccggttc
cgagcagatccgagccaccattgagcgagatggtcagctccagaccttcctcgacttcggtggtatcgtc
cttgctaacgcttgtggcccctgcattggtcagtgggaccgacgagacatcaagaagggtgagaagaaca
ccattgtctcttcttacaaccgaaacttcactggccgaaacgattctaaccctgccacccacgctttcgt
cacctctcccgatctcgtcaccgcttttcgccattgctggtgacctccgattcaaccctctcactgactcc
ctgaaggattctgagggtaaggagttcaagctcaaggagcccactggaaagggtctgcccgaccgaggtt
acgaccccggcatggacacctaccaggctccccccgccgaccgatctgccgtcgaggttgatgtttcccc
cacttccgaccgactccagatcctcaagcccttcaagccttgggacggcaaggacggtattgacatgccc
atcctcatcaagtctcttggtaagaccaccactgaccatatctctcaggccggtccctggcttaagtacc
gaggccatctccagaacatctccaacaactacatgattggagccatcaacgctgagaacgaggaggccaa
caacgtccgaaaccagatcactggcgagtggggaggagttcccgagactgccattgcttaccgagacaac
ggtatccgatgggttgttgtcggaggtgataacttcggtgagggttcttctcgagagcacgctgctcttg
agccccgattcctcggtggtttcgccatcatcaccaagtcttttgcccgaattcacgagactaacctgaa
gaagcagggtctcctgccccttaacttcgtcaacggtgctgactacgacaagatccagccctccgataag
atctccattcttggtcttaaggaccttgcccccggcaagaacgtcaccattgaggttaccccaaggacg
gtgccaagtggaccaccgaggtttctcacacctacaactctgagcagctcgagtggttcaagtacggctc
tgccctcaacaagatggctgcctccaagaaataa
```

(SEQ ID NO.: 76)

Amino Acid =
MLASRVSIKAPRLARSLATTTNASLNLDSKVRMNNWEANNFLNFKKHTENVQIVKERLNRPLTYAEKILY -continued

GHLDKPHEQEIVRGQSYLKLRPDRAACQDATAQMAILQFMSAGIPTVQTPTTVHCDHLIQAVGGEQDLA

RAIDINKEVYNFLGTASAKYDIGFWKAGSGIIHQIILENYAFPGALLIGSDSHTPNAGGLGMLAIGVGGA

DVVDVMAGLPWELKAPKIIGVKLTGKLSGWTSPKDIILKVAGILTVKGGTGAIVEYFGDGVDNLSCTGMG

TICNMGAEIGATTSTFPFNERMADYLNATGRKEIADFARLYNHFLSADEGCEYDQLIEIDLNTLEPYVNG

PFTPDLATPISKLKDVAVENGWPLEVKVGLIGSCTNSSYEDMERSASIAKDAMAHGLKSKSIYTVTPGSE

QIRATIERDGQLQTFLDFGGIVLANACGPCIGQWDRRDIKKGEKNTIVSSYNRNFTGRNDSNPATHAFVT

SPDLVTAFAIAGDLRFNPLTDSLKDSEGKEFKLKEPTGKGLPDRGYDPGMDTYQAPPADRSAVEVDVSPT

SDRLQILKPFKPWDGKDGIDMPILIKSLGKTTTDHISQAGPWLKYRGHLQNISNNYMIGAINAENEEANN

VRNQITGEWGGVPETAIAYRDNGIRWVVVGGDNFGEGSSREHAALEPRFLGGFAIITKSFARIHETNLKK

QGLLPLNFVNGADYDKIQPSDKISILGLKDLAPGKNVTIEVTPKDGAKWTTEVSHTYNSEQLEWFKYGSA

LNKMAASKK*

YLYOX1 YALI0E20449g (SEQ ID NO.: 77)

Nucleotide =
atggatctggcgaaaatcaccgacggcttcgtcaagcacgagacctcgtcgtcgtcctcttcttgctcca ccaccaacacagggcccaccccagacttgtctccagtgacgccctccaaggaatgtgagaagcggccacg agaggacgaccctgaagagtcgcacgacacgagcgccggcgccaacagcaacaacaacgctagcgtgtct ctcatgtccaccccagagcccaagtcgtcgtctcccccggactgtcgcatttcgcacacctgatgcaaa agtcggacaccatgtaccgacagaacctcaactcggaccagtacatctactcggacgaggagaaggagaa ccacaagacttcgggcaagccccacaccccccaggtgcctcatacgccctccagtgtgccgacacaacaa ccccaatatgcatttatttcacattccatcacctcgtacccgtcgaacgagcctcagattgacaacgcac ggctggcgcgccgaaaacgacgccgaacgtctcccacggaactcgcgctgctggagcaggagtttgcccg caaccagaagcctcccaagcacattcgcgtcgacattgcccgccgagtcgacatgactgaaaaggctgtg caggtgtggttccagaacaagcggcagagcgtgcgaaagagcatgaacaagagcatgaccgatgacacct ctttcgccgactcttcgttcgctgaaactacctttgacgagacagacggtaactccacattcctgtccaa ttccaacgtcagcaccagcgtaagcaacaagtcaatcacttcttccatcacagacaacaagtcgcccctg gcacagtcaaccaccgccgactctggtgccaacgccaacgccaacgccaacgccaacaacaaca ccgcatccacttcctccacaaacgactccgaaattgcatccgtcgccccaaaacaaacggcagctcatt ctctgttttcgaagataccccgagactcccgcgaaaagaaacccagtgctccgcgactgtccatgcgt ggtgggaaggctactgttatctacgccggcaagcccaagggtgtcacgctgtcctcgggaagacgtcttg gggtccctgccacaccctcctctcccgccaacaacaatcttggcctgggaggctcgcctctggccacatc gtctcctatgacccagcggaccgcgtcgcaactgaaccaggcatctgcatcttctcccctatcggctgtt aagtccaagtcttttggaactgccgaggaaagcctggctgcgacgctcaagaagcggcttccgtccatgc actacgacctgcccgtgaccaacaagacgtcgtctgtgcgccatggcgtgagctctcccgtggtcgacgc cggcagccgtgaggccgagtgtatttccaatctcctctctcttcgaaacggaggacgatggtaa YLUGA2 YALI0F26191g (SEQ ID NO.: 78)

Nucleotide =
atgttgcgagccctgaataccgtccagcgactttccagcacccgagccatgtccacctcttccatttcgt ctctgcttaagaaccccaatcttctgcgaaaccagggctatgtcaatggtcagtgggtctcctccaagac cggagacactttcagcgttgagaacccagccactggcgagactctgggccaggtgcccgagttctctgtc gccgaggccgatgaggctgtccagcacgcacagactgccttcaagaccttcaaacataccactggacgag agcgatccaagatgctgcgaaagtggtacgatctgatgcaggagaatgctggtgatctggccaccctggt gactctggagaacggtaagtccctcgctgacgccaagggcgagattggctacggagcatctttcttcgag -continued tggttctccgaggaagctcctcgaatctacggagacatcattccatccgccaaccccgccaaccgaatct acacaatcaagcagcccatcggagtctgcggaatcatcacccctggaacttcccctcggccatgatcac ccgaaaggctgctgctgctgttgctgctggctgtaccatggtgatcaagcctggttccgaaacctcctac tctgcccttgctctggcttacctggctgaacaggccggcatccctaagggtgttgtcaacgtggtcacta ctaagaagaacactcgagcttttggtaacgccctgtgcgagaacccgaccgtcaaaaaggtttctttcac gggctccactggtgtcggaaagacccctatgggcgcatcggcctccactcttaagaagctgtcctttgag ctcggtggcaacgctcccttcattgtgtttgaggacgccgatattgaccgggctgtcgacggagctattg cgtccaagttccgaggcactggccagacctgtgtctgtgcaaaccgaatttatgtgcacgagagcatcgc cgagaagtttgctgagcgaatggcagccgtggtcaaggacttcaaggttggaaacggtctcgaccctaac accacccatggccctcttatccacgagggagccaagggcaagatccaggagcaggttgacgatgctgtca agaagggaggaaaggtactcattggaggctccgacgcccctgagatcggaaaggcctttttccagcctac cgtcatttccggggccaagtctgatatgctgattgcctccgaggagacgtttggtcccattgctgccatc ttcccctttaagaccgacgctgaggtcattgagcttgccaacaaggcagaggtcggtctggccggctact tctactccaaggacgtgtaccgaatccaacaggttgccgaggctctcgaggtcggaatggtcggtgttaa caccggtctgatgacggagtgtgctctgccctttggcggtatcaaggagtctggctttggccgagagggc tccaagtacggcctggatgactacatggtgctcaagactattgttgtgtctggcgtcgagccccacattc agccttaa YLRME1 YALI0E17215g
(SEQ ID NO.: 79)
Nucleotide =
Atgtattcattcgacttcaactttgacacggcatatccgccacagactgaatattccaaacaagacgact gtctgggatacatgccatcacgcctccttacctggactggagctcgctgacattcccgccggttaata cgcacccatcgtcgataacgtgctcccggaagaaccctcggagccctcggacgtgtcttcttcttccgga gaagaaagcccctacttttcgacgaatactgcaccattccctctctggtcgaccagctcaaagaaaacc ccaacatttgggccatggcaaacaccgtcaagaaaggagcctacgtgtgtagccactgcactaagcaggg caccccgtcaagttcaaaaccatggtcgactttgccacccacctcgactcgcattctcatgaccgaagc tgcaaatgcgccgacacaaaatgtccctggtccattgtgggcttctctactcgatcggaaatgcgaagac acacaaactcggtccatcgacaaacacccttcacatgcaaaatctgtgaccgcgggtttgtacgagaaga ctctctcaaacggcatgtcaaactactccacatttctcccctcaaaaccagacgaaagagtacctga YLOSH6 YALI0A02354g
(SEQ ID NO.: 80)
Nucleotide =
atgcaccaccacctcaaccccaaggcgctcttttctggtgagtatggcggacagaaatggacggaggaac gtggcagagccgattgaccagccacgcaggccgaccaagcccattgagtgagccattggacgtccttgg cccgaatagacgctctctcccaggtttgccggaaaaacgagctgttatatccgaacgagctgtttgtgcc caaaaaagcccctactaaccccaggccgaaaggagagcacctctcccagacacaagccgcgtccggct ccggagccgtgtctccaggccgacctctggattcgtccaccaacgtcgaagatgtggatgagcttgacgg agacggccagaacatcatcatgggaattatcgcgcagctgcgacccggcgctgatctgtctcgaatcaca cttcccaccttcattctcgagcgaaagtccatgctcgagcgaatcacaaactccctgcagcaccccacat atgtcattgaggcccacgccaccaaggaccccatgcagcggttcatccaagtggtaaagtggtaccactc cggctggcacatcacccccaaggccgtcaaaaagcccctgaacccattctcggcgagttcttcacatgc tactgggactacgacgacggttcccacggatactacatctccgagcagacctccaccacccctcccaagt catcctacttttacatgatccctgagcacaacatccgagtcgacggtacactggctcccaagtcccgttt -continued cctgggtaactcagctgcttctctcatggagggcgccaccattctcaagttcctggacattgtagatgcc aagggcgctcccgaggagtacgaaatcacttcgcccaatgcctacgcccgaggtattctctttgaacggc tcaagtacgagtactgcgaccactcgatcatcaagtgtcccgctctggacctgactctggacctggactt caaggccaagggcttcatttccggtacatacaatgccttcgagggccagatcaagaagatctccaccggc gaggccttttacgatgtttatggaaagtgggatgaaatcatcgagctcaagaacctcaagaccggcgaga agtcggtgctgtttgacgtgactaaggccgccctgcaccctcccaaggtgcgacccatcgctgagcaggc cgccaccgagtcccgacgactgtgggagcccgtcaccgacgctcttgctaagcgagaccacaccgttgct accgacgaaaagttcaagattgaggacaaacagcgaacgctggccaaggagcgagaagagcacggcgtca agttcctgcccaaactgttcaagcccgcccccgctcccctggacttcattctgtataaggatctgcacgg cactcccgaagagatcaccaaggagattctcagcatagtccccattctgcccggccaacagttcaccaag gactttgaaatgtccggcgagaagaaatacaagctggagaagagcggccaggccagcagcgagactcagc ccaccgccacgaccactgcggctgcccccaagcaggcgctgtcccacaacccctgctaacggccagac tcccctggccaagacttctgatcttcaggaggctcttcccaccgaagaggacgagttccacgacgcccag tag YLIRC20 YALI0C07150g (SEQ ID NO.: 81)

Nucleotide =
atgacaagtgatgcgataaacgccatggaaaacgacagtacgacggtggtagaggtggaaacgacatttg tgaacgataacgtggtccgtggcttcctcgatgttgcacgtgatacgctgccagacgtccaaggactcct tccactggtccaagtgcagctggtggcggatatctcaagagagatgctggagggcgaagaagtgctggaa atcaccgatccagagtcacatggcgtcaaaaataccgaagcaggtgacgaaacgaactcacgtgacccca tcgtcgcttctgcgcctgctaccctggttcctaacgagagcacattagagattcatgtcacgcccaagta caccaccaaggacaagaaacgaggccgcaaaaagaccaagaaggacgaagattggttggtaacatgcttg ggtgttgttcaactaggaaacgtggaaaccagtgaccacgtgcttaccgctttgaaacaggctctttcgg tagccaaatttaacccgcgaaatcgagtcagtgtcttttcagtgaatcctcacgtcactgttaccaaaaa caatggtgtttacagcatttccatcacttttggagtctttgcgaagccttttgatggccacgtcaaccct gagatccatatggcaggtcacctcaacattgtgaatgtcatccgacagttcctgggcgtaactaagataa aacagctacataagaacgactatgtgactcctgaatacttctacgagtgcctggaactcaaggatgatac cgaggttgagatcaacagagatcttcagccggaagggatgagatcaaaacttttggattaccagcttgaa actgtggggtgggttctggatagaaaagggagaatcgcgtgagaagacgatagagggaattccttcac catggaaacggttcagggctcatggtatcaactggttggttgattttgtgggtctcaacattggtcctga gaaggaggtgatggagattttgacacgagatacgaaaccaacaactgaggaccccgagattcaagcagta tcacgtgacgcagattttaaggctggatatggacttattgctgatgaaatgggtcttggaaagacagttg agctactagctgtagtcctgaataaccccagacctgaatttccaccgcaaacacactacgatctgtactc tgacagagacgtgttacctaccaagacgactctcattttatgtcctgccagtatcagtcaacagtggatt gctgaggttactaaacatgctcccagtctctctgtctttctgtacactggtcgagcagctttggatgctc aaagagagaaggaaggtactcccgataccgatattgaggttggaattgactcagatactgattcagaagg ccctcttgtttcaaaacatgcacaatttctctctcagttcgacattgtagtcacatcctatgaagttgca tctcgcgaggttgccaacgctcttracaaccctctgagaggtcgtgtaactcgcaccaagacgaagctaa agtcgaaagatacccgagatgtcgatctcgtgcaagaccggctttccctccaatctccactgagtcagct tcagttctggcgtgtgattctggacgaggttcagatggtgggaaacacggtctccaacgcagctgttgta gctcgtattattccccgagtgcatgcatggggagtcagtggtactcctataaagaagggcatgcctgact -continued

```
tacttggcatgtgtgtgttttgagatgtgaacccggcgagttttatggaagaagtgattgtgagtatac taaaggaacagtcagagtggcatgtgacaaaaaaacaaaaaaccatatggctcaatgaagggctacgact aacacagatgcgtataactactcttggcaaaacggatacctcagcacaactatgacagcatctggagtaa gtcatcaaaaacactgggagatgctcatgcttgacaagcctcggtttcgagacgttattcgtcaaatgtc tattcgacatactaagcgacaggtcagagatcaactagtattgcctcctcaggaaagacaccatgtgaga ctcagattcaatctagtcgaggaagaaaactaccgacacctgcgtgaaggtgttgagagtgccgtcagtg aggcagtggctagttctctcatgagagaagagagggaagctacacgtgaggcagctgtggtggataggta tggcgttctgccttcaagtgtcactcccccctgtgagcaacagacctagaggcactttcaacatcggaggc tctaatccctatgctagtatcatggcgaatatcaacaacacagtcattgaacctgaaattgagattgatc ccagtatcacttctagtggagagggtgacggccaacatgtctacactacctggtcgggtgctgtagacac gtatggtggtgagtctagcggtacagctgctagtagcaccgatgctgacggcgatgataacgctcaatct cccacatctgatacagctagcaacactgacatcaatgttagtgctattcccgatatagaggtatccccga ctgccacccctacagcctccaccagatcccaaaatggaacttctgctcctccagcatcttccgctcctgc ggatttaacaacagcaaccctctcttcctggctgttacggttacgacaaacctgctgccatcctcgagtc ggttctggtaacaagaaggctctcggaaacggtattcttcaaactgtcagtcacgtgctggacgccatgt gcgaccaggcgctcacccagctgctgaacgacgagcgaagtctgtttgtcgaagagctggagaaggcacg agttcacgagttcaacaaacaaccagacattggactcacagtgcttcagtcacgtgtttctgaagtcgag gttcgaactggtgagatccgagatatggctgttgctgcggctacgcggtatgctatgaagaagaaggagg taatttccgagtggaagcgtattggtgaggttgataacaagcgcaagttggaggagagtgatgacggtgc tgctaatgttaagaaagtcaaggtcgaaaaagaggagaaggaggaagaagtggcaaaggaggaggtttcc gaagattttaaaatggagggaactgagaacaactccattttggagctccaactgcttttctgggctctg attcggagtctgagagcactggtaagatgtccaaaccattacaaaagtacctgaacaactccgaggaact tcagacggagaaggagcgaaaacaggcttttctgcaccggtacaggagctggatggatcttatgcatcgg tactattttttcattgctacttttcatttccaagttggagaagcgtgagtatgacaaagatttgtaatga cgtggtggttctactggggtcatgagaggtcatgagacatactaacacagtaaaaaagtggctgaggaga agaaagaaaaagaggatgggaaggacgatgaagagaaggaagatgaagagaaggaagagattgaggtcaa gaaagaggaggatgaagggaccaagagtgacgagtgagtatagagatatcatgagtggcagaataacttg tgccattcgctcctcttatgtatatgtgtactaacacagtctggaaacgcactattacacgctggcagaa caaatccgaacccagctacttcaacgccctattgagagagtagaccaagacgtgggtcgacttgaacggg ccaaggagctggagatggttcagatccctgttgataccttgactcgagatctagtacaggcttctcctttt ccttgaggcacgtgttctcgggtctactcgagatcatcaaccaacagtccgaatatcttgaagaatggatg accagagttcgagagctgttggttgcacgtgacgagaaggacgtgaaagaaacagataagaagaagaata aaggagatgtcgagaaagttgaaggcgaaaacactgatccttatgcttctggattagacaaccaacaata tgcgtcggactaccttgatgctatatcgtacctgctgcaactcagagatgaagctctcaatgccaagact acggcctcagcagccgacaagatccaagttaacttgtggtaccacaatgactacgaagaagagcttaccg atcttcaggtggccctcaaggaagctctggacgcttgtcatgtgagtcccactcttggtgccctcaaacc tatcgttgctgctctgaagacggactctggagctgtttcattgtcaatttacaacccgaaatggcctccc aagttgctgtccaagctcaatccgatcgttaagacagttacctcgacaaccaaggcttgcagagacctgt tgtcagtcgttagaagctgtttcaactcgaaggttgtctattacaagcagctgcagcaactgtctgacaa tgtgagcagtctggaggaactcatcgagcctggttatgtcacactggaacgcctgaacgccaaaataaac catctcgtacctttaatcaagcgtacaaagggccgaatcacatacttacagagtctcaaaggtgatgatg
```

-continued

```
acacaactggagtttccaacatgactggaattcataaaatgtgtgtcatctgtcaggatgattatattat cgtgggatccatcactgtctgtggccattacttttgcagaaactgcctggaagagtggtggcagacacat aatacgtgtccaatgtgcaagactgtattgtcccgcgacgatgtgttctctttcacccaacaggacaagg aagacaagtcacgtgcaggttctttcgctgctcggatcaatcaagatgacgccattggagcaatgtatgc gccagtgtcggaggacactcaacagttgatgagcaaacagagcatcaagagtgcgtatggcacaaagatt gaccacgttatcaagtatatcaagatgctcactcatcgggctcctggcactcagattgtcatctttctc agtgggcagagattctcacattgttagcttcagccctcactgagaacaagattgcatacgcggagccgaa aacactgatgtctttcttgcaatcggaagaagtcacgtgtttcctcttgaacgcaaagttccagtccact ggcctgactcttgtaaatgccactcacgtcattctatgcgagcccattctcaacgctgctcttgaggctc aggccatcagtcgaatccaccgaatgggccagactcagactacccacgtgactatcttcactatggccga tactgttgaagaagaggttctgcgtcttgctattaacaagcggttgaaaagtatggacggtgatgagacg tttgaggagaatgaatctcgacatgtgacatcaggagtgggtgcgctcgccaccgataaatccggagagg tggtcaaccgtcaggatatgtgggacgctttgtttcccagtgacgggtaa
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```

What is claimed is:

1. A method of producing a lipid, lipid precursor, or oleochemical comprising:
   a) culturing a genetically modified yeast cell in a growth medium; and
   b) isolating said lipid, lipid precursor, or oleochemical, wherein the dry weight of said genetically modified yeast cell comprises greater than 60% wt/wt lipids, lipid precursors, and oleochemicals; and
   wherein said genetically modified yeast cell comprises (i) a recombinant acyl-CoA:diacylglycerol acyltransferase 1 (DGA1) gene and a UGA2 succinate semialdehyde dehydrogenase (UGA2) gene comprising a mutation, wherein said mutation results in a loss of function of succinate semialdehyde dehydrogenase of 20% or more compared to succinate semialdehyde dehydrogenase encoded by UGA2 without the mutation; or (ii) a recombinant acyl-CoA:diacylglycerol acyltransferase 2 (DGA2) gene and a UGA2 succinate semialdehyde dehydrogenase (UGA2) gene comprising a mutation, wherein said mutation results in a loss of function of succinate semialdehyde dehydrogenase of 20% or more compared to succinate semialdehyde dehydrogenase encoded by UGA2 without the mutation.

2. The method of claim 1, wherein said growth medium comprises a majority carbon source selected from the group consisting of glucose, glycerol, xylose, fructose, mannose, ribose, sucrose, and lignocellulosic biomass.

3. The method of claim 1, wherein said growth medium comprises lignocellulosic biomass as the majority carbon source.

4. The method of claim 1, wherein said growth medium comprises cobalt, iron, magnesium, potassium, zinc, nickel, molybdenum, manganese, copper, or boron.

5. The method of claim 1, wherein said growth medium comprises $5.77 \times 10^{-5}$ M to $1.73 \times 10^{-4}$ M cobalt, 0.001 M to 0.003 M magnesium, $4.52 \times 10^{-5}$ M to $1.35 \times 10^{-4}$ M potassium, $4.05 \times 10^{-5}$ M to $1.22 \times 10^{-4}$ zinc, $3.55 \times 10^{-5}$ M to $1.06 \times 10^{-4}$ manganese, $9.07 \times 10^{-5}$ M to $2.91 \times 10^{-4}$ boron, $3.76 \times 10^{-5}$ M to $1.10 \times 10^{-5}$ molybdenum, $2.28 \times 10^{-5}$ M to $6.84 \times 10^{-5}$ nickel, $3.60 \times 10^{-5}$ M to $1.08 \times 10^{-4}$ iron, or $4.70 \times 10^{-5}$ M to $1.41 \times 10^{-4}$ copper.

6. The method of claim 1, wherein said genetically modified yeast cell comprises a recombinant Lipid synthesis regulator (MGA2) gene, a genetically modified Lipid synthesis regulator (MGA2) gene, a recombinant Leucine Biosynthesis gene (LEU2), a genetically modified multifunctional enzyme (MFEI) gene, a genetically modified PEX10 Transcription Factor (PEX10) gene or a recombinant AMP Deaminase (AMPD) gene.

7. The method of claim 1, wherein said genetically modified yeast cell comprises a genetically modified multifunctional enzyme (MFE1) gene and a genetically modified PEX10 Transcription Factor (PEX10) gene.

8. The method of claim 1, wherein said genetically modified yeast cell comprises a recombinant Leucine Biosynthesis gene (LEU2), a genetically modified multifunctional enzyme (MFEI) gene and a genetically modified PEX10 Transcription Factor (PEX10) gene.

9. The method of claim 1, wherein said genetically modified yeast cell comprises a genetically modified multifunctional enzyme (MFEI) gene, a genetically modified PEX10 Transcription Factor (PEX10) gene and a recombinant AMP Deaminase (AMPD) gene.

10. The method of claim 1, wherein said genetically modified yeast cell comprises a recombinant Leucine Biosynthesis gene (LEU2), a genetically modified multifunctional enzyme (MFEI) gene, a genetically modified PEX10 Transcription Factor (PEX10) gene and a recombinant AMP Deaminase (AMPD)) gene.

* * * * *